(12) United States Patent
Rewcastle et al.

(10) Patent No.: US 9,108,980 B2
(45) Date of Patent: *Aug. 18, 2015

(54) PYRIMIDINYL AND 1,3,5-TRIAZINYL BENZIMIDAZOLE SULFONAMIDES AND THEIR USE IN CANCER THERAPY

(71) Applicant: VETDC, Inc., Fort Collins, CO (US)

(72) Inventors: Gordon William Rewcastle, Auckland (NZ); Swarnalatha Akuratiya Gamage, Auckland (NZ); Jack Urquhart Flanagan, Auckland (NZ); Anna Claire Giddens, Auckland (NZ); Kit Yee Tsang, Auckland (NZ)

(73) Assignee: VETDC, INC., Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/324,570

(22) Filed: Jul. 7, 2014

(65) Prior Publication Data

US 2015/0038486 A1    Feb. 5, 2015

Related U.S. Application Data

(63) Continuation of application No. 13/914,385, filed on Jun. 10, 2013, now Pat. No. 8,772,287, which is a continuation of application No. 12/748,251, filed on Mar. 26, 2010, now Pat. No. 8,461,158.

(Continued)

(51) Int. Cl.
*A61K 31/5355* (2006.01)
*C07D 403/04* (2006.01)
(Continued)

(52) U.S. Cl.
CPC .......... *C07D 491/08* (2013.01); *A61K 31/5355* (2013.01); *A61K 31/541* (2013.01);
(Continued)

(58) Field of Classification Search
CPC .. C07D 403/04; C07D 403/14; C07D 413/14; C07D 487/04; C07D 491/08; A61K 31/5355
USPC ........................ 544/113; 514/234.5
See application file for complete search history.

(56) References Cited

U.S. PATENT DOCUMENTS 5,750,292 A    5/1998 Sato et al.
6,251,900 B1   6/2001 Kawashima et al.
(Continued)

FOREIGN PATENT DOCUMENTS

CN    101137382    3/2008
EP    0711804      5/1996
(Continued)

OTHER PUBLICATIONS

Barber et al. (2005) Nature Medicine 11(9):933-935 "PI3Kγ inhibition blocks glomerulonephritis and extends lifespan in a mouse model of systemic lupus".

Berrie (2001) Exp. Opin. Invest. Drugs 10:1085-1098 "Phosphoinositide 3-kinase inhibition in cancer treatment".

(Continued)

*Primary Examiner* — Rebecca Anderson
(74) *Attorney, Agent, or Firm* — Swanson & Bratschun, L.L.C.

(57) ABSTRACT

Provided herein are pyrimidinyl and 1,3,5-triazinyl benzimidazole sulfonamides, e.g., compounds of Formulae IA, IB, and IC, and their pharmaceutical compositions, preparation, and use as agents or drugs for cancer therapy, either alone or in combination with radiation and/or other anticancer drugs.

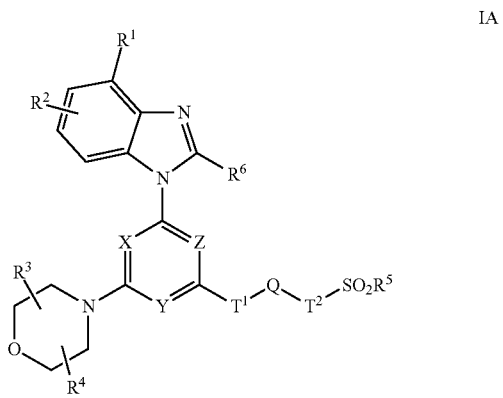

IA

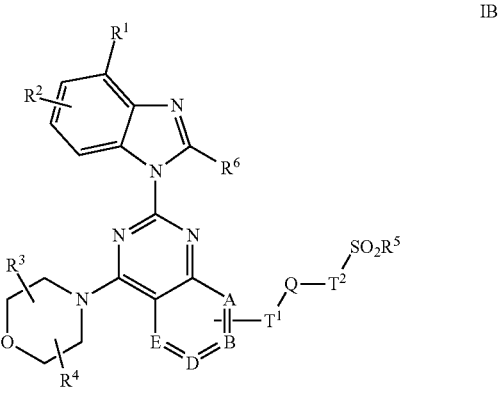

IB

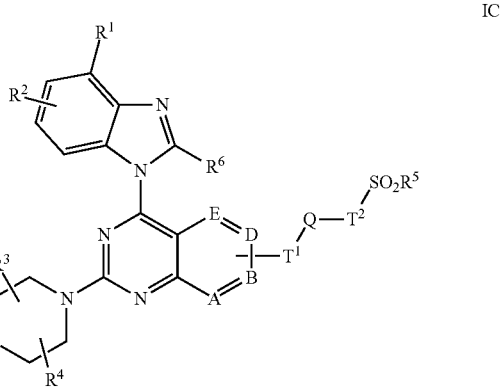

IC

22 Claims, No Drawings

Related U.S. Application Data

(60) Provisional application No. 61/164,359, filed on Mar. 27, 2009, provisional application No. 61/223,687, filed on Jul. 7, 2009, provisional application No. 61/247,454, filed on Sep. 30, 2009.

(51) Int. Cl.

| | | |
|---|---|---|
| *C07D 403/14* | (2006.01) | |
| *C07D 413/14* | (2006.01) | |
| *C07D 487/04* | (2006.01) | |
| *C07D 491/08* | (2006.01) | |
| *C07D 473/34* | (2006.01) | |
| *C07D 498/08* | (2006.01) | |
| *A61K 31/541* | (2006.01) | |
| *A61K 45/06* | (2006.01) | |

(52) U.S. Cl.
CPC ............ *A61K 45/06* (2013.01); *C07D 403/04* (2013.01); *C07D 403/14* (2013.01); *C07D 413/14* (2013.01); *C07D 473/34* (2013.01); *C07D 487/04* (2013.01); *C07D 498/08* (2013.01)

(56) References Cited

U.S. PATENT DOCUMENTS

| | | |
|---|---|---|
| 7,071,189 B2 | 7/2006 | Kawashima et al. |
| 7,153,853 B2 | 12/2006 | Kawashima et al. |
| 7,307,077 B2 | 12/2007 | Kawashima et al. |
| 8,461,158 B2 | 6/2013 | Rewcastle et al. |
| 8,772,287 B2 * | 7/2014 | Rewcastle et al. ......... 514/234.5 |
| 2007/0244110 A1 | 10/2007 | Yaguchi et al. |
| 2008/0113987 A1 | 5/2008 | Haruta et al. |
| 2008/0287431 A1 | 11/2008 | Kawashima et al. |
| 2009/0181963 A1 | 7/2009 | Dehnhardt et al. |
| 2009/0192176 A1 | 7/2009 | Zask et al. |
| 2009/0233926 A1 | 9/2009 | Butterworth et al. |
| 2009/0270390 A1 | 10/2009 | Butterworth et al. |
| 2009/0325954 A1 | 12/2009 | Butterworth et al. |
| 2010/0022534 A1 | 1/2010 | Butterworth et al. |
| 2011/0053907 A1 | 3/2011 | Rewcastle et al. |
| 2012/0165309 A1 | 6/2012 | Takahashi et al. |

FOREIGN PATENT DOCUMENTS

| | | |
|---|---|---|
| EP | 1864665 | 12/2007 |
| EP | 2050749 | 4/2009 |
| JP | 11174638 | 2/1999 |
| JP | A-2011-515462 | 5/2011 |
| JP | A-2011-527342 | 10/2011 |
| WO | WO 99/05138 | 2/1999 |
| WO | WO 01/81346 | 11/2001 |
| WO | WO 02/088112 | 11/2002 |
| WO | WO 2004/037812 | 5/2004 |
| WO | WO 2004/048365 | 6/2004 |
| WO | WO 2005/028467 | 3/2005 |
| WO | WO 2005/095389 | 10/2005 |
| WO | WO 2006/095906 | 9/2006 |
| WO | WO 2006/122806 | 11/2006 |
| WO | WO 2007/066099 | 6/2007 |
| WO | WO 2007/066103 | 6/2007 |
| WO | WO 2007/084786 | 7/2007 |
| WO | WO 2007/127183 | 8/2007 |
| WO | WO 2007/127175 | 11/2007 |
| WO | WO 2007/129161 | 11/2007 |
| WO | WO 2008/018426 | 2/2008 |
| WO | WO 2008/032027 | 3/2008 |
| WO | WO 2008/032028 | 3/2008 |
| WO | WO 2008/032033 | 3/2008 |
| WO | WO 2008/032036 | 3/2008 |
| WO | WO 2008/032041 | 3/2008 |
| WO | WO 2008/032060 | 3/2008 |
| WO | WO 2008/032064 | 3/2008 |
| WO | WO 2008/032072 | 3/2008 |
| WO | WO 2008/032077 | 3/2008 |
| WO | WO 2008/032086 | 3/2008 |
| WO | WO 2008/032089 | 3/2008 |
| WO | WO 2008/032091 | 3/2008 |
| WO | WO 2008/098058 | 8/2008 |
| WO | WO 2008/115974 | 9/2008 |
| WO | WO 2008/116129 | 9/2008 |
| WO | WO 2009/045174 | 4/2009 |
| WO | WO 2009/045175 | 4/2009 |
| WO | WO 2009/066775 | 5/2009 |
| WO | WO 2009/093981 | 7/2009 |
| WO | WO 2009/097490 | 8/2009 |
| WO | WO 2009/099163 | 8/2009 |
| WO | WO 2009/120094 | 10/2009 |
| WO | WO 2009/143313 | 11/2009 |
| WO | WO 2009/143317 | 11/2009 |
| WO | WO 2009/157880 | 12/2009 |
| WO | WO 2010/005558 | 1/2010 |
| WO | WO 2010/092962 | 8/2010 |

OTHER PUBLICATIONS

Billottet et al. (2006) Oncogene 25:6648-6659 "A selective inhibitor of the p110δ isoform of PI 3-kinase inhibits AML cell proliferation and survival and increases the cytotoxic effects of VP16.

Byrn et al. (1999) Solid-state Chemistry of Drugs, Second Edition, Chapter 11: "Hydrates and Solvates" pp. 233-247.

Camps et al. (2005) Nature Medicine 11(9):936-943 "Blockade of P13Kγ suppresses joint inflammation and damage in mouse models of rheumatoid arthritis".

Foukas and Sheperd (2004) Biochemical Society Transactions 32(part 2):330-331 "Phosphoinositide 3-kinase: the protein kinase that time forgot".

Fry (1994) Biochimica et Biophysica Acta 1226:237-268 "Structure, regulation and function of phosphoinositide 3-kinases".

Fry (2001) Breast Cancer Res 3:304-312 "Phosphoinositide 3-kinase signalling in breast cancer: how big a role might it play?"

Gymnopoulos et al. (2007) Proc. Natl. Acad. Sci. 104(13):5569-5574 "Rare cancer-specific mutations in PIK3CA show gain of function".

Hayakawa et al. (2007) Bioorg. Med. Chem. 15:403-412 "Synthesis and biological evaluation of imidazo[1,2-a]pyridine derivatives as novel PI3 kinase p110alpha inhibitors".

Hayakawa et al. (2007) Bioorganic & Medicinal Chemistry 15:5837-5844 "Synthesis and biological evaluation of sulfonylhydrazone-substituted imidazo[1,2-*a*]pyridines as novel PI3 kinase p110α inhibitors".

Hayakawa et al. (2007) Bioorganic & Medicinal Chemistry Letters 17:2438-2442 "Synthesis and biological evaluation of pyrido[3',2':4,5]furo[3,2-*d*]pyrimidine derivatives as novel PI3 kinase p110α inhibitors".

Horner et al. (1953) Justus Liebigs Annalen der Chemie 579:212-234 "Derivate des Chinoxalins als Isostere der Pteridine".

Hu et al. (2002) Cancer Research 62:1087-1092 "Inhibition of Phosphatidylinositol 3'-Kinase Increases Efficacy of Paclitaxel in in Vitro and in Vivo Ovarian Cancer Models".

Huang et al. (2007) Science 318:1744-1748 "The Structure of a Human P10α/P85α Complex Elucidates the Effects of Oncogenic PI3Kα Mutations".

Ikenoue et al. (2005) Cancer Res. 65(11):4562-4567 "Functional Analysis of PIK3CA Gene Mutations in Human Colorectal Cancer".

Jackson et al. (2005) Nature Medicine 11(5):507-514 "PI 3-kinase p110β: a new target for antithrombotic therapy".

Kang et al. (2005) Proc. Natl. Acad. Sci. 102(3):802-807 "Phosphatidylinositol 3-kinase mutations identified in human cancer are oncogenic".

Knight et al. (2006) Cell 125:733-747 "A Pharmacological Map of the P13-K Family Defines a Role for P110α in Insulin Signaling".

Kong and Yamori (2007) Cancer Sci. 98(10):1638-1642 "ZSTK474 is an ATP-competitive inhibitor of class I phosphatidylinositol 3 kinase isoforms".

Lanni et al. (2007) Bioorganic & Medicinal Chemistry Letters 17:756-760 "Design and synthesis of phenethyl benzo[1.4]oxazine-3-ones as potent inhibitors of PI3Kinaseγ".

(56) References Cited

OTHER PUBLICATIONS

Löwik and Lowe (2001) European Journal of Organic Chemistry 2825-2839 "Synthesis of Macrocyclic, Triazine-Based Receptor Molecules".
Maira et al. (2008) Mol. Cancer Ther. 7(7):1851-1863 "Identification and characterization of NVP-BEZ235, a new orally available dual phosphatidylinositol 3-kinase/mammalian target of rapamycin inhibitor with potent in vivo antitumor activity".
Marshall et al. (2004) Oncology Research 14:297-304 "Estimation of Radiation-Induced Interphase Cell Death in Cultures of Human Tumor Material and in Cell Lines".
Matsuno et al. (2000) Chem. Pharm. Bull. 48(11):1778-1781 "Synthesis and Antitumor Activity of Benzimidazolyl-1,3,5-Triazine and Benzimidazolylpyrimidine Derivatives".
Miled et al. (2007) Science 317:239-242 "Mechanism of Two Classes of Cancer Mutations in the Phosphoinositide 3-Kinase Catalytic Subunit".
Raynaud et al. (2007) Cancer Res. 67(12):5840-5850 "Pharmacologic Characterization of a Potent Inhibitor of Class I Phosphatidylinositide 3-Kinases".
Sabat et al. (2006) Bioorganic & Medicinal Chemistry Letters 16:5973-5977 "The development of 2-benzimidazole substituted pyrimidine based inhibitors of lymphocyte specific kinase (Lck)".
Samuels et al. (2004) Science 304:554 "High Frequency of Mutations of the PIK3CA Gene in Human Cancers".
Semba et al. (2002) Clinical Cancer Research 8:1957-1963 "The in Vitro and in Vivo Effects of 2-(4-Morpholinyl)-8-phenyl-chromone (LY294002), a Specific Inhibitor of Phosphatidylinositol 3'-Kinase, in Human Colon Cancer Cells".
Shepherd (2005) Acta Physiol Scand 183:3-12 "Mechanisms regulating phosphoinositide 3-kinase signalling in insulin-sensitive tissues".
Stauffer et al. (2005) Curr. Med. Chem.—Anticancer Agents 5:449-462 "Blocking the PI3K/PKB Pathway in Tumor Cells".
Stephens et al. (2005) Current Opinion in Pharmacology 5:357-365 "Phosphoinositide 3-kinases as drug targets in cancer".
Stirdivant et al. (1997) Bioorganic & Medicinal Chemistry 5(1):65-74 "Cloning and Mutagenesis of the P110α Subunit of Human Phosphoinositide 3'-Hydroxykinase".
Toshiyuki et al., (2000) Chem. Pharm. (48): 1778-1781. "Synthesis and antitumor activity of benzimidazolyl-1,3,5-trizaine and benzimidazolylpyrimidine derivatives."
Vanhaesebroeck and Waterfield (1999) Experimental Cell Research 253:239-254 "Signaling by Distinct Classes of Phosphoinositide 3-Kinases".
Volinia et al. (1994) Genomics 24:472-477 "Molecular cloning, cDNA Sequence, and Chromosomal Localization of the Human Phosphatidylinositol 3-Kinase p110α (PIK3CA) Gene".
Walker et al. (2000) Molecular Cell 6:909-919 "Structural Determinants of Phosphoinositide 3-Kinase Inhibition by Wortmannin, LY294002, Quercetin, Myricetin, and Staurosporine".
Wipf et al. (2004) Org. Biomol. Chem. 2:1911-1920 "Synthesis and biological evaluation of synthetic viridins derived from C(20)-heteroalkylation of the steroidal PI-3-kinase inhibitor wortmannin".
Yaguchi et al. (2006) Journal of the National Cancer Institute 98(8):545-556 "Antitumor Activity of ZSTK474, a New Phosphatidylinositol 3-Kinase Inhibitor".
Yokoyama et al. (2008) Bioorganic & Medicinal Chemistry 16:7968-7974 "Potent CCR4 antagonists: Synthesis, evaluation, and docking study of 2,4-diaminquinazolines".
Zask et al. (2008) J. Med. Chem. 51:1319-1323 "Synthesis and Structure-Activity Relationships of Ring-Opened 17-Hydroxywortmannins: Potent Phosphoinositide 3-Kinase Inhibitors with Improved Properties and Anticancer Efficacy".
Zhu et al. (2006) J. Med. Chem. 49:1373-1378 "Pegylated Wortmannin and 17-Hydroxywortmannin Conjugates as Phosphoinositide 3-Kinase Inhibitors Active in Human Tumor Xenograft Models".
Chinese Office Action for Application No. 201080023218.9 dated Sep. 2, 2014, 14 pages.
Japanese Office Action for Application No. 2012-501953 dated Jul. 9, 2014, 12 pages.
Jaworska et al. "Review of Methods for Assessing the Applicabilty Domains of SARS and QSARS" ptcl.chem.ox.ac.uk/MSDS structure activity relationship; 1-8, (2004).
Lala et al. "Role of nitric oxide in tumor progression: Lessons from experimental tumors" Cancer and Metastasis Reviews (1998), 17(1): 91-106.
Golub et al. "Molecular Classification of Cancer: Class Disclovery and Class Prediction by Gene Expression Monitoring" Science (1999), vol. 286; 531-537.

\* cited by examiner

PYRIMIDINYL AND 1,3,5-TRIAZINYL BENZIMIDAZOLE SULFONAMIDES AND THEIR USE IN CANCER THERAPY

CROSS REFERENCE TO RELATED APPLICATIONS

This application is a continuation of U.S. application Ser. No. 13/914,385, filed Jun. 20, 2013, which will issue as U.S. Pat. No. 8,772,287 on Jul. 8, 2014, which is a continuation of U.S. application Ser. No. 12/748,251, filed Mar. 26, 2010, which issued as U.S. Pat. No. 8,461,158 on Jun. 11, 2013, which claims priority under 35 U.S.C. §119(e) to U.S. Provisional Application Nos. 61/164,359, filed Mar. 27, 2009; 61/223,687, filed Jul. 7, 2009; and 61/247,454, filed Sep. 30, 2009; the disclosure of each of which is incorporated herein by reference in its entirety.

FIELD

Provided herein are pyrimidinyl and 1,3,5-triazinyl benzimidazole sulfonamides, and their pharmaceutical compositions, preparation, and use as agents or drugs for cancer therapy, either alone or in combination with radiation and/or other anticancer drugs.

BACKGROUND

Phosphoinositide-3-kinases (PI3Ks) are a group of lipid kinases, which phosphorylate the 3-hydroxyl of phosphoinositides. They are classified into at least three classes (Classes I, II, and III) and play an important role in cellular signaling (Stephens et al., *Curr. Opin. Pharmacol.* 2005, 5, 357). Class I enzymes are further classified into Classes Ia and Ib based on their mechanism of activation; Class Ia PI3Ks are heterodimeric structures consisting of a catalytic subunit (p110α, p110β, or p110δ) in complex with a regulatory p85 subunit, while the class-Ib PI3K (p110γ) is structurally similar but lacks the p85 regulatory subunit, and instead is activated by βγ subunits of heterotrimeric G-proteins (Walker et al., *Mol. Cell.* 2000, 6, 909). The human protein sequence of the p110α isoform is described in Volina et al., *Genomics* 1994, 24, 472; and Stirdivant et al., *Bioorg. Med. Chem.* 1997, 5, 65.

PI3Ks play a variety of roles in normal tissue physiology (Foukas & Shepherd, *Biochem. Soc. Trans.* 2004, 32, 330; Shepherd, *Acta Physiol. Scand.* 2005, 183, 3), with p110α having a specific role in cancer growth, p110β in thrombus formation mediated by integrin $\alpha_{IIb}\beta_3$ (Jackson et al., *Nat. Med.* 2005, 11, 507), and p110γ in inflammation, rheumatoid arthritis (Camps et al., *Nat. Med.* 2005, 11, 936) and other chronic inflammation states (Barber et al., *Nat. Med.* 2005, 11, 933). The PI3K enzymes produce phosphoinositide 3,4,5-triphosphate (PIP3) from the corresponding diphosphate (PIP2), thus recruiting AKT (protein kinase B) through its Pleckstrin homology (PH) domain to the plasma membrane. Once bound, AKT is phosphorylated and activated by other membrane bound kinases and is central to a cascade of events that lead to inhibition of apoptosis (Berrie, *Exp. Opin. Invest. Drugs* 2001, 10, 1085).

The p110α isoform is selectively amplified and activated in a number of cancer types (Stephens et al., *Curr. Opin. Pharmacol.* 2005, 5, 357; Stauffer et al., *Curr. Med. Chem.—Anti-Cancer Agents* 2005, 5, 449). In addition, there is a high frequency of non-random mutations in specific sites, primarily in the C2 domain and or the activation loop, of the kinase in several human cancer cell lines, including colon, brain, breast, and stomach (Samuels et al., *Science* 2004, 304, 554). This results in a constitutively active enzyme (Ikenoue et al., *Cancer Res.* 2005, 65, 4562; Kang et al., *Proc. Natl. Acad. Sci. USA* 2005, 102, 802), making p110α one of the most highly mutated oncogenes found in human tumors. Structural studies have shown that many of the mutations occur at residues lying at the interfaces between p110α and p85α or between the kinase domain of p110α and other domains within the catalytic subunit (Miled et al., *Science* 2007, 317, 239; Huang et al., *Science* 2007, 318, 1744).

While PI3K isoenzymes play important roles in many cellular processes, published experimental studies in mice with human tumor xenografts show that the pan-PI3K inhibitor LY294002 is well-tolerated, reduces signaling through the PI3K pathway, causes reduction of tumor volume, and is more active in cell lines over-expressing mutant forms of p110α than parental control cells (Semba et al., *Clin. Cancer Res.* 2002, 8, 1957; Hu et al., *Cancer Res.* 2002, 62, 1087).

Thus, PI3K, especially the p110α isoform, is an interesting target for drug intervention. Several classes of compounds have been identified as reversible inhibitors; for example, LY 294002 (non-selective) (Walker et al., *Mol. Cell.* 2000, 6, 909), PI103 (slightly α-selective) (Knight et al., *Cell* 2006, 125, 733; Hayakawa et al., *Bioorg. Med. Chem. Lett.* 2007, 17, 2438; Raynaud et al., *Cancer Res.* 2007, 67, 5840), ZSTK474 (non-selective) (Yaguchi et al., *J. Natl. Cancer Inst.* 2006, 98, 545; Kong et al., *Cancer Sci.* 2007, 98, 1639), TGX221 (β-selective) (Jackson et al., *Nat. Med.* 2005, 11, 507), oxazines (γ-selective) (Lanni et al., *Bioorg. Med. Chem. Lett.* 2007, 17, 756), IC87114 (δ-selective) (Sadhu et al. WO 2001/81346; Billottet et al., *Oncogene* 2006, 25, 6648), AS605240 (γ-selective) (Camps et al., *Nat. Med.* 2005, 11, 936), the imidazo[1,2-a]pyridines (α-selective) (Hayakawa et al., *Bioorg. Med. Chem.* 2007, 15, 403; Hayakawa et al., *Bioorg. Med. Chem.* 2007, 15, 5837), and the imidazo[4,5-c]quinoline NVP-BEZ235 (Garcia-Echeverria, et al., WO 2006/122806).

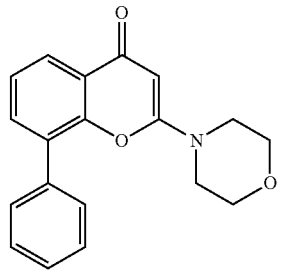

LY294002

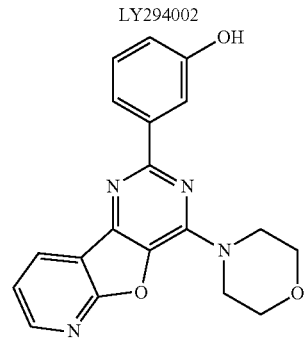

PI103

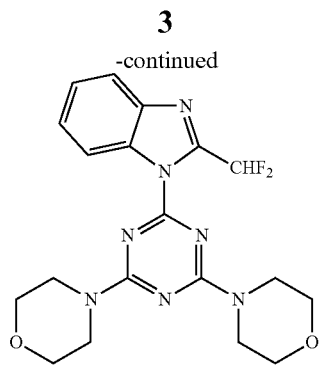
ZSTK474
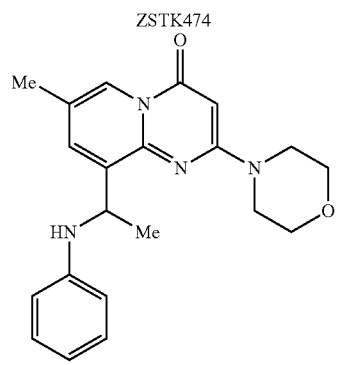
TGX221
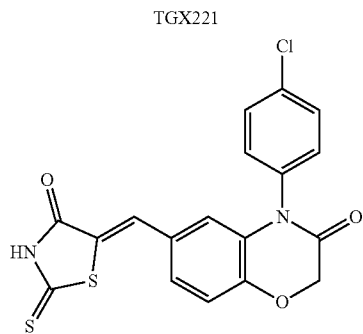
IC87114
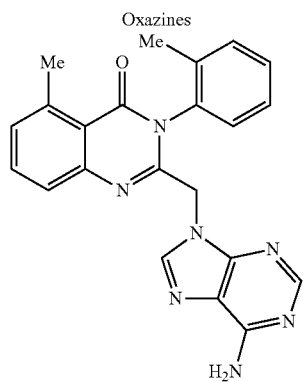
Oxazines
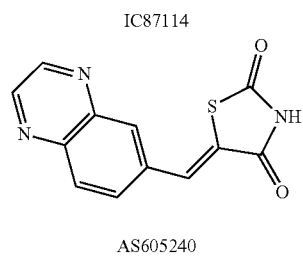
AS605240
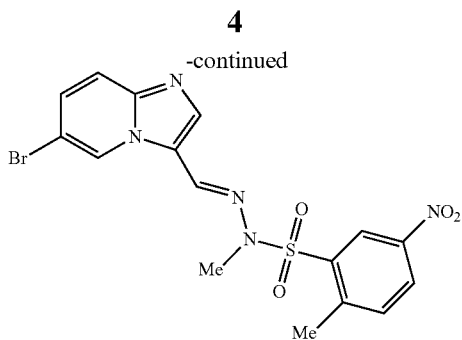
Imidazol[1,2-a]pyridine
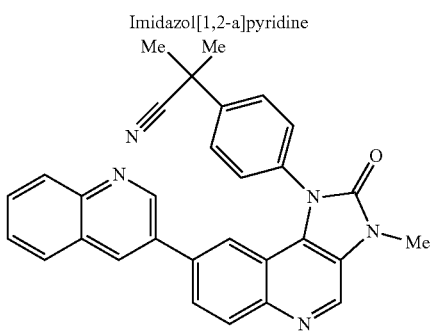
NVP-BEZ235
Despite the advances in developing PI3K inhibitors, there is a need for PI3K inhibitors for treatment of cancer.
SUMMARY OF THE DISCLOSURE
Provided herein is a compound of Formula IA, IB, or IC:
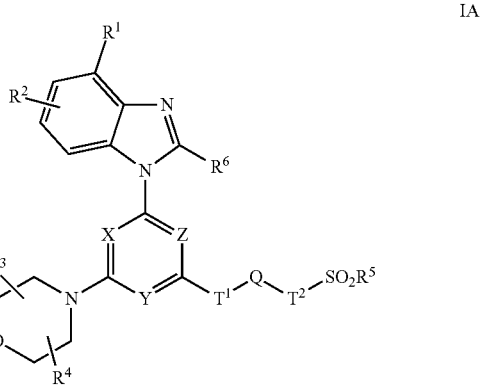
IA
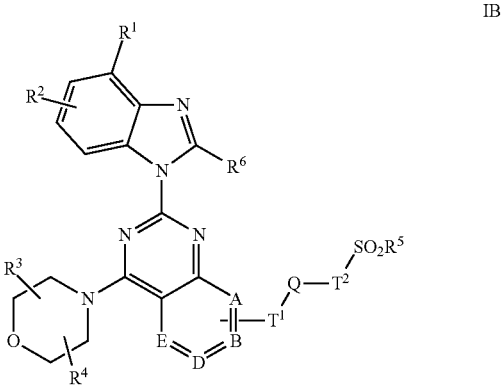
IB

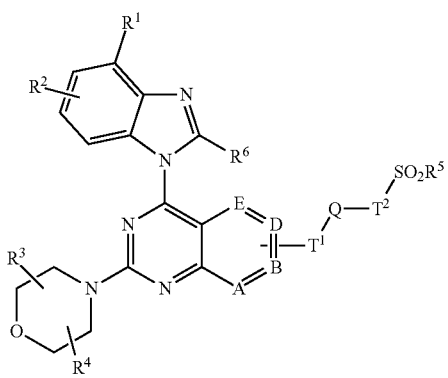

IC or an enantiomer, a mixture of enantiomers, or a mixture of two or more diastereomers thereof; or a pharmaceutically acceptable salt, solvate, hydrate, or prodrug thereof; wherein:

each $R^1$ and $R^2$ is independently (a) hydrogen, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1b}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; wherein each $R^{1a}$, $R^{1b}$, $R^{1c}$, and $R^{1d}$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^{1b}$ and $R^{1c}$ together with the N atom to which they are attached form heterocyclyl;

each $R^3$ and $R^4$ is independently hydrogen or $C_{1-6}$ alkyl; or $R^3$ and $R^4$ are linked together to form a bond, $C_{1-6}$ alkylene, $C_{1-6}$ heteroalkylene, $C_{2-6}$ alkenylene, or $C_{2-6}$ heteroalkenylene;

each $R^5$ is independently $C_{1-6}$ alkyl, $C_{2-6}$ alkenyl, $C_{2-6}$ alkynyl, $C_{3-7}$ cycloalkyl, $C_{3-7}$ cycloalkyl-$C_{1-6}$ alkyl, $C_{6-14}$ aryl, $C_{7-15}$ aralkyl, heteroaryl, heteroaryl-$C_{1-6}$ alkyl, heterocyclyl, heterocyclyl-$C_{1-6}$ alkyl, or —N$R^{5m}R^{5n}$, where $R^{5m}$ and $R^{5n}$ are each independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl;

each $R^6$ is independently hydrogen or $C_{1-6}$ alkyl;

each A, B, D, and E is independently a bond, C, O, N, S, N$R^7$, C(O), C$R^7$, or C$R^7R^{7'}$, where each $R^7$ and $R^{7'}$ is independently hydrogen, halo, $C_{1-6}$ alkyl, $C_{2-6}$ alkenyl, or $C_{2-6}$ alkynyl; wherein the bonds between A, B, D, and E may be saturated or unsaturated; with the proviso that no more than one of A, B, D, and E are a bond;

each Q is $C_{1-6}$ alkylene, $C_{2-6}$ alkenylene, $C_{2-6}$ alkynylene, $C_{3-7}$ cycloalkylene, $C_{6-14}$ arylene, heteroarylene, or heterocyclylene;

each $T^1$ is independently a bond, $C_{1-6}$ alkylene, —O—, or —N$R^8$—;

each $T^2$ is independently a bond, $C_{1-6}$ alkylene, or —N$R^8$—;

with the proviso that at least one of the two atoms that are directly attached to the —SO$_2$— group is nitrogen;

each $R^8$ is independently hydrogen, $C_{1-6}$ alkyl, $C_{2-6}$ alkenyl, or $C_{2-6}$ alkynyl; and X, Y, and Z are each independently a nitrogen atom or C$R^9$, with the proviso that at least two of X, Y, and Z are nitrogen atoms; where $R^9$ is hydrogen or $C_{1-6}$ alkyl;

wherein each alkyl, alkylene, heteroalkylene, alkenyl, alkenylene, heteroalkenylene, alkynyl, alkynylene, cycloalkyl, cycloalkylene, aryl, arylene, heteroaryl, heteroarylene, heterocyclyl, and heterocyclylene in $R^1$, $R^2$, $R^3$, $R^4$, $R^5$, $R^6$, $R^7$, $R^{7'}$, $R^8$, $R^9$, $R^{1a}$, $R^{1b}$, $R^{1c}$, $R^{1d}$, $R^{5m}$, $R^{5n}$, Q, $T^1$, and $T^2$, is optionally substituted with one or more groups, in one embodiment, one, two, three, or four groups, each independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents $Q^1$; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^1$; or (iii) $R^b$ and $R^c$ together with the N atom to which they are attached form heterocyclyl, optionally substituted with one or more, in one embodiment, one, two, three, or four, substituents $Q^1$;

wherein each $Q^1$ is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^h$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

Provided herein is a compound of Formula IA, IB, or IC:

IA

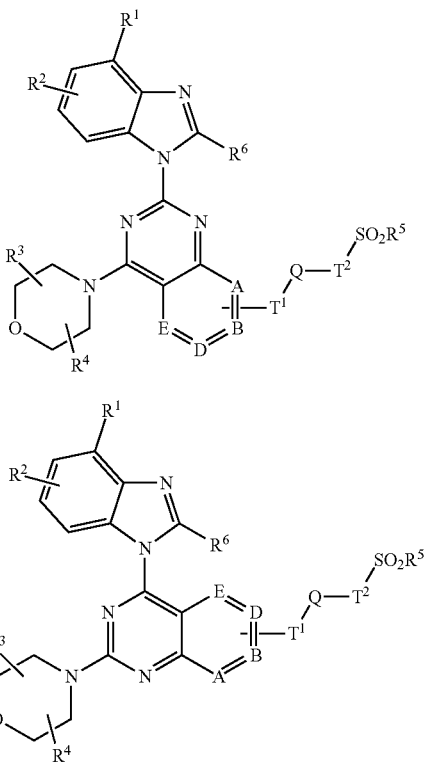

or an enantiomer, a mixture of enantiomers, or a mixture of two or more diastereomers thereof; or a pharmaceutically acceptable salt, solvate, hydrate, or prodrug thereof; wherein:

each $R^1$ and $R^2$ is independently (a) hydrogen, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1b}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; wherein each $R^{1a}$, $R^{1b}$, $R^{1c}$, and $R^{1d}$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^{1b}$ and $R^{1c}$ together with the N atom to which they are attached form heterocyclyl;

each $R^3$ and $R^4$ is independently hydrogen or $C_{1-6}$ alkyl; or $R^3$ and $R^4$ are linked together to form a bond, $C_{1-6}$ alkylene, $C_{1-6}$ heteroalkylene, $C_{2-6}$ alkenylene, or $C_{2-6}$ heteroalkenylene;

each $R^5$ is independently $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl;

each $R^6$ is independently hydrogen or $C_{1-6}$ alkyl;

each A, B, D, and E is independently a bond, C, O, N, S, N$R^7$, C$R^7$, or C$R^7R^{7'}$, where each $R^7$ and $R^{7'}$ is independently hydrogen, halo, $C_{1-6}$ alkyl, $C_{2-6}$ alkenyl, or $C_{2-6}$ alkynyl; wherein the bonds between A, B, D, and E may be saturated or unsaturated; with the proviso that no more than one of A, B, D, and E are a bond;

each Q is $C_{1-6}$ alkylene, $C_{2-6}$ alkenylene, $C_{2-6}$ alkynylene, $C_{3-7}$ cycloalkylene, $C_{6-14}$ arylene, heteroarylene, or heterocyclylene;

each $T^1$ is independently a bond, —O—, or —N$R^8$—;
each $T^2$ is independently a bond or —N$R^8$—, with the proviso that the atom that is attached to —SO$_2R^5$ is nitrogen;
each $R^8$ is independently hydrogen, $C_{1-6}$ alkyl, $C_{2-6}$ alkenyl, or $C_{2-6}$ alkynyl; and
X, Y, and Z are each independently a nitrogen atom or C$R^9$, with the proviso that at least two of X, Y, and Z are nitrogen atoms; where $R^9$ is hydrogen or $C_{1-6}$ alkyl;

wherein each alkyl, alkylene, heteroalkylene, alkenyl, alkenylene, heteroalkenylene, alkynyl, alkynylene, cycloalkyl, cycloalkylene, aryl, arylene, heteroaryl, heteroarylene, heterocyclyl, and heterocyclylene in $R^1$, $R^2$, $R^3$, $R^4$, $R^5$, $R^6$, $R^7$, $R^{7'}$, $R^8$, $R^9$, $R^{1a}$, $R^{1b}$, $R^{1c}$, $R^{1d}$, and Q is optionally substituted with one or more groups, in one embodiment, one, two, three, or four groups, each independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents $Q^1$; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^1$; or (iii) $R^b$ and $R^c$ together with the N atom to which they are attached form heterocyclyl, optionally substituted with one or more, in one embodiment, one, two, three, or four, substituents $Q^1$;

wherein each $Q^1$ is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^h$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

Also provided herein is a compound of Formula IA, IB, or IC:

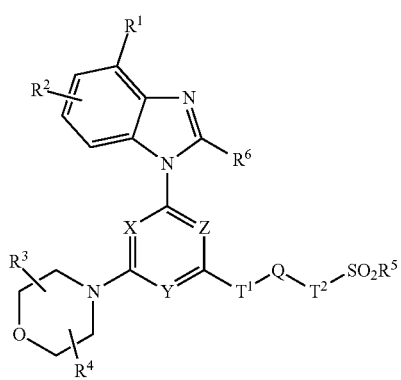

-continued

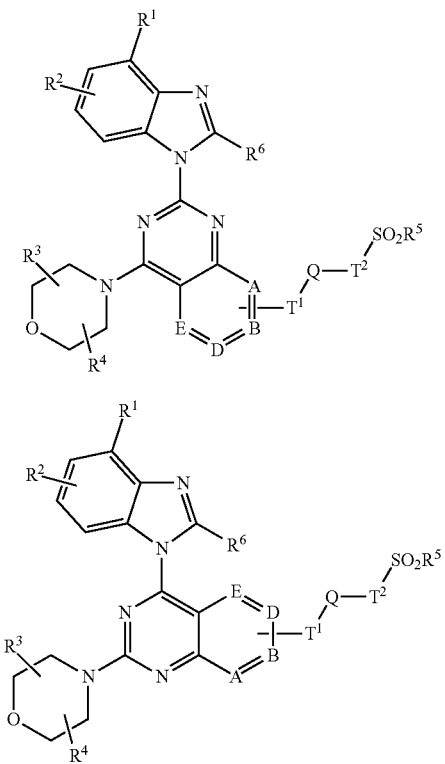

or an enantiomer, a mixture of enantiomers, or a mixture of two or more diastereomers thereof; or a pharmaceutically acceptable salt, solvate, hydrate, or prodrug thereof; wherein:

each $R^1$ and $R^2$ is independently (a) hydrogen, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1b}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; wherein each $R^{1a}$, $R^{1b}$, $R^{1c}$, and $R^{1d}$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^1$; or (iii) $R^{1b}$ and $R^{1c}$ together with the N atom to which they are attached form heterocyclyl, optionally substituted with one or more, in one embodiment, one, two, three, or four, substituents $Q^1$;

each $R^3$ and $R^4$ is independently hydrogen or $C_{1-6}$ alkyl;

each $R^5$ is independently $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl;

each $R^6$ is independently hydrogen or $C_{1-6}$ alkyl;

each A, B, D, and E is independently (i) a bond; (ii) a nitrogen, oxygen, or sulfur atom; or (iii) C$R^7$, where $R^7$ is hydrogen, halo, $C_{1-6}$ alkyl, $C_{2-6}$ alkenyl, or $C_{2-6}$ alkynyl; wherein the bonds between A, B, D, and E may be saturated or unsaturated; with the proviso that no more than one of A, B, D, and E are a bond;

each Q is $C_{1-6}$ alkylene, $C_{2-6}$ alkenylene, $C_{2-6}$ alkynylene, $C_{3-7}$ cycloalkylene, $C_{6-14}$ arylene, heteroarylene, or heterocyclylene;

each $T^1$ is independently a bond, —O—, or —N$R^8$—;
each $T^2$ is independently a bond or —N$R^8$—, with the proviso that the atom that is attached to —SO$_2R^5$ is nitrogen;
each $R^8$ is independently hydrogen, $C_{1-6}$ alkyl, $C_{2-6}$ alkenyl, or $C_{2-6}$ alkynyl; and
X, Y, and Z are each independently a nitrogen atom or C$R^9$, with the proviso that at least two of X, Y, and Z are nitrogen atoms; where $R^9$ is hydrogen or $C_{1-6}$ alkyl;

wherein each alkyl, alkylene, alkenyl, alkenylene, alkynyl, alkynylene, cycloalkyl, cycloalkylene, aryl, arylene, heteroaryl, heteroarylene, heterocyclyl, and heterocyclylene is optionally substituted with one or more groups, each independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents $Q^1$; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^1$; or (iii) $R^b$ and $R^c$ together with the N atom to which they are attached form heterocyclyl, optionally substituted with one or more, in one embodiment, one, two, three, or four, substituents $Q^1$;

wherein each $Q^1$ is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^h$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

Additionally provided herein is a compound of Formula Ia, Ib, or Ic:

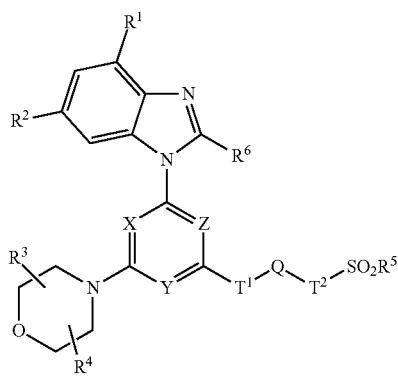

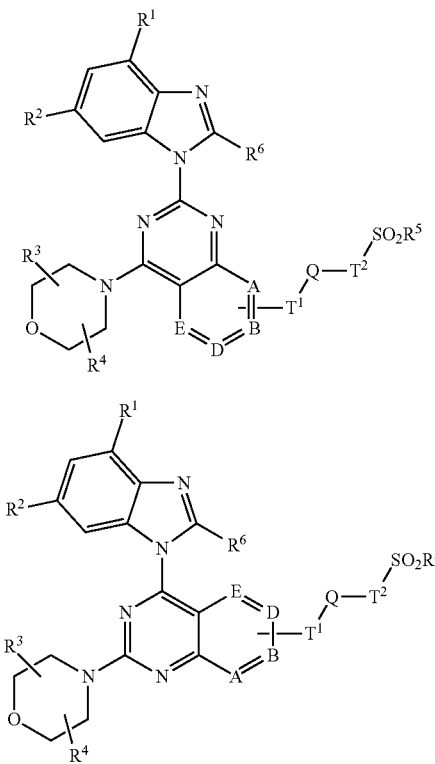

or an enantiomer, a mixture of enantiomers, or a mixture of two or more diastereomers thereof; or a pharmaceutically acceptable salt, solvate, hydrate, or prodrug thereof; wherein:

each $R^1$ and $R^2$ is independently (a) hydrogen, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1b}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^d$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; wherein each $R^{1a}$, $R^{1b}$, $R^{1c}$, and $R^{1d}$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^1$; or (iii) $R^{1b}$ and $R^{1c}$ together with the N atom to which they are attached form heterocyclyl, optionally substituted with one or more, in one embodiment, one, two, three, or four, substituents $Q^1$;

each $R^3$ and $R^4$ is independently hydrogen or $C_{1-6}$ alkyl;

each $R^5$ is independently $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl;

each $R^6$ is independently hydrogen or $C_{1-6}$ alkyl;

each A, B, D, and E is independently (i) a bond; (ii) a nitrogen, oxygen, or sulfur atom; or (iii) $CR^7$, where $R^7$ is hydrogen, halo, $C_{1-6}$ alkyl, $C_{2-6}$ alkenyl, or $C_{2-6}$ alkynyl; wherein the bonds between A, B, D, and E may be saturated or unsaturated; with the proviso that no more than one of A, B, D, and E are a bond;

each Q is $C_{1-6}$ alkylene, $C_{2-6}$ alkenylene, $C_{2-6}$ alkynylene, $C_{3-7}$ cycloalkylene, $C_{6-14}$ arylene, heteroarylene, or heterocyclylene;

each $T^1$ is independently a bond, —O—, or —N$R^8$—;

each $T^2$ is independently a bond or —N$R^8$—, with the proviso that the atom that is attached to —SO$_2R^5$ is nitrogen;

each $R^8$ is independently hydrogen, $C_{1-6}$ alkyl, $C_{2-6}$ alkenyl, or $C_{2-6}$ alkynyl; and X, Y, and Z are each independently a nitrogen atom or $CR^9$, with the proviso that at least two of X, Y, and Z are nitrogen atoms; where $R^9$ is hydrogen or $C_{1-6}$ alkyl;

wherein each alkyl, alkylene, alkenyl, alkenylene, alkynyl, alkynylene, cycloalkyl, cycloalkylene, aryl, arylene, heteroaryl, heteroarylene, heterocyclyl, and heterocyclylene is optionally substituted with one or more groups, each independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents $Q^1$; and (c) —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^1$; or (iii) $R^b$ and $R^c$ together with the N atom to which they are attached form heterocyclyl, optionally substituted with one or more, in one embodiment, one, two, three, or four, substituents $Q^1$;

wherein each $Q^1$ is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(N$R^e$)N$R^fR^g$, —O$R^e$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^h$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

Provided herein are pharmaceutical compositions comprising a compound disclosed herein, e.g., a compound of Formula IA, IB, or IC, including an enantiomer, a mixture of enantiomers, or a mixture of two or more diastereomers; or a pharmaceutically acceptable salt, solvate, hydrate, or prodrug thereof; in combination with one or more pharmaceutically acceptable carriers.

Provided herein is a method for treating, preventing, or ameliorating one or more symptoms of a PI3K-mediated disorder, disease, or condition in a subject, comprising administering to the subject a therapeutically effective amount of a compound disclosed herein, e.g., a compound of Formula IA, IB, or IC, an enantiomer, a mixture of enantiomers, a mixture of two or more diastereomers; or a pharmaceutically acceptable salt, solvate, hydrate, or prodrug thereof.

Provided herein is a method for modulating PI3K activity, comprising contacting a PI3K with a therapeutically effective amount of a compound disclosed herein, e.g., a compound of Formula IA, IB, or IC, including an enantiomer, a mixture of enantiomers, or a mixture of two or more diastereomers; or a pharmaceutically acceptable salt, solvate, hydrate, or prodrug thereof.

DETAILED DESCRIPTION

To facilitate understanding of the disclosure set forth herein, a number of terms are defined below.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition, Lippincott Williams & Wilkins: Philadelphia, Pa., 2005; *Handbook of Pharmaceutical Excipients,* 5th Edition, Rowe et al., Eds., The Pharmaceutical Press and the American Pharmaceutical Association: 2005; and *Handbook of Pharmaceutical Additives,* 3rd Edition, Ash and Ash Eds., Gower Publishing Company: 2007; *Pharmaceutical Preformulation and Formulation,* 2nd Edition, Gibson Ed., CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "PI3K" refers to a phosphoinositide 3-kinase or mutant thereof, which is capable of phosphorylating the inositol ring of PI in the D-3 position. The term "PI3K mutant" is intended to include proteins substantially homologous to a native PI3K, i.e., proteins having one or more naturally or non-naturally occurring amino acid deletions, insertions, or substitutions (e.g., PI3K derivatives, homologs, and fragments), as compared to the amino acid sequence of a native PI3K. The amino acid sequence of a PI3K mutant is at least about 80% identical, at least about 90% identical, or at least about 95% identical to a native PI3K. Examples of PI3K include, but are not limited to, p110α, p110β, p110δ, p110γ, PI3K-C2α, PI3K-C2β, PI3K-C2γ, Vps34, mTOR, ATM, ATR, and DNA-PK. See, Fry, *Biochem. Biophys. Acta* 1994, 1226, 237-268; Vanhaesebroeck and Waterfield, *Exp. Cell. Res.* 1999, 253, 239-254; and Fry, *Breast Cancer Res.* 2001, 3, 304-312. PI3Ks are classified into at least three classes. Class I includes p110α, p110β, p110δ, and p110γ. Class II includes PI3K-C2α, PI3K-C2β, and PI3K-C2γ. Class III includes Vps34. Class IV includes mTOR, ATM, ATR, and DNA-PK. In certain embodiments, the PI3K is a Class I kinase. In certain embodiments, the PI3K is p110α, p110β, p110δ, or p110γ. In certain embodiments, the PI3K is a mutant of a Class I kinase. In certain embodiments, the PI3K is a p110α mutant. Examples of p110α mutants include, but are not limited to, R38H, G106V, K111N, K227E, N345K, C420R, P539R, E542K, E545A, E545G, E545K, Q546K, Q546P, E453Q, H710P, I800L, T1025S, M1043I, M1043V, H1047L, H1047R, and H1047Y (Ikenoue et al., *Cancer Res.* 2005, 65, 4562-4567; Gymnopoulos et al., *Proc. Natl. Acad. Sci.,* 2007, 104, 5569-5574). In certain embodiments, the PI3K is a Class II kinase. In certain embodiments, the PI3K is PI3K-C2α, PI3K-C2β, or PI3K-C2γ. In certain embodiments, the PI3K is a Class III kinase. In certain embodiments, the PI3K is Vps34. In certain embodiments, the PI3K is a Class IV kinase. In certain embodiments, the PI3K is mTOR, ATM, ATR, or DNA-PK.

The terms "PI3K-mediated disorder or disease" and "a condition, disorder or disease mediated by PI3K" refer to a condition, disorder, or disease characterized by inappropriate, e.g., less than or greater than normal, PI3K activity. Inappropriate PI3K functional activity might arise as the result of PI3K expression in cells which normally do not express PI3K, increased PI3K expression or degree of intracellular activation; or decreased PI3K expression. A PI3K-mediated condition, disorder or disease may be completely or partially mediated by inappropriate PI3K activity. In particular, a PI3K-mediated condition, disorder or disease is one in which modulation of a PI3K enzyme activity results in some effect on the underlying condition or disorder, e.g., a PI3K inhibitor results in some improvement in at least some of patients being treated.

The term "alkyl" refers to a linear or branched saturated monovalent hydrocarbon radical, wherein the alkylene may optionally be substituted as described herein. The term "alkyl" also encompasses both linear and branched alkyl, unless otherwise specified. In certain embodiments, the alkyl is a linear saturated monovalent hydrocarbon radical that has 1 to 20 ($C_{1-20}$), 1 to 15 ($C_{3-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms.

The term "alkylene" refers to a linear or branched saturated divalent hydrocarbon radical, wherein the alkylene may optionally be substituted as described herein. The term "alkylene" encompasses both linear and branched alkylene, unless otherwise specified. In certain embodiments, the alkylene is a linear saturated divalent hydrocarbon radical that has 1 to 20 ($C_{1-20}$), 1 to 15 ($C_{\_15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkylene groups are also referred as "lower alkylene." Examples of alkylene groups include, but are not limited to, methylene, ethylene, propylene (including all isomeric forms), n-propylene, isopropylene, butylene (including all isomeric forms), n-butylene, isobutylene, t-butylene, pentylene (including all isomeric forms), and hexylene (including all isomeric forms). For example, $C_{1-6}$ alkylene refers to a linear saturated divalent hydrocarbon radical of 1 to 6 carbon atoms or a branched saturated divalent hydrocarbon radical of 3 to 6 carbon atoms.

The term "heteroalkylene" refers to a linear or branched saturated divalent hydrocarbon radical that contains one or more heteroatoms each independently selected from O, S, and N in the hydrocarbon chain. For example, $C_{1-6}$ heteroalkylene refers to a linear saturated divalent hydrocarbon radical of 1 to 6 carbon atoms or a branched saturated divalent hydrocarbon radical of 3 to 6 carbon atoms. In certain embodiments, the heteroalkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ heteroalkylene groups are also referred as "lower heteroalkylene." Examples of heteroalkylene groups include, but are not limited to, —$CH_2O$—, —$CH_2OCH_2$—, —$CH_2CH_2O$—, —$CH_2NH$—, —$CH_2NHCH_2$—, —$CH_2CH_2NH$—, —$CH_2S$—, —$CH_2SCH_2$—, and —$CH_2CH_2S$—. In certain embodiments, heteroalkylene may also be optionally substituted as described herein.

The term "alkenyl" refers to a linear or branched monovalent hydrocarbon radical, which contains one or more, in one embodiment, one to five, carbon-carbon double bonds. The alkenyl may be optionally substituted as described herein. The term "alkenyl" also embraces radicals having "cis" and "trans" configurations, or alternatively, "Z" and "E" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkenylene" refers to a linear or branched divalent hydrocarbon radical, which contains one or more, in one embodiment, one to five, carbon-carbon double bonds. The alkenylene may be optionally substituted as described herein. Similarly, the term "alkenylene" also embraces radicals having "cis" and "trans" configurations, or alternatively, "E" and "Z" configurations. As used herein, the term "alkenylene" encompasses both linear and branched alkenylene, unless otherwise specified. For example, $C_{2-6}$ alkenylene refers to a linear unsaturated divalent hydrocarbon radical of 2 to 6 carbon atoms or a branched unsaturated divalent hydrocarbon radical of 3 to 6 carbon atoms. In certain embodiments, the alkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenylene groups include, but are not limited to, ethenylene, allylene, propenylene, butenylene, and 4-methylbutenylene.

The term "heteroalkenylene" refers to a linear or branched divalent hydrocarbon radical, which contains one or more, in one embodiment, one to five, in another embodiment, one, carbon-carbon double bond(s), and which contains one or more heteroatoms each independently selected from O, S, and N in the hydrocarbon chain. The heteroalkenylene may be optionally substituted as described herein. The term "heteroalkenylene" embraces radicals having a "cis" or "trans" configuration or a mixture thereof, or alternatively, a "Z" or "E" configuration or a mixture thereof, as appreciated by those of ordinary skill in the art. For example, $C_{2-6}$ heteroalkenylene refers to a linear unsaturated divalent hydrocarbon radical of 2 to 6 carbon atoms or a branched unsaturated divalent hydrocarbon radical of 3 to 6 carbon atoms. In certain embodiments, the heteroalkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of heteroalkenylene groups include, but are not limited to, —CH=CHO—, —CH=CHOCH$_2$—, —CH=CHCH$_2$O—, —CH=CHS—, —CH=CHSCH$_2$—, —CH=CHCH$_2$S—, or —CH=CHCH$_2$NH—.

The term "alkynyl" refers to a linear or branched monovalent hydrocarbon radical, which contains one or more, in one embodiment, one to five, carbon-carbon triple bonds. The alkynyl may be optionally substituted as described herein. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH) and propargyl (—$CH_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms.

The term "alkynylene" refers to a linear or branched divalent hydrocarbon radical, which contains one or more, in one embodiment, one to five, carbon-carbon triple bonds. The alkynylene may be optionally substituted as described herein. The term "alkynylene" also encompasses both linear and branched alkynylene, unless otherwise specified. In certain embodiments, the alkynylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynylene groups include, but are not limited to, ethynylene (—C≡C—) and propargylene (—$CH_2$C≡C—). For example, $C_{2-6}$ alkynylene refers to a linear unsaturated divalent hydrocarbon radical of 2 to 6 carbon atoms or a branched unsaturated divalent hydrocarbon radical of 3 to 6 carbon atoms.

The term "cycloalkyl" refers to a cyclic saturated bridged and/or non-bridged monovalent hydrocarbon radical, which may be optionally substituted as described herein. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, bicyclo[2.1.1]hexyl, bicyclo[2.2.1]heptyl, decalinyl, and adamantyl.

The term "cycloalkylene" refers to a cyclic saturated bridged and/or non-bridged divalent hydrocarbon radical, which may be optionally substituted as described herein. In certain embodiments, the cycloalkylene has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkylene groups include, but are not limited to, cyclopropylene (e.g., 1,1-cyclopropylene and 1,2-cyclopropylene), cyclobutylene (e.g., 1,1-cyclobutylene, 1,2-cyclobutylene, or 1,3-cyclobutylene), cyclopentylene (e.g., 1,1-cyclopentylene, 1,2-cyclopentylene, or 1,3-cyclopentylene), cyclohexylene (e.g., 1,1-cyclohexylene, 1,2-cyclohexylene, 1,3-cyclohexylene, or 1,4-cyclohexylene), cycloheptylene (e.g., 1,1-cycloheptylene, 1,2-cycloheptylene, 1,3-cycloheptylene, or 1,4-cycloheptylene), decalinylene, and adamantylene.

The term "aryl" refers to a monocyclic aromatic group and/or multicyclic monovalent aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may be optionally substituted as described herein.

The term "arylene" refers to a monocyclic and/or multicyclic divalent aromatic group that contain at least one aromatic hydrocarbon ring. In certain embodiments, the arylene has from 6 to 20 ($C_{6-20}$), from 6 to 15 ($C_{6-15}$), or from 6 to 10 ($C_{6-10}$) ring atoms. Examples of arylene groups include, but are not limited to, phenylene, naphthylene, fluorenylene, azulenylene, anthrylene, phenanthrylene, pyrenylene, biphenylene, and terphenylene. Arylene also refers to bicyclic or tricyclic carbon rings, where one of the rings is aromatic and the others of which may be saturated, partially unsaturated, or aromatic, for example, dihydronaphthylene, indenylene, indanylene, or tetrahydro-naphthylene (tetralinyl). In certain embodiments, arylene may also be optionally substituted as described herein.

The term "aralkyl" or "aryl-alkyl" refers to a monovalent alkyl group substituted with aryl. In certain embodiments, the alkyl and aryl moieties are optionally substituted as described herein.

The term "heteroaryl" refers to a monocyclic aromatic group and/or multicyclic aromatic group that contain at least one aromatic ring, wherein at least one aromatic ring contains one or more heteroatoms independently selected from O, S, and N. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted as described herein.

The term "heteroarylene" refers to a divalent aromatic group and/or multicyclic aromatic group that contain at least one aromatic ring, wherein at least one aromatic ring contains one or more heteroatoms independently selected from O, S, and N. Each ring of a heteroarylene group can contain one or two O atoms, one or two S atoms, and/or one to four N atoms, provided that the total number of heteroatoms in each ring is four or less and each ring contains at least one carbon atom. In certain embodiments, the heteroarylene has from 5 to 20, from 5 to 15, or from 5 to 10 ring atoms. Examples of monocyclic heteroarylene groups include, but are not limited to, furanylene, imidazolylene, isothiazolylene, isoxazolylene, oxadiazolylene, oxadiazolylene, oxazolylene, pyrazinylene, pyrazolylene, pyridazinylene, pyridylene, pyrimidinylene, pyrrolylene, thiadiazolylene, thiazolylene, thienylene, tetrazolylene, triazinylene, and triazolylene. Examples of bicyclic heteroarylene groups include, but are not limited to, benzofuranylene, benzimidazolylene, benzoisoxazolylene, benzopyranylene, benzothiadiazolylene, benzothiazolylene, benzothienylene, benzothiophenylene, benzotriazolylene, benzoxazolylene, furopyridylene, imidazopyridinylene, imidazothiazolylene, indolizinylene, indolylene, indazolylene, isobenzofuranylene, isobenzothienylene, isoindolylene, isoquinolinylene, isothiazolylene, naphthyridinylene, oxazolopyridinylene, phthalazinylene, pteridinylene, purinylene, pyridopyridylene, pyrrolopyridylene, quinolinylene, quinoxalinylene, quinazolinylene, thiadiazolopyrimidylene, and thienopyridylene. Examples of tricyclic heteroaryl groups include, but are not limited to, acridinylene, benzindolylene, carbazolylene, dibenzofuranylene, perimidinylene, phenanthrolinylene, phenanthridinylene, phenarsazinylene, phenazinylene, phenothiazinylene, phenoxazinylene, and xanthenylene. In certain embodiments, heteroaryl may also be optionally substituted as described herein.

The term "heterocyclyl" or "heterocyclic" refers to a monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted as described herein.

The term "heterocyclylene" refers to a divalent non-aromatic ring system and/or multicyclic ring system that contain at least one non-aromatic ring, wherein one or more of the non-aromatic ring atoms are heteroatoms independently selected from O, S, or N; and the remaining ring atoms are carbon atoms. In certain embodiments, the heterocyclylene group has from 3 to 20, from 3 to 15, from 3 to 10, from 3 to 8, from 4 to 7, or from 5 to 6 ring atoms. In certain embodiments, the heterocyclylene is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclylene may be attached to the main structure at any heteroatom or carbon atom which results in the creation of a stable compound. Examples of such heterocyclene groups include, but are not limited to, azepinylene, benzodioxanylene, benzodioxolylene, benzofuranonylene, benzopyranonylene, benzopyranylene, benzotetrahydrofuranylene, benzotetrahydrothienylene, benzothiopyranylene, benzoxazinylene, β-carbolinylene, chromanylene, chromonylene, cinnolinylene, coumarinylene, decahydroisoquinolinylene, dihydrobenzisothiazinylene, dihydrobenzisoxazinylene, dihydrofurylene, dihydroisoindolylene, dihydropyranylene, dihydropyrazolylene, dihydropyrazinylene, dihydropyridinylene, dihydropyrimidinylene, dihydropyrrolylene, dioxolanylene, 1,4-dithianylene, furanonylene, imidazolidinylene, imidazolinylene, indolinylene, isobenzotetrahydrofuranylene, isobenzotetrahydrothienylene, isochromanylene, isocoumarinylene, isoindolinylene, isothiazolidinylene, isoxazolidinylene, morpholinylene, octahydroindolylene, octahydroisoindolylene, oxazolidinonylene, oxazolidinylene, oxiranylene, piperazinylene, piperidinylene, 4-piperidonylene, pyrazolidinylene, pyrazolinylene, pyrrolidinylene, pyrrolinylene, quinuclidinylene, tetrahydrofurylene, tetrahydroisoquinolinylene, tetrahydropyranylene, tetrahydrothienylene, thiamorpholinylene, thiazolidinylene, tetrahydroquinolinylene, and 1,3,5-trithianylene. In certain embodiments, heterocyclic may also be optionally substituted as described herein.

The term "halogen", "halide" or "halo" refers to fluorine, chlorine, bromine, and/or iodine.

The term "optionally substituted" is intended to mean that a group, such as an alkyl, alkylene, alkenyl, alkenylene, alkynyl, alkynylene, cycloalkyl, cycloalkylene, aryl, arylene, heteroaryl, heteroarylene, heterocyclyl, or heterocyclylene group, may be substituted with one or more substituents independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents $Q^1$; and (b) halo, cyano (—CN), nitro (—NO$_2$), —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^1$; or (iii) R$^b$ and R$^c$ together with the N atom to which they are attached form heteroaryl or heterocyclyl, optionally substituted with one or more, in one embodiment, one, two, three, or four, substituents $Q^1$. As used herein, all groups that can be substituted are "optionally substituted," unless otherwise specified.

In one embodiment, each $Q^1$ is independently selected from the group consisting of (a) cyano, halo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, OC(=NR$^e$)NR$^f$R$^g$, —OS(O)R$^e$, —OS(O)$_2$R$^e$, —OS(O) NR$^f$R$^g$, —OS(O)$_2$NR$^f$R$^g$, —NR$^f$R$^g$, —NR$^e$C(O)R$^h$, —NR$^e$C (O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S (O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) R$^f$ and R$^g$ together with the N atom to which they are attached form heteroaryl or heterocyclyl.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer and about 5% or less of the less preferred enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "solvate" refers to a compound provided herein or a salt thereof, which further includes a stoichiometric or non-stoichiometric amount of solvent bound by non-covalent intermolecular forces. Where the solvent is water, the solvate is a hydrate.

The phrase "an enantiomer, a mixture of enantiomers, or a mixture of two or more diastereomers thereof; or a pharmaceutically acceptable salt, solvate, hydrate, or prodrug thereof" has the same meaning as the phrase "a single enantiomer, a mixture of enantiomers, or a mixture of diastereomers of the compound referenced therein; or a pharmaceutically acceptable salt, solvate, hydrate, or prodrug of the compound referenced therein, or an enantiomer, a mixture of enantiomers, or a mixture of diastereomers of the compound referenced therein."

Compounds

In one embodiment, provided herein is a compound of Formula IA, IB, or IC:

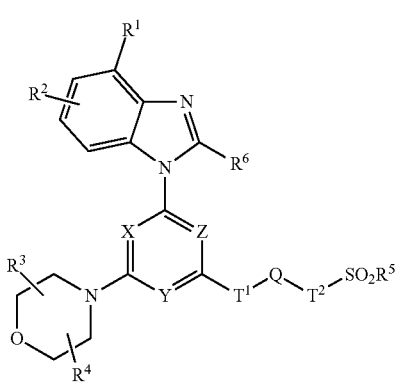

IA

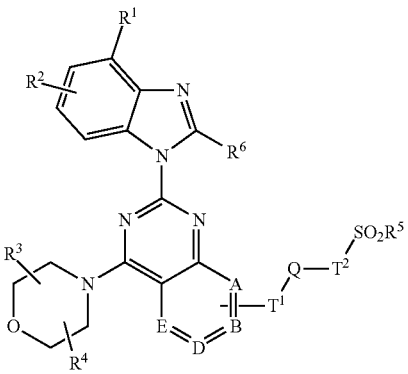

IB

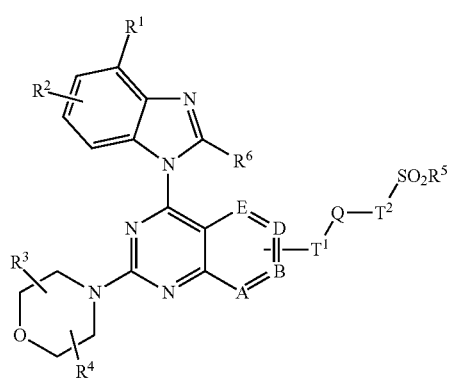

IC or an enantiomer, a mixture of enantiomers, or a mixture of two or more diastereomers thereof; or a pharmaceutically acceptable salt, solvate, hydrate, or prodrug thereof; wherein:
each R$^1$ and R$^2$ is independently (a) hydrogen, cyano, halo, or nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (c) —C(O)R$^{1a}$, —C(O)OR$^{1b}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^d$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^c$, or —S(O)$_2$NR$^{1b}$R$^{1c}$; wherein each R$^{1a}$, R$^{1b}$, R$^{1c}$, and R$^{1d}$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) R$^{1b}$ and R$^{1c}$ together with the N atom to which they are attached form heterocyclyl;

each R$^3$ and R$^4$ is independently hydrogen or C$_{1-6}$ alkyl; or R$^3$ and R$^4$ are linked together to form a bond, C$_{1-6}$ alkylene, C$_{1-6}$ heteroalkylene, C$_{2-6}$ alkenylene, or C$_{2-6}$ heteroalkenylene;

each R$^5$ is independently C$_{1-6}$ alkyl, C$_{2-6}$ alkenyl, C$_{2-6}$ alkynyl, C$_{3-7}$ cycloalkyl, C$_{3-7}$ cycloalkyl-C$_{1-6}$ alkyl, C$_{6-14}$ aryl, C$_{7-15}$ aralkyl, heteroaryl, heteroaryl-C$_{1-6}$ alkyl, heterocyclyl, heterocyclyl-C$_{1-6}$ alkyl, or —NR$^{5m}$R$^{5n}$, where R$^{5m}$ and R$^{5n}$ are each independently hydrogen, C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl;

each R$^6$ is independently hydrogen or C$_{1-6}$ alkyl;

each A, B, D, and E is independently a bond, C, O, N, S, NR$^7$, C(O), CR$^7$, or CR$^7$R$^{7'}$, where each R$^7$ and R$^{7'}$ is independently hydrogen, halo, C$_{1-6}$ alkyl, C$_{2-6}$ alkenyl, or C$_{2-6}$ alkynyl; wherein the bonds between A, B, D, and E may be saturated or unsaturated; with the proviso that no more than one of A, B, D, and E are a bond;

each Q is $C_{1-6}$ alkylene, $C_{2-6}$ alkenylene, $C_{2-6}$ alkynylene, $C_{3-7}$ cycloalkylene, $C_{6-14}$ arylene, heteroarylene, or heterocyclylene;

each $T^1$ is independently a bond, $C_{1-6}$ alkylene, —O—, or —$NR^8$—;

each $T^2$ is independently a bond, $C_{1-6}$ alkylene, or —$NR^8$—; with the proviso that at least one of the two atoms that are directly attached to the —$SO_2$— group is nitrogen;

each $R^8$ is independently hydrogen, $C_{1-6}$ alkyl, $C_{2-6}$ alkenyl, or $C_{2-6}$ alkynyl; and X, Y, and Z are each independently a nitrogen atom or $CR^9$, with the proviso that at least two of X, Y, and Z are nitrogen atoms; where $R^9$ is hydrogen or $C_{1-6}$ alkyl;

wherein each alkyl, alkylene, heteroalkylene, alkenyl, alkenylene, heteroalkenylene, alkynyl, alkynylene, cycloalkyl, cycloalkylene, aryl, arylene, heteroaryl, heteroarylene, heterocyclyl, and heterocyclylene in $R^1$, $R^2$, $R^3$, $R^4$, $R^5$, $R^6$, $R^7$, $R^{7'}$, $R^8$, $R^9$, $R^{1a}$, $R^{1b}$, $R^{1c}$, $R^{1d}$, $R^{5m}$, $R^{5n}$, Q, $T^1$, and $T^2$, is optionally substituted with one or more groups, in one embodiment, one, two, three, or four groups, each independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents $Q^1$; and (c) —$C(O)R^a$, —$C(O)OR^a$, —$C(O)NR^bR^c$, —$C(NR^a)NR^bR^c$, —$OR^a$, —$OC(O)R^a$, —$OC(O)OR^a$, —$OC(O)NR^bR^c$, $OC(=NR^a)NR^bR^c$, —$OS(O)R^a$, —$OS(O)_2R^a$, —$OS(O)NR^bR^c$, —$OS(O)_2NR^bR^c$, —$NR^bR^c$, —$NR^aC(O)R^d$, —$NR^aC(O)OR^d$, —$NR^aC(O)NR^bR^c$, —$NR^aC(=NR^d)NR^bR^c$, —$NR^aS(O)R^d$, —$NR^aS(O)_2R^d$, —$NR^aS(O)NR^bR^c$, —$NR^aS(O)_2NR^bR^c$, —$SR^a$, —$S(O)R^a$, —$S(O)_2R^a$, —$S(O)NR^bR^c$, and —$S(O)_2NR^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^1$; or (iii) $R^b$ and $R^c$ together with the N atom to which they are attached form heterocyclyl, optionally substituted with one or more, in one embodiment, one, two, three, or four, substituents $Q^1$;

wherein each $Q^1$ is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —$C(O)R^e$, —$C(O)OR^e$, —$C(O)NR^fR^g$, —$C(NR^e)NR^fR^g$, —$OR^e$, —$OC(O)R^e$, —$OC(O)OR^e$, —$OC(O)NR^fR^g$, —$OC(=NR^e)NR^fR^g$, —$OS(O)R^e$, —$OS(O)_2R^e$, —$OS(O)NR^fR^g$, —$OS(O)_2NR^fR^g$, —$NR^fR^g$, —$NR^eC(O)R^h$, —$NR^eC(O)OR^h$, —$NR^eC(O)NR^fR^g$, —$NR^eC(=NR^h)NR^fR^g$, —$NR^eS(O)R^h$, —$NR^eS(O)_2R^h$, —$NR^eS(O)NR^fR^g$, —$NR^eS(O)_2NR^fR^g$, —$SR^e$, —$S(O)R^e$, —$S(O)_2R^e$, —$S(O)NR^fR^g$, and —$S(O)_2NR^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In another embodiment, provided herein is a compound of Formula IA, IB, or IC:

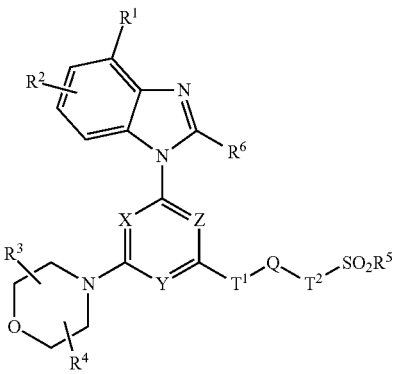

IA

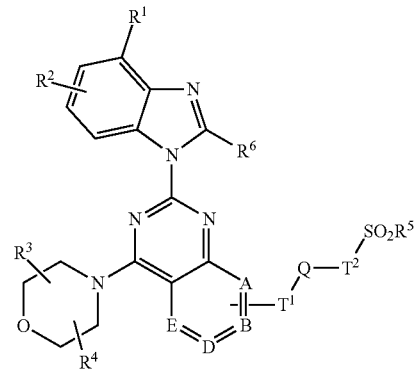

IB

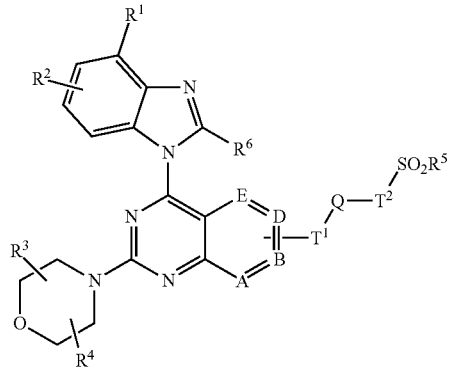

IC or an enantiomer, a mixture of enantiomers, or a mixture of two or more diastereomers thereof; or a pharmaceutically acceptable salt, solvate, hydrate, or prodrug thereof; wherein:

each $R^1$ and $R^2$ is independently (a) hydrogen, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —$C(O)R^{1a}$, —$C(O)OR^{1b}$, —$C(O)NR^{1b}R^{1c}$, —$C(NR^{1a})NR^{1b}R^{1c}$, —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, —$OS(O)_2NR^{1b}R^{1c}$, —$NR^{1b}R^{1c}$, —$NR^{1a}C(O)R^{1d}$, —$NR^{1a}C(O)OR^d$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$SR^{1a}$, —$S(O)R^{1a}$, —$S(O)_2R^{1a}$, —$S(O)NR^{1b}R^c$, or —$S(O)_2NR^{1b}R^{1c}$; wherein each $R^{1a}$, $R^{1b}$, $R^{1c}$, and $R^{1d}$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^{1b}$ and $R^{1c}$ together with the N atom to which they are attached form heterocyclyl;

each R³ and R⁴ is independently hydrogen or C₁₋₆ alkyl; or R³ and R⁴ are linked together to form a bond, C₁₋₆ alkylene, C₁₋₆ heteroalkylene, C₂₋₆ alkenylene, or C₂₋₆ heteroalkenylene;

each R⁵ is independently C₁₋₆ alkyl, C₂₋₆ alkenyl, C₂₋₆ alkynyl, C₃₋₇ cycloalkyl, C₆₋₁₄ aryl, C₇₋₁₅ aralkyl, heteroaryl, or heterocyclyl;

each R⁶ is independently hydrogen or C₁₋₆ alkyl;

each A, B, D, and E is independently a bond, C, O, N, S, NR⁷, CR⁷, or CR⁷R⁷′, where each R⁷ and R⁷′ is independently hydrogen, halo, C₁₋₆ alkyl, C₂₋₆ alkenyl, or C₂₋₆ alkynyl; wherein the bonds between A, B, D, and E may be saturated or unsaturated; with the proviso that no more than one of A, B, D, and E are a bond;

each Q is C₁₋₆ alkylene, C₂₋₆ alkenylene, C₂₋₆ alkynylene, C₃₋₇ cycloalkylene, C₆₋₁₄ arylene, heteroarylene, or heterocyclylene;

each T¹ is independently a bond, —O—, or —NR⁸—;

each T² is independently a bond or —NR⁸—, with the proviso that the atom that is attached to —SO₂R⁵ is nitrogen;

each R⁸ is independently hydrogen, C₁₋₆ alkyl, C₂₋₆ alkenyl, or C₂₋₆ alkynyl; and X, Y, and Z are each independently a nitrogen atom or CR⁹, with the proviso that at least two of X, Y, and Z are nitrogen atoms; where R⁹ is hydrogen or C₁₋₆ alkyl;

wherein each alkyl, alkylene, heteroalkylene, alkenyl, alkenylene, heteroalkenylene, alkynyl, alkynylene, cycloalkyl, cycloalkylene, aryl, arylene, heteroaryl, heteroarylene, heterocyclyl, and heterocyclylene in R¹, R², R³, R⁴, R⁵, R⁶, R⁷, R⁷′, R⁸, R⁹, R¹ᵃ, R¹ᵇ, R¹ᶜ, R¹ᵈ, and Q is optionally substituted with one or more groups, in one embodiment, one, two, three, or four groups, each independently selected from (a) cyano, halo, and nitro; (b) C₁₋₆ alkyl, C₂₋₆ alkenyl, C₂₋₆ alkynyl, C₃₋₇ cycloalkyl, C₆₋₁₄ aryl, C₇₋₁₅ aralkyl, heteroaryl, and heterocyclyl, each optionally substituted with one or more, in one embodiment, one, two, three, or four, substituents Q¹; and (c) —C(O)Rᵃ, —C(O)ORᵃ, —C(O)NRᵇRᶜ, —C(NRᵃ)NRᵇRᶜ, —ORᵃ, —OC(O)Rᵃ, —OC(O)ORᵃ, —OC(O)NRᵇRᶜ, —OC(=NRᵃ)NRᵇRᶜ, —OS(O)Rᵃ, —OS(O)₂Rᵃ, —OS(O)NRᵇRᶜ, —OS(O)₂NRᵇRᶜ, —NRᵇRᶜ, —NRᵃC(O)Rᵈ, —NRᵃC(O)ORᵈ, —NRᵃC(O)NRᵇRᶜ, —NRᵃC(=NRᵈ)NRᵇRᶜ, —NRᵃS(O)Rᵈ, —NRᵃS(O)₂Rᵈ, —NRᵃS(O)NRᵇRᶜ, —NRᵃS(O)₂NRᵇRᶜ, —SRᵃ, —S(O)Rᵃ, —S(O)₂Rᵃ, —S(O)NRᵇRᶜ, and —S(O)₂NRᵇRᶜ, wherein each Rᵃ, Rᵇ, Rᶜ, and Rᵈ is independently (i) hydrogen; (ii) C₁₋₆ alkyl, C₂₋₆ alkenyl, C₂₋₆ alkynyl, C₃₋₇ cycloalkyl, C₆₋₁₄ aryl, C₇₋₁₅ aralkyl, heteroaryl, or heterocyclyl, each optionally substituted with one or more, in one embodiment, one, two, three, or four, substituents Q¹; or (iii) Rᵇ and Rᶜ together with the N atom to which they are attached form heterocyclyl, optionally substituted with one or more, in one embodiment, one, two, three, or four, substituents Q¹;

wherein each Q¹ is independently selected from the group consisting of (a) cyano, halo, and nitro; (b) C₁₋₆ alkyl, C₂₋₆ alkenyl, C₂₋₆ alkynyl, C₃₋₇ cycloalkyl, C₆₋₁₄ aryl, C₇₋₁₅ aralkyl, heteroaryl, and heterocyclyl; and (c) —C(O)Rᵉ, —C(O)ORᵉ, —C(O)NRᶠRᵍ, —C(NRᵉ)NRᶠRᵍ, —ORᵉ, —OC(O)Rᵉ, —OC(O)ORᵉ, —OC(O)NRᶠRᵍ, —OC(=NRᵉ)NRᶠRᵍ, —OS(O)Rᵉ, —OS(O)₂Rᵉ, —OS(O)NRᶠRᵍ, —OS(O)₂NRᶠRᵍ, —NRᶠRᵍ, —NRᵉC(O)Rʰ, —NRᵉC(O)ORʰ, —NRᵉC(O)NRᶠRᵍ, —NRᵉC(=NRʰ)NRᶠRᵍ, —NRᵉS(O)Rʰ, —NRᵉS(O)₂Rʰ, —NRᵉS(O)NRᶠRᵍ, —NRᵉS(O)₂NRᶠRᵍ, —SRᵉ, —S(O)Rᵉ, —S(O)₂Rᵉ, —S(O)NRᶠRᵍ, and —S(O)₂NRᶠRᵍ; wherein each Rᵉ, Rᶠ, Rᵍ, and Rʰ is independently (i) hydrogen; (ii) C₁₋₆ alkyl, C₂₋₆ alkenyl, C₂₋₆ alkynyl, C₃₋₇ cycloalkyl, C₆₋₁₄ aryl, C₇₋₁₅ aralkyl, heteroaryl, or heterocyclyl; or (iii) Rᶠ and Rᵍ together with the N atom to which they are attached form heterocyclyl.

In yet another embodiment, provided herein is a compound of Formula IA, IB, or IC:

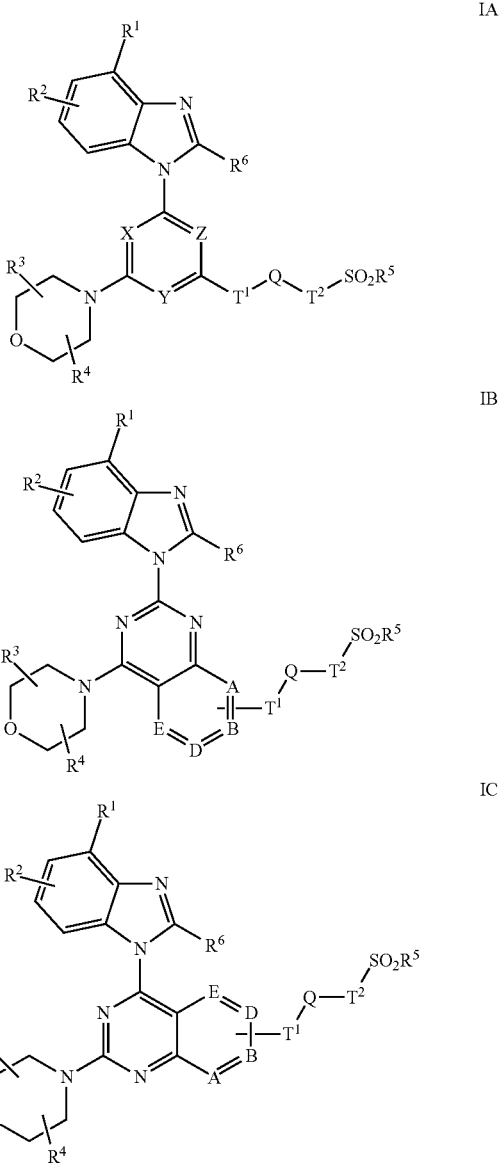

or an enantiomer, a mixture of enantiomers, or a mixture of two or more diastereomers thereof; or a pharmaceutically acceptable salt, solvate, hydrate, or prodrug thereof; wherein:

each R¹ and R² is independently (a) hydrogen, cyano, halo, or nitro; (b) C₁₋₆ alkyl, C₂₋₆ alkenyl, C₂₋₆ alkynyl, C₃₋₇ cycloalkyl, C₆₋₁₄ aryl, C₇₋₁₅ aralkyl, heteroaryl, or heterocyclyl; or (c) —C(O)R¹ᵃ, —C(O)OR¹ᵇ, —C(O)NR¹ᵇR¹ᶜ, —C(NR¹ᵃ)NR¹ᵇR¹ᶜ, —OR¹ᵃ, OC(O)R¹ᵃ, —OC(O)OR¹ᵃ, —OC(O)NR¹ᵇR¹ᶜ, —OC(=NR¹ᵃ)NR¹ᵇR¹ᶜ, —OS(O)R¹ᵃ, —OS(O)₂R¹ᵃ, —OS(O)NR¹ᵇR¹ᶜ, —OS(O)₂NR¹ᵇR¹ᶜ, —NR¹ᵃC(O)R¹ᵈ, —NR¹ᵃC(O)ORᵈ, —NR¹ᵃC(O)NR¹ᵇR¹ᶜ, —NR¹ᵃC(=NR¹ᵈ)NR¹ᵇR¹ᶜ, NR¹ᵃS(O)R¹ᵈ, —NR¹ᵃS(O)₂R¹ᵈ, —NR¹ᵃS(O)NR¹ᵇR¹ᶜ, —NR¹ᵃS(O)₂NR¹ᵇR¹ᶜ, —SR¹ᵃ, —S(O)R¹ᵃ, —S(O)₂R¹ᵃ, —S(O)NR¹ᵇRᶜ, or —S(O)₂NR¹ᵇR¹ᶜ; wherein each R¹ᵃ, R¹ᵇ, R¹ᶜ, and R¹ᵈ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^1$; or (iii) $R^{1b}$ and $R^{1c}$ together with the N atom to which they are attached form heterocyclyl, optionally substituted with one or more, in one embodiment, one, two, three, or four, substituents $Q^1$;

each $R^3$ and $R^4$ is independently hydrogen or $C_{1-6}$ alkyl;

each $R^5$ is independently $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl;

each $R^6$ is independently hydrogen or $C_{1-6}$ alkyl;

each A, B, D, and E is independently (i) a bond; (ii) a nitrogen, oxygen, or sulfur atom; or (iii) $CR^7$, where $R^7$ is hydrogen, halo, $C_{1-6}$ alkyl, $C_{2-6}$ alkenyl, or $C_{2-6}$ alkynyl; wherein the bonds between A, B, D, and E may be saturated or unsaturated; with the proviso that no more than one of A, B, D, and E are a bond;

each Q is $C_{1-6}$ alkylene, $C_{2-6}$ alkenylene, $C_{2-6}$ alkynylene, $C_{3-7}$ cycloalkylene, $C_{6-14}$ arylene, heteroarylene, or heterocyclylene;

each $T^1$ is independently a bond, —O—, or —$NR^8$—;

each $T^2$ is independently a bond or —$NR^8$—, with the proviso that the atom that is attached to —$SO_2R^5$ is nitrogen;

each $R^8$ is independently hydrogen, $C_{1-6}$ alkyl, $C_{2-6}$ alkenyl, or $C_{2-6}$ alkynyl; and X, Y, and Z are each independently a nitrogen atom or $CR^9$, with the proviso that at least two of X, Y, and Z are nitrogen atoms; where $R^9$ is hydrogen or $C_{1-6}$ alkyl;

wherein each alkyl, alkylene, alkenyl, alkenylene, alkynyl, alkynylene, cycloalkyl, cycloalkylene, aryl, arylene, heteroaryl, heteroarylene, heterocyclyl, and heterocyclylene is optionally substituted with one or more groups, each independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents $Q^1$; and (c) —C(O)$R^a$, —C(O)O$R^a$, —C(O)$NR^bR^c$, —C($NR^a$)$NR^bR^c$, —O$R^a$, —OC(O)$R^a$, —OC(O)O$R^a$, —OC(O)$NR^bR^c$, —OC(=$NR^a$)$NR^bR^c$, —OS(O)$R^a$, —OS(O)$_2R^a$, —OS(O)$NR^bR^c$, —OS(O)$_2NR^bR^c$, —$NR^bR^c$, —$NR^aC(O)R^d$, —$NR^aC(O)OR^d$, —$NR^aC(O)NR^bR^c$, —$NR^aC(=NR^d)NR^bR^c$, —$NR^aS(O)R^d$, —$NR^aS(O)_2R^d$, —$NR^aS(O)NR^bR^c$, —$NR^aS(O)_2NR^bR^c$, —$SR^a$, —S(O)$R^a$, —S(O)$_2R^a$, —S(O)$NR^bR^c$, and —S(O)$_2NR^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^1$; or (iii) $R^b$ and $R^c$ together with the N atom to which they are attached form heterocyclyl, optionally substituted with one or more, in one embodiment, one, two, three, or four, substituents $Q^1$;

wherein each $Q^1$ is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)$NR^fR^g$, —C($NR^e$)$NR^fR^g$, —O$R^e$, —OC(O)$R^e$, —OC(O)O$R^e$, —OC(O)$NR^fR^g$, —OC(=$NR^e$)$NR^fR^g$, —OS(O)$R^e$, —OS(O)$_2R^e$, —OS(O)$NR^fR^g$, —OS(O)$_2NR^fR^g$, —$NR^fR^g$, —$NR^eC(O)R^h$, —$NR^eC(O)OR^h$, —$NR^eC(O)NR^fR^g$, —$NR^eC(=NR^h)NR^fR^g$, —$NR^eS(O)R^h$, —$NR^eS(O)_2R^h$, —$NR^eS(O)NR^fR^g$, —$NR^eS(O)_2NR^fR^g$, —$SR^e$, —S(O)$R^e$, —S(O)$_2R^e$, —S(O)$NR^fR^g$, and —S(O)$_2NR^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heterocyclyl.

In yet another embodiment, provided herein is a compound of Formula Ia, Ib, or Ic:

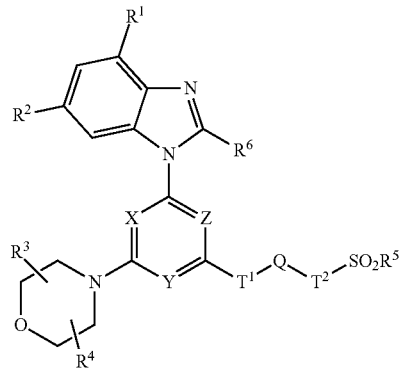

Ia

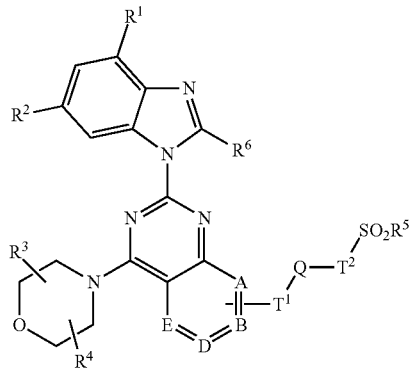

Ib

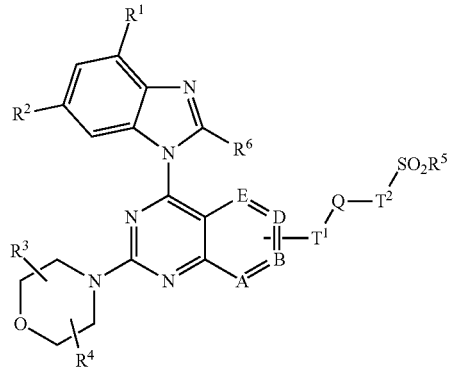

Ic or an enantiomer, a mixture of enantiomers, or a mixture of two or more diastereomers thereof; or a pharmaceutically acceptable salt, solvate, hydrate, or prodrug thereof; wherein:

each $R^1$ and $R^2$ is independently (a) hydrogen, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)O$R^{1b}$, —C(O)$NR^{1b}R^{1c}$, —C($NR^{1a}$)$NR^{1b}R^{1c}$, —O$R^{1a}$, —OC(O)$R^{1a}$, —OC(O)O$R^{1a}$, —OC(O)$NR^{1b}R^{1c}$, —OC(=$NR^{1a}$)$NR^{1b}R^{1c}$, —OS(O)$R^{1a}$, —OS(O)$_2R^{1a}$, —OS(O)$NR^{1b}R^{1c}$, —OS(O)$_2NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2$ NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; wherein each R$^{1a}$, R$^{1b}$, R$^{1c}$, and R$^{1d}$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) R$^{1b}$ and R$^{1c}$ together with the N atom to which they are attached form heterocyclyl;

each R$^3$ and R$^4$ is independently hydrogen or C$_{1-6}$ alkyl; or R$^3$ and R$^4$ are linked together to form a bond, C$_{1-6}$ alkylene, C$_{1-6}$ heteroalkylene, C$_{2-6}$ alkenylene, or C$_{2-6}$ heteroalkenylene;

each R$^5$ is independently C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl;

each R$^6$ is independently hydrogen or C$_{1-6}$ alkyl;

each A, B, D, and E is independently a bond, C, O, N, S, NR$^7$, CR$^7$, or CR$^7$R$^{7'}$, where each R$^7$ and R$^{7'}$ is independently hydrogen, halo, C$_{1-6}$ alkyl, C$_{2-6}$ alkenyl, or C$_{2-6}$ alkynyl; wherein the bonds between A, B, D, and E may be saturated or unsaturated; with the proviso that no more than one of A, B, D, and E are a bond;

each Q is C$_{1-6}$ alkylene, C$_{2-6}$ alkenylene, C$_{2-6}$ alkynylene, C$_{3-7}$ cycloalkylene, C$_{6-14}$ arylene, heteroarylene, or heterocyclylene;

each T$^1$ is independently a bond, —O—, or —NR$^8$—;

each T$^2$ is independently a bond or —NR$^8$—, with the proviso that the atom that is attached to —SO$_2$R$^5$ is nitrogen;

each R$^8$ is independently hydrogen, C$_{1-6}$ alkyl, C$_{2-6}$ alkenyl, or C$_{2-6}$ alkynyl; and X, Y, and Z are each independently a nitrogen atom or CR$^9$, with the proviso that at least two of X, Y, and Z are nitrogen atoms; where R$^9$ is hydrogen or C$_{1-6}$ alkyl;

wherein each alkyl, alkylene, heteroalkylene, alkenyl, alkenylene, heteroalkenylene, alkynyl, alkynylene, cycloalkyl, cycloalkylene, aryl, arylene, heteroaryl, heteroarylene, heterocyclyl, and heterocyclylene in R$^1$, R$^2$, R$^3$, R$^4$, R$^5$, R$^6$, R$^7$, R$^{7'}$, R$^8$, R$^9$, R$^{1a}$, R$^{1b}$, R$^{1c}$, R$^{1d}$, and Q is optionally substituted with one or more groups, in one embodiment, one, two, three, or four groups, each independently selected from (a) cyano, halo, and nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl, each optionally substituted with one or more, in one embodiment, one, two, three, or four, substituents Q$^1$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more, in one embodiment, one, two, three, or four, substituents Q$^1$; or (iii) R$^b$ and R$^c$ together with the N atom to which they are attached form heterocyclyl, optionally substituted with one or more, in one embodiment, one, two, three, or four, substituents Q$^1$;

wherein each Q$^1$ is independently selected from the group consisting of (a) cyano, halo, and nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl.

In yet another embodiment, provided herein is a compound of Formula Ia, Ib, or Ic:

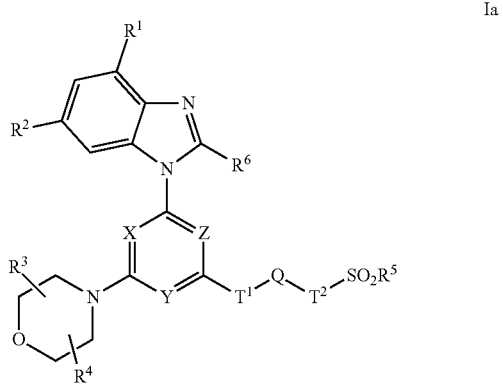

Ia

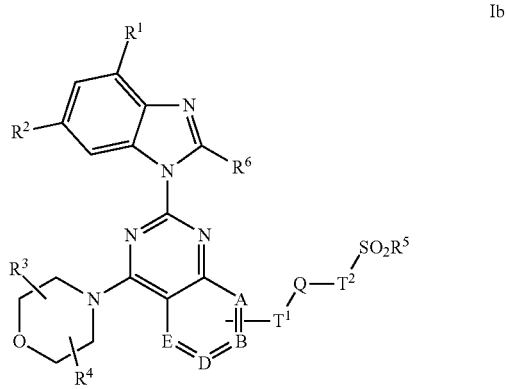

Ib

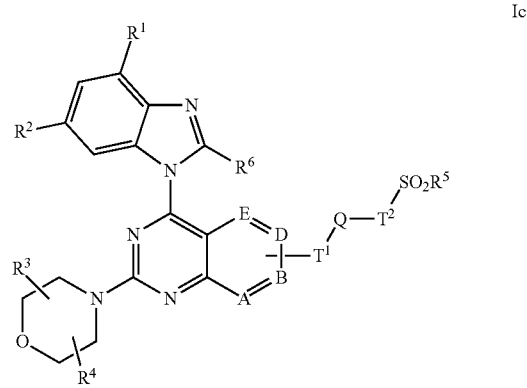

Ic or an enantiomer, a mixture of enantiomers, or a mixture of two or more diastereomers thereof; or a pharmaceutically acceptable salt, solvate, hydrate, or prodrug thereof; wherein:

each R$^1$ and R$^2$ is independently (a) hydrogen, cyano, halo, or nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (c) —C(O)R$^{1a}$, —C(O)OR$^{1b}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; wherein each R$^{1a}$, R$^{1b}$, R$^{1c}$, and R$^{1d}$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more, in one embodiment, one, two, three, or four, substituents Q$^1$; or (iii) R$^{1b}$ and R$^{1c}$ together with the N atom to which they are attached form heterocyclyl, optionally substituted with one or more, in one embodiment, one, two, three, or four, substituents Q$^1$;

each R$^3$ and R$^4$ is independently hydrogen or C$_{1-6}$ alkyl;

each R$^5$ is independently C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl;

each R$^6$ is independently hydrogen or C$_{1-6}$ alkyl;

each A, B, D, and E is independently (i) a bond; (ii) a nitrogen, oxygen, or sulfur atom; or (iii) CR$^7$, where R$^7$ is hydrogen, halo, C$_{1-6}$ alkyl, C$_{2-6}$ alkenyl, or C$_{2-6}$ alkynyl; wherein the bonds between A, B, D, and E may be saturated or unsaturated; with the proviso that no more than one of A, B, D, and E are a bond;

each Q is C$_{1-6}$ alkylene, C$_{2-6}$ alkenylene, C$_{2-6}$ alkynylene, C$_{3-7}$ cycloalkylene, C$_{6-14}$ arylene, heteroarylene, or heterocyclylene;

each T$^1$ is independently a bond, —O—, or —NR$^8$—;

each T$^2$ is independently a bond or —NR$^8$—, with the proviso that the atom that is attached to —SO$_2$R$^5$ is nitrogen;

each R$^8$ is independently hydrogen, C$_{1-6}$ alkyl, C$_{2-6}$ alkenyl, or C$_{2-6}$ alkynyl; and X, Y, and Z are each independently a nitrogen atom or CR$^9$, with the proviso that at least two of X, Y, and Z are nitrogen atoms; where R$^9$ is hydrogen or C$_{1-6}$ alkyl;

wherein each alkyl, alkylene, alkenyl, alkenylene, alkynyl, alkynylene, cycloalkyl, cycloalkylene, aryl, arylene, heteroaryl, heteroarylene, heterocyclyl, and heterocyclylene is optionally substituted with one or more groups, each independently selected from (a) cyano, halo, and nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl, each optionally substituted with one or more, in one embodiment, one, two, three, or four, substituents Q$^1$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more, in one embodiment, one, two, three, or four, substituents Q$^1$; or (iii) R$^b$ and R$^c$ together with the N atom to which they are attached form heterocyclyl, optionally substituted with one or more, in one embodiment, one, two, three, or four, substituents Q$^1$;

wherein each Q$^1$ is independently selected from the group consisting of (a) cyano, halo, and nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl.

In one embodiment, in Formula Ia, Ib, or Ic, each R$^1$ and R$^2$ is independently hydrogen, —OR$^{1a}$, or —NR$^{1b}$R$^{1c}$; where R$^{1a}$, R$^{1b}$, and R$^{1c}$ are each independently (a) hydrogen; or (b) C$_{1-6}$ alkyl, C$_{2-6}$ alkenyl, or C$_{2-6}$ alkynyl, each optionally substituted with one or more substituents Q$^1$; or R$^{1b}$ and R$^{1c}$ together with the N atom to which they are attached form heterocyclyl, optionally substituted with one or more substituents Q$^1$;

each R$^3$ and R$^4$ is independently hydrogen or C$_{1-6}$ alkyl, optionally substituted with one or more substituents Q$^1$;

each R$^5$ is independently C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more substituents Q$^1$;

each R$^6$ is independently C$_{1-6}$ alkyl, optionally substituted with one or more substituents Q$^1$;

each A, B, D, and E is independently (i) a bond; (ii) a nitrogen, oxygen, or sulfur atom; or (iii) CH; wherein the bonds between A, B, D, and E may be saturated or unsaturated; with the proviso that no more than one of A, B, D, and E are a bond;

Q is C$_{1-6}$ alkylene, C$_{2-6}$ alkenylene, C$_{2-6}$ alkynylene, C$_{3-7}$ cycloalkylene, C$_{6-14}$ arylene, heteroarylene, or heterocyclylene, each optionally substituted with one or more substituents Q$^1$;

each T$^1$ is independently a bond, —O—, or —NR$^8$—;

each T$^2$ is independently a bond or —NR$^8$—, with the proviso that the atom that is attached to —SO$_2$R$^5$ is nitrogen;

each R$^8$ is independently (a) hydrogen; or (b) C$_{1-6}$ alkyl, C$_{2-6}$ alkenyl, or C$_{2-6}$ alkynyl, each optionally substituted with one or more substituents Q$^1$; and X, Y, and Z are each independently a nitrogen atom or CR$^9$, with the proviso that at least two of X, Y, and Z are nitrogen atoms; where R$^9$ is hydrogen or C$_{1-6}$ alkyl, optionally substituted with one or more substituents Q$^1$.

In another embodiment, in Formula Ia, Ib, or Ic, each R$^1$ and R$^2$ is independently hydrogen, —OR$^{1a}$, or —NR$^{1b}$R$^{1c}$; where R$^{1a}$, R$^{1b}$, and R$^{1c}$ are each independently (a) hydrogen; or (b) C$_{1-6}$ alkyl, C$_{2-6}$ alkenyl, or C$_{2-6}$ alkynyl, each optionally substituted with one or more substituents Q$^1$, each independently selected from the group consisting of —OR$^e$ and —NR$^f$R$^g$;

each R$^3$ and R$^4$ is independently hydrogen or C$_{1-6}$ alkyl, optionally substituted with one or more substituents Q$^1$, each independently selected from the group consisting of —OR$^e$ and —NR$^f$R$^g$;

each R$^5$ is independently C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each optionally substituted with one or more substituents Q$^1$, each independently selected from the group consisting of halo, heteroaryl, heterocyclyl, —OR$^e$, and —NR$^f$R$^g$;

each R$^6$ is independently C$_{1-6}$ alkyl, optionally substituted with one or more substituents Q$^1$, each independently selected from the group consisting of —OR$^e$ and —NR$^f$R$^g$;

each A, B, D, and E is independently (i) a bond; (ii) a nitrogen, oxygen, or sulfur atom; or (iii) CH; wherein the bonds between A, B, D, and E may be saturated or unsaturated; with the proviso that no more than one of A, B, D, and E are a bond;

Q is $C_{1-6}$ alkylene, $C_{2-6}$ alkenylene, $C_{2-6}$ alkynylene, $C_{3-7}$ cycloalkylene, $C_{6-14}$ arylene, heteroarylene, or heterocyclylene, each optionally substituted with one or more substituents $Q^1$;

each $T^1$ is independently a bond, —O—, or —NR$^8$—;

each $T^2$ is independently a bond or —NR$^8$—, with the proviso that the atom that is attached to —SO$_2$R$^5$ is nitrogen;

each $R^8$ is independently (a) hydrogen; or (b) $C_{1-6}$ alkyl, $C_{2-6}$ alkenyl, or $C_{2-6}$ alkynyl, each optionally substituted with one or more substituents $Q^1$, each independently selected from the group consisting of cyano, —C(O)R$^e$, —C(O)OR$^e$, —C(O)NR$^f$R$^g$, —OR$^e$, —OC(O)R$^e$, —OC(O)OR$^e$, —OC(O)NR$^f$R$^g$, —NR$^f$R$^g$, —NR$^e$C(O)R$^h$, —NR$^e$C(O)OR$^f$, —S(O)$_2$R$^e$, and —S(O)$_2$NR$^f$R$^g$;

X, Y, and Z are each independently a nitrogen atom or CR$^9$, with the proviso that at least two of X, Y, and Z are nitrogen atoms; where R$^9$ is hydrogen or $C_{1-6}$ alkyl; and each R$^e$, R$^f$, R$^g$, and R$^h$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl.

In yet another embodiment, in Formula Ia, Ib, or Ic, each $R^1$ is independently hydrogen or —OR$^{1a}$, where R$^{1a}$ is $C_{1-6}$ alkyl, optionally substituted with one or more —NR$^f$R$^g$; where R$^f$ and R$^g$ are each independently hydrogen or $C_{1-6}$ alkyl;

each $R^2$, $R^3$, and $R^4$ is independently hydrogen or $C_{1-6}$ alkyl;

each $R^5$ is independently $C_{1-6}$ alkyl or $C_{1-6}$ alkenyl, each optionally substituted with one or more substituents $Q^1$, each independently selected from the group consisting of chloro, heterocyclyl, and —NR$^f$R$^g$;

$R^6$ is $C_{1-6}$ alkyl, optionally substituted with one or more halo;

A, B, D, and E are each independently (i) a bond; (ii) a nitrogen, oxygen, or sulfur atom; or (iii) CH; wherein the bonds between A, B, D, and E may be saturated or unsaturated; with the proviso that no more than one of A, B, D, and E are a bond;

Q is heterocyclylene;

each $T^1$ is independently a bond, —O—, or —NR$^8$—;

each $T^2$ is independently a bond or —NR$^8$—, with the proviso that the atom that is attached to —SO$_2$R$^5$ is nitrogen;

each $R^8$ is independently (a) hydrogen; or (b) $C_{1-6}$ alkyl, $C_{2-6}$ alkenyl, or $C_{2-6}$ alkynyl, each optionally substituted with one or more substituents $Q^1$, each independently selected from the group consisting of cyano, —C(O)R$^e$, —C(O)OR$^e$, —C(O)NR$^f$R$^g$, —OR$^e$, —OC(O)R$^e$, —OC(O)OR$^e$, —OC(O)NR$^f$R$^g$, —NR$^f$R$^g$, —NR$^e$C(O)R$^h$, —NR$^e$C(O)OR$^f$, —S(O)$_2$R$^e$, and —S(O)$_2$NR$^f$R$^g$;

X, Y, and Z are each independently a nitrogen atom or CR$^9$, with the proviso that at least two of X, Y, and Z are nitrogen atoms; and $R^9$ is independently hydrogen or $C_{1-6}$ alkyl.

In yet another embodiment, in Formula Ia, Ib, or Ic, each $R^1$ is independently hydrogen, methoxy, or dimethylaminopropoxy;

$R^2$, $R^3$, and $R^4$ are hydrogen;

each $R^5$ is independently methyl, ethenyl, chloropropyl, dimethylaminomethyl, dimethylaminoethyl, dimethylaminopropyl, morpholinylmethyl, morpholinylethyl, morpholinylpropyl, (methylpiperazinyl)methyl, (methylpiperazinyl)ethyl, (methylpiperazinyl)propyl, (methylsulfonylpiperazinylmethyl, (methylsulfonylpiperazinyl)ethyl, or (methylsulfonylpiperazinyl)propyl;

$R^6$ is difluoromethyl;

A, B, D, and E are each independently (i) a bond; (ii) a nitrogen, oxygen, or sulfur atom; or (iii) CH; wherein the bonds between A, B, D, and E may be saturated or unsaturated; with the proviso that no more than one of A, B, D, and E are a bond;

Q is azetidinylene, cyclopropylene, cyclobutylene, cyclopentylene, cyclohexylene, pyrrollidinylene, pyrrolylene, pyrazolylene, piperidinylene, piperazinylene, phenylene, thiazolylylene, or pyridylene;

each $T^1$ is independently a bond, —O—, or —NR$^8$—;

each $T^2$ is independently a bond or —NR$^8$—, with the proviso that the atom that is attached to —SO$_2$R$^5$ is nitrogen;

each $R^8$ is independently hydrogen or methyl; and

X, Y, and Z are each independently a nitrogen atom or CH, with the proviso that at least two of X, Y, and Z are nitrogen atoms.

In yet another embodiment, in Formula Ia, Ib, or Ic, each $R^1$ is independently hydrogen, methoxy, or 3-dimethylaminopropoxy;

$R^2$, $R^3$, and $R^4$ are hydrogen;

each $R^5$ is independently methyl, ethenyl, 3-chloropropyl, dimethylaminomethyl, 2-dimethylaminoethyl, 3-dimethylpropylamino, 4-morpholinylmethyl, 2-(4-morpholinyl)ethyl, 3-(4-morpholinyl)propyl, (4-methyl-1-piperazinyl)methyl, 2-(4-methyl-1-piperazinyl)ethyl, 3-(4-methyl-1-piperazinyl)propyl, 4-(methylsulfonyl)-1-piperazinyl-methyl, 2-(4-(methylsulfonyl)-1-piperazinyl)ethyl, or 3-(4-(methylsulfonyl)-1-piperazinyl)propyl;

$R^6$ is difluoromethyl;

A, B, D, and E are each independently (i) a bond; (ii) a nitrogen, oxygen, or sulfur atom; or (iii) CH; wherein the bonds between A, B, D, and E may be saturated or unsaturated; with the proviso that no more than one of A, B, D, and E are a bond;

Q is 1,4-piperidinylene or 1,4-piperazinylene;

each $T^1$ is independently a bond, —O—, or —NR$^8$—;

each $T^2$ is independently a bond or —NR$^8$—, with the proviso that the atom that is attached to —SO$_2$R$^5$ is nitrogen;

each $R^8$ is independently hydrogen or methyl; and

X, Y, and Z are each independently a nitrogen atom or CH, with the proviso that at least two of X, Y, and Z are nitrogen atoms.

In yet another embodiment, in Formula Ia, Ib, or Ic, each $R^1$ is independently hydrogen, methoxy, or 3-dimethylaminopropoxy;

$R^2$, $R^3$, and $R^4$ are hydrogen;

each $R^5$ is independently methyl, ethenyl, 3-chloropropyl, dimethylaminomethyl, 2-dimethylaminoethyl, 3-dimethylpropyl, 4-morpholinylmethyl, 2-(4-morpholinyl)ethyl, 3-(4-morpholinyl)propyl, (4-methyl-1-piperazinyl)methyl, 2-(4-methyl-1-piperazinyl)ethyl, 3-(4-methyl-1-piperazinyl)propyl, 4-(methylsulfonyl)-1-piperazinyl-methyl, 2-(4-(methylsulfonyl)-1-piperazinyl)ethyl, or 3-(4-(methylsulfonyl)-1-piperazinyl)propyl;

$R^6$ is difluoromethyl;

A, B, D, and E are each independently (i) a bond; (ii) a nitrogen, oxygen, or sulfur atom; or (iii) CH; wherein the bonds between A, B, D, and E may be saturated or unsaturated; with the proviso that no more than one of A, B, D, and E are a bond;

Q is 1,4-piperidinylene or 1,4-piperazinylene;

each $T^1$ is independently a bond, —O—, or —NR$^8$—;

each $T^2$ is independently a bond or —NR$^8$—, with the proviso that the atom that is attached to —SO$_2$R$^5$ is nitrogen;

each $R^8$ is independently hydrogen or methyl; and

X, Y, and Z are each independently a nitrogen atom or CH, with the proviso that at least two of X, Y, and Z are nitrogen atoms.

In yet another embodiment, in Formula Ia, Ib, or Ic, each $R^1$ is independently hydrogen or —$OR^{1a}$, where $R^{1a}$ is $C_{1-6}$ alkyl, optionally substituted with one or more —$NR^fR^g$; where $R^f$ and $R^g$ are each independently hydrogen or $C_{1-6}$ alkyl;

each $R^2$ is independently hydrogen, $C_{1-6}$ alkyl, or —$NR^{1b}R^{1c}$; where $R^{1b}$ and $R^{1c}$ are each independently (a) hydrogen; or (b) $C_{1-6}$ alkyl, $C_{2-6}$ alkenyl, or $C_{2-6}$ alkynyl, each optionally substituted with one or more substituents $Q^1$, each independently selected from the group consisting of —$OR^e$ and —$NR^fR^g$;

each $R^3$ and $R^4$ is independently hydrogen or $C_{1-6}$ alkyl;

each $R^5$ is independently $C_{1-6}$ alkyl or $C_{1-6}$ alkenyl, each optionally substituted with one or more substituents $Q^1$, each independently selected from the group consisting of chloro, heterocyclyl, and —$NR^fR^g$;

$R^6$ is $C_{1-6}$ alkyl, optionally substituted with one or more halo;

A, B, D, and E are each independently (i) a bond; (ii) a nitrogen, oxygen, or sulfur atom; or (iii) CH; wherein the bonds between A, B, D, and E may be saturated or unsaturated; with the proviso that no more than one of A, B, D, and E are a bond;

Q is heterocyclylene;

each $T^1$ is independently a bond, —O—, or —$NR^8$—;

each $T^2$ is independently a bond or —$NR^8$—, with the proviso that the atom that is attached to —$SO_2R^5$ is nitrogen;

each $R^8$ is independently (a) hydrogen; or (b) $C_{1-6}$ alkyl, $C_{2-6}$ alkenyl, or $C_{2-6}$ alkynyl, each optionally substituted with one or more substituents $Q^1$, each independently selected from the group consisting of cyano, —$C(O)R^e$, —$C(O)OR^e$, —$C(O)NR^fR^g$, —$OR^e$, —$OC(O)R^e$, —$OC(O)OR^e$, —$OC(O)NR^fR^g$, —$NR^fR^g$, —$NR^eC(O)R^h$, —$NR^eC(O)OR^f$, —$S(O)_2R^e$, and —$S(O)_2NR^fR^g$;

X, Y, and Z are each independently a nitrogen atom or $CR^9$, with the proviso that at least two of X, Y, and Z are nitrogen atoms; and $R^9$ is independently hydrogen or $C_{1-6}$ alkyl.

In yet another embodiment, in Formula Ia, Ib, or Ic, each $R^1$ is independently hydrogen, methoxy, or dimethylaminopropoxy;

each $R^2$ is independently hydrogen or amino;

$R^3$ and $R^4$ are hydrogen;

each $R^5$ is independently methyl, ethenyl, chloropropyl, dimethylaminomethyl, dimethylaminoethyl, dimethylaminopropyl, morpholinylmethyl, morpholinylethyl, morpholinylpropyl, (methylpiperazinyl)methyl, (methylpiperazinyl)ethyl, (methylpiperazinyl)propyl, (methylsulfonylpiperazinyl)methyl, (methylsulfonylpiperazinyl)ethyl, or (methylsulfonylpiperazinyl)propyl;

$R^6$ is difluoromethyl;

A, B, D, and E are each independently (i) a bond; (ii) a nitrogen, oxygen, or sulfur atom; or (iii) CH; wherein the bonds between A, B, D, and E may be saturated or unsaturated; with the proviso that no more than one of A, B, D, and E are a bond;

Q is azetidinylene, cyclopropylene, cyclobutylene, cyclopentylene, cyclohexylene, pyrrollidinylene, pyrrolylene, pyrazolylene, piperidinylene, piperazinylene, phenylene, thiazolylylene, or pyridylene;

each $T^1$ is independently a bond, —O—, or —$NR^8$—;

each $T^2$ is independently a bond or —$NR^8$—, with the proviso that the atom that is attached to —$SO_2R^5$ is nitrogen;

each $R^8$ is independently hydrogen or methyl; and

X, Y, and Z are each independently a nitrogen atom or CH, with the proviso that at least two of X, Y, and Z are nitrogen atoms.

In still another embodiment, Formula Ia, Ib, or Ic, each $R^1$ is independently hydrogen, methoxy, or 3-dimethylaminopropoxy;

each $R^2$ is independently hydrogen or amino;

$R^3$ and $R^4$ are hydrogen;

each $R^5$ is independently methyl, ethenyl, 3-chloropropyl, dimethylaminomethyl, 2-dimethylaminoethyl, 3-dimethylaminopropyl, 4-morpholinylmethyl, 2-(4-morpholinyl)ethyl, 3-(4-morpholinyl)propyl, (4-methyl-1-piperazinyl)methyl, 2-(4-methyl-1-piperazinyl)ethyl, 3-(4-methyl-1-piperazinyl)propyl, 4-(methylsulfonyl)-1-piperazinylmethyl, 2-(4-(methylsulfonyl)-1-piperazinyl)ethyl, or 3-(4-(methylsulfonyl)-1-piperazinyl)propyl;

$R^6$ is difluoromethyl;

A, B, D, and E are each independently (i) a bond; (ii) a nitrogen, oxygen, or sulfur atom; or (iii) CH; wherein the bonds between A, B, D, and E may be saturated or unsaturated; with the proviso that no more than one of A, B, D, and E are a bond;

Q is 1,3-piperidinylene, 1,4-piperidinylene, or 1,4-piperazinylene;

each $T^1$ is independently a bond, —O—, or —$NR^8$—;

each $T^2$ is independently a bond or —$NR^8$—, with the proviso that the atom that is attached to —$SO_2R^5$ is nitrogen;

each $R^8$ is independently hydrogen or methyl; and

X, Y, and Z are each independently a nitrogen atom or CH, with the proviso that at least two of X, Y, and Z are nitrogen atoms.

In one embodiment, in Formula IA, IB, IC, Ia, Ib, or Ic, each $R^1$ and $R^2$ is independently hydrogen, —$OR^{1a}$, or —$NR^{1b}R^{1c}$; where $R^{1a}$, $R^{1b}$, and $R^{1c}$ are each independently (a) hydrogen; or (b) $C_{1-6}$ alkyl, $C_{2-6}$ alkenyl, or $C_{2-6}$ alkynyl, each optionally substituted with one or more substituents; or $R^{1b}$ and $R^{1c}$ together with the N atom to which they are attached form heterocyclyl, optionally substituted with one or more substituents;

each $R^3$ and $R^4$ is independently hydrogen or $C_{1-6}$ alkyl, optionally substituted with one or more substituents; or $R^3$ and $R^4$ are linked together to form a bond or $C_{1-6}$ alkylene, optionally substituted with one or more substituents;

each $R^5$ is independently $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more substituents;

each $R^6$ is independently $C_{1-6}$ alkyl, optionally substituted with one or more substituents;

A, B, D, and E are each independently a bond, C, O, N, S, NH, CH, or $CH_2$; wherein the bonds between A, B, D, and E may be saturated or unsaturated; with the proviso that no more than one of A, B, D, and E are a bond;

Q is $C_{1-6}$ alkylene, $C_{2-6}$ alkenylene, $C_{2-6}$ alkynylene, $C_{3-7}$ cycloalkylene, $C_{6-14}$ arylene, heteroarylene, or heterocyclylene, each optionally substituted with one or more substituents;

each $T^1$ is independently a bond, —O—, or —$NR^8$—;

each $T^2$ is independently a bond or —$NR^8$—, with the proviso that the atom that is attached to —$SO_2R^5$ is nitrogen;

each $R^8$ is independently (a) hydrogen; or (b) $C_{1-6}$ alkyl, $C_{2-6}$ alkenyl, or $C_{2-6}$ alkynyl, each optionally substituted with one or more substituents; and X, Y, and Z are each independently a nitrogen atom or $CR^9$, with the proviso that at least two of X, Y, and Z are nitrogen atoms; where $R^9$ is hydrogen or $C_{1-6}$ alkyl, optionally substituted with one or more substituents.

In another embodiment, in Formula IA, IB, IC, Ia, Ib, or Ic, each $R^1$ and $R^2$ is independently hydrogen, —$OR^{1a}$, or —$NR^{1b}R^{1c}$; where $R^{1a}$, $R^{1b}$, and $R^{1c}$ are each independently (a) hydrogen; or (b) $C_{1-6}$ alkyl, $C_{2-6}$ alkenyl, or $C_{2-6}$ alkynyl, each optionally substituted with one or more substituents, each independently selected from the group consisting of —$OR^e$ and —$NR^fR^g$;

each $R^3$ and $R^4$ is independently hydrogen or $C_{1-6}$ alkyl, optionally substituted with one or more substituents, each independently selected from the group consisting of —$OR^e$ and —$NR^fR^g$; or $R^3$ and $R^4$ are linked together to form a bond or $C_{1-6}$ alkylene, optionally substituted with one or more substituents each $R^5$ is independently $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more substituents, each independently selected from the group consisting of halo, heteroaryl, heterocyclyl, —$OR^e$, and —$NR^fR^g$, wherein heteroaryl and heterocyclyl are further optionally substituted with one or more substituents;

each $R^6$ is independently $C_{1-6}$ alkyl, optionally substituted with one or more substituents, each independently selected from the group consisting of —$OR^e$ and —$NR^fR^g$;

A, B, D, and E are each independently a bond, C, O, N, S, NH, CH, or $CH_2$; wherein the bonds between A, B, D, and E may be saturated or unsaturated; with the proviso that no more than one of A, B, D, and E are a bond;

Q is $C_{1-6}$ alkylene, $C_{2-6}$ alkenylene, $C_{2-6}$ alkynylene, $C_{3-7}$ cycloalkylene, $C_{6-14}$ arylene, heteroarylene, or heterocyclylene, each optionally substituted with one or more substituents;

each $T^1$ is independently a bond, —O—, or —$NR^8$—;

each $T^2$ is independently a bond or —$NR^8$—, with the proviso that the atom that is attached to —$SO_2R^5$ is nitrogen;

each $R^8$ is independently (a) hydrogen; or (b) $C_{1-6}$ alkyl, $C_{2-6}$ alkenyl, or $C_{2-6}$ alkynyl, each optionally substituted with one or more substituents, each independently selected from the group consisting of cyano, heterocycle, —$C(O)R^e$, —$C(O)OR^e$, —$C(O)NR^fR^g$, —$OR^e$, —$OC(O)R^e$, —$OC(O)OR^e$, —$OC(O)NR^fR^g$, —$NR^fR^g$, —$NR^eC(O)R^h$, —$NR^eC(O)OR^f$, —$S(O)_2R^e$, and —$S(O)_2NR^fR^g$, where heterocyclyl is optionally substituted with one or more substituents;

X, Y, and Z are each independently a nitrogen atom or $CR^9$, with the proviso that at least two of X, Y, and Z are nitrogen atoms; where $R^9$ is hydrogen or $C_{1-6}$ alkyl; and each $R^e$, $R^f$, $R^g$, and $R^h$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl.

In yet another embodiment, in Formula IA, IB, IC, Ia, Ib, or Ic, each $R^1$ is independently hydrogen or —$OR^{1a}$, where $R^{1a}$ is $C_{1-6}$ alkyl, optionally substituted with one or more —$NR^fR^g$; where $R^f$ and $R^g$ are each independently hydrogen or $C_{1-6}$ alkyl;

each $R^2$ is independently hydrogen or $C_{1-6}$ alkyl;

$R^3$, and $R^4$ is independently hydrogen or $C_{1-6}$ alkyl; or $R^3$ and $R^4$ are linked together to form a bond or $C_{1-6}$ alkylene;

each $R^5$ is independently $C_{1-6}$ alkyl or $C_{1-6}$ alkenyl, each optionally substituted with one or more substituents, each independently selected from the group consisting of chloro, heterocyclyl, and —$NR^fR^g$, wherein heterocyclyl is further optionally substituted with one or more substituents, each of which is independently oxo, methyl, or methylsulfonyl;

$R^6$ is $C_{1-6}$ alkyl, optionally substituted with one or more halo;

A, B, D, and E are each independently a bond, C, O, N, S, NH, CH, or $CH_2$; wherein the bonds between A, B, D, and E may be saturated or unsaturated; with the proviso that no more than one of A, B, D, and E are a bond;

Q is heterocyclylene;

each $T^1$ is independently a bond, —O—, or —$NR^8$—;

each $T^2$ is independently a bond or —$NR^8$—, with the proviso that the atom that is attached to —$SO_2R^5$ is nitrogen;

each $R^8$ is independently (a) hydrogen; or (b) $C_{1-6}$ alkyl, $C_{2-6}$ alkenyl, or $C_{2-6}$ alkynyl, each optionally substituted with one or more substituents, each independently selected from the group consisting of cyano, heterocyclyl, —$C(O)R^e$, —$C(O)OR^e$, —$C(O)NR^fR^g$, —$OR^e$, —$OC(O)R^e$, —$OC(O)OR^e$, —$OC(O)NR^fR^g$, —$NR^fR^g$, —$NR^eC(O)R^h$, —$NR^eC(O)OR^f$, —$S(O)_2R^e$, and —$S(O)_2NR^fR^g$, where heterocyclyl is optionally substituted with one or more substituents;

X, Y, and Z are each independently a nitrogen atom or $CR^9$, with the proviso that at least two of X, Y, and Z are nitrogen atoms; and $R^9$ is independently hydrogen or $C_{1-6}$ alkyl.

In yet another embodiment, in Formula IA, IB, IC, Ia, Ib, or Ic, each $R^1$ is independently hydrogen, methoxy, or dimethylaminopropoxy;

$R^2$ is hydrogen;

$R^3$ and $R^4$ are hydrogen; or $R^3$ and $R^4$ are linked together to form methylene or ethylene;

each $R^5$ is independently methyl, ethenyl, chloropropyl, dimethylaminomethyl, dimethylaminoethyl, dimethylaminopropyl, morpholinylmethyl, morpholinylethyl, morpholinylpropyl, (methylpiperazinyl)methyl, (methylpiperazinyl)ethyl, (methyl-piperazinyl)propyl, (methylsulfonylpiperazinylmethyl, (methylsulfonylpiperazinyl)ethyl, (methylsulfonylpiperazinyl)propyl, (oxido-thiomorpholinyl)ethyl, or (dioxido-thiomorpholinyl)ethyl;

$R^6$ is difluoromethyl;

A, B, D, and E are each independently a bond, C, O, N, S, NH, CH, or $CH_2$; wherein the bonds between A, B, D, and E may be saturated or unsaturated; with the proviso that no more than one of A, B, D, and E are a bond;

Q is azetidinylene, cyclopropylene, cyclobutylene, cyclopentylene, cyclohexylene, pyrrolidinylene, pyrrolylene, pyrazolylene, piperidinylene, piperazinylene, phenylene, thiazolylylene, or pyridylene;

each $T^1$ is independently a bond, —O—, or —$NR^8$—;

each $T^2$ is independently a bond or —$NR^8$—, with the proviso that the atom that is attached to —$SO_2R^5$ is nitrogen;

each $R^8$ is independently hydrogen, methyl, ethenyl, chloropropyl, dimethylaminomethyl, dimethylaminoethyl, dimethylaminopropyl, morpholinylmethyl, morpholinylethyl, morpholinylpropyl, (methylpiperazinyl)methyl, (methylpiperazinyl)ethyl, (methylpiperazinyl)propyl, (methylsulfonylpiperazinylmethyl, (methylsulfonylpiperazinyl)-ethyl, or (methylsulfonylpiperazinyl)propyl; and X, Y, and Z are each independently a nitrogen atom or CH, with the proviso that at least two of X, Y, and Z are nitrogen atoms.

In yet another embodiment, in Formula IA, IB, IC, Ia, Ib, or Ic, each $R^1$ is independently hydrogen, methoxy, or 3-dimethylaminopropoxy;

$R^2$ is hydrogen;

$R^3$ and $R^4$ are hydrogen; or $R^3$ and $R^4$ are linked together to form ethylene;

each $R^5$ is independently methyl, ethenyl, 3-chloropropyl, dimethylaminomethyl, 2-dimethylaminoethyl, 3-dimethylpropylamino, 4-morpholinylmethyl, 2-(4-morpholinyl)ethyl, 3-(4-morpholinyl)propyl, (4-methyl-1-piperazinyl)methyl, 2-(4-methyl-1-piperazinyl)ethyl, 3-(4-methyl-1-piperazinyl)

propyl, 4-(methylsulfonyl)-1-piperazinyl-methyl, 2-(4-(methylsulfonyl)-1-piperazinyl)ethyl, 3-(4-(methylsulfonyl)-1-piperazinyl)propyl, 3-(1-oxido-thiomorpholin-4-yl)ethyl, or 3-(1,1-dioxido-thiomorpholin-4-yl)ethyl;

$R^6$ is difluoromethyl;

A, B, D, and E are each independently a bond, C, O, N, S, NH, CH, or $CH_2$; wherein the bonds between A, B, D, and E may be saturated or unsaturated; with the proviso that no more than one of A, B, D, and E are a bond;

Q is 1,4-piperidinylene or 1,4-piperazinylene;

each $T^1$ is independently a bond, —O—, or —$NR^8$—;

each $T^2$ is independently a bond or —$NR^8$—, with the proviso that the atom that is attached to —$SO_2R^5$ is nitrogen;

each $R^8$ is independently hydrogen, methyl, ethenyl, chloropropyl, dimethylaminomethyl, dimethylaminoethyl, dimethylaminopropyl, morpholinylmethyl, morpholinylethyl, morpholinylpropyl, (methylpiperazinyl)methyl, (methylpiperazinyl)ethyl, (methylpiperazinyl)propyl, (methylsulfonylpiperazinylmethyl, (methylsulfonylpiperazinyl)-ethyl, or (methylsulfonylpiperazinyl)propyl; and X, Y, and Z are each independently a nitrogen atom or CH, with the proviso that at least two of X, Y, and Z are nitrogen atoms.

In yet another embodiment, in Formula IA, IB, IC, Ia, Ib, or Ic, each $R^1$ is independently hydrogen, methoxy, or 3-dimethylaminopropoxy;

$R^2$ is hydrogen;

$R^3$ and $R^4$ are hydrogen; or $R^3$ and $R^4$ are linked together to form ethylene;

each $R^5$ is independently methyl, ethenyl, 3-chloropropyl, dimethylaminomethyl, 2-dimethylaminoethyl, 3-dimethylpropyl, 4-morpholinylmethyl, 2-(4-morpholinyl)ethyl, 3-(4-morpholinyl)propyl, (4-methyl-1-piperazinyl)methyl, 2-(4-methyl-1-piperazinyl)ethyl, 3-(4-methyl-1-piperazinyl)propyl, 4-(methylsulfonyl)-1-piperazinyl-methyl, 2-(4-(methylsulfonyl)-1-piperazinyl)ethyl, 3-(4-(methylsulfonyl)-1-piperazinyl)propyl, 3-(1-oxido-thiomorpholin-4-yl)ethyl, or 3-(1,1-dioxido-thiomorpholin-4-yl)ethyl;

$R^6$ is difluoromethyl;

A, B, D, and E are each independently a bond, C, O, N, S, NH, CH, or $CH_2$; wherein the bonds between A, B, D, and E may be saturated or unsaturated; with the proviso that no more than one of A, B, D, and E are a bond;

Q is 1,4-piperidinylene or 1,4-piperazinylene;

each $T^1$ is independently a bond, —O—, or —$NR^8$—;

each $T^2$ is independently a bond or —$NR^8$—, with the proviso that the atom that is attached to —$SO_2R^5$ is nitrogen;

each $R^8$ is independently hydrogen, methyl, ethenyl, chloropropyl, dimethylaminomethyl, dimethylaminoethyl, dimethylaminopropyl, morpholinylmethyl, morpholinylethyl, morpholinylpropyl, (methylpiperazinyl)methyl, (methylpiperazinyl)ethyl, (methylpiperazinyl)propyl, (methylsulfonylpiperazinylmethyl, (methylsulfonylpiperazinyl)-ethyl, or (methylsulfonylpiperazinyl)propyl; and X, Y, and Z are each independently a nitrogen atom or CH, with the proviso that at least two of X, Y, and Z are nitrogen atoms.

In yet another embodiment, in Formula IA, IB, IC, Ia, Ib, or Ic, each $R^1$ is independently hydrogen or —$OR^{1a}$, where $R^{1a}$ is $C_{1-6}$ alkyl, optionally substituted with one or more —$NR^fR^g$; where $R^f$ and $R^g$ are each independently hydrogen or $C_{1-6}$ alkyl;

each $R^2$ is independently hydrogen, $C_{1-6}$ alkyl, or —$NR^{1b}R^{1c}$; where $R^{1b}$ and $R^{1c}$ are each independently (a) hydrogen; or (b) $C_{1-6}$ alkyl, $C_{2-6}$ alkenyl, or $C_{2-6}$ alkynyl, each optionally substituted with one or more substituents, each independently selected from the group consisting of —$OR^e$ and —$NR^fR^g$;

each $R^3$ and $R^4$ is independently hydrogen or $C_{1-6}$ alkyl; or $R^3$ and $R^4$ are linked together to form a bond or $C_{1-6}$ alkylene, optionally substituted with one or more substituents;

each $R^5$ is independently $C_{1-6}$ alkyl or $C_{1-6}$ alkenyl, each optionally substituted with one or more substituents, each independently selected from the group consisting of chloro, heterocyclyl, and —$NR^fR^g$, wherein heterocyclyl is further optionally substituted with one or more substituents;

$R^6$ is $C_{1-6}$ alkyl, optionally substituted with one or more halo;

A, B, D, and E are each independently a bond, C, O, N, S, NH, CH, or $CH_2$; wherein the bonds between A, B, D, and E may be saturated or unsaturated; with the proviso that no more than one of A, B, D, and E are a bond;

Q is heterocyclylene;

each $T^1$ is independently a bond, —O—, or —$NR^8$—;

each $T^2$ is independently a bond or —$NR^8$—, with the proviso that the atom that is attached to —$SO_2R^5$ is nitrogen;

each $R^8$ is independently (a) hydrogen; or (b) $C_{1-6}$ alkyl, $C_{2-6}$ alkenyl, or $C_{2-6}$ alkynyl, each optionally substituted with one or more substituents, each independently selected from the group consisting of cyano, heterocyclyl, —$C(O)R^e$, —$C(O)OR^e$, —$C(O)NR^fR^g$, —$OR^e$, —$OC(O)R^e$, —$OC(O)OR^e$, —$OC(O)NR^fR^g$, —$NR^fR^g$, —$NR^eC(O)R^h$, —$NR^eC(O)OR^f$, —$S(O)_2R^e$, and —$S(O)_2NR^fR^g$, where heterocyclyl is optionally substituted with one or more substituents;

X, Y, and Z are each independently a nitrogen atom or $CR^9$, with the proviso that at least two of X, Y, and Z are nitrogen atoms; and $R^9$ is independently hydrogen or $C_{1-6}$ alkyl.

In yet another embodiment, in Formula IA, IB, IC, Ia, Ib, or Ic, each $R^1$ is independently hydrogen, methoxy, or dimethylaminopropoxy;

each $R^2$ is independently hydrogen or amino;

$R^3$ and $R^4$ are hydrogen; or $R^3$ and $R^4$ are linked together to form ethylene;

each $R^5$ is independently methyl, ethenyl, chloropropyl, dimethylaminomethyl, dimethylaminoethyl, dimethylaminopropyl, morpholinylmethyl, morpholinylethyl, morpholinylpropyl, (methylpiperazinyl)methyl, (methylpiperazinyl)ethyl, (methylpiperazinyl)propyl, (methylsulfonylpiperazinylmethyl, (methylsulfonylpiperazinyl)ethyl, (methylsulfonylpiperazinyl)propyl, (oxido-thiomorpholinyl)ethyl, or (dioxido-thiomorpholinyl)ethyl;

$R^6$ is difluoromethyl;

A, B, D, and E are each independently a bond, C, O, N, S, NH, CH, or $CH_2$;

wherein the bonds between A, B, D, and E may be saturated or unsaturated; with the proviso that no more than one of A, B, D, and E are a bond;

Q is azetidinylene, cyclopropylene, cyclobutylene, cyclopentylene, cyclohexylene, pyrrolidinylene, pyrrolylene, pyrazolylene, piperidinylene, piperazinylene, phenylene, thiazolylylene, or pyridylene;

each $T^1$ is independently a bond, —O—, or —$NR^8$—;

each $T^2$ is independently a bond or —$NR^8$—, with the proviso that the atom that is attached to —$SO_2R^5$ is nitrogen;

each $R^8$ is independently hydrogen, methyl, ethenyl, chloropropyl, dimethylaminomethyl, dimethylaminoethyl, dimethylaminopropyl, morpholinylmethyl, morpholinylethyl, morpholinylpropyl, (methylpiperazinyl)methyl, (methylpiperazinyl)ethyl, (methylpiperazinyl)propyl, (methylsulfonylpiperazinylmethyl, (methylsulfonylpiperazinyl)-ethyl, or (methylsulfonylpiperazinyl)propyl; and X, Y, and Z are each independently a nitrogen atom or CH, with the proviso that at least two of X, Y, and Z are nitrogen atoms.

In still another embodiment, Formula IA, IB, IC, Ia, Ib, or Ic, each $R^1$ is independently hydrogen, methoxy, or 3-dimethylaminopropoxy;

each $R^2$ is independently hydrogen or amino;

$R^3$ and $R^4$ are hydrogen; or $R^3$ and $R^4$ are linked together to form ethylene;

each $R^5$ is independently methyl, ethenyl, 3-chloropropyl, dimethylaminomethyl, 2-dimethylaminoethyl, 3-dimethylaminopropyl, 4-morpholinylmethyl, 2-(4-morpholinyl)ethyl, 3-(4-morpholinyl)propyl, (4-methyl-1-piperazinyl)methyl, 2-(4-methyl-1-piperazinyl)ethyl, 3-(4-methyl-1-piperazinyl)propyl, 4-(methylsulfonyl)-1-piperazinylmethyl, 2-(4-(methylsulfonyl)-1-piperazinyl)ethyl, 3-(4-(methylsulfonyl)-1-piperazinyl)propyl, 3-(1-oxido-thiomorpholin-4-yl)ethyl, or 3-(1,1-dioxido-thiomorpholin-4-yl)ethyl;

$R^6$ is difluoromethyl;

A, B, D, and E are each independently a bond, C, O, N, S, NH, CH, or $CH_2$; wherein the bonds between A, B, D, and E may be saturated or unsaturated; with the proviso that no more than one of A, B, D, and E are a bond;

Q is 1,3-piperidinylene, 1,4-piperidinylene, or 1,4-piperazinylene;

each $T^1$ is independently a bond, —O—, or —$NR^8$—;

each $T^2$ is independently a bond or —$NR^8$—, with the proviso that the atom that is attached to —$SO_2R^5$ is nitrogen;

each $R^8$ is independently hydrogen, methyl, ethenyl, chloropropyl, dimethylaminomethyl, dimethylaminoethyl, dimethylaminopropyl, morpholinylmethyl, morpholinylethyl, morpholinylpropyl, (methylpiperazinyl)methyl, (methylpiperazinyl)ethyl, (methylpiperazinyl)propyl, (methylsulfonylpiperazinylmethyl, (methylsulfonylpiperazinyl)ethyl, or (methylsulfonylpiperazinyl)propyl; and X, Y, and Z are each independently a nitrogen atom or CH, with the proviso that at least two of X, Y, and Z are nitrogen atoms.

In one embodiment, the compound of Formula Ia has the structure of Formula II:

II or an enantiomer, a mixture of enantiomers, or a mixture of two or more diastereomers thereof; or a pharmaceutically acceptable salt, solvate, hydrate, or prodrug thereof; wherein $R^1$, $R^2$, $R^3$, $R^4$, $R^5$, $R^6$, Q, $T^1$, and $T^2$ are each as defined herein.

In another embodiment, the compound of Formula Ia has the structure of Formula III:

III or an enantiomer, a mixture of enantiomers, or a mixture of two or more diastereomers thereof; or a pharmaceutically acceptable salt, solvate, hydrate, or prodrug thereof; wherein:

$R^1$, $R^2$, $R^3$, $R^4$, $R^5$, $R^6$, X, Y, and Z are each as defined herein;

$T^1$ is —O— or —$NR^8$—; where $R^8$ is hydrogen or $C_{1-6}$ alkyl, optionally substituted with one or more substituents $Q^1$; and G and J are each independently a bond, —$CH_2$—, or —$CH_2CH_2$—.

In yet another embodiment, the compound of Formula Ia has the structure of Formula III, or an enantiomer, a mixture of enantiomers, or a mixture of two or more diastereomers thereof; or a pharmaceutically acceptable salt, solvate, hydrate, or prodrug thereof; wherein:

$R^1$, $R^2$, $R^3$, $R^4$, $R^5$, $R^6$, X, Y, and Z are each as defined herein;

$T^1$ is a bond, —O—, or —$NR^8$—; where $R^8$ is hydrogen or $C_{1-6}$ alkyl, optionally substituted with one or more substituents $Q^1$; and G and J are each independently a bond, —$CH_2$—, or —$CH_2CH_2$—.

In yet another embodiment, the compound of Formula Ia has the structure of Formula III:

III or an enantiomer, a mixture of enantiomers, or a mixture of two or more diastereomers thereof; or a pharmaceutically acceptable salt, solvate, hydrate, or prodrug thereof; wherein:

$R^1$, $R^2$, $R^3$, $R^4$, $R^5$, $R^6$, X, Y, and Z are each as defined herein;

$T^1$ is —O— or —NR$^8$—; where R$^8$ is hydrogen or C$_{1-6}$ alkyl; and

G and J are each independently a bond, —CH$_2$—, or —CH$_2$CH$_2$—.

In yet another embodiment, the compound of Formula Ia has the structure of Formula III, or an enantiomer, a mixture of enantiomers, or a mixture of two or more diastereomers thereof; or a pharmaceutically acceptable salt, solvate, hydrate, or prodrug thereof; wherein:

R$^1$, R$^2$, R$^3$, R$^4$, R$^5$, R$^6$, X, Y, and Z are each as defined herein;

T$^1$ is a bond, —O—, or —NR$^8$—; where R$^8$ is hydrogen or C$_{1-6}$ alkyl; and G and J are each independently a bond, —CH$_2$—, or —CH$_2$CH$_2$—. In yet another embodiment, the compound of Formula Ia has the structure of Formula IV:

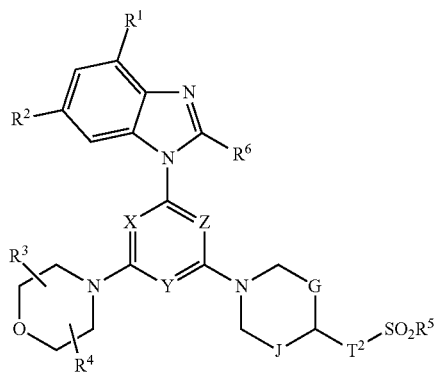

IV or an enantiomer, a mixture of enantiomers, or a mixture of two or more diastereomers thereof; or a pharmaceutically acceptable salt, solvate, hydrate, or prodrug thereof; wherein:

R$^1$, R$^2$, R$^3$, R$^4$, R$^5$, R$^6$, T$^2$, X, Y, and Z are each as defined herein; and G and J are each independently a bond, —CH$_2$—, or —CH$_2$CH$_2$—.

In yet another embodiment, the compound of Formula Ia has the structure of Formula V:

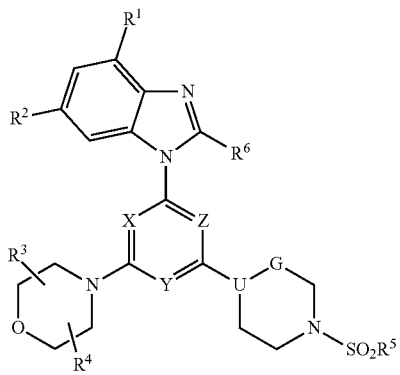

V or an enantiomer, a mixture of enantiomers, or a mixture of two or more diastereomers thereof; or a pharmaceutically acceptable salt, solvate, hydrate, or prodrug thereof; wherein:

R$^1$, R$^2$, R$^3$, R$^4$, R$^5$, R$^6$, X, Y, and Z are each as defined herein;

G is —CH$_2$—, or —CH$_2$CH$_2$—; and

U is N or CH.

In yet another embodiment, the compound of Formula Ib has the structure of Formula VI:

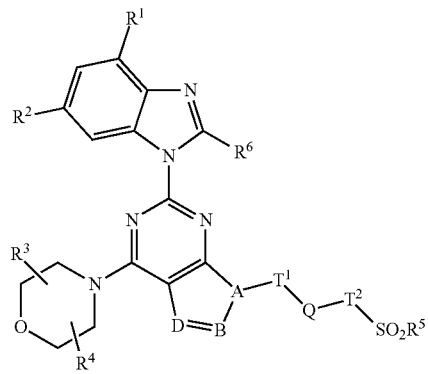

VI or an enantiomer, a mixture of enantiomers, or a mixture of two or more diastereomers thereof; or a pharmaceutically acceptable salt, solvate, hydrate, or prodrug thereof; wherein R$^1$, R$^2$, R$^3$, R$^4$, R$^5$, R$^6$, A, B, D, Q, T$^1$, and T$^2$ are each as defined herein.

In yet another embodiment, the compound of Formula Ic has the structure of Formula VII:

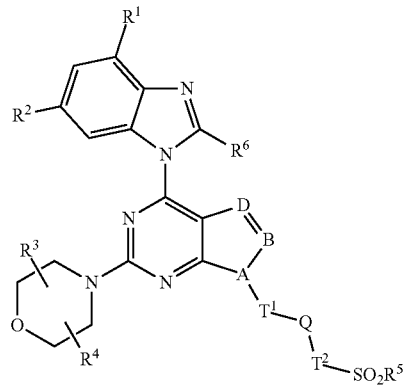

VII or an enantiomer, a mixture of enantiomers, or a mixture of two or more diastereomers thereof; or a pharmaceutically acceptable salt, solvate, hydrate, or prodrug thereof; wherein R$^1$, R$^2$, R$^3$, R$^4$, R$^5$, R$^6$, A, B, D, Q, T$^1$, and T$^2$ are each as defined herein.

In still another embodiment, provided here is a compound of Formula VIII:

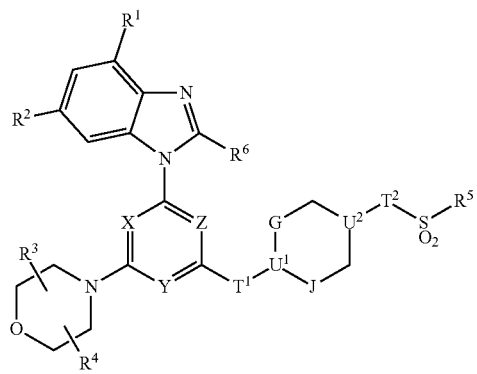

(VIII)

or an enantiomer, a mixture of enantiomers, or a mixture of two or more diastereomers thereof; or a pharmaceutically acceptable salt, solvate, hydrate, or prodrug thereof; wherein:

$R^1$, $R^2$, $R^3$, $R^4$, $R^6$, G, J, $T^1$, $T^2$, X, Y, and Z are each as defined herein;

$R^5$ is $C_{1-6}$ alkyl, substituted with one or more halo; and $U^1$ and $U^2$ are each independently N or CH.

In one embodiment, provided herein is a compound of Formula VIII, wherein:

$R^1$ is —$OR^{1a}$, where $R^{1a}$ is $C_{1-6}$ alkyl, optionally substituted with one or more substituents as described herein;

$R^2$ is hydrogen;

$R^3$ and $R^4$ are hydrogen;

$R^5$ is chloromethyl;

$R^6$ is $C_{1-6}$ alkyl, substituted with one or more halo;

G and J are both methylene; or one of them is a bond and the other is ethylene;

$T^1$ is a bond or N(3-dimethylaminopropyl);

$T^2$ is a bond, NH, or N(3-dimethylaminopropyl);

$U^1$ and $U^2$ are each independently N or CH; and

X, Y, and Z are N.

In another embodiment, provided herein is a compound of Formula VIII, wherein:

$R^1$ is methoxy;

$R^2$ is hydrogen;

$R^3$ and $R^4$ are hydrogen;

$R^5$ is chloromethyl;

$R^6$ is difluoromethyl;

G and J are both methylene; or G is a bond, and J is ethylene;

$T^1$ is a bond or N(3-dimethylaminopropyl);

$T^2$ is a bond, NH, or N(3-dimethylaminopropyl);

$U^1$ and $U^2$ are each independently N or CH; and

X, Y, and Z are N.

The groups, $R^1$, $R^2$, $R^3$, $R^4$, $R^5$, $R^6$, A, B, D, E, G, J, Q, $T^1$, $T^2$, U, X, Y, and Z in Formulae provided herein, e.g., Formulae IA, IB, IC, Ia, Ib, Ic, II, III, IV, V, VI, VII, and VIII, are further defined in the embodiments described herein. All combinations of the embodiments provided herein for such groups are within the scope of this disclosure.

In certain embodiments, each $R^1$ is independently hydrogen, cyano, halo, or nitro. In certain embodiments, each $R^1$ is independently $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more substituents $Q^1$. In certain embodiments, each $R^1$ is independently —$C(O)R^{1a}$, —$C(O)OR^{1b}$, —$C(O)NR^{1b}R^{1c}$, or —$C(NR^{1a})NR^{1b}R^{1c}$, wherein $R^{1a}$, $R^{1b}$, and $R^{1c}$ are each as defined herein. In certain embodiments, each $R^1$ is independently —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, or —$OS(O)_2NR^{1b}R^{1c}$, wherein $R^{1a}$, $R^{1b}$, and $R^{1c}$ are each as defined herein. In certain embodiments, each $R^1$ is independently —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^d)NR^{1b}R^{1c}$, —$NR^{1a}S(O)R^{1d}$, —$NR^{1a}S(O)_2R^d$, —$NR^{1a}S(O)NR^{1b}R^{1c}$, or —$NR^{1a}S(O)_2NR^{1b}R^{1c}$, wherein $R^{1a}$, $R^{1b}$, $R^{1c}$, and $R^{1d}$ are each as defined herein. In certain embodiments, each $R^1$ is independently —$SR^{1a}$, —$S(O)R^{1a}$, —$S(O)_2R^{1a}$, —$S(O)NR^{1b}R^{1c}$, or —$S(O)_2NR^{1b}R^{1c}$; wherein $R^{1a}$, $R^{1b}$, and $R^{1c}$ are each as defined herein. In certain embodiments, each $R^1$ is independently hydrogen, methoxy, ethoxy, propoxy, isopropoxy, or dimethylaminopropoxy. In certain embodiments, each $R^1$ is independently hydrogen, methoxy, or 3-dimethylaminopropoxy.

In certain embodiments, each $R^2$ is independently hydrogen, cyano, halo, or nitro. In certain embodiments, each $R^2$ is independently $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more substituents $Q^1$. In certain embodiments, each $R^2$ is independently —$C(O)R^{1a}$, —$C(O)OR^{1b}$, —$C(O)NR^{1b}R^{1c}$, or —$C(NR^{1a})NR^{1b}R^{1c}$, wherein $R^{1a}$, $R^b$, and $R^{1c}$ are each as defined herein. In certain embodiments, each $R^2$ is independently —$OR^{1a}$, —$OC(O)R^{1a}$, —$OC(O)OR^{1a}$, —$OC(O)NR^{1b}R^{1c}$, —$OC(=NR^{1a})NR^{1b}R^{1c}$, —$OS(O)R^{1a}$, —$OS(O)_2R^{1a}$, —$OS(O)NR^{1b}R^{1c}$, or —$OS(O)_2NR^{1b}R^{1c}$, wherein $R^{1a}$, $R^{1b}$, and $R^{1c}$ are each as defined herein. In certain embodiments, each $R^2$ is independently —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^d$, —$NR^{1a}S(O)NR^{1b}R^{1c}$, or —$NR^{1a}S(O)_2NR^{1b}R^{1c}$, wherein $R^{1a}$, $R^{1b}$, $R^{1c}$, and $R^{1d}$ are each as defined herein. In certain embodiments, each $R^2$ is independently —$NR^{1b}R^{1c}$ wherein $R^{1b}$ and $R^{1c}$ are each as defined herein. In certain embodiments, $R^2$ is amino (—$NH_2$). In certain embodiments, each $R^2$ is independently —$SR^{1a}$, —$S(O)R^{1a}$, —$S(O)_2R^{1a}$, —$S(O)NR^{1b}R^{1c}$, or —$S(O)_2NR^{1b}R^{1c}$; wherein $R^{1a}$, $R^{1b}$, and $R^{1c}$ are each as defined herein. In certain embodiments, each $R^2$ is independently hydrogen, methoxy, ethoxy, propoxy, isopropoxy, or dimethylaminopropoxy. In certain embodiments, $R^2$ is hydrogen.

In certain embodiments, each $R^3$ is independently hydrogen or $C_{1-6}$ alkyl, optionally substituted with one or more substituents $Q^1$. In certain embodiments, each $R^3$ is independently hydrogen, methyl, ethyl, or propyl (e.g., n-propyl, isopropyl, or 2-isopropyl). In certain embodiments, $R^3$ is hydrogen.

In certain embodiments, each $R^4$ is independently hydrogen or $C_{1-6}$ alkyl, optionally substituted with one or more substituents $Q^1$. In certain embodiments, each $R^4$ is independently hydrogen, methyl, ethyl, or propyl (e.g., n-propyl, isopropyl, or 2-isopropyl). In certain embodiments, $R^4$ is hydrogen.

In certain embodiments, $R^3$ and $R^4$ are linked together to form a bond. In certain embodiments, $R^3$ and $R^4$ are linked together to form $C_{1-6}$ alkylene, optionally substituted with one or more substituents. In certain embodiments, $R^3$ and $R^4$ are linked together to form methylene, ethylene, or propylene, each optionally substituted with one or more substituents.

In certain embodiments, each $R^5$ is independently $C_{1-6}$ alkyl, $C_{2-6}$ alkenyl, or $C_{2-6}$ alkynyl, each optionally substituted with one or more substituents $Q^1$. In certain embodiments, each $R^5$ is independently $C_{3-7}$ cycloalkyl, $C_{6-14}$ aryl, or $C_{7-15}$ aralkyl, each optionally substituted with one or more substituents $Q^1$. In certain embodiments, each $R^5$ is independently heteroaryl or heterocyclyl, each optionally substituted with one or more substituents $Q^1$. In certain embodiments, each $R^5$ is independently $C_{3-7}$ cycloalkyl-$C_{1-6}$ alkyl, optionally substituted with one or more substituents. In certain embodiments, each $R^5$ is independently heteroaryl-$C_{1-6}$ alkyl, optionally substituted with one or more substituents. In certain embodiments, each $R^5$ is independently heterocyclyl-$C_{1-6}$ alkyl, optionally substituted with one or more substituents. In certain embodiments, each $R^5$ is independently methyl, trifluoromethyl, ethenyl, chloropropyl, dimethylaminomethyl, dimethylaminoethyl, dimethylaminopropyl, pyrrolidinylethyl, morpholinylmethyl, morpholinylmethyl, morpholinylethyl, morpholinylpropyl, piperidinylethyl, methylpiperazinyl, (methylpiperazinyl)methyl, (methylpiperazinyl)ethyl, (hydroxyethyl-piperazinyl)ethyl, (methylpiperazinyl)propyl, (methylsulfonylpiperazinyl)methyl, (methylsulfonylpiperazinyl)ethyl, (methylsulfonylpiperazinyl)

propyl, (oxido-thiomorpholinyl)ethyl, or (dioxido-thiomorpholinyl)ethyl, 8-oxa-3-azabicyclo[3.2.1]octanyl-ethyl, (imidazylyl)ethyl, pyridinyl, or (pyridinyl)ethyl. In certain embodiments, each $R^5$ is independently methyl, ethenyl, 3-chloropropyl, dimethylaminomethyl, 2-dimethylaminoethyl, 3-dimethylaminopropyl, 2-pyrrolidin-1-yl-ethyl, 4-morpholinylmethyl, 2-(4-morpholinyl)ethyl, 3-(4-morpholinyl)propyl, 2-(piperidin-1-yl)ethyl, 4-methyl-1-piperazinyl, (4-methyl-1-piperazinyl)methyl, 2-(4-methyl-1-piperazinyl)ethyl, 2-(4-hydroxyethyl-1-piperazinyl)ethyl, 3-(4-methyl-1-piperazinyl)propyl, 4-(methylsulfonyl)-1-piperazinyl-methyl, 2-(4-(methylsulfonyl)-1-piperazinyl)ethyl, 3-(4-(methylsulfonyl)-1-piperazinyl)propyl, 3-(1-oxido-thiomorpholin-4-yl)ethyl, 3-(1,1-dioxido-thiomorpholin-4-yl)ethyl, 2-(8-oxa-3-azabicyclo[3.2.1]octan-3-yl)ethyl, 2-(imidazyl-1-yl)-ethyl, 3-pyridinyl, 2-(pyridin-2-yl)ethyl, or 2-(pyridin-4-yl)ethyl.

In certain embodiments, each $R^5$ is independently $C_{1-6}$ alkyl, optionally substituted with one or more substituents $Q^1$. In certain embodiments, each $R^5$ is independently $C_{1-6}$ alkyl, substituted with one or more halo groups. In certain embodiments, each $R^5$ is independently $C_{1-6}$ alkyl, substituted with one or more groups, each of which is independently selected from fluoro, chloro, bromo, or iodo. In certain embodiments, each $R^5$ is independently chloromethyl. In certain embodiments, each $R^5$ is independently —$(CR^{5a}R^{5b})_m$—$R^{5c}$, where $R^{5a}$ and $R^{5b}$ are each independently (a) hydrogen, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; each optionally substituted with one or more substituents; $R^{5c}$ is hydrogen, —$NR^{5d}R^{5e}$, or heterocyclyl; $R^{5d}$ and $R^{5e}$ are each independently hydrogen or $C_{1-6}$ alkyl; and m is an integer of 0, 1, 2, or 3; and where each alkyl and heterocyclyl is independently, optionally substituted with one or more substituents as described herein. In certain embodiments, $R^{5a}$ is hydrogen. In certain embodiments, $R^{5b}$ is hydrogen. In certain embodiments, $R^{5a}$ and $R^{5b}$ are hydrogen. In certain embodiments, $R^{5c}$ is hydrogen. In certain embodiments, $R^{5c}$ is —$NR^{5d}R^{5e}$, where $R^{5d}$ and $R^{5e}$ are each independently hydrogen or $C_{1-6}$ alkyl, optionally substituted with one or more substituents as described herein. In certain embodiments, $R^{5d}$ is hydrogen or methyl. In certain embodiments, $R^{5e}$ is hydrogen or methyl. In certain embodiments, $R^{5c}$ is amino, methylamino, or dimethylamino. In certain embodiments, $R^{5c}$ is heterocyclyl, optionally substituted with one or more substituents as described herein. In certain embodiments, $R^{5c}$ is pyrrolidinyl, piperidinyl, piperazinyl, or morpholinyl, each optionally substituted with one or more substituents as described herein. In certain embodiments, $R^{5c}$ is pyrrolidinyl, piperidinyl, piperazinyl, morpholinyl, thiomorpholinyl, each optionally substituted with one or more substituents, wherein each substituent is independently oxo, methyl, or methylsulfonyl. In certain embodiments, $R^{5c}$ is hydrogen, dimethylamino, pyrrolidinyl, methyl-piperazinyl, piperazinyl, hydroxyethyl-piperazinyl, methylsulfonyl-piperazinyl, morpholinyl, oxido-thiomorpholinyl, dioxido-thiomorpholinyl, or 8-oxa-3-azabicyclo[3.2.1]octanyl. In certain embodiments, $R^{5c}$ is hydrogen, dimethylamino, pyrrolidin-1-yl, piperazin-1-yl, 4-methyl-piperazin-1-yl, 4-(2-hydroxyethyl)-1-piperazinyl, 4-methylsulfonyl-1-piperazinyl, 4-morpholinyl, 1-oxido-thiomorpholin-4-yl, 1,1-dioxido-thiomorpholin-4-yl, or 8-oxa-3-azabicyclo[3.2.1]octan-3-yl. In certain embodiments, m is 1. In certain embodiments, m is 2.

In certain embodiments, $R^5$ is —$NR^{5m}R^{5n}$, where $R^{5m}$ and $R^{5n}$ are each as defined herein. In certain embodiments, $R^5$ is (dimethylamino)ethylamino. In certain embodiments, $R^5$ is methylamino, dimethylamino, 2-(dimethylamino)ethylamino.

In certain embodiments, $R^{5m}$ is hydrogen. In certain embodiments, $R^{5m}$ is $C_{1-6}$ alkyl, optionally substituted with one or more substituents $Q^1$. In certain embodiments, $R^{5m}$ is methyl or ethyl, optionally substituted with one or more substituents $Q^1$. In certain embodiments, $R^{5m}$ is dimethylaminoethyl. In certain embodiments, $R^{5m}$ is 2-dimethylaminoethyl. In certain embodiments, $R^{5m}$ is $C_{2-6}$ alkenyl, optionally substituted with one or more substituents $Q^1$. In certain embodiments, $R^{5m}$ is $C_{2-6}$ alkynyl, optionally substituted with one or more substituents $Q^1$. In certain embodiments, $R^{5m}$ is $C_{3-7}$ cycloalkyl, optionally substituted with one or more substituents $Q^1$. In certain embodiments, $R^{5m}$ is $C_{6-14}$ aryl, optionally substituted with one or more substituents $Q^1$. In certain embodiments, $R^{5m}$ is $C_{7-15}$ aralkyl, optionally substituted with one or more substituents $Q^1$. In certain embodiments, $R^{5m}$ is heteroaryl, optionally substituted with one or more substituents $Q^1$. In certain embodiments, $R^{5m}$ is heterocyclyl, optionally substituted with one or more substituents $Q^1$.

In certain embodiments, $R^{5m}$ is hydrogen. In certain embodiments, $R^{5m}$ is $C_{1-6}$ alkyl, optionally substituted with one or more substituents $Q^1$. In certain embodiments, $R^{5m}$ is methyl or ethyl, optionally substituted with one or more substituents $Q^1$. In certain embodiments, $R^{5m}$ is dimethylaminoethyl. In certain embodiments, $R^{5m}$ is 2-dimethylaminoethyl. In certain embodiments, $R^{5m}$ is $C_{2-6}$ alkenyl, optionally substituted with one or more substituents $Q^1$. In certain embodiments, $R^{5m}$ is $C_{2-6}$ alkynyl, optionally substituted with one or more substituents $Q^1$. In certain embodiments, $R^{5m}$ is $C_{3-7}$ cycloalkyl, optionally substituted with one or more substituents $Q^1$. In certain embodiments, $R^{5m}$ is $C_{6-14}$ aryl, optionally substituted with one or more substituents $Q^1$. In certain embodiments, $R^{5m}$ is $C_{7-15}$ aralkyl, optionally substituted with one or more substituents $Q^1$. In certain embodiments, $R^{5m}$ is heteroaryl, optionally substituted with one or more substituents $Q^1$. In certain embodiments, $R^{5m}$ is heterocyclyl, optionally substituted with one or more substituents $Q^1$.

In certain embodiments, $R^6$ is hydrogen. In certain embodiments, each $R^6$ is independently $C_{1-6}$ alkyl, optionally substituted with one or more substituents $Q^1$. In certain embodiments, each $R^6$ is independently $C_{1-6}$ alkyl, optionally substituted with one or more halo. In certain embodiments, each $R^6$ is independently $C_{1-6}$ alkyl, optionally substituted with one to three halo. In certain embodiments, each $R^6$ is independently methyl, fluoromethyl, difluoromethyl, or trifluoromethyl.

In certain embodiments, G is a bond. In certain embodiments, G is —$CH_2$—. In certain embodiments, G is —$CH_2CH_2$—.

In certain embodiments, J is a bond. In certain embodiments, J is —$CH_2$—. In certain embodiments, J is —$CH_2CH_2$—.

In certain embodiments, G and J are both bonds. In certain embodiments, G and J are both —$CH_2$—.

In certain embodiments, each Q is independently $C_{1-6}$ alkylene, $C_{2-6}$ alkenylene, or $C_{2-6}$ alkynylene, each optionally substituted with one or more substituents $Q^1$. In certain embodiments, Q is $C_{3-7}$ cycloalkylene, optionally substituted with one or more substituents $Q^1$. In certain embodiments, Q is $C_{6-14}$ arylene, optionally substituted with one or more substituents $Q^1$. In certain embodiments, Q is heteroarylene, optionally substituted with one or more substituents $Q^1$. In certain embodiments, Q is heterocyclylene, optionally substituted with one or more substituents $Q^1$. In certain embodiments, Q is cyclopropylene, cyclobutylene, cyclopentylene, cyclohexylene, phenylene, azetidinylene, pyrrolidinylene, piperidinylene, piperazinylene, pyrrolylene, thiazolylylene, pyrazolylene, or pyridylene.

In certain embodiments, $T^1$ is a bond. In certain embodiments, $T^1$ is $C_{1-6}$ alkylene, which is optionally substituted with one or more substituents as described herein. In certain embodiments, $T^1$ is methylene. In certain embodiments, $T^1$ is —O—. In certain embodiments, $T^1$ is —NR$^8$—, wherein R$^8$ is as defined herein. In certain embodiments, $T^1$ is —NH— or —N(CH$_3$)—. In certain embodiments, $R^8$ is $C_{1-6}$ alkyl, optionally substituted with one or more —NR$^b$R$^c$ or heterocyclyl, which is further optionally substituted with one or more substituents, wherein R$^b$ and R$^c$ are each as defined herein. In certain embodiments, $R^8$ is independently methyl, ethenyl, chloropropyl, dimethylaminomethyl, dimethylaminoethyl, dimethylaminopropyl, morpholinylmethyl, morpholinylethyl, morpholinylpropyl, (methylpiperazinyl)methyl, (methylpiperazinyl)ethyl, (methylpiperazinyl)propyl, (methylsulfonylpiperazinylmethyl, (methylsulfonylpiperazinyl)-ethyl, or (methylsulfonylpiperazinyl)propyl. In certain embodiments, $R^8$ is hydrogen, methyl, dimethylaminopropyl, morpholinyl-propyl, or methylsulfonyl-piperazinyl-propyl. In certain embodiments, $R^8$ is hydrogen, methyl, 3-dimethylaminopropyl, 3-(4-morpholinyl)propyl, or 3-(4-methylsulfonyl-piperazin-1-yl)propyl.

In certain embodiments, $R^8$ of $T^1$ is independently $C_{1-6}$ alkyl, optionally substituted with one or more substituents as described herein. In certain embodiments, $R^8$ of $T^1$ is independently —(CR$^{8a}$R$^{8b}$)$_n$—R$^{8a}$, where R$^{8a}$ and R$^{8b}$ are each independently (a) hydrogen, cyano, halo, or nitro; or (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; each optionally substituted with one or more substituents $Q^1$; $R^{8c}$ is hydrogen, —NR$^{8d}$R$^{8e}$, or heterocyclyl; R$^{8d}$ and R$^{8e}$ are each independently hydrogen or $C_{1-6}$ alkyl; and n is an integer of 0, 1, 2, or 3; and where each alkyl and heterocyclyl is independently, optionally substituted with one or more substituents as described herein. In certain embodiments, $R^{8a}$ is hydrogen. In certain embodiments, $R^{8b}$ is hydrogen. In certain embodiments, $R^{8a}$ and $R^{8b}$ are hydrogen. In certain embodiments, $R^{8c}$ is hydrogen. In certain embodiments, $R^{8c}$ is —NR$^{8d}$R$^{8e}$, where R$^{8d}$ and R$^{8e}$ are each independently hydrogen or $C_{1-6}$ alkyl, optionally substituted with one or more substituents as described herein. In certain embodiments, $R^{8d}$ is hydrogen or methyl. In certain embodiments, $R^{8e}$ is hydrogen or methyl. In certain embodiments, $R^{8c}$ is amino, methylamino, or dimethylamino. In certain embodiments, $R^{8c}$ is heterocyclyl, optionally substituted with one or more substituents as described herein. In certain embodiments, $R^{8c}$ is pyrrolidinyl, piperidinyl, piperazinyl, or morpholinyl, each optionally substituted with one or more substituents as described herein. In certain embodiments, $R^{8c}$ is pyrrolidinyl, piperidinyl, piperazinyl, or morpholinyl, each optionally substituted with one or more substituents, wherein each substituent is independently methyl or methylsulfonyl. In certain embodiments, $R^{8c}$ is hydrogen, dimethylamino, piperazinyl, methylsulfonyl-piperazinyl, or morpholinyl. In certain embodiments, $R^{8c}$ is hydrogen, dimethylamino, piperazin-1-yl, 4-methylsulfonyl-4-piperazinyl, or 4-morpholinyl. In certain embodiments, n is 1. In certain embodiments, n is 2. In certain embodiments, n is 3.

In certain embodiments, each Q is $C_{1-6}$ alkylene, $C_{2-6}$ alkenylene, $C_{2-6}$ alkynylene, $C_{3-7}$ cycloalkylene, $C_{6-14}$ arylene, heteroarylene, or heterocyclylene, each of which is optionally substituted with one or more substituents as described herein. In certain embodiments, Q is $C_{1-6}$ alkylene, which is optionally substituted with one or more substituents as described herein. In certain embodiments, Q is $C_{2-6}$ alkenylene, which is optionally substituted with one or more substituents as described herein. In certain embodiments, Q is $C_{2-6}$ alkynylene, which is optionally substituted with one or more substituents as described herein. In certain embodiments, Q is $C_{3-7}$ cycloalkylene, which is optionally substituted with one or more substituents as described herein. In certain embodiments, Q is cyclohexylene, which is optionally substituted with one or more substituents as described herein. In certain embodiments, Q is cis- or trans-cyclohexylene, which is optionally substituted with one or more substituents as described herein. In certain embodiments, Q is 1,4-cyclohexylene, which is optionally substituted with one or more substituents as described herein. In certain embodiments, Q is cis- or trans-1,4-cyclohexylene, which is optionally substituted with one or more substituents as described herein. In certain embodiments, Q is $C_{6-14}$ arylene, which is optionally substituted with one or more substituents as described herein. In certain embodiments, Q is phenylene, which is optionally substituted with one or more substituents as described herein. In certain embodiments, Q is 1,4-phenylene, which is optionally substituted with one or more substituents as described herein. In certain embodiments, Q is heteroarylene, which is optionally substituted with one or more substituents as described herein. In certain embodiments, Q is pyridinylene, which is optionally substituted with one or more substituents as described herein. In certain embodiments, Q is 1,3-pyridinylene, which is optionally substituted with one or more substituents as described herein. In certain embodiments, Q is heterocyclylene, which is optionally substituted with one or more substituents as described herein. In certain embodiments, Q is azetidinylene, pyrrolidinylene, piperidinylene, or piperazinylene, each of which is optionally substituted with one or more substituents as described herein. In certain embodiments, Q is azetidinylene, pyrrolidinylene, piperidinylene, or piperazinylene. In certain embodiments, Q is 1,3-azetidinylene, 1,3-pyrrolidinylene, 1,3-piperidinylene, 1,4-piperidinylene, or 1,4-piperazinylene, each of which is optionally substituted with one or more substituents as described herein. In certain embodiments, Q is 1,3-piperidinylene, 1,4-piperidinylene, or 1,4-piperazinylene.

In certain embodiments, $T^2$ is a bond. In certain embodiments, $T^2$ is $C_{1-6}$ alkylene, which is optionally substituted with one or more substituents as described herein. In certain embodiments, $T^2$ is methylene. In certain embodiments, $T^2$ is —NR$^8$—, wherein R$^8$ is as defined herein. In certain embodiments, $T^2$ is —NH— or —N(CH$_3$)—. In certain embodiments, $R^8$ is $C_{1-6}$ alkyl, optionally substituted with one or more —NR$^b$R$^c$ or heterocyclyl, which is further optionally substituted with one or more substituents, wherein R$^b$ and R$^c$ are each as defined herein. In certain embodiments, $R^8$ is independently methyl, ethenyl, chloropropyl, dimethylaminomethyl, dimethylaminoethyl, dimethylaminopropyl, morpholinylmethyl, morpholinylethyl, morpholinylpropyl, (methylpiperazinyl)methyl, (methylpiperazinyl)ethyl, (methylpiperazinyl)propyl, (methylsulfonylpiperazinylmethyl, (methylsulfonylpiperazinyl)-ethyl, or (methylsulfonylpiperazinyl)propyl. In certain embodiments, $R^8$ is hydrogen, methyl, dimethylaminopropyl, morpholinyl-propyl, or methylsulfonyl-piperazinyl-propyl. In certain embodiments, $R^8$ is hydrogen, methyl, 3-dimethylaminopropyl, 3-(4-morpholinyl)propyl, or 3-(4-methylsulfonyl-piperazin-1-yl)propyl.

In certain embodiments, $R^8$ of $T^2$ is independently $C_{1-6}$ alkyl, optionally substituted with one or more substituents as described herein. In certain embodiments, $R^8$ of $T^2$ is independently —(CR$^{8a}$R$^{8b}$)$_n$—R$^{8b}$, where R$^{8a}$ and R$^{8b}$ are each independently (a) hydrogen, cyano, halo, or nitro; or (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; each optionally substituted with one or more substituents $Q^1$; $R^{8c}$ is hydrogen, —$NR^{8d}R^{8e}$, or heterocyclyl; $R^{8d}$ and $R^{8e}$ are each independently hydrogen or $C_{1-6}$ alkyl; and n is an integer of 0, 1, 2, or 3; and where each alkyl and heterocyclyl is independently, optionally substituted with one or more substituents as described herein. In certain embodiments, $R^{8a}$ is hydrogen. In certain embodiments, $R^{8b}$ is hydrogen. In certain embodiments, $R^{8a}$ and $R^{8b}$ are hydrogen. In certain embodiments, $R^{8c}$ is hydrogen. In certain embodiments, $R^{8c}$ is —$NR^{8d}R^{8e}$, where $R^{8d}$ and $R^{8e}$ are each independently hydrogen or $C_{1-6}$ alkyl, optionally substituted with one or more substituents as described herein. In certain embodiments, $R^{8d}$ is hydrogen or methyl. In certain embodiments, $R^{8e}$ is hydrogen or methyl. In certain embodiments, $R^{8c}$ is amino, methylamino, or dimethylamino. In certain embodiments, $R^{8c}$ is heterocyclyl, optionally substituted with one or more substituents as described herein. In certain embodiments, $R^{8c}$ is pyrrolidinyl, piperidinyl, piperazinyl, or morpholinyl, each optionally substituted with one or more substituents as described herein. In certain embodiments, $R^{8c}$ is pyrrolidinyl, piperidinyl, piperazinyl, or morpholinyl, each optionally substituted with one or more substituents, wherein each substituent is independently methyl or methylsulfonyl. In certain embodiments, $R^{8c}$ is hydrogen, dimethylamino, piperazinyl, methylsulfonyl-piperazinyl, or morpholinyl. In certain embodiments, $R^{8c}$ is hydrogen, dimethylamino, piperazin-1-yl, 4-methylsulfonyl-4-piperazinyl, or 4-morpholinyl. In certain embodiments, n is 1. In certain embodiments, n is 2. In certain embodiments, n is 3.

In certain embodiments, U is N. In certain embodiments, U is CH.

In certain embodiments, X is nitrogen or $CR^9$, wherein $R^9$ is as defined herein. In certain embodiments, X is nitrogen or CH. In certain embodiments, Y is nitrogen or $CR^9$, wherein $R^9$ is as defined herein. In certain embodiments, Y is nitrogen or CH. In certain embodiments, Z is nitrogen or $CR^9$, wherein $R^9$ is as defined herein. In certain embodiments, Z is nitrogen or CH.

In certain embodiments, X, Y, and Z are nitrogen. In certain embodiments, X and Y are nitrogen, and Z is CH. In certain embodiments, X and Z are nitrogen, and Y is CH. In certain embodiments, Y and Z are nitrogen, and X is CH.

In certain embodiments, each A is independently a bond. In certain embodiments, each A is independently C, N, O, or S. In certain embodiments, each A is independently a nitrogen, oxygen, or sulfur atom. In certain embodiments, each A is independently $NR^7$, where $R^7$ is as defined herein. In certain embodiments, each A is independently NH. In certain embodiments, each A is independently C(O). In certain embodiments, each A is independently $CR^7$, where $R^7$ is as defined herein. In certain embodiments, each A is independently $CR^7$, where $R^7$ is hydrogen, halo, or $C_{1-6}$ alkyl. In certain embodiments, each A is independently CH. In certain embodiments, each A is independently $CR^7R^{7'}$, where $R^7$ and $R^{7'}$ are each as defined herein. In certain embodiments, each A is independently $CH_2$.

In certain embodiments, each B is independently a bond. In certain embodiments, each B is independently C, N, O, or S. In certain embodiments, each B is independently a nitrogen, oxygen, or sulfur atom. In certain embodiments, each B is independently $NR^7$, where $R^7$ is as defined herein. In certain embodiments, each B is independently NH. In certain embodiments, each B is independently C(O). In certain embodiments, each B is independently $CR^7$, where $R^7$ is as defined herein. In certain embodiments, each B is independently $CR^7$, where $R^7$ is hydrogen, halo, or $C_{1-6}$ alkyl. In certain embodiments, each B is independently CH. In certain embodiments, each B is independently $CR^7R^{7'}$, where $R^7$ and $R^{7'}$ are each as defined herein. In certain embodiments, each B is independently $CH_2$.

In certain embodiments, each D is independently a bond. In certain embodiments, each D is independently C, N, O, or S. In certain embodiments, each D is independently a nitrogen, oxygen, or sulfur atom. In certain embodiments, each D is independently $NR^7$, where $R^7$ is as defined herein. In certain embodiments, each D is independently NH. In certain embodiments, each D is independently C(O). In certain embodiments, each D is independently $CR^7$, where $R^7$ is as defined herein. In certain embodiments, each D is independently $CR^7$, where $R^7$ is hydrogen, halo, or $C_{1-6}$ alkyl. In certain embodiments, each D is independently CH. In certain embodiments, each D is independently $CR^7R^{7'}$, where $R^7$ and $R^{7'}$ are each as defined herein. In certain embodiments, each D is independently $CH_2$.

In certain embodiments, each E is independently a bond. In certain embodiments, each E is independently C, N, O, or S. In certain embodiments, each E is independently a nitrogen, oxygen, or sulfur atom. In certain embodiments, each E is independently $NR^7$, where $R^7$ is as defined herein. In certain embodiments, each E is independently NH. In certain embodiments, each E is independently C(O). In certain embodiments, each E is independently $CR^7$, where $R^7$ is as defined herein. In certain embodiments, each E is independently $CR^7$, where $R^7$ is hydrogen, halo, or $C_{1-6}$ alkyl. In certain embodiments, each E is independently CH. In certain embodiments, each E is independently $CR^7R^{7'}$, where $R^7$ and $R^{7'}$ are each as defined herein. In certain embodiments, each E is independently $CH_2$.

In one embodiment, provided herein is a compound selected from:

2-(difluoromethyl)-1-[4-[4-(methylsulfonyl)-1-piperazinyl]-6-(4-morpholinyl)-1,3,5-triazin-2-yl]-1H-benzimidazole;

2-(difluoromethyl)-4-methoxy-1-[4-[4-(methylsulfonyl)-1-piperazinyl]-6-(4-morpholinyl)-1,3,5-triazin-2-yl]-1H-benzimidazole;

2-(difluoromethyl)-4-methoxy-1-{4-(4-morpholinyl)-6-[4-(vinylsulfonyl)-1-piperazinyl]-1,3,5-triazin-2-yl}-1H-benzimidazole;

1-[4-{4-[(3-chloropropyl)sulfonyl]-1-piperazinyl}-6-(4-morpholinyl)-1,3,5-triazin-2-yl]-2-(difluoromethyl)-4-methoxy-1H-benzimidazole;

({4-[4-[2-(difluoromethyl)-4-methoxy-1H-benzimidazol-1-yl]-6-(4-morpholinyl)-1,3,5-triazin-2-yl]-1-piperazinyl}sulfonyl)-N,N-dimethylmethylamine;

N-[2-({4-[4-[2-(difluoromethyl)-4-methoxy-1H-benzimidazol-1-yl]-6-(4-morpholinyl)-1,3,5-triazin-2-yl]-1-piperazinyl}sulfonyl)ethyl]-N,N-dimethylamine;

N-[3-({4-[4-[2-(difluoromethyl)-4-methoxy-1H-benzimidazol-1-yl]-6-(4-morpholinyl)-1,3,5-triazin-2-yl]-1-piperazinyl}sulfonyl)propyl]-N,N-dimethylamine;

2-(difluoromethyl)-4-methoxy-1-(4-(4-morpholinyl)-6-{4-[(4-morpholinylmethyl)sulfonyl]-1-piperazinyl}-1,3,5-triazin-2-yl)-1H-benzimidazole;

2-(difluoromethyl)-4-methoxy-1-[4-(4-morpholinyl)-6-(4-{[2-(4-morpholinyl)ethyl]sulfonyl}-1-piperazinyl)-1,3,5-triazin-2-yl]-1H-benzimidazole;

2-(difluoromethyl)-4-methoxy-1-[4-(4-morpholinyl)-6-(4-{[3-(4-morpholinyl)propyl]sulfonyl}-1-piperazinyl)-1,3,5-triazin-2-yl]-1H-benzimidazole;

2-(difluoromethyl)-4-methoxy-1-[4-(4-{[(4-methyl-1-piperazinyl)methyl]sulfonyl}-1-piperazinyl)-6-(4-morpholinyl)-1,3,5-triazin-2-yl]-1H-benzimidazole;
2-(difluoromethyl)-4-methoxy-1-[4-(4-{[2-(4-methyl-1-piperazinyl)ethyl]sulfonyl}-1-piperazinyl)-6-(4-morpholinyl)-1,3,5-triazin-2-yl]-1H-benzimidazole;
2-(difluoromethyl)-4-methoxy-1-[4-(4-{[3-(4-methyl-1-piperazinyl)propyl]sulfonyl}-1-piperazinyl)-6-(4-morpholinyl)-1,3,5-triazin-2-yl]-1H-benzimidazole;
2-(difluoromethyl)-4-methoxy-1-[4-[4-({[4-(methylsulfonyl)-1-piperazinyl]methyl}sulfonyl)-1-piperazinyl]-6-(4-morpholinyl)-1,3,5-triazin-2-yl]-1H-benzimidazole;
2-(difluoromethyl)-4-methoxy-1-[4-[4-({2-[4-(methylsulfonyl)-1-piperazinyl]ethyl}sulfonyl)-1-piperazinyl]-6-(4-morpholinyl)-1,3,5-triazin-2-yl]-1H-benzimidazole;
2-(difluoromethyl)-4-methoxy-1-[4-[4-({3-[4-(methylsulfonyl)-1-piperazinyl]propyl}sulfonyl)-1-piperazinyl]-6-(4-morpholinyl)-1,3,5-triazin-2-yl]-1H-benzimidazole;
N-{1-[4-[2-(difluoromethyl)-4-methoxy-1H-benzimidazol-1-yl]-6-(4-morpholinyl)-1,3,5-triazin-2-yl]-4-piperidinyl}methanesulfonamide;
N-{1-[4-[2-(difluoromethyl)-4-methoxy-1H-benzimidazol-1-yl]-6-(4-morpholinyl)-1,3,5-triazin-2-yl]-4-piperidinyl}-N-methylmethanesulfonamide;
N-[4-[2-(difluoromethyl)-4-methoxy-1H-benzimidazol-1-yl]-6-(4-morpholinyl)-1,3,5-triazin-2-yl]-N-[1-(methylsulfonyl)-4-piperidinyl]amine;
N-[4-[2-(difluoromethyl)-4-methoxy-1H-benzimidazol-1-yl]-6-(4-morpholinyl)-1,3,5-triazin-2-yl]-N-methyl-N-[1-(methylsulfonyl)-4-piperidinyl]amine;
2-(difluoromethyl)-4-methoxy-1-[4-[4-(methylsulfonyl)-1-piperazinyl]-6-(4-morpholinyl)-1,3,5-triazin-2-yl]-1H-benzimidazol-6-ylamine;
2-(difluoromethyl)-4-methoxy-1-[4-[1-(methylsulfonyl)-4-piperidinyl]-6-(4-morpholinyl)-1,3,5-triazin-2-yl]-1H-benzimidazole;
N-[2-({4-[4-[2-(difluoromethyl)-4-methoxy-1H-benzimidazol-1-yl]-6-(4-morpholinyl)-1,3,5-triazin-2-yl]-1-piperidinyl}sulfonyl)ethyl]-N,N-dimethylamine;
2-(difluoromethyl)-4-methoxy-1-[4-[1-(methylsulfonyl)-3-piperidinyl]-6-(4-morpholinyl)-1,3,5-triazin-2-yl]-1H-benzimidazole;
2-(difluoromethyl)-4-methoxyl-[4-{[1-(methylsulfonyl)-4-piperidinyl]oxy}-6-(4-morpholinyl)-1,3,5-triazin-2-yl]-1H-benzimidazole;
N$^1$-[4-[2-(difluoromethyl)-4-methoxy-1H-benzimidazol-1-yl]-6-(4-morpholinyl)-1,3,5-triazin-2-yl]-N$^3$,N$^3$-dimethyl-N$^1$-[1-(methylsulfonyl)-3-piperidinyl]-1,3-propanediamine;
4-[2-(difluoromethyl)-4-methoxy-1H-benzimidazol-1-yl]-N-[1-(methylsulfonyl)-3-piperidinyl]-6-(4-morpholinyl)-N-[3-(4-morpholinyl)propyl]-1,3,5-triazin-2-amine;
N$^1$-[4-[2-(difluoromethyl)-4-methoxy-1H-benzimidazol-1-yl]-6-(4-morpholinyl)-1,3,5-triazin-2-yl]-N$^3$,N$^3$-dimethyl-N$^1$-[1-(methylsulfonyl)-4-piperidinyl]-1,3-propanediamine;
4-[2-(difluoromethyl)-4-methoxy-1H-benzimidazol-1-yl]-N-[1-(methylsulfonyl)-4-piperidinyl]-6-(4-morpholinyl)-N-[3-(4-morpholinyl)propyl]-1,3,5-triazin-2-amine;
4-[2-(difluoromethyl)-4-methoxy-1H-benzimidazol-1-yl]-N-{3-[4-(methylsulfonyl)-1-piperazinyl]propyl}-N-[1-(methylsulfonyl)-4-piperidinyl]-6-(4-morpholinyl)-1,3,5-triazin-2-amine;
N-{(3S)-1-[4-[2-(difluoromethyl)-4-methoxy-1H-benzimidazol-1-yl]-6-(4-morpholinyl)-1,3,5-triazin-2-yl]piperidinyl}-N-[3-(dimethylamino)propyl]methanesulfonamide;
N-[2-({4-[4-[2-(difluoromethyl)-4-methoxy-1H-benzimidazol-1-yl]-6-(4-morpholinyl)-1,3,5-triazin-2-yl]-1-piperazinyl}sulfonyl)ethyl]-N,N-diethylamine;
2-(difluoromethyl)-4-methoxy-1-[4-(4-morpholinyl)-6-(4-{[2-(1-piperidinyl)ethyl]sulfonyl}-1-piperazinyl)-1,3,5-triazin-2-yl]-1H-benzimidazole;
2-{4-[2-({4-[4-[2-(difluoromethyl)-4-methoxy-1H-benzimidazol-1-yl]-6-(4-morpholinyl)-1,3,5-triazin-2-yl]-1-piperazinyl}sulfonyl)ethyl]-1-piperazinyl}ethanol;
2-(difluoromethyl)-1-[4-(4-{[2-(1H-imidazol-1-yl)ethyl]sulfonyl}-1-piperazinyl)-6-(4-morpholinyl)-1,3,5-triazin-2-yl]-4-methoxy-1H-benzimidazole;
2-(difluoromethyl)-4-methoxy-1-[4-(4-morpholinyl)-6-(4-{[2-(2-pyridinyl)ethyl]sulfonyl}-1-piperazinyl)-1,3,5-triazin-2-yl]-1H-benzimidazole;
2-(difluoromethyl)-4-methoxy-1-[4-(4-morpholinyl)-6-(4-{[2-(4-pyridinyl)ethyl]sulfonyl}-1-piperazinyl)-1,3,5-triazin-2-yl]-1H-benzimidazole;
2-(difluoromethyl)-4-methoxy-1-{4-(4-morpholinyl)-6-[4-(3-pyridinylsulfonyl)-1-piperazinyl]-1,3,5-triazin-2-yl}-1H-benzimidazole;
N-{1-[4-[2-(difluoromethyl)-4-methoxy-1H-benzimidazol-1-yl]-6-(4-morpholinyl)-1,3,5-triazin-2-yl]-4-piperidinyl}-2-(dimethylamino)ethanesulfonamide;
N-{1-[4-[2-(difluoromethyl)-4-methoxy-1H-benzimidazol-1-yl]-6-(4-morpholinyl)-1,3,5-triazin-2-yl]-4-piperidinyl}-2-(dimethylamino)-N-methylethanesulfonamide;
N-{4-[4-[2-(difluoromethyl)-4-methoxy-1H-benzimidazol-1-yl]-6-(4-morpholinyl)-1,3,5-triazin-2-yl]phenyl}-2-(dimethylamino)ethanesulfonamide;
N-{4-[4-[2-(difluoromethyl)-4-methoxy-1H-benzimidazol-1-yl]-6-(4-morpholinyl)-1,3,5-triazin-2-yl]phenyl}-2-(dimethylamino)-N-methylethanesulfonamide;
N-{1-[4-[2-(difluoromethyl)-4-methoxy-1H-benzimidazol-1-yl]-6-(4-morpholinyl)-1,3,5-triazin-2-yl]-3-azetidinyl}-2-(dimethylamino)ethanesulfonamide;
N-{1-[4-[2-(difluoromethyl)-4-methoxy-1H-benzimidazol-1-yl]-6-(4-morpholinyl)-1,3,5-triazin-2-yl]-3-azetidinyl}-2-(dimethylamino)-N-methylethanesulfonamide;
trans-N-(4-{[4-[2-(difluoromethyl)-4-methoxy-1H-benzimidazol-1-yl]-6-(4-morpholinyl)-1,3,5-triazin-2-yl]amino}cyclohexyl)methanesulfonamide;
cis-N-(4-{[4-[2-(difluoromethyl)-4-methoxy-1H-benzimidazol-1-yl]-6-(4-morpholinyl)-1,3,5-triazin-2-yl]amino}cyclohexyl)methanesulfonamide;
N-({1-[4-[2-(difluoromethyl)-4-methoxy-1H-benzimidazol-1-yl]-6-(4-morpholinyl)-1,3,5-triazin-2-yl]-4-piperidinyl}methyl)methanesulfonamide;
N-({1-[4-[2-(difluoromethyl)-4-methoxy-1H-benzimidazol-1-yl]-6-(4-morpholinyl)-1,3,5-triazin-2-yl]-3-piperidinyl}methyl)methanesulfonamide;
4-[2-(difluoromethyl)-4-methoxy-1H-benzimidazol-1-yl]-N-{[1-(methylsulfonyl)-4-piperidinyl]methyl}-6-(4-morpholinyl)-1,3,5-triazin-2-amine;
N-[2-({4-[4-[2-(difluoromethyl)-1H-benzimidazol-1-yl]-6-(4-morpholinyl)-1,3,5-triazin-2-yl]-1-piperazinyl}sulfonyl)ethyl]-N,N-dimethylamine;
N-[2-({4-[4-[6-amino-2-(difluoromethyl)-4-methoxy-1H-benzimidazol-1-yl]-6-(4-morpholinyl)-1,3,5-triazin-2-yl]-1-piperazinyl}sulfonyl)ethyl]-N,N-dimethylamine;
2-(difluoromethyl)-4-methoxy-1-{4-[4-(methylsulfonyl)-1-piperazinyl]-6-tetrahydro-2H-pyran-4-yl-1,3,5-triazin-2-yl}-1H-benzimidazole;
2-(difluoromethyl)-4-methoxy-1-(4-(4-morpholinyl)-6-{4-[(trifluoromethyl)-sulfonyl]-1-piperazinyl}-1,3,5-triazin-2-yl)-1H-benzimidazole;

N-{1-[4-[2-(difluoromethyl)-4-methoxy-1H-benzimidazol-1-yl]-6-(4-morpholinyl)-1,3,5-triazin-2-yl]-4-piperidinyl}trifluoromethanesulfonamide;

N-{1-[4-[2-(difluoromethyl)-4-methoxy-1H-benzimidazol-1-yl]-6-(4-morpholinyl)-1,3,5-triazin-2-yl]-3-azetidinyl}(trifluoro)methanesulfonamide;

4-4-[2-(difluoromethyl)-4-methoxy-1H-benzimidazol-1-yl]-6-(4-morpholinyl)-1,3,5-triazin-2-yl]-N,N-dimethyl-1-piperazinesulfonamide;

1-[4-[2-(difluoromethyl)-4-methoxy-1H-benzimidazol-1-yl]-6-(4-morpholinyl)-1,3,5-triazin-2-yl]-N,N-dimethyl-4-piperidinesulfonamide;

1-[4-[2-(difluoromethyl)-4-methoxy-1H-benzimidazol-1-yl]-6-(4-morpholinyl)-1,3,5-triazin-2-yl]-N-methyl-4-piperidinesulfonamide;

1-[4-[2-(difluoromethyl)-4-methoxy-1H-benzimidazol-1-yl]-6-(4-morpholinyl)-1,3,5-triazin-2-yl]-N-[2-(dimethylamino)ethyl]-4-piperidinesulfonamide;

1-[4-[2-(difluoromethyl)-4-methoxy-1H-benzimidazol-1-yl]-6-(4-morpholinyl)-1,3,5-triazin-2-yl]-N-methyl-3-pyrrolidinesulfonamide;

1-[4-[2-(difluoromethyl)-4-methoxy-1H-benzimidazol-1-yl]-6-(4-morpholinyl)-1,3,5-triazin-2-yl]-N-[2-(dimethylamino)ethyl]-3-pyrrolidinesulfonamide;

2-(difluoromethyl)-4-methoxy-1-[4-{4-[(4-methyl-1-piperazinyl) sulfonyl]phenyl}-6-(4-morpholinyl)-1,3,5-triazin-2-yl]-1H-benzimidazole;

N-(5-{[4-[2-(difluoromethyl)-4-methoxy-1H-benzimidazol-1-yl]-6-(4-morpholinyl)-1,3,5-triazin-2-yl]amino}-2-pyridinyl)methanesulfonamide; and N-(5-{[4-[2-(difluoromethyl)-4-methoxy-1H-benzimidazol-1-yl]-6-(4-morpholinyl)-1,3,5-triazin-2-yl]amino}-2-pyridinyl)-N-methylmethanesulfonamide;

and enantiomers, mixtures of enantiomers, or mixtures of two or more diastereomers thereof; and pharmaceutically acceptable salts, solvates, hydrates, and prodrugs thereof.

In another embodiment, provided herein is a compound selected from:

4-[2-(difluoromethyl)-4-methoxy-1H-benzimidazol-1-yl]-N-[1-(methylsulfonyl)-4-piperidinyl]-6-(4-morpholinyl)-1,3,5-triazin-2-amine;

3-{4-[2-(difluoromethyl)-4-methoxy-1H-benzimidazol-1-yl]-6-[4-(methylsulfonyl)-1-piperazinyl]-1,3,5-triazin-2-yl}-8-oxa-3-azabicyclo[3.2.1]octane;

2-(difluoromethyl)-4-methoxy-1-[4-[4-(methylsulfonyl)-1-piperazinyl]-6-(4-morpholinyl)-2-pyrimidinyl]-1H-benzimidazole;

4-[2-(difluoromethyl)-4-methoxy-1H-benzimidazol-1-yl]-N-[1-(methylsulfonyl)-3-azetidinyl]-6-(4-morpholinyl)-1,3,5-triazin-2-amine;

4-[2-(difluoromethyl)-4-methoxy-1H-benzimidazol-1-yl]-N-methyl-N-[1-(methylsulfonyl)-3-azetidinyl]-6-(4-morpholinyl)-1,3,5-triazin-2-amine;

N-{1-[4-[2-(difluoromethyl)-4-methoxy-1H-benzimidazol-1-yl]-6-(4-morpholinyl)-1,3,5-triazin-2-yl]-3-azetidinyl}methanesulfonamide;

N-{1-[4-[2-(difluoromethyl)-4-methoxy-1H-benzimidazol-1-yl]-6-(4-morpholinyl)-1,3,5-triazin-2-yl]-3-azetidinyl}-N-methylmethanesulfonamide;

4-[2-(difluoromethyl)-4-methoxy-1H-benzimidazol-1-yl]-N-[(3R)-1-(methylsulfonyl)pyrrolidinyl]-6-(4-morpholinyl)-1,3,5-triazin-2-amine;

4-[2-(difluoromethyl)-4-methoxy-1H-benzimidazol-1-yl]-N-methyl-N-[(3R)-1-(methylsulfonyl)pyrrolidinyl]-6-(4-morpholinyl)-1,3,5-triazin-2-amine;

4-[2-(difluoromethyl)-4-methoxy-1H-benzimidazol-1-yl]-N-[(3S)-1-(methylsulfonyl)pyrrolidinyl]-6-(4-morpholinyl)-1,3,5-triazin-2-amine;

4-[2-(difluoromethyl)-4-methoxy-1H-benzimidazol-1-yl]-N-methyl-N-[(3S)-1-(methylsulfonyl)pyrrolidinyl]-6-(4-morpholinyl)-1,3,5-triazin-2-amine;

N-{(3R)-1-[4-[2-(difluoromethyl)-4-methoxy-1H-benzimidazol-1-yl]-6-(4-morpholinyl)-1,3,5-triazin-2-yl]pyrrolidinyl}methanesulfonamide;

N-{(3R)-1-[4-[2-(difluoromethyl)-4-methoxy-1H-benzimidazol-1-yl]-6-(4-morpholinyl)-1,3,5-triazin-2-yl]pyrrolidinyl}-N-methylmethanesulfonamide;

N-{(3S)-1-[4-[2-(difluoromethyl)-4-methoxy-1H-benzimidazol-1-yl]-6-(4-morpholinyl)-1,3,5-triazin-2-yl]pyrrolidinyl}methanesulfonamide;

N-{(3S)-1-[4-[2-(difluoromethyl)-4-methoxy-1H-benzimidazol-1-yl]-6-(4-morpholinyl)-1,3,5-triazin-2-yl]pyrrolidinyl}-N-methylmethanesulfonamide;

4-[2-(difluoromethyl)-4-methoxy-1H-benzimidazol-1-yl]-N-[(3R)-1-(methylsulfonyl)piperidinyl]-6-(4-morpholinyl)-1,3,5-triazin-2-amine;

4-[2-(difluoromethyl)-4-methoxy-1H-benzimidazol-1-yl]-N-methyl-N-[(3R)-1-(methylsulfonyl)piperidinyl]-6-(4-morpholinyl)-1,3,5-triazin-2-amine;

4-[2-(difluoromethyl)-4-methoxy-1H-benzimidazol-1-yl]-N-[(3S)-1-(methylsulfonyl)piperidinyl]-6-(4-morpholinyl)-1,3,5-triazin-2-amine;

4-[2-(difluoromethyl)-4-methoxy-1H-benzimidazol-1-yl]-N-methyl-N-[(3S)-1-(methylsulfonyl)piperidinyl]-6-(4-morpholinyl)-1,3,5-triazin-2-amine;

N-{(3R)-1-[4-[2-(difluoromethyl)-4-methoxy-1H-benzimidazol-1-yl]-6-(4-morpholinyl)-1,3,5-triazin-2-yl]piperidinyl}methanesulfonamide;

N-{(3R)-1-[4-[2-(difluoromethyl)-4-methoxy-1H-benzimidazol-1-yl]-6-(4-morpholinyl)-1,3,5-triazin-2-yl]piperidinyl}-N-methylmethanesulfonamide;

N-{(3S)-1-[4-[2-(difluoromethyl)-4-methoxy-1H-benzimidazol-1-yl]-6-(4-morpholinyl)-1,3,5-triazin-2-yl]piperidinyl}methanesulfonamide;

N-{(3S)-1-[4-[2-(difluoromethyl)-4-methoxy-1H-benzimidazol-1-yl]-6-(4-morpholinyl)-1,3,5-triazin-2-yl]piperidinyl}-N-methylmethanesulfonamide;

2-(difluoromethyl)-4-methoxy-1-[4-(4-morpholinyl)-6-(4-{[2-(1-oxido-4-thiomorpholinyl)ethyl]sulfonyl}-1-piperazinyl)-1,3,5-triazin-2-yl]-1H-benzimidazole;

2-(difluoromethyl)-1-[4-(4-{[2-(1,1-dioxido-4-thiomorpholinyl)ethyl]sulfonyl}-1-piperazinyl)-6-(4-morpholinyl)-1,3,5-triazin-2-yl]-4-methoxy-1H-benzimidazole;

N-{2-[(4-{[4-[2-(difluoromethyl)-4-methoxy-1H-benzimidazol-1-yl]-6-(4-morpholinyl)-1,3,5-triazin-2-yl]oxy}-1-piperidinyl)sulfonyl]ethyl}-N,N-dimethylamine;

2-(difluoromethyl)-4-methoxy-1-{4-(4-morpholinyl)-6-[(1-{[2-(4-morpholinyl)ethyl]sulfonyl}-4-piperidinyl)oxy]—1,3,5-triazin-2-yl}-1H-benzimidazole;

2-(difluoromethyl)-4-methoxy-1-[4-{[1-({2-[4-(methylsulfonyl)-1-piperazinyl]ethyl}sulfonyl)-4-piperidinyl]oxy}-6-(4-morpholinyl)-1,3,5-triazin-2-yl]-1H-benzimidazole;

N-{1-[4-[2-(difluoromethyl)-4-methoxy-1H-benzimidazol-1-yl]-6-(4-morpholinyl)-1,3,5-triazin-2-yl]-4-piperidinyl}-N-[3-(dimethylamino)propyl]-methanesulfonamide;

N-{1-[4-[2-(difluoromethyl)-4-methoxy-1H-benzimidazol-1-yl]-6-(4-morpholinyl)-1,3,5-triazin-2-yl]-4-piperidinyl}-N-[3-(4-morpholinyl)propyl]-methanesulfonamide;

2-(difluoromethyl)-4-methoxy-1-[4-(4-morpholinyl)-6-(4-{[2-(1-pyrrolidinyl)ethyl]sulfonyl}-1-piperazinyl)-1,3,5-triazin-2-yl]-1H-benzimidazole; and 3-[2-({4-[4-[2-(Difluoromethyl)-4-methoxy-1H-benzimidazol-1-yl]-6-(4-morpholinyl)-1,3,5-triazin-2-yl]-1-piperazinyl}sulfonyl)ethyl]-8-oxa-3-azabicyclo[3.2.1]octane;

and enantiomers, mixtures of enantiomers, or mixtures of two or more diastereomers thereof; and pharmaceutically acceptable salts, solvates, hydrates, and prodrugs thereof.

In yet another embodiment, provided herein is a compound selected from:

2-(difluoromethyl)-1-[4-(4-morpholinyl)-6-(1-piperazinyl)-1,3,5-triazin-2-yl]-1H-benzimidazole;

2-(difluoromethyl)-4-methoxy-1-[4-(4-morpholinyl)-6-(1-piperazinyl)-1,3,5-triazin-2-yl]-1H-benzimidazole;

2-(difluoromethyl)-4-methoxy-1-{4-(4-morpholinyl)-6-[4-(vinylsulfonyl)-1-piperazinyl]-1,3,5-triazin-2-yl}-1H-benzimidazole;

N-[3-({2-(difluoromethyl)-1-[4-[4-(methylsulfonyl)-1-piperazinyl]-6-(4-morpholinyl)-1,3,5-triazin-2-yl]-1H-benzimidazol-4-yl}oxy)propyl]-N,N-dimethylamine;

4-[2-(difluoromethyl)-4-methoxy-1H-benzimidazol-1-yl]-N-methyl-N-[1-(methylsulfonyl)-4-piperidinyl]-6-(4-morpholinyl)-1,3,5-triazin-2-amine;

2-[2-(difluoromethyl)-4-methoxy-1H-benzimidazol-1-yl]-N-methyl-N-[1-(methylsulfonyl)-4-piperidinyl]-6-(4-morpholinyl)-4-pyrimidinamine;

N-[3-({2-(difluoromethyl)-1-[4-{[1-(methylsulfonyl)-4-piperidinyl]oxy}-6-(4-morpholinyl)-1,3,5-triazin-2-yl]-1H-benzimidazol-4-yl}oxy)propyl]-N,N-dimethylamine;

6-[2-(difluoromethyl)-4-methoxy-1H-benzimidazol-1-yl]-1-[1-(methylsulfonyl)-4-piperidinyl]-4-(4-morpholinyl)-1H-pyrazolo[3,4-d]pyrimidine;

2-[2-(difluoromethyl)-4-methoxy-1H-benzimidazol-1-yl]-9-[1-(methylsulfonyl)-4-piperidinyl]-6-(4-morpholinyl)-7,9-dihydro-8H-purin-8-one;

2-[2-(difluoromethyl)-4-methoxy-1H-benzimidazol-1-yl]-9-[1-(methylsulfonyl)-4-piperidinyl]-6-(4-morpholinyl)-9H-purine;

5-[2-(difluoromethyl)-4-methoxy-1H-benzimidazol-1-yl]-3-[1-(methylsulfonyl)-4-piperidinyl]-7-(4-morpholinyl)-3H-[1,2,3]triazolo[4,5-d]pyrimidine; and N-[2-({4-[6-[2-(difluoromethyl)-4-methoxy-1H-benzimidazol-1-yl]-4-(4-morpholinyl)-1H-pyrazolo[3,4-d]pyrimidin-1-yl]-1-piperidinyl}sulfonyl)ethyl]-N,N-dimethylamine;

and enantiomers, mixtures of enantiomers, or mixtures of two or more diastereomers thereof; and pharmaceutically acceptable salts, solvates, hydrates, and prodrugs thereof.

In yet another embodiment, provided herein is a compound selected from:

$N^1$-{1-[(chloromethyl)sulfonyl]-4-piperidinyl}-$N^1$-[4-[2-(difluoromethyl)-4-methoxy-1H-benzimidazol-1-yl]-6-(4-morpholinyl)-1,3,5-triazin-2-yl]-$N^3$,$N^3$-dimethyl-1,3-propanediamine;

chloro-N-{1-[4-[2-(difluoromethyl)-4-methoxy-1H-benzimidazol-1-yl]-6-(4-morpholinyl)-1,3,5-triazin-2-yl]-4-piperidinyl}-N-[3-(dimethylamino)propyl]methanesulfonamide;

chloro-N-{1-[4-[2-(difluoromethyl)-4-methoxy-1H-benzimidazol-1-yl]-6-(4-morpholinyl)-1,3,5-triazin-2-yl]-4-piperidinyl}methanesulfonamide; and chloro-N-{(3S)-1-[4-[2-(difluoromethyl)-4-methoxy-1H-benzimidazol-1-yl]-6-(4-morpholinyl)-1,3,5-triazin-2-yl]-3-piperidinyl}methanesulfonamide;

and enantiomers, mixtures of enantiomers, or mixtures of two or more diastereomers thereof; and pharmaceutically acceptable salts, solvates, hydrates, and prodrugs thereof.

The compounds provided herein are intended to encompass all possible stereoisomers, unless a particular stereochemistry is specified. Where the compound provided herein contains an alkenyl or alkenylene group, the compound may exist as one or mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

In certain embodiments, the compounds provided herein are pharmacologically acceptable salts of the compounds with one or more of hydrochloric, sulfuric, phosphoric, acetic, citric, oxalic, malonic, salicylic, malic, fumaric, succinic, ascorbic, maleic, methanesulfonic, and isoethonic acids; or with one or more of potassium carbonate, sodium or potassium hydroxide, ammonia, triethylamine, and triethanolamine.

The compound provided herein may also be provided as a prodrug, which is a functional derivative of the compound, for example, of Formula I and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

In certain embodiments, the compounds provided herein are reversible inhibitors of PI3K. In certain embodiments, the compounds provided herein are irreversible inhibitors of PI3K. In certain embodiments, the compounds provided herein are selective reversible inhibitors of PI3K isoforms. In certain embodiments, the compounds provided herein are selective irreversible inhibitors of PI3K isoforms.

In certain embodiments, the compounds provided herein are reversible inhibitors of p110α. In certain embodiments, the compounds provided herein are irreversible inhibitors of p110α. In certain embodiments, the compounds provided herein are selective reversible inhibitors of p110α. In certain embodiments, the compounds provided herein are selective irreversible inhibitors of p110α.

Without being bound by any theory, it is believed that, in certain embodiments, the compounds provided herein interact with the His-855, which is unique to p110α. Without being bound by any theory, it is believed that, in certain embodiments, the compounds provided herein react with the His-855, which is unique to p110α. Without being bound by any theory, it is believed that, in certain embodiments, the compounds provided herein alkylate the His-855, which is unique to p110α.

Without being bound by any theory, it is believed that, in certain embodiments, the compounds provided herein are adapted to irreversibly inhibit the p110α isoform of PI3K. Without being bound by any theory, it is believed that, in certain embodiments, the compounds provided herein are adapted to target the His-855 group which is considered to form part of the ATP binding pocket of the p110α isoform of PI3K, but not of the other isoforms. Without being bound by any theory, it is believed that, in certain embodiments, by targeting the His-855 of p110α, the compounds provided herein selectively and irreversibly inhibit this PI3K isoform.

Irreversible inhibition of an enzyme target has a number of potential advantages: e.g., (a) kinase inhibitors that shut down the ATP site by reversible competitive blockade of ATP have to bind very tightly to the enzyme and/or maintain high plasma levels for prolonged periods, in order to compete with ATP binding, since ATP levels in cells are high; (b) the enzyme is shut down permanently, and the pathway is only reactivated upon resynthesis of the enzyme, which may take some time; (c) it allows longer times between doses, for a more achievable dosage regime; (d) it provides an additional mechanism for selectivity, in one embodiment, between different isoforms of an enzyme.

In certain embodiments, the sulfonamide compounds provided herein exhibit greater pharmacological stability than the corresponding carboxamides. In certain embodiments, the sulfonamide compounds provided herein exhibit an increase of no less than 2-fold, 3-fold, 4-fold, or 5-fold in pharmacological stability than the corresponding carboxamides. In certain embodiments, the sulfonamide compounds provided herein exhibit greater stability in human plasma than the corresponding carboxamides. In certain embodiments, the sulfonamide compounds provided herein exhibit an increase of no less than 2-fold, 3-fold, 4-fold, or 5-fold in stability in human plasma than the corresponding carboxamides.

Methods of Synthesis

The compound provided herein can be prepared, isolated, or obtained by any method known to one of skill in the art, and the following examples are only representative and do not exclude other related procedures.

For example, the compounds of Formula Ia, Ib, or Ic can be prepared via the formation of a bond between the $T^2$ and $SO_2R^5$ groups (Method A) as shown in Scheme 1.

Scheme 1
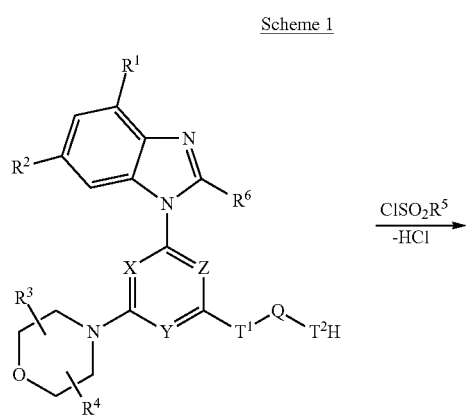
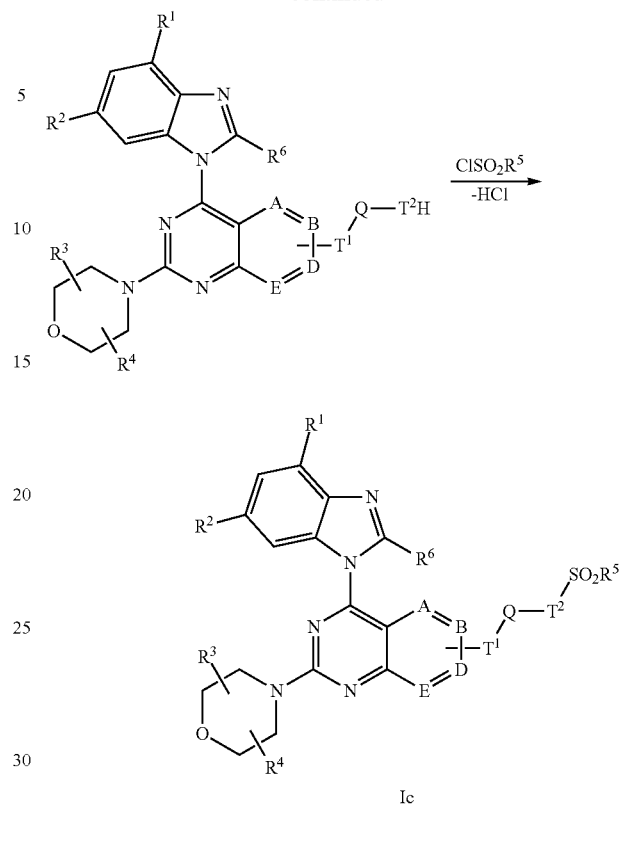
The compounds of Formula Ia, Ib, or Ic can also be prepared via the formation of a bond between the benzimidazole group and the pyrimidinyl or 1,3,5-triazilnyl ring (Method B) as shown in Scheme 2.
Scheme 2
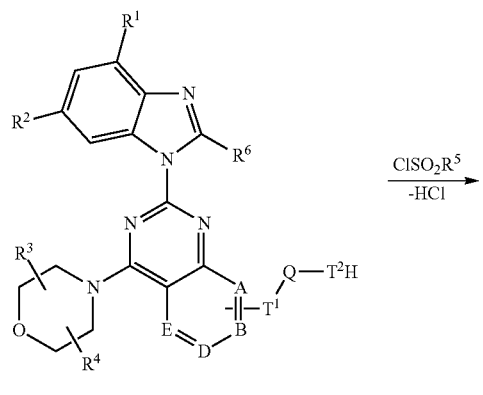
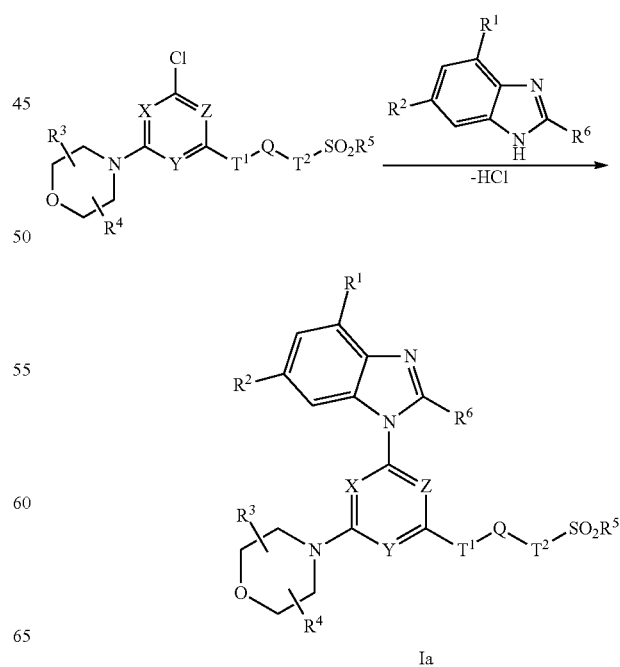

-continued

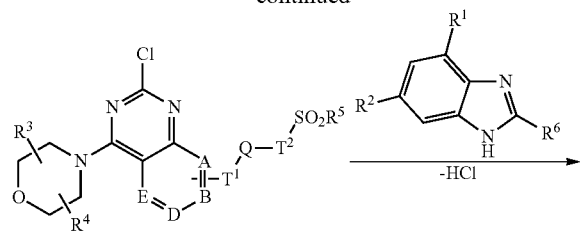

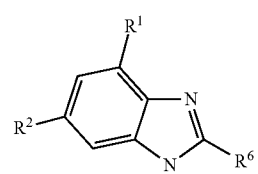

Ib

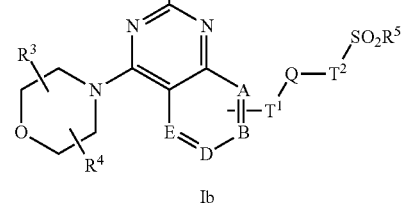

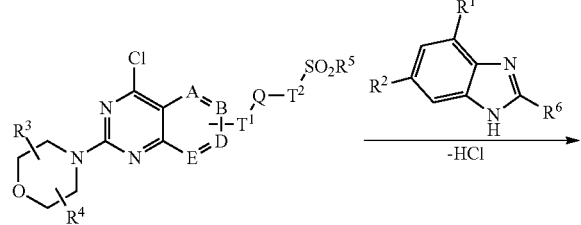

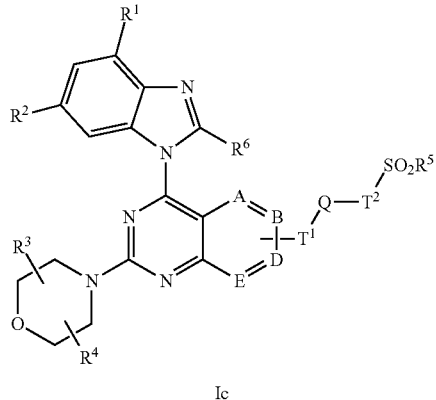

Ic

Furthermore, the compounds of Formula Ia can be prepared via the formation of a bond between Q and the pyrimidinyl or 1,3,5-triazinyl ring (Method C) as shown in Scheme 3.

Scheme 3

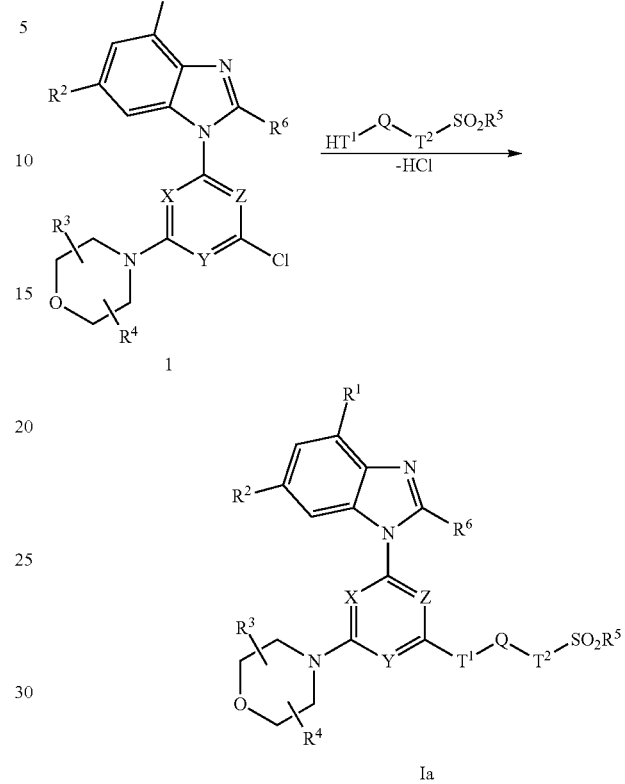

Ia

The halo-1,3,5-triazine or halo-pyrimidine used in Method C can be prepared, isolated, or obtained by any method known to one of skill in the art. For example, the halo-1,3,5-triazine 1 can be prepared via aromatic substitution reactions of chlorotriazine with two different amines as shown in Scheme 4.

Scheme 4

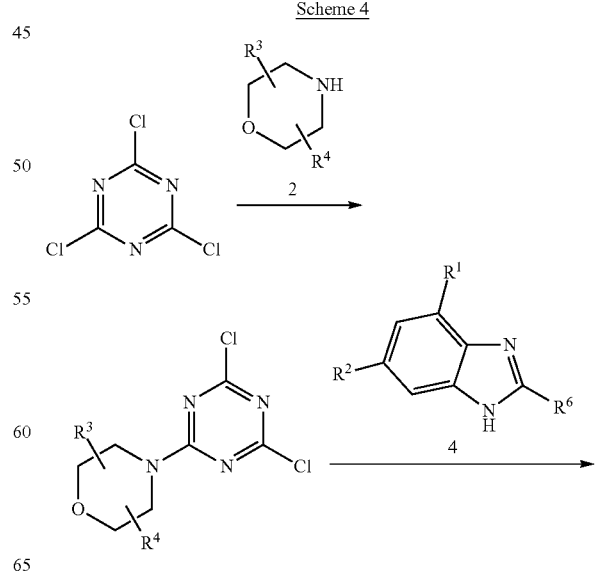

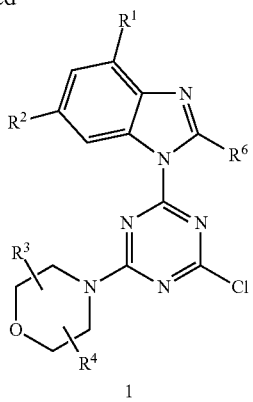

The benzimidazole 4 used in Scheme 4 can also be prepared, isolated, or obtained by any method known to one of skill in the art. For example, the benzimidazole 4 can be as shown in Scheme 5.

Scheme 5

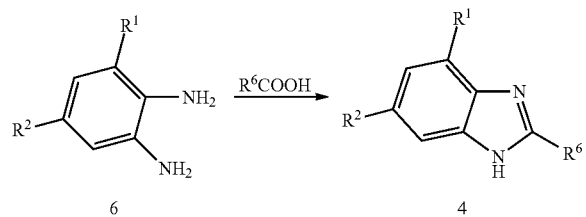

The compounds of Formula Ia, Ib, or Ic can also be prepared via the modification of existing substituents on the compounds (Method D).

Pharmaceutical Compositions

In one embodiment, provided herein is a pharmaceutical composition comprising a compound of Formula IA, IB, or IC as defined herein, and a pharmaceutically acceptable excipient, adjuvant, carrier, buffer, or stabiliser.

In one embodiment, the pharmaceutically acceptable excipient, adjuvant, carrier, buffer, or stabiliser is non-toxic and does not interfere with the efficacy of the active ingredient. The precise nature of the carrier or other material will depend on the route of administration, which may be oral or by injection, such as cutaneous, subcutaneous, or intravenous injection.

In one embodiment, the pharmaceutical compositions are provided in a dosage form for oral administration, which comprise a compound provided herein, and one or more pharmaceutically acceptable excipients or carriers. The pharmaceutical compositions provided herein that are formulated for oral administration may be in tablet, capsule, powder, or liquid form. A tablet may comprise a solid carrier or an adjuvant. Liquid pharmaceutical compositions generally comprise a liquid carrier such as water, petroleum, animal or vegetable oils, or mineral oil or synthetic oil. Physiological saline solution, dextrose or other saccharide solution, or glycols such as ethylene glycol, propylene glycol, or polyethylene glycol may be included. A capsule may comprise a solid carrier such as gelatin.

In another embodiment, the pharmaceutical compositions are provided in a dosage form for parenteral administration, and one or more pharmaceutically acceptable excipients or carriers. Where pharmaceutical compositions may be formulated for intravenous, cutaneous or subcutaneous injection, the active ingredient will be in the form of a parenterally acceptable aqueous solution, which is pyrogen-free and has a suitable pH, isotonicity, and stability. Those of relevant skill in the art are well able to prepare suitable solutions using, for example, isotonic vehicles, such as Sodium Chloride injection, Ringer's injection, or Lactated Ringer's injection. Preservatives, stabilisers, buffers, antioxidants, and/or other additives may be included as required.

In yet another embodiment, the pharmaceutical compositions are provided in a dosage form for topical administration, which comprise a compound provided herein, and one or more pharmaceutically acceptable excipients or carriers.

The pharmaceutical compositions can also be formulated as modified release dosage forms, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, Remington: The Science and Practice of Pharmacy, supra; Modified-Release Drug Delivery Technology, 2nd Edition, Rathbone et al., Eds., Marcel Dekker, Inc.: New York, N.Y., 2008).

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In another embodiment, the pharmaceutical compositions provided herein further comprise one or more chemotherapeutic agents as defined herein.

In yet another embodiment, provided herein is the use of a compound of Formula IA, IB, or IC in the manufacture of a medicament for the treatment of cancer. In certain embodiments, the medicament is in tablet, capsule, powder, or liquid form. In certain embodiments, the medicament is formulated as described herein.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained-, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcellulose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphorism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form can be fabricated using a matrix controlled release device known to those skilled in the art (see, Takada et al. in "Encyclopedia of Controlled Drug Delivery," Vol. 2, Mathiowitz Ed., Wiley, 1999).

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(–)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly (acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 m to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

In one embodiment, provided is a method of treating, preventing, or ameliorating one or more symptoms of a disorder, disease, or condition associated with PI3K activity in a subject, which comprises administering to the subject a therapeutically effective amount of a compound provided herein, e.g., a compound of Formula IA, IB, or IC, including an enantiomer, a mixture of enantiomers, or a mixture of two or more diastereomers thereof; or a pharmaceutically acceptable salt, solvate, hydrate, or prodrug thereof.

In another embodiments, provided is a method of treating, preventing, or ameliorating one or more symptoms of a disorder, disease, or condition responsive to the modulation of PI3K activity in a subject, which comprises administering to the subject a therapeutically effective amount of a compound provided herein, e.g., a compound of Formula IA, IB, or IC, including an enantiomer, a mixture of enantiomers, or a mixture of two or more diastereomers thereof; or a pharmaceutically acceptable salt, solvate, hydrate, or prodrug thereof.

In yet another embodiment, provided is a method of treating, preventing, or ameliorating one or more symptoms of a disorder, disease, or condition mediated by a PI3K enzyme in a subject, which comprises administering to the subject a therapeutically effective amount of a compound provided herein, e.g., a compound of Formula IA, IB, or IC, including an enantiomer, a mixture of enantiomers, or a mixture of two or more diastereomers thereof; or a pharmaceutically acceptable salt, solvate, hydrate, or prodrug thereof.

In yet another embodiment, provided is a method of treating, preventing, or ameliorating one or more symptoms of cancer in a subject, which comprises administering to the subject a therapeutically effective amount of a compound provided herein, e.g., a compound of Formula IA, IB, or IC, including an enantiomer, a mixture of enantiomers, or a mixture of two or more diastereomers thereof; or a pharmaceutically acceptable salt, solvate, hydrate, or prodrug thereof.

In yet another embodiment, provided herein are uses of a compound provided herein, e.g., a compound of Formula IA, IB, or IC, including an enantiomer, a mixture of enantiomers, or a mixture of two or more diastereomers thereof; or a pharmaceutically acceptable salt, solvate, hydrate, or prodrug thereof, in the manufacture of a medicament for the treatment of cancer.

In certain embodiments, the compound selectively targets the p110α subunit of PI3K. In certain embodiments, the compound selectively inhibits the PI3K via its interaction with its p110α subunit. In certain embodiments, the compound selectively alkylates the p110α, subunit of PI3K.

In certain embodiments, the PI3K is a wild type PI3K. In certain embodiments, the PI3K is a PI3K mutant.

In certain embodiments, the PI3K is a Class I kinase. In certain embodiments, the PI3K is p110α, p110β, p110δ, or p110γ. In certain embodiments, the PI3K is a wild type of a Class I kinase. In certain embodiments, the PI3K is a mutant of a Class I kinase.

In certain embodiments, the PI3K is p110α. In certain embodiments, the PI3K is a wild type of p110α. In certain embodiments, the PI3K is a p110α mutant. In certain embodiments, the p110α mutant is R38H, G106V, K111N, K227E, N345K, C420R, P539R, E542K, E545A, E545G, E545K, Q546K, Q546P, E453Q, H710P, I800L, T1025S, M1043I, M1043V, H1047L, H1047R, or H1047Y. In certain embodiments, the p110α mutant is R38H, K111N, N345K, C420R, P539R, E542K, E545A, E545G, E545K, Q546K, Q546P, I800L, T1025S, M1043I, H1047L, H1047R, or H1047Y. In certain embodiments, the p110α mutant is C420R, E542K, E545A, E545K, Q546K, I800L, M1043I, H1047L, or H1047Y.

In certain embodiments, the PI3K is a Class IV kinase. In certain embodiments, the PI3K is a wild type of a Class IV kinase. In certain embodiments, the PI3K is a mutant of a Class IV kinase. In certain embodiments, the PI3K is mTOR, ATM, ATR, or DNA-PK. In certain embodiments, the PI3K is mTOR.

In one embodiment, the subject is a mammal. In another embodiment, the subject is a human. In yet another embodiment, the subject is a primate other than a human, a farm animal such as cattle, a sport animal, or a pet such as a horse, dog, or cat.

The disorders, diseases, or conditions treatable with a compound provided herein, include, but are not limited to, (1) inflammatory or allergic diseases, including systemic anaphylaxis and hypersensitivity disorders, atopic dermatitis, urticaria, drug allergies, insect sting allergies, food allergies (including celiac disease and the like), and mastocytosis; (2) inflammatory bowel diseases, including Crohn's disease, ulcerative colitis, ileitis, and enteritis; (3) vasculitis, and Behcet's syndrome; (4) psoriasis and inflammatory dermatoses, including dermatitis, eczema, atopic dermatitis, allergic contact dermatitis, urticaria, viral cutaneous pathologies including those derived from human papillomavirus, HIV or RLV infection, bacterial, flugal, and other parasital cutaneous pathologies, and cutaneous lupus erythematosus; (5) asthma and respiratory allergic diseases, including allergic asthma, exercise induced asthma, allergic rhinitis, otitis media, allergic conjunctivitis, hypersensitivity lung diseases, and chronic obstructive pulmonary disease; (6) autoimmune diseases, including arthritis (including rheumatoid and psoriatic), systemic lupus erythematosus, type I diabetes, myasthenia gravis, multiple sclerosis, Graves' disease, and glomerulonephritis; (7) graft rejection (including allograft rejection and graft-v-host disease), e.g., skin graft rejection, solid organ transplant rejection, bone marrow transplant rejection; (8) fever; (9) cardiovascular disorders, including acute heart failure, hypotension, hypertension, angina pectoris, myocardial infarction, cardiomyopathy, congestive heart failure, atherosclerosis, coronary artery disease, restenosis, and vascular stenosis; (10) cerebrovascular disorders, including traumatic brain injury, stroke, ischemic reperfusion injury and aneurysm; (11) cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system; (12) fibrosis, connective tissue disease, and sarcoidosis, (13) genital and reproductive conditions, including erectile dysfunction; (14) gastrointestinal disorders, including gastritis, ulcers, nausea, pancreatitis, and vomiting; (15) neurologic disorders, including Alzheimer's disease; (16) sleep disorders, including insomnia, narcolepsy, sleep apnea syndrome, and Pickwick Syndrome; (17) pain; (18) renal disorders; (19) ocular disorders, including glaucoma, and (20) infectious diseases, including HIV.

In certain embodiments, the cancer treatable with the methods provided herein includes, but is not limited to, (1) leukemias, including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome or a symptom thereof (such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia, and chronic myelomonocytic leukemia (CMML), (2) chronic leukemias, including, but not limited to, chronic myelocytic (granulocytic) leukemia, chronic lymphocytic leukemia, and hairy cell leukemia; (3) polycythemia vera; (4) lymphomas, including, but not limited to, Hodgkin's disease and non-Hodgkin's disease; (5) multiple myelomas, including, but not limited to, smoldering multiple myeloma, nonsecretory myeloma, osteosclerotic myeloma, plasma cell leukemia, solitary plasmacytoma, and extramedullary plasmacytoma; (6) Waldenström's macroglobulinemia; (7) monoclonal gammopathy of undetermined significance; (8) benign monoclonal gammopathy; (9) heavy chain disease; (10) bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, and synovial sarcoma; (11) brain tumors, including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; (12) breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; (13) adrenal cancer, including, but not limited to, pheochromocytom and adrenocortical carcinoma; (14) thyroid cancer, including, but not limited to, papillary or follicular thyroid cancer, medullary thyroid cancer, and anaplastic thyroid cancer; (15) pancreatic cancer, including, but not limited to, insulinoma, gastrinoma, glucagonoma, vipoma, somatostatin-secreting tumor, and carcinoid or islet cell tumor; (16) pituitary cancer, including, but limited to, Cushing's disease, prolactin-secreting tumor, acromegaly, and diabetes insipius; (17) eye cancer, including, but not limited, to ocular melanoma such as iris melanoma, choroidal melanoma, and ciliary body melanoma, and retinoblastoma; (18) vaginal cancer, including, but not limited to, squamous cell carcinoma, adenocarcinoma, and melanoma; (19) vulvar cancer, including, but not limited to, squamous cell carcinoma, melanoma, adenocarcinoma, basal cell carcinoma, sarcoma, and Paget's disease; (20) cervical cancers, including, but not limited to, squamous cell carcinoma, and adenocarcinoma; (21) uterine cancer, including, but not limited to, endometrial carcinoma and uterine sarcoma; (22) ovarian cancer, including, but not limited to, ovarian epithelial carcinoma, borderline tumor, germ cell tumor, and stromal tumor; (23) esophageal cancer, including, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; (24) stomach cancer, including, but not limited to, adenocarcinoma, fungating (polypoid), ulcerating, superficial spreading, diffusely spreading, malignant lymphoma, liposarcoma, fibrosarcoma, and carcinosarcoma; (25) colon cancer; (26) rectal cancer; (27) liver cancer, including, but not limited to, hepatocellular carcinoma and hepatoblastoma; (28) gallbladder cancer, including, but not limited to, adenocarcinoma; (29) cholangiocarcinomas, including, but not limited to, pappillary, nodular, and diffuse; (30) lung cancer, including, but not limited to, non-small cell lung cancer, squamous cell carcinoma (epidermoid carcinoma), adenocarcinoma, large-cell carcinoma, and small-cell lung cancer; (31) testicular cancer, including, but not limited to, germinal tumor, seminoma, anaplastic, classic (typical), spermatocytic, nonseminoma, embryonal carcinoma, teratoma carcinoma, and choriocarcinoma (yolk-sac tumor); (32) prostate cancer, including, but not limited to, adenocarcinoma, leiomyosarcoma, and rhabdomyosarcoma; (33) penal cancer; (34) oral cancer, including, but not limited to, squamous cell carcinoma; (35) basal cancer; (36) salivary gland cancer, including, but not limited to, adenocarcinoma, mucoepidermoid carcinoma, and adenoidcystic carcinoma; (37) pharynx cancer, including, but not limited to, squamous cell cancer and verrucous; (38) skin cancer, including, but not limited to, basal cell carcinoma, squamous cell carcinoma and melanoma, superficial spreading melanoma, nodular melanoma, lentigo malignant melanoma, and acral lentiginous melanoma; (39) kidney cancer, including, but not limited to, renal cell cancer, adenocarcinoma, hypernephroma, fibrosarcoma, and transitional cell cancer (renal pelvis and/or uterer); (40) Wilms' tumor; (41) bladder cancer, including, but not limited to, transitional cell carcinoma, squamous cell cancer, adenocarcinoma, and carcinosarcoma; and other cancer, including, not limited to, myxosarcoma, osteogenic sarcoma, endotheliosarcoma, lymphangio-endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, and papillary adenocarcinomas (See Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

Depending on the disorder, disease, or condition to be treated, and the subject's condition, the compounds or pharmaceutical compositions provided herein can be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical (e.g., transdermal or local) routes of administration and can be formulated, alone or together, in suitable dosage unit with pharmaceutically acceptable excipients, carriers, adjuvants, and vehicles appropriate for each route of administration. Also provided is administration of the compounds or pharmaceutical compositions provided herein in a depot formulation, in which the active ingredient is released over a predefined time period.

In the treatment, prevention, or amelioration of one or more symptoms of the disorders, diseases, or conditions described herein, an appropriate dosage level generally is ranging from about 0.001 to 100 mg per kg subject body weight per day (mg/kg per day), from about 0.01 to about 75 mg/kg per day, from about 0.1 to about 50 mg/kg per day, from about 0.5 to about 25 mg/kg per day, or from about 1 to about 20 mg/kg per day, which can be administered in single or multiple doses. Within this range, the dosage can be ranging from about 0.005 to about 0.05, from about 0.05 to about 0.5, from about 0.5 to about 5.0, from about 1 to about 15, from about 1 to about 20, or from about 1 to about 50 mg/kg per day.

For oral administration, the pharmaceutical compositions provided herein can be formulated in the form of tablets containing from about 1.0 to about 1,000 mg of the active ingredient, in one embodiment, about 1, about 5, about 10, about 15, about 20, about 25, about 50, about 75, about 100, about 150, about 200, about 250, about 300, about 400, about 500, about 600, about 750, about 800, about 900, and about 1,000 mg of the active ingredient for the symptomatic adjustment of the dosage to the patient to be treated. The pharmaceutical compositions can be administered on a regimen of 1 to 4 times per day, including once, twice, three times, and four times per day.

It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also provided herein are methods of modulating PI3K activity, comprising contacting a PIK3 enzyme with a compound provided herein, e.g., a compound of Formula IA, IB, or IC, including an enantiomer, a mixture of enantiomers, or a mixture of two or more diastereomers thereof; or a pharmaceutically acceptable salt, solvate, hydrate, or prodrug thereof. In one embodiment, the PIK3 enzyme is inside a cell.

In certain embodiments, the PI3K is a wild type PI3K. In certain embodiments, the PI3K is a PI3K mutant.

In certain embodiments, the PI3K is a Class I kinase. In certain embodiments, the PI3K is p110α, p110β, p110δ, or p110γ. In certain embodiments, the PI3K is a wild type of a Class I kinase. In certain embodiments, the PI3K is a mutant of a Class I kinase.

In certain embodiments, the PI3K is p110α. In certain embodiments, the PI3K is a wild type of p110α. In certain embodiments, the PI3K is a p110α mutant. In certain embodiments, the p110α mutant is R38H, G106V, K111N, K227E, N345K, C420R, P539R, E542K, E545A, E545G, E545K, Q546K, Q546P, E453Q, H710P, I800L, T1025S, M1043I, M1043V, H1047L, H1047R, or H1047Y. In certain embodiments, the p110 mutant is R38H, K111N, N345K, C420R, P539R, E542K, E545A, E545G, E545K, Q546K, Q546P, I800L, T1025S, M1043I, H1047L, H1047R, or H1047Y. In certain embodiments, the p110 mutant is C420R, E542K, E545A, E545K, Q546K, I800L, M1043I, H1047L, or H1047Y.

In certain embodiments, the PI3K is a Class IV kinase. In certain embodiments, the PI3K is a wild type of a Class IV kinase. In certain embodiments, the PI3K is a mutant of a Class IV kinase. In certain embodiments, the PI3K is mTOR, ATM, ATR, or DNA-PK. In certain embodiments, the PI3K is mTOR.

In certain embodiments, the compounds provided herein, e.g., a compound of Formula IA, IB, or IC, including an enantiomer, a mixture of enantiomers, or a mixture of two or more diastereomers thereof; or a pharmaceutically acceptable salt, solvate, hydrate, or prodrug thereof, show inhibitory activity against a PI3K and a mutant thereof.

In certain embodiments, the compounds provided herein, e.g., a compound of Formula IA, IB, or IC, including an enantiomer, a mixture of enantiomers, or a mixture of two or more diastereomers thereof; or a pharmaceutically acceptable salt, solvate, hydrate, or prodrug thereof, show inhibitory activity against a wild type of a PI3K. In certain embodiments, the PI3K is p110α. In certain embodiments, the PI3K is mTOR.

In certain embodiments, the compounds provided herein, e.g., a compound of Formula IA, IB, or IC, including an enantiomer, a mixture of enantiomers, or a mixture of two or more diastereomers thereof; or a pharmaceutically acceptable salt, solvate, hydrate, or prodrug thereof, show inhibitory activity against a PI3K mutant. In certain embodiments, the PI3K mutant is a p110α mutant. In certain embodiments, the p110α mutant is C420R, E542K, E545A, E545K, Q546K, I800L, M1043I, H1047L, or H1047Y.

The compounds provided herein, e.g., a compound of Formula IA, IB, or IC, including an enantiomer, a mixture of enantiomers, or a mixture of two or more diastereomers thereof; or a pharmaceutically acceptable salt, solvate, hydrate, or prodrug thereof, can also be combined or used in combination with other agents or therapies useful in the treatment, prevention, or amelioration of one or more symptoms of the disorders, diseases, or conditions for which the compounds provided herein are useful, including asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, infectious diseases, and those pathologies noted herein.

Suitable other therapeutic agents can also include, but are not limited to, (1) alpha-adrenergic agents; (2) antiarrhythmic agents; (3) anti-atherosclerotic agents, such as ACAT inhibitors; (4) antibiotics, such as anthracyclines, bleomycins, mitomycin, dactinomycin, and plicamycin; (5) anticancer agents and cytotoxic agents, e.g., alkylating agents, such as nitrogen mustards, alkyl sulfonates, nitrosoureas, ethylenimines, and triazenes; (6) anticoagulants, such as acenocoumarol, argatroban, bivalirudin, lepirudin, fondaparinux, heparin, phenindione, warfarin, and ximelagatran; (7) antidiabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; (8) antifungal agents, such as amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole; (9) antiinflammatories, e.g., non-steroidal antiinflammatory agents, such as aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin; (10) antimetabolites, such as folate antagonists, purine analogues, and pyrimidine analogues; (11) anti-platelet agents, such as GPIIb/IIIa blockers (e.g., abciximab, eptifibatide, and tirofiban), P2Y(AC) antagonists (e.g., clopidogrel, ticlopidine and CS-747), cilostazol, dipyridamole, and aspirin; (12) antiproliferatives, such as methotrexate, FK506 (tacrolimus), and mycophenolate mofetil; (13) anti-TNF antibodies or soluble TNF receptor, such as etanercept, rapamycin, and leflunimide; (14) aP2 inhibitors; (15) beta-adrenergic agents, such as carvedilol and metoprolol; (16) bile acid sequestrants, such as questran; (17) calcium channel blockers, such as amlodipine besylate; (18) chemotherapeutic agents; (19) cyclooxygenase-2 (COX-2) inhibitors, such as celecoxib and rofecoxib; (20) cyclosporins; (21) cytotoxic drugs, such as azathioprine and cyclophosphamide; (22) diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; (23) endothelin converting enzyme (ECE) inhibitors, such as phosphoramidon; (24) enzymes, such as L-asparaginase; (25) Factor VIIa Inhibitors and Factor Xa Inhibitors; (26) farnesyl-protein transferase inhibitors; (27) fibrates; (28) growth factor inhibitors, such as modulators of PDGF activity; (29) growth hormone secretagogues; (30) HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); neutral endopeptidase (NEP) inhibitors; (31) hormonal agents, such as glucocorticoids (e.g., cortisone), estrogens/antiestrogens, androgens/antiandrogens, progestins, and luteinizing hormone-releasing hormone antagonists, and octreotide acetate; (32) immunosuppressants; (33) mineralocorticoid receptor antagonists, such as spironolactone and eplerenone; (34) microtubule-disruptor agents, such as ecteinascidins; (35) microtubule-stabilizing agents, such as pacitaxel, docetaxel, and epothilones A-F; (36) MTP Inhibitors; (37) niacin; (38) phosphodiesterase inhibitors, such as PDE III inhibitors (e.g., cilostazol) and PDE V inhibitors (e.g., sildenafil, tadalafil, and vardenafil); (39) plant-derived products, such as vinca alkaloids, epipodophyllotoxins, and taxanes; (40) platelet activating factor (PAF) antagonists; (41) platinum coordination complexes, such as cisplatin, satraplatin, and carboplatin; (42) potassium channel openers; (43) prenyl-protein transferase inhibitors; (44) protein tyrosine kinase inhibitors; (45) renin inhibitors; (46) squalene synthetase inhibitors; (47) steroids, such as aldosterone, beclometasone, betamethasone, deoxycorticosterone acetate, fludrocortisone, hydrocortisone (cortisol), prednisolone, prednisone, methylprednisolone, dexamethasone, and triamcinolone; (48) TNF-alpha inhibitors, such as tenidap; (49) thrombin inhibitors, such as hirudin; (50) thrombolytic agents, such as anistreplase, reteplase, tenecteplase, tissue plasminogen activator (tPA), recombinant tPA, streptokinase, urokinase, prourokinase, and anisoylated plasminogen streptokinase activator complex (APSAC); (51) thromboxane receptor antagonists, such as ifetroban; (52) topoisomerase inhibitors; (53) vasopeptidase inhibitors (dual NEP-ACE inhibitors), such as omapatrilat and gemopatrilat; and (54) other miscellaneous agents, such as, hydroxyurea, procarbazine, mitotane, hexamethylmelamine, and gold compounds.

In certain embodiments, the other therapies that may be used in combination with the compounds provided herein include, but are not limited to, surgery, endocrine therapy, biologic response modifiers (e.g., interferons, interleukins, and tumor necrosis factor (TNF)), hyperthermia and cryotherapy, and agents to attenuate any adverse effects (e.g., antiemetics).

In certain embodiments, the other therapeutic agents that may be used in combination with the compounds provided herein include, but are not limited to, alkylating drugs (mechlorethamine, chlorambucil, cyclophosphamide, melphalan, and ifosfamide), antimetabolites (cytarabine (also known as cytosine arabinoside or Ara-C), HDAC (high dose cytarabine), and methotrexate), purine antagonists and pyrimidine antagonists (6-mercaptopurine, 5-fluorouracil, cytarbine, and gemcitabine), spindle poisons (vinblastine, vincristine, and vinorelbine), podophyllotoxins (etoposide, irinotecan, and topotecan), antibiotics (daunorubicin, doxorubicin, bleomycin, and mitomycin), nitrosoureas (carmustine and lomustine), enzymes (asparaginase), and hormones (tamoxifen, leuprolide, flutamide, and megestrol), imatinib, adriamycin, dexamethasone, and cyclophosphamide. For a more comprehensive discussion of updated cancer therapies; See, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

In another embodiment, the method provided herein comprises administration of a compound of Formula IA, IB, or IC, together with administering one or more chemotherapeutic agents and/or therapies selected from: alkylation agents (e.g., cisplatin, carboplatin); antimetabolites (e.g., methotrexate and 5-FU); antitumour antibiotics (e.g., adriamymycin and bleomycin); antitumour vegetable alkaloids (e.g., taxol and etoposide); antitumour hormones (e.g., dexamethasone and tamoxifen); antitumour immunological agents (e.g., interferon $\alpha$, $\beta$, and $\gamma$); radiation therapy; and surgery. In certain embodiments, the one or more chemotherapeutic agents and/or therapies are administered to the subject before, during, or after the administration of the compound of Formula IA, IB, or IC as defined herein.

Such other agents, or drugs, can be administered, by a route and in an amount commonly used therefor, simultaneously or sequentially with the compounds provided herein, e.g., a compound of Formula IA, IB, or IC, including a single enantiomer, a mixture of enantiomers, or a mixture of diastereomers thereof; or a pharmaceutically acceptable salt, solvate, or prodrug thereof. When a compound provided herein is used contemporaneously with one or more other drugs, a pharmaceutical composition containing such other drugs in addition to the compound provided herein can be utilized, but is not required. Accordingly, the pharmaceutical compositions provided herein include those that also contain one or more other active ingredients or therapeutic agents, in addition to a compound provided herein.

The weight ratio of a compound provided herein to the second active ingredient can be varied, and will depend upon the effective dose of each ingredient. Generally, an effective dose of each will be used. Thus, for example, when a compound provided herein is combined with a NSAID, the weight ratio of the compound to the NSAID can range from about 1,000:1 to about 1:1,000, or about 200:1 to about 1:200. Combinations of a compound provided herein and other active ingredients will generally also be within the aforementioned range, but in each case, an effective dose of each active ingredient should be used.

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes a container and a dosage form of a compound provided herein, including a single enantiomer or a mixture of diastereomers thereof; or a pharmaceutically acceptable salt, solvate, or prodrug thereof.

In certain embodiments, the kit includes a container comprising a dosage form of the compound provided herein, including a single enantiomer or a mixture of diastereomers thereof; or a pharmaceutically acceptable salt, solvate, or prodrug thereof, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); μL (microliters); M (molar); mM (millimolar); μM (micromolar); eq. (equivalent); mmol (millimoles); Hz (Hertz); MHz (megahertz); hr or hrs (hours); min (minutes); MS (mass spectrometry); APCI (atmospheric pressure chemical ionization); mp (melting point); DMF (dimethylormamide); DMSO (dimethylsulfoxide); DMSO-$d_6$ (deuterated dimethylsulfoxide); EtOAc (ethyl acetate); EtOH (ethanol); MeOH (methanol); THF (tetrahydrofuran); DIPEA (N,N-diisopropylethylamine); TFA (trifluoroacetic acid); Me (methyl); Et (ethyl); PdCl$_2$(dppf), ((1,1'-bis(diphenylphosphino)ferrocene)dichloropalladium(II)); and EDTA (ethylenediaminetetraacetic acid).

For all of the following examples, standard work-up and purification methods known to those skilled in the art can be utilized. Unless otherwise indicated, all temperatures are expressed in ° C. (degrees Centigrade). All reactions conducted at room temperature unless otherwise noted. Synthetic methodologies illustrated herein are intended to exemplify the applicable chemistry through the use of specific examples and are not indicative of the scope of the disclosure.

General Experimental Information.

Elemental analyses (combustion analysis) were carried out in the Microchemical Laboratory, University of Otago, Dunedin, NZ. Melting points were determined on an Electrothermal 9100 Melting Point Apparatus. NMR spectra were obtained on a Bruker Avance-400 spectrometer at 400 MHz for 1H and 100 MHz for $^{13}$C spectra, referenced to TMS (Si(CH$_3$)$_4$). Mass spectra were determined on a VG-70SE mass spectrometer using an ionizing potential of 70 eV at a nominal resolution of 1000. High-resolution spectra were obtained at nominal resolutions of 3000, 5000, or 10000 as appropriate. All MS spectra were obtained as electron impact (EI) using perfluorokerosene (PFK) as a reference unless otherwise stated. Column chromatography was carried out on silica gel (Merck 230-400 mesh), unless otherwise stated.

Example 1

Synthesis of 2-(difluoromethyl)-1-[4-[4-(methylsulfonyl)-1-piperazinyl]-6-(4-morpholinyl)-1,3,5-triazin-2-yl]-1H-benzimidazole

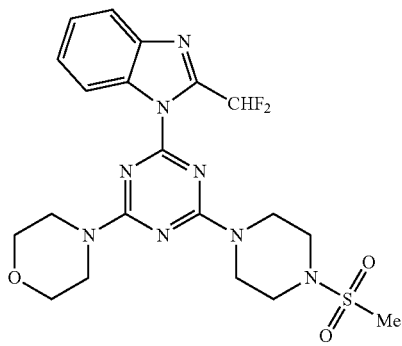 [SMILES: CS(=O)(=O)N1CCN(c2nc(N3CCOCC3)nc(-n3c(C(F)F)nc4ccccc43)n2)CC1]

A solution of 100 mg (0.24 mmol) of 2-(difluoromethyl)-1-[4-(4-morpholinyl)-6-(1-piperazinyl)-1,3,5-triazin-2-yl]-1H-benzimidazole (WO 2006/095906) and 0.51 g (50 mmol) of Et$_3$N in 20 mL of THF was cooled to 0° C. and 41 mg (0.36 mmol) of methanesulfonyl chloride was added. The mixture was allowed to warm to room temperature, and after 1 hr water was added. The precipitate was collected, washed with water, and dried to give 110 mg (93% yield) of 2-(difluoromethyl)-1-[4-[4-(methylsulfonyl)-1-piperazinyl]-6-(4-morpholinyl)-1,3,5-triazin-2-yl]-1H-benzimidazole: mp (MeOH) 248-250° C.; $^1$H NMR (CDCl$_3$) δ 8.30 (br d, J=8.3 Hz, 1H), 7.90 (br d, J=7.3 Hz, 1H), 7.52 (t, $J_{HF}$=53.6 Hz, 1H), 7.46-7.40 (m, 2H), 4.03 (m, 4H), 3.89 (m, 4H), 3.80 (m, 4H), 3.34 (m, 4H), 2.82 (s, 3H); Anal. Calcd. for C$_{20}$H$_{24}$F$_2$N$_8$O$_4$S: C, 48.6; H, 4.9; N, 22.7. Found: C, 48.8; H, 4.9; N, 22.85%.

Example 2

Synthesis of 2-(difluoromethyl)-4-methoxy-1-[4-[4-(methylsulfonyl)-1-piperazinyl]-6-(4-morpholinyl)-1,3,5-triazin-2-yl]-1H-benzimidazole

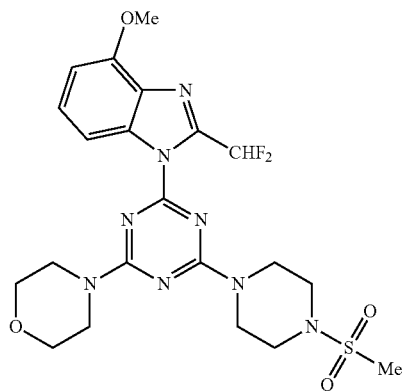 [SMILES: COc1cccc2c1nc(C(F)F)n2-c1nc(N2CCOCC2)nc(N2CCN(S(C)(=O)=O)CC2)n1]

2-Amino-3-methoxynitrobenzene (15.10 g, 0.09 mol) was hydrogenated over palladium on carbon in methanol, and the solution was filtered through celite into a methanolic HCl solution. The solvent was removed under vacuum and the resulting hydrochloride salt was combined with difluoroacetic acid (19.2 g, 0.18 mol) and 4 M HCl (100 mL). The mixture was heated under reflux for 3 hrs, diluted with water, decolorized with charcoal, and filtered through celite. Neutralization with aqueous ammonia gave 2-difluoromethyl-4-methoxy-1H-benzimidazole (15.2 g, 84%) as a solid: $^1$H NMR (CDCl$_3$) (tautomeric mixture) δ 9.95-9.70 (m, exchangeable with D$_2$O, 1H), 7.44 (br d, J=7.9 Hz, 0.4H), 7.31-7.24 (m, 1H), 7.12 (br d, J=8.0 Hz, 0.5H), 6.89 (t, $J_{HF}$=53.8 Hz, 1H), 6.82-6.74 (m, 1H), 4.03 and 3.98 (2s, 3H).

A mixture of 3.96 g (20 mmol) of 2-difluoromethyl-4-methoxy-1H-benzimidazole, 4.70 g (20 mmol) of 2,4-dichloro-6-(4-morpholinyl)-1,3,5-triazine, and 22 g (80 mmol) of powdered K$_2$CO$_3$ in 150 mL of DMF was stirred rapidly for 3 hrs, and then diluted with water. The resulting precipitate was collected, washed with water and then with cold ethanol, and dried to give 6.82 g (86%) of 1-[4-chloro-6-(4-morpholinyl)-1,3,5-triazin-2-yl]-2-(difluoromethyl)-4-methoxy-1H-benzimidazole: mp (CHCl$_3$/EtOH) 263-266° C.; $^1$H NMR (CDCl$_3$) δ 7.99 (d, J=8.4 Hz, 1H), 7.48 (t, $J_{HF}$=53.4 Hz, 1H), 7.40 (t, J=8.3 Hz, 1H), 6.86 (d, J=8.1 Hz, 1H), 4.05 (s, 3H), 3.96 (m, 4H), 3.82 (m, 4H); Anal. Calcd. for C$_{16}$H$_{15}$ClF$_2$N$_6$O$_2$: C, 48.4; H, 3.8; N, 21.2. Found: C, 48.3; H, 3.8; N, 21.1%.

A mixture of 1.98 g (5 mmol) of 1-[4-chloro-6-(4-morpholinyl)-1,3,5-triazin-2-yl]-2-(difluoromethyl)-4-methoxy-1H-benzimidazole, 1.16 g (6.25 mmol) of tert-butyl 1-piperazinecarboxylate, and 1.29 g (10 mmol) of DIPEA in 100 mL of THF was stirred at room temperature for 1 hr, and the solution was concentrated under vacuum. The residue was diluted with water (100 mL) containing 1 mL of acetic acid. The resulting precipitate was collected, washed with water, and dried to give 2.71 g (99% yield) of tert-butyl 4-[4-[2-(difluoromethyl)-4-methoxy-1H-benzimidazol-1-yl]-6-(4-morpholinyl)-1,3,5-triazin-2-yl]-1-piperazinecarboxylate: mp (MeOH) 221-223° C.; $^1$H NMR (CDCl$_3$) δ 7.88 (dd, J=8.4, 0.6 Hz, 1H), 7.47 (t, J=53.5 Hz, 1H), 7.35 (t, J=8.2 Hz, 1H), 6.81 (d, J=7.7 Hz, 1H), 4.05 (s, 3H), 3.87 (m, 8H), 3.78 (m, 4H), 3.53 (m, 4H), 1.50 (s, 9H); Anal. Calcd. for $C_{25}H_{32}F_2N_8O_4$: C, 54.9; H, 5.9; N, 20.5. Found: C, 54.9; H, 5.9; N, 20.5%.

Reaction of tert-butyl 4-[4-[2-(difluoromethyl)-4-methoxy-1H-benzimidazol-1-yl]-6-(4-morpholinyl)-1,3,5-triazin-2-yl]-1-piperazinecarboxylate from the previous step with an excess of TFA (10 mL) in CH$_2$Cl$_2$ (50 mL) at room temperature for 2 hrs, followed by treatment with aq. NH$_3$ gave 2-(difluoromethyl)-4-methoxy-1-[4-(4-morpholinyl)-6-(1-piperazinyl)-1,3,5-triazin-2-yl]-1H-benzimidazole in 100% yield: mp (EtOH) 228-231° C.; $^1$H NMR (CDCl$_3$) δ 7.90 (d, J=7.9 Hz, 1H), 7.50 (t, $J_{HF}$=53.5 Hz, 1H), 7.34 (t, J=8.3 Hz, 1H), 6.81 (d, J=7.8 Hz, 1H), 4.05 (s, 3H), 3.87 (m, 8H), 3.78 (m, 4H), 2.95 (m, 4H); Anal. Calcd. for $C_{20}H_{24}F_2N_8O_2$: C, 53.8; H, 5.4; N, 25.1. Found: C, 53.8; H, 5.6; N, 25.3%.

A solution of 107 mg (0.24 mmol) of 2-(difluoromethyl)-4-methoxy-1-[4-(4-morpholinyl)-6-(1-piperazinyl)-1,3,5-triazin-2-yl]-1H-benzimidazole in a mixture of 20 mL of THF and 20 mL of pyridine was cooled to 0° C. and 41 mg (0.36 mmol) of methanesulfonyl chloride was added. The mixture was allowed to warm to room temperature, and after 1 hr, water was added. The precipitate was collected, washed with water, and dried to give 95 mg (75% yield) of 2-(difluoromethyl)-4-methoxy-1-[4-[4-(methylsulfonyl)-1-piperazinyl]-6-(4-morpholinyl)-1,3,5-triazin-2-yl]-1H-benzimidazole: mp (MeOH) 311-314° C.; $^1$H NMR (CDCl$_3$) δ 7.86 (dd, J=8.4, 0.6 Hz, 1H), 7.43 (t, $J_{HF}$=53.5 Hz, 1H), 7.36 (t, J=8.2 Hz, 1H), 6.82 (d, J=7.8 Hz, 1H), 4.05 (s, 3H), 4.03 (m, 4H), 3.89 (m, 4H), 3.79 (m, 4H), 3.33 (m, 4H), 2.81 (s, 3H); Anal. Calcd. for $C_{21}H_{26}F_2N_8O_4S$: C, 48.1; H, 5.0; N, 21.4. Found: C, 48.0; H, 4.9; N, 21.2%.

Example 3

Synthesis of 2-(difluoromethyl)-4-methoxy-1-{4-(4-morpholinyl)-6-[4-(vinylsulfonyl)-1-piperazinyl]-1,3,5-triazin-2-yl}-1H-benzimidazole

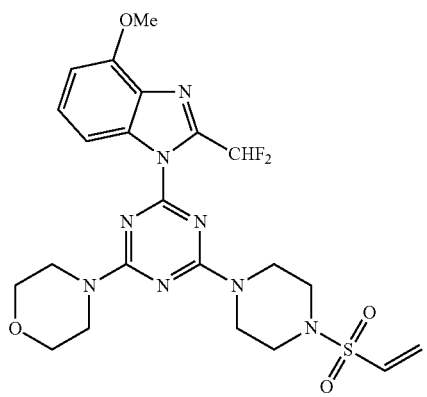 [SMILES: C=CS(=O)(=O)N1CCN(c2nc(N3CCOCC3)nc(-n3c(C(F)F)nc4c(OC)cccc43)n2)CC1]

A solution of 0.224 g (0.5 mmol) of 2-(difluoromethyl)-4-methoxy-1-[4-(4-morpholinyl)-6-(1-piperazinyl)-1,3,5-triazin-2-yl]-1H-benzimidazole (Example 2) and 25 mg of DMAP in 10 mL of pyridine was cooled to 0° C. and 0.122 g (0.75 mmol) of 2-chloroethanesulfonyl chloride was added dropwise over 5 min. The mixture was stirred at 0° C. for 2 hrs and water was added to give a precipitate which was collected and dried. Chromatography on silica eluting with CH$_2$Cl$_2$/EtOAc (4:1) gave 183 mg (31% yield) of 2-(difluoromethyl)-4-methoxy-1-{4-(4-morpholinyl)-6-[4-(vinylsulfonyl)-1-piperazinyl]-1,3,5-triazin-2-yl}-1H-benzimidazole: mp (MeOH) 242-244° C.; $^1$H NMR (CDCl$_3$) δ 7.85 (dd, J=8.4, 0.7 Hz, 1H), 7.43 (t, $J_{HF}$=53.5 Hz, 1H), 7.35 (t, J=8.2 Hz, 1H), 6.82 (d, J=7.7 Hz, 1H), 6.43 (dd, J=16.6, 9.8 Hz, 1H), 6.29 (d, J=16.6 Hz, 1H), 6.07 (d, J=9.8 Hz, 1H), 4.05 (s, 3H), 4.01 (m, 4H), 3.87 (m, 4H), 3.78 (m, 4H), 3.26 (m, 4H); MS (APCI$^+$) m/z 538.4; Anal. Calcd. for $C_{22}H_{26}F_2N_8O_4S$: C, 49.25; H, 4.9; N, 20.9. Found: C, 49.1; H, 5.0; N, 20.4%.

Example 4

Synthesis of N-[3-({2-(difluoromethyl)-1-[4-[4-(methylsulfonyl)-1-piperazinyl]-6-(4-morpholinyl)-1,3,5-triazin-2-yl]-1H-benzimidazol-4-yl}oxy)propyl]-N,N-dimethylamine

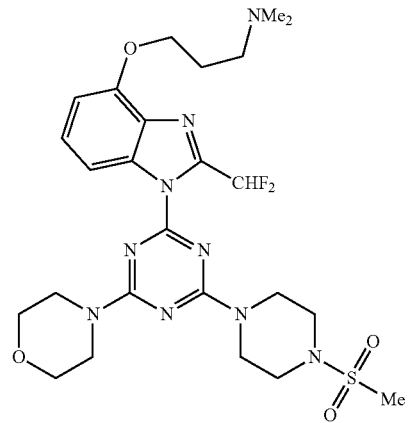 [SMILES: CN(C)CCCOc1cccc2c1nc(C(F)F)n2-c1nc(N2CCOCC2)nc(N2CCN(S(C)(=O)=O)CC2)n1]

Reaction of 4-(tert-butyldimethylsilyloxy)-2-(difluoromethyl)-1H-benzimidazole with 2,4-dichloro-6-(4-morpholinyl)-1,3,5-triazine as in Example 2, but using acetone as solvent, followed by chromatography on silica gel eluting with CH$_2$Cl$_2$/hexanes 3:1 gave 4-(tert-butyldimethylsilyloxy)-1-[4-chloro-6-(4-morpholinyl)-1,3,5-triazin-2-yl]-2-(difluoromethyl)-1H-benzimidazole: mp (hexanes) 143-145° C.; $^1$H NMR (CDCl$_3$) δ 7.99 (d, J=8.4 Hz, 1H), 7.46 (t, $J_{HF}$=53.5 Hz, 1H), 7.32 (t, J=8.2 Hz, 1H), 6.88 (d, J=8.0 Hz, 1H), 3.96 (m, 3.5H), 3.88 (m, 0.5H), 3.81 (m, 3.5H), 3.75 (m, 0.5H), 1.05 (s, 9H), 0.29 (s, 6H); MS (APCI$^+$) 497.9/499.9 MH$^+$. Anal. Calcd. for $C_{21}H_{27}ClF_2N_6O_2Si$: C, 50.75; H, 5.5; N, 16.9. Found: C, 50.7; H, 5.6; N, 17.0%.

Reaction of 4-(tert-butyldimethylsilyloxy)-1-[4-chloro-6-(4-morpholinyl)-1,3,5-triazin-2-yl]-2-(difluoromethyl)-1H-benzimidazole with 2.2 equivalents of tert-butyl 1-piperazinecarboxylate in THF at room temperature gave a quantitative yield of tert-butyl 4-[4-[4-(tert-butyldimethylsilyloxy)-2-(difluoromethyl)-1H-benzimidazol-1-yl]-6-(4-morpholinyl)-1,3,5-triazin-2-yl]piperazine-1-carboxylate as an oil: $^1$H NMR (CDCl$_3$) δ 7.91 (d, J=8.2 Hz, 1H), 7.45 (t, $J_{HF}$=53.6 Hz, 1H), 7.26 (t, J=8.1 Hz, 1H), 6.83 (d, J=7.9 Hz, 1H), 3.85 (m, 8H), 3.77 (m, 4H), 3.53 (m, 4H), 1.50 (s, 9H), 1.05 (s, 9H), 0.30 (s, 6H); MS (APCI$^+$) 648.7 [MH$^+$].

Reaction of tert-butyl 4-[4-[4-(tert-butyldimethylsilyloxy)-2-(difluoromethyl)-1H-benzimidazol-1-yl]-6-(4-morpholinyl)-1,3,5-triazin-2-yl]piperazine-1-carboxylate from the previous step with tetrabutylammonium fluoride in THF at 0° C. gave a quantitative yield of tert-butyl 4-[4-[2-(difluoromethyl)-4-hydroxy-1H-benzimidazol-1-yl]-6-(4-morpholinyl)-1,3,5-triazin-2-yl]piperazine-1-carboxylate: mp (MeOH) 228-230° C.; $^1$H NMR (CDCl$_3$) δ 7.81 (d, J=8.4 Hz, 1H), 7.55 (t, $J_{HF}$=53.6 Hz, 1H), 7.32 (t, J=8.2 Hz, 1H), 6.90 (d, J=8.0 Hz, 1H), 3.88 (m, 8H), 3.79 (m, 4H), 3.53 (m, 4H), 1.50 (s, 9H); MS (APCI$^+$) 534.1 [MH$^+$]; Anal. Calcd. for $C_{24}H_{30}F_2N_8O_4$: C, 54.1; H, 5.7; N, 21.0. Found: C, 54.15; H, 5.8; N, 21.3%.

A mixture of 0.60 g (1.1 mmol) of tert-butyl 4-[4-[2-(difluoromethyl)-4-hydroxy-1H-benzimidazol-1-yl]-6-(4-morpholinyl)-1,3,5-triazin-2-yl]piperazine-1-carboxylate, 0.47 g (3.3 mmol) of 3-bromo-1-propanol, and 0.80 g (5.5 mmol) of powdered $K_2CO_3$ in 20 mL dry DMF was stirred at room temperature for 8 hrs. Dilution with water gave 0.66 g, (99% yield) of tert-butyl 4-[4-[2-(difluoromethyl)-4-(3-hydroxypropoxy)-1H-benzimidazol-1-yl]-6-(4-morpholinyl)-1,3,5-triazin-2-yl]-1-piperazinecarboxylate: $^1$H NMR (CDCl$_3$) δ 7.94 (dd, J=8.4. 0.7 Hz, 1H), 7.49 (t, $J_{HF}$=53.4 Hz, 1H), 7.34 (t, J=8.1 Hz, 1H), 6.92 (dd, J=8.0, 0.6 Hz, 1H), 4.47 (t, J=5.9 Hz, 2H), 3.98 (t, J=5.4 Hz, 2H), 3.87 (m, 8H), 3.79 (m, 4H), 3.54 (m, 4H), 3.30 (m, exchangeable with D$_2$O, 1H), 2.14 (pentet, J=5.8 Hz, 2H), 1.50 (s, 9H).

A mixture of tert-butyl 4-[4-[2-(difluoromethyl)-4-(3-hydroxypropoxy)-1H-benzimidazol-1-yl]-6-(4-morpholinyl)-1,3,5-triazin-2-yl]-1-piperazinecarboxylate from the previous step and 0.34 g (3.3 mmol) of Et$_3$N in 20 mL of THF was cooled to 0° C. and 0.32 g (2.8 mmol) of methanesulfonyl chloride was added dropwise. After 1 hr, 6 g of 40% aqueous Me$_2$NH was added, and the resulting mixture was stirred at room temperature for 36 hrs. The THF was removed under vacuum and the residue was diluted with water and extracted into CH$_2$Cl$_2$. Drying and removal of the solvent gave tert-butyl 4-[4-{2-(difluoromethyl)-4-[3-(dimethylamino)propoxy]-1H-benzimidazol-1-yl}-6-(4-morpholinyl)-1,3,5-triazin-2-yl]-1-piperazinecarboxylate as an oil: $^1$H NMR (CDCl$_3$) δ 7.87 (dd, J=8.4. 0.6 Hz, 1H), 7.48 (t, $J_{HF}$=53.5 Hz, 1H), 7.33 (t, J=8.2 Hz, 1H), 6.85 (d, J=7.8 Hz, 1H), 4.31 (t, J=6.7 Hz, 2H), 3.87 (m, 8H), 3.79 (m, 4H), 3.53 (m, 4H), 2.51 (t, J=7.2 Hz, 2H), 2.26 (s, 6H), 2.13 (pentet, J=7.0 Hz, 2H), 1.50 (s, 9H).

Treatment of tert-butyl 4-[4-{2-(difluoromethyl)-4-[3-(dimethylamino)propoxy]-1H-benzimidazol-1-yl}-6-(4-morpholinyl)-1,3,5-triazin-2-yl]-1-piperazinecarboxylate from the previous step with TFA in CH$_2$Cl$_2$ gave N-[3-({2-(difluoromethyl)-1-[4-(4-morpholinyl)-6-(1-piperazinyl)-1,3,5-triazin-2-yl]-1H-benzimidazol-4-yl}oxy)propyl]-N,N-dimethylamine as a solid: $^1$H NMR (CDCl$_3$) δ 7.89 (dd, J=8.4. 0.7 Hz, 1H), 7.50 (t, $J_{HF}$=53.5 Hz, 1H), 7.31 (t, J=8.2 Hz, 1H), 6.84 (d, J=8.0 Hz, 1H), 4.32 (t, J=6.8 Hz, 2H), 3.86 (m, 8H), 3.78 (m, 4H), 2.95 (m, 4H), 2.53 (t, J=7.2 Hz, 2H), 2.27 (s, 6H), 2.13 (pentet, J=6.9 Hz, 2H).

A stirred mixture of 297 mg (0.57 mmol) of N-[3-({2-(difluoromethyl)-1-[4-(4-morpholinyl)-6-(1-piperazinyl)-1,3,5-triazin-2-yl]-1H-benzimidazol-4-yl}oxy)propyl]-N,N-dimethylamine and 1 g of powdered $K_2CO_3$ in CH$_2$Cl$_2$ was cooled to 0° C. and 0.4 g of methanesulphonyl chloride was added. The mixture was allowed to warm to room temperature, and after 2 hrs it was diluted with water and the organic layer was separated and dried. Chromatography on alumina, eluting first with CH$_2$Cl$_2$/EtOAc (1:1) and then with EtOAc gave 200 mg (59% yield) of N-[3-({2-(difluoromethyl)-1-[4-[4-(methylsulfonyl)-1-piperazinyl]-6-(4-morpholinyl)-1,3,5-triazin-2-yl]-1H-benzimidazol-4-yl}oxy)propyl]-N,N-dimethylamine: $^1$H NMR (CDCl$_3$) δ 7.84 (dd, J=8.4. 0.6 Hz, 1H), 7.43 (t, $J_{HF}$=53.5 Hz, 1H), 7.33 (t, J=8.2 Hz, 1H), 6.86 (d, J=7.7 Hz, 1H), 4.32 (t, J=6.8 Hz, 2H), 4.02 (m, 4H), 3.88 (m, 4H), 3.78 (m, 4H), 3.33 (m, 4H), 2.81 (s, 3H), 2.54 (t, J=7.2 Hz, 2H), 2.28 (s, 6H), 2.14 (pentet, J=7.0 Hz, 2H); Hydrochloride: mp (EtOH) 243-247° C.; Anal. Calcd. for $C_{25}H_{36}ClF_2N_9O_4S·1.5H_2O$: C, 45.6; H, 6.0; Cl, 5.4; N, 19.1. Found: C, 45.5; H, 6.1; Cl, 5.2; N, 19.2%.

Example 5

Synthesis of 4-[2-(difluoromethyl)-4-methoxy-1H-benzimidazol-1-yl]-N-methyl-N-[1-(methylsulfonyl)-4-piperidinyl]-6-(4-morpholinyl)-1,3,5-triazin-2-amine

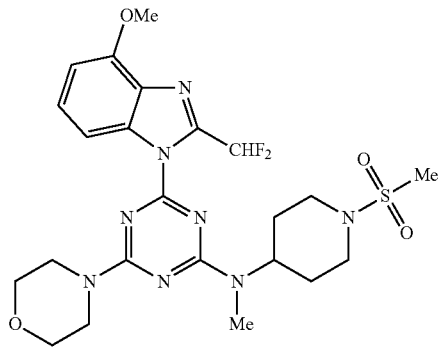

A mixture of 0.397 g (1 mmol) of 1-[4-chloro-6-(4-morpholinyl)-1,3,5-triazin-2-yl]-2-(difluoromethyl)-4-methoxy-1H-benzimidazole (Example 2), 0.24 g (1.2 mmol) of tert-butyl 4-amino-1-piperidinecarboxylate, and 0.194 g (1.5 mmol) of DIPEA in 25 mL of THF was stirred at room temperature overnight. Dilution with water and extraction with CH$_2$Cl$_2$, followed by chromatography on silica eluting with CH$_2$Cl$_2$/EtOAc (4:1) gave 0.51 g (91% yield) of tert-butyl 4-{[4-[2-(difluoromethyl)-4-methoxy-1H-benzimidazol-1-yl]-6-(4-morpholinyl)-1,3,5-triazin-2-yl]amino}-1-piperidinecarboxylate: mp (hexanes/CH$_2$Cl$_2$) 142-145° C.; $^1$H NMR (CDCl$_3$) (rotamer mixture; ratio ca. 3:2) δ 7.96 and 7.95 (2d, J=8.3 and 7.9 Hz, 1H), 7.54 and 7.52 (2t, $J_{HF}$=53.6 Hz, 1H), 7.34 (br t, J=8.1 Hz, 1H), 6.81 (t, J=6.9 Hz, 1H), 5.22 and 5.17 (2d, J=7.4 and 7.6 Hz, exchangeable with D$_2$O, 1H), 4.10 (m, 3H), 4.05 (s, 3H), 3.87 (m, 4H), 3.78 (m, 4H), 2.93 (t, J=12.1 Hz, 2H) 2.06 (m, 2H), 1.48 (s, 9H), 1.43 (m, 2H); Anal. Calcd. for $C_{26}H_{34}F_2N_8O_4$: C, 55.7; H, 6.1; N, 20.0. Found: C, 55.6; H, 6.2; N, 20.0%.

A solution of 0.30 g (5.4 mmol) of tert-butyl 4-{[4-[2-(difluoromethyl)-4-methoxy-1H-benzimidazol-1-yl]-6-(4-morpholinyl)-1,3,5-triazin-2-yl]amino}-1-piperidinecarboxylate in 10 mL of DMF was treated sequentially with excess NaH and iodomethane at room temperature for 2 hrs. Dilution with water and workup in CH$_2$Cl$_2$, followed by chromatography on silica eluting with CH$_2$Cl$_2$/EtOAc (4:1) gave 0.286 g (93% yield) of tert-butyl 4-[[4-[2-(difluoromethyl)-4-methoxy-1H-benzimidazol-1-yl]-6-(4-morpholinyl)-1,3,5-triazin-2-yl](methyl)amino]-1-piperidinecarboxylate: mp (MeOH/CH$_2$Cl$_2$) 200-202° C.; $^1$H NMR (CDCl$_3$) (rotamer mixture; ratio ca. 3:2) δ 7.98 and 7.91 (2d, J=8.4 Hz, 1H), 7.57 and 7.47 (2t, J$_{HF}$=53.5 Hz, 1H), 7.34 (t, J=8.2 Hz, 1H), 6.81 (d, J=7.9 Hz, 1H), 4.82 and 4.70 (2m, 1H), 4.29 (m, 2H), 4.05 (s, 3H), 3.88 (m, 4H), 3.79 (m, 4H), 3.10 and 3.05 (2s, 3H), 2.84 (m, 2H), 1.73 (m, 4H), 1.49 (s, 9H); Anal. Calcd. for C$_{27}$H$_{36}$F$_2$N$_8$O$_4$: C, 56.4; H, 6.3; N, 19.5. Found: C, 56.6; H, 6.4; N, 19.6%.

Treatment of 0.173 g (0.3 mmol) of tert-butyl 4-[[4-[2-(difluoromethyl)-4-methoxy-1H-benzimidazol-1-yl]-6-(4-morpholinyl)-1,3,5-triazin-2-yl](methyl)amino]-1-piperidinecarboxylate with TFA in CH$_2$Cl$_2$ at room temperature gave 0.143 g (100% yield) of crude 4-[2-(difluoromethyl)-4-methoxy-1H-benzimidazol-1-yl]-N-methyl-6-(4-morpholinyl)-N-(4-piperidinyl)-1,3,5-triazin-2-amine: $^1$H NMR (CDCl$_3$) (rotamers; ratio ca. 3:2) δ 7.99 and 7.94 (2d, J=8.4 Hz, 1H), 7.59 and 7.52 (2t, J$_{HF}$=53.6 Hz, 1H), 7.34 (t, J=8.2 Hz, 1H), 6.81 (d, J=8.0 Hz, 1H), 4.80-4.63 (m, 1H), 4.06 (s, 3H), 3.88 (m, 4H), 3.79 (m, 4H), 3.25 (m, 2H), 3.13 and 3.09 (2s, 3H), 2.88-2.73 (m, 2H), 1.98-1.72 (m, 4H), 1.49 (s, 9H).

Reaction of 4-[2-(difluoromethyl)-4-methoxy-1H-benzimidazol-1-yl]-N-methyl-6-(4-morpholinyl)-N-(4-piperidinyl)-1,3,5-triazin-2-amine from the previous step with methanesulphonyl chloride as in Example 4 gave 4-[2-(difluoromethyl)-4-methoxy-1H-benzimidazol-1-yl]-N-methyl-N-[1-(methylsulfonyl)-4-piperidinyl]-6-(4-morpholiny)-1,3,5-triazin-2-amine in 56% yield: mp (CH$_2$Cl$_2$/MeOH) 190-192° C.; $^1$H NMR (DMSO-d$_6$) (rotamers) δ 7.97 and 7.89 (2d, J=8.3, 8.5 Hz, 1H), 7.69 and 7.74 (2t, J$_{HF}$=52.9 Hz, 1H), 7.46-7.39 (m, 1H), 6.95 (d, J=7.8 Hz, 1H), 4.69-4.61 (m, 1H), 3.98 (s, 3H), 3.80-3.69 (m, 10H), 3.09 and 2.95 (2s, 3H), 2.93-2.92 (2s, 3H), 2.92-2.78 (m, 2H), 1.93-1.67 (m, 4H); Anal. Calcd. for C$_{23}$H$_{30}$F$_2$N$_8$O$_4$S: C, 50.0; H, 5.5; N, 20.3. Found: C, 49.5; H, 5.3; N, 20.0%.

Example 6

Synthesis of 2-[2-(difluoromethyl)-4-methoxy-1H-benzimidazol-1-yl]-N-methyl-N-[1-(methylsulfonyl)-4-piperidinyl]-6-(4-morpholinyl)-4-pyrimidinamine

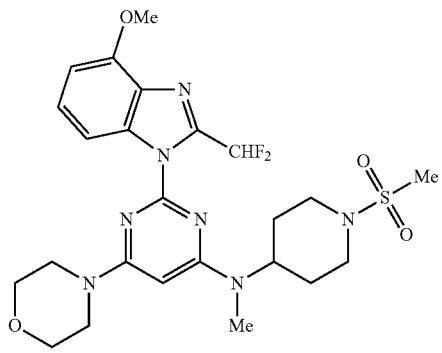 [SMILES: COc1cccc2c1nc(C(F)F)n2-c1nc(N2CCOCC2)cc(N(C)C2CCN(S(C)(=O)=O)CC2)n1]

A mixture of 95 mg (2 mmol) of 2-[2-(difluoromethyl)-4-methoxy-1H-benzimidazol-1-yl]-N-methyl-6-(4-morpholinyl)-N-(4-piperidinyl)-4-pyrimidinamine and 61 mg (6 mmol) of Et$_3$N in 15 mL THF was cooled to 0° C. and 46 mg (4 mmol) of methanesulphonyl chloride was added. The stirred mixture was allowed to warm to room temperature, and after 2 hrs it was diluted with water to give a precipitate of 98 mg (89% yield) of 2-[2-(difluoromethyl)-4-methoxy-1H-benzimidazol-1-yl]-N-methyl-N-[1-(methylsulfonyl)-4-piperidinyl]-6-(4-morpholinyl)-4-pyrimidinamine: mp (MeOH) 191-193° C.; $^1$H NMR (CDCl$_3$) δ 7.77 (dd, J=8.4. 0.6 Hz, 1H), 7.37 (t, J$_{HF}$=53.4 Hz, 1H), 7.31 (t, J=8.2 Hz, 1H), 6.79 (d, J=7.6 Hz, 1H), 5.40 (s, 1H), 4.96 (m, 1H), 4.05 (s, 3H), 3.99-3.93 (m, 2H), 3.83 (m, 4H), 3.64 (m, 4H), 2.90 (s, 3H), 2.82 (s, 3H), 2.81 (dt, J=12.0, 2.4 Hz, 2H), 1.91 (dq J=12.3, 4.3 Hz, 2H), 1.85-1.76 (m, 2H); Anal. Calcd. for C$_{24}$H$_{31}$F$_2$N$_7$O$_4$S: C, 52.3; H, 5.7; N, 17.8. Found: C, 52.5; H, 5.7; N, 17.9%.

Example 7

Synthesis of N-[3-({2-(difluoromethyl)-1-[4-{[1-(methylsulfonyl)-4-piperidinyl]oxy}-6-(4-morpholinyl)-1,3,5-triazin-2-yl]-1H-benzimidazol-4-yl}oxy)propyl]-N,N-dimethylamine

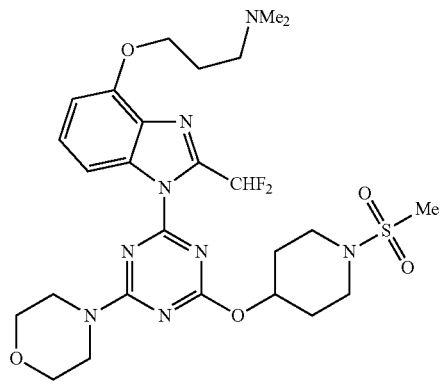 [SMILES: CN(C)CCCOc1cccc2c1nc(C(F)F)n2-c1nc(OC2CCN(S(C)(=O)=O)CC2)nc(N2CCOCC2)n1]

A mixture of 0.60 g (1.1 mmol) of tert-butyl 4-[4-[2-(difluoromethyl)-4-hydroxy-1H-benzimidazol-1-yl]-6-(4-morpholinyl)-1,3,5-triazin-2-yl]piperazine-1-carboxylate (Example 5), 0.47 g (3.3 mmol) of 3-bromo-1-propanol, and 0.80 g (5.5 mmol) of powdered K$_2$CO$_3$ in 20 mL dry DMF was stirred at room temperature for 8 hrs. Dilution with water, filtration, and dry gave 0.66 g (99% yield) of tert-butyl 4-[4-[2-(difluoromethyl)-4-(3-hydroxypropoxy)-1H-benzimidazol-1-yl]-6-(4-morpholinyl)-1,3,5-triazin-2-yl]-1-piperazinecarboxylate: $^1$H NMR (CDCl$_3$) δ 7.94 (dd, J=8.4. 0.7 Hz, 1H), 7.49 (t, J$_{HF}$=53.4 Hz, 1H), 7.34 (t, J=8.1 Hz, 1H), 6.92 (dd, J=8.0, 0.6 Hz, 1H), 4.47 (t, J=5.9 Hz, 2H), 3.98 (t, J=5.4 Hz, 2H), 3.87 (m, 8H), 3.79 (m, 4H), 3.54 (m, 4H), 3.30 (m, exchangeable with D$_2$O, 1H), 2.14 (pentet, J=5.8 Hz, 2H), 1.50 (s, 9H).

A mixture of tert-butyl 4-[4-[2-(difluoromethyl)-4-(3-hydroxypropoxy)-1H-benzimidazol-1-yl]-6-(4-morpholinyl)-1,3,5-triazin-2-yl]-1-piperazinecarboxylate from the previous step and 0.34 g (3.3 mmol) of Et$_3$N in 20 mL of THF was cooled to 0° C. and 0.32 g (2.8 mmol) of methanesulfonyl chloride was added dropwise. After 1 hr, 6 g of 40% aqueous Me$_2$NH was added, and the resulting mixture was stirred at room temperature for 36 hrs. The THF was removed under vacuum and the residue was diluted with water and extracted into CH$_2$Cl$_2$. Drying and removal of the solvent gave tert-butyl 4-[4-{2-(difluoromethyl)-4-[3-(dimethylamino)propoxy]-1H-benzimidazol-1-yl}-6-(4-morpholinyl)-1,3,5-triazin-2-yl]-1-piperazinecarboxylate as an oil: $^1$H NMR (CDCl$_3$) δ 7.87 (dd, J=8.4. 0.6 Hz, 1H), 7.48 (t, J$_{HF}$=53.5 Hz, 1H), 7.33 (t, J=8.2 Hz, 1H), 6.85 (d, J=7.8 Hz, 1H), 4.31 (t, J=6.7 Hz, 2H), 3.87 (m, 8H), 3.79 (m, 4H), 3.53 (m, 4H), 2.51 (t, J=7.2 Hz, 2H), 2.26 (s, 6H), 2.13 (pentet, J=7.0 Hz, 2H), 1.50 (s, 9H).

Treatment of tert-butyl 4-[4-{2-(difluoromethyl)-4-[3-(dimethylamino)propoxy]-1H-benzimidazol-1-yl}-6-(4-morpholinyl)-1,3,5-triazin-2-yl]-1-piperazinecarboxylate from the previous step with TFA in CH$_2$Cl$_2$ gave N-[3-({2-(difluoromethyl)-1-[4-(4-morpholinyl)-6-(1-piperazinyl)-1,3,5-triazin-2-yl]-1H-benzimidazol-4-yl}oxy)propyl]-N,N-dimethylamine as a solid: $^1$H NMR (CDCl$_3$) δ 7.89 (dd, J=8.4. 0.7 Hz, 1H), 7.50 (t, $J_{HF}$=53.5 Hz, 1H), 7.31 (t, J=8.2 Hz, 1H), 6.84 (d, J=8.0 Hz, 1H), 4.32 (t, J=6.8 Hz, 2H), 3.86 (m, 8H), 3.78 (m, 4H), 2.95 (m, 4H), 2.53 (t, J=7.2 Hz, 2H), 2.27 (s, 6H), 2.13 (pentet, J=6.9 Hz, 2H).

Reaction of N-[3-({2-(difluoromethyl)-1-[4-(4-morpholinyl)-6-(1-piperazinyl)-1,3,5-triazin-2-yl]-1H-benzimidazol-4-yl}oxy)propyl]-N,N-dimethylamine from the previous step with methanesulphonyl chloride and powdered K$_2$CO$_3$ in CH$_2$Cl$_2$, followed by chromatography on alumina eluting with CH$_2$Cl$_2$/EtOAc (1:1) g, and acidification with HCl in MeOH gave N-[3-({2-(difluoromethyl)-1-[4-{[1-(methylsulfonyl)-4-piperidinyl]oxy}-6-(4-morpholinyl)-1,3,5-triazin-2-yl]-1H-benzimidazol-4-yl}oxy)propyl]-N,N-dimethylamine hydrochloride in 71% yield: $^1$H NMR (DMSO-d$_6$) δ 10.07 (br s, exchangeable with D$_2$O, 1H), 7.99 (d, J=8.2 Hz, 1H), 7.73 (t, $J_{HF}$=52.7 Hz, 1H), 7.46 (t, J=8.2 Hz, 1H), 7.02 (d, J=8.0 Hz, 1H), 5.27-5.21 (m, 1H), 4.34 (t, J=6.1 Hz, 2H), 3.86-3.85 (m, 4H), 3.74-3.71 (m, 4H), 3.44-3.38 (m, 2H), 3.20-3.14 2.93 (s, 3H), 2.82 (s, 6H), (m 2H), 2.28-2.26 (m, 2H), 2.15-2.10 (m, 2H); Anal. Calcd. for C$_{26}$H$_{29}$ClF$_2$N$_8$O$_5$S.0.75H$_2$O: C, 47.3; H, 5.9; Cl, 5.4; N, 17.0. Found: C, 47.3; H, 5.8; Cl, 5.4; N, 17.0%.

Example 8

Synthesis of 6-[2-(difluoromethyl)-4-methoxy-1H-benzimidazol-1-yl]-1-[1-(methylsulfonyl)-4-piperidinyl]-4-(4-morpholinyl)-1H-pyrazolo[3,4-d]pyrimidine

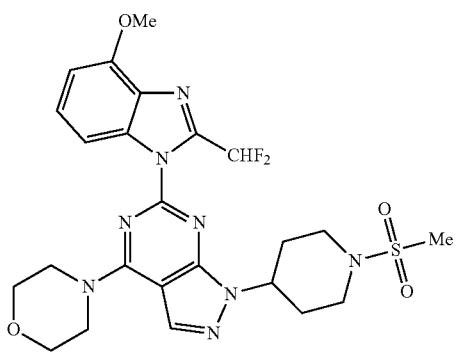 [SMILES: COc1cccc2c1nc(C(F)F)n2-c1nc(N2CCOCC2)c2cnn(C3CCN(S(C)(=O)=O)CC3)c2n1]

A stirred mixture of 0.44 g (2.2 mmol) of 2-(difluoromethyl)-4-methoxy-1H-benzimidazole, 0.47 g (1.1 mmol) of tert-butyl 4-[6-chloro-4-(4-morpholinyl)-1H-pyrazolo[3,4-d]pyrimidin-1-yl]-1-piperidinecarboxylate (WO 2008/115974), and 0.61 g (4.4 mmol) of powdered K$_2$CO$_3$ in 10 mL of DMSO was heated at 160° C. for 20 hrs. After cooling, the mixture was diluted with water, and the precipitate was collected by filtration, washed with water, and dried. Chromatography on silica eluting with CH$_2$Cl$_2$/EtOAc (17:3) gave 0.20 g (31% yield) of tert-butyl 4-[6-[2-(difluoromethyl)-4-methoxy-1H-benzimidazol-1-yl]-4-(4-morpholinyl)-1H-pyrazolo[3,4-d]pyrimidin-1-yl]-1-piperidinecarboxylate: mp (MeOH) 245-247° C.; $^1$H NMR (CDCl$_3$) δ 7.99 (s, 1H), 7.84 (dd, J=8.4, 0.6 Hz, 1H), 7.47 (t, J=53.6 Hz, 1H), 7.37 (t, J=8.2 Hz, 1H), 6.83 (d, J=7.8 Hz, 1H), 4.87 (tt, J=11.4, 4.1 Hz, 1H), 4.32 (m, 2H), 4.07 (s, 3H), 4.06 (m, 4H), 3.91 (m, 4H), 2.99 (m, 2H), 2.23 (dq, J=12.3, 4.5 Hz, 2H), 2.02 (m, 2H), 1.49 (s, 9H); Anal. Calcd. for C$_{28}$H$_{34}$F$_2$N$_8$O$_4$: C, 57.5; H, 5.9; N, 19.2. Found: C, 57.2; H, 6.0; N, 19.0%.

Treatment of tert-butyl 4-[6-[2-(difluoromethyl)-4-methoxy-1H-benzimidazol-1-yl]-4-(4-morpholinyl)-1H-pyrazolo[3,4-d]pyrimidin-1-yl]-1-piperidinecarboxylate from the previous step with TFA in CH$_2$Cl$_2$ at room temperature gave 6-[2-(difluoromethyl)-4-methoxy-1H-benzimidazol-1-yl]-4-(4-morpholinyl)-1-(4-piperidinyl)-1H-pyrazolo[3,4-d]pyrimidine in 97% yield: $^1$H NMR (CDCl$_3$) δ 8.00 (s, 1H), 7.86 (dd, J=8.4, 0.6 Hz, 1H), 7.51 (t, $J_{HF}$=53.6 Hz, 1H), 7.38 (t, J=8.2 Hz, 1H), 6.83 (d, J=7.7 Hz, 1H), 4.83 (tt, J=11.6, 4.1 Hz, 1H), 4.07 (s, 3H), 4.06 (m, 4H), 3.91 (m, 4H), 3.31 (m, 2H), 2.87 (dt, J=12.7, 2.5 Hz, 2H), 2.21 (dq, J=12.3, 4.2 Hz, 2H), 2.04 (m, 2H).

A mixture of 75 mg (155 mmol) of 6-[2-(difluoromethyl)-4-methoxy-1H-benzimidazol-1-yl]-4-(4-morpholinyl)-1-(4-piperidinyl)-1H-pyrazolo[3,4-d]pyrimidine and 65 mg (465 mmol) of powdered K$_2$CO$_3$ in CH$_2$Cl$_2$ was cooled to 0° C., and 27 mg (233 mmol) of methanesulfonyl chloride was added. The mixture was allowed to warm to room temperature, and after 2 hrs it was diluted with water and washed with aq. NH$_3$. The organic layer was dried (Na$_2$SO$_4$) and concentrated under vacuum to give 80 mg (92% yield) of 6-[2-(difluoromethyl)-4-methoxy-1H-benzimidazol-1-yl]-1-[1-(methylsulfonyl)-4-piperidinyl]-4-(4-morpholinyl)-1H-pyrazolo[3,4-d]pyrimidine: mp (MeOH) 273-276° C.; $^1$H NMR (CDCl$_3$) δ 8.01 (s, 1H), 7.82 (dd, J=8.4, 0.6 Hz, 1H), 7.46 (t, $J_{HF}$=53.6 Hz, 1H), 7.38 (t, J=8.2 Hz, 1H), 6.83 (d, J=7.8 Hz, 1H), 4.85 (tt, J=11.1, 4.1 Hz, 1H), 4.07 (s, 3H), 4.06 (m, 4H), 4.02 (m, 1H), 3.99 (m, 1H), 3.92 (m, 4H), 3.02 (dt, J=12.2, 2.5 Hz, 2H), 2.88 (s, 3H), 2.44 (dq, J=11.6, 4.2 Hz, 2H), 2.17 (m, 2H); Anal. Calcd. for C$_{24}$H$_{28}$F$_2$N$_8$O$_4$S: C, 51.2; H, 5.0; N, 19.9. Found: C, 50.85; H, 5.0; N, 19.7%.

Example 9

Synthesis of 2-(difluoromethyl)-4-methoxy-1-[4-[4-(methylsulfonyl)-1-piperazinyl]-6-(4-morpholinyl)-1,3,5-triazin-2-yl]-1H-benzimidazol-6-ylamine

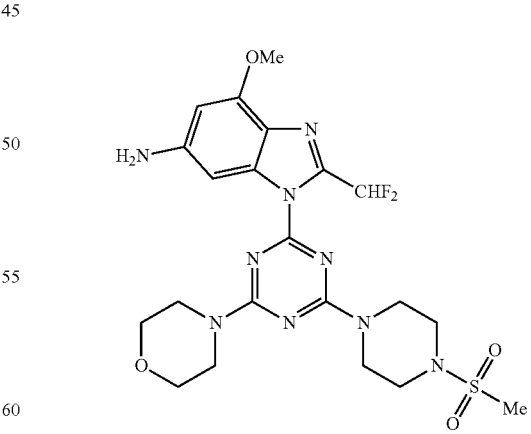

A mixture of 2,3-diamino-5-nitroanisole (Horner et al., Annalen 1953, 579, 212) (1.10 g, 6 mmol) and difluoroacetic acid (2.31 g, 24 mmol) in polyphosphoric acid (PPA) (50 g) was heated at 130° C. in an oil bath for 1 hr. The hot solution was poured into water, and the pH was adjusted to neutral with cooling to give 2-(difluoromethyl)-4-methoxy-6-nitro-1H-benzimidazole (1.33 g, 91%): mp (EtOH/H$_2$O) 192-194° C.; $^1$H NMR (DMSO-d$_6$) δ 814.18 (br, exchangeable with D$_2$O, 1H), 8.18 (br, 1H), 7.65 (dd, J=1.4 Hz, 1H), 7.30 (t, J$_{HF}$=52.9 Hz, 1H), 4.07 (s, 3H); Anal. Calcd. for C$_9$H$_7$F$_2$N$_3$O$_3$: C, 44.45; H, 2.9; N, 17.3. Found: C, 44.75; H, 3.0; N, 17.3%.

A solution of 2-(difluoromethyl)-4-methoxy-6-nitro-1H-benzimidazole (1.22 g, 5 mmol) in MeOH (50 mL) was hydrogenated over 10% Pd on C (50 mg). After filtration to remove the catalyst Pd/C, the solution was evaporated to dryness. The residue was combined with di-tert-butyl dicarbonate (3.2 g, 15 mmol) in dioxane (20 mL), and the mixture was heated under reflux for 5 hrs. The solvent was removed under vacuum and the residue was dissolved in MeOH (30 mL) containing aqueous NaOH (2 M, 12.5 mL, 5 equiv.). The mixture was stirred at room temperature for 1 hr, neutralized with HOAc, and evaporated to dryness. The residue was extracted with EtOAc, washed with NaHCO$_3$ solution, and dried over Na$_2$SO$_4$. Chromatography on silica eluting with CH$_2$Cl$_2$/EtOAc (9:1) gave 1.54 g (98% yield) of tert-butyl 2-(difluoromethyl)-4-methoxy-1H-benzimidazol-6-yl-carbamate: mp (i-Pr$_2$O) 189-191° C.; $^1$H NMR (DMSO-d$_6$) δ13.0 (br, exchangeable with D$_2$O, 1H), 9.31 (br s, exchangeable with D$_2$O, 1H), 7.42 (br s, 1H), 7.15 (t, J$_{HF}$=53.4 Hz, 1H), 6.90 (br, 1H), 3.90 (s, 3H), 1.49 (s, 9H); Anal. Calcd. For C$_{14}$H$_{17}$F$_2$N$_3$O$_3$: C, 53.7; H, 5.5; N, 13.4. Found: C, 53.9; H, 5.6; N, 13.4%.

A mixture of tert-butyl 2-(difluoromethyl)-4-methoxy-1H-benzimidazol-6-yl-carbamate (0.47 g, 1.5 mmol), 2,4-dichloro-6-(4-morpholinyl)-1,3,5-triazine (0.35 g, 1.5 mmol), and powdered K$_2$CO$_3$ (0.83 g, 6 mmol) in DMF (10 mL) was stirred at room temperature for 30 min. The reaction mixture was then diluted with water. The resulting precipitate was collected, washed with water and then MeOH, and dried to give 0.45 g (59% yield) of tert-butyl 1-[4-chloro-6-(4-morpholinyl)-1,3,5-triazin-2-yl]-2-(difluoromethyl)-4-methoxy-1H-benzimidazol-6-yl-carbamate: mp (CH$_2$Cl$_2$/MeOH)>300° C.; $^1$HNMR (CDCl$_3$) δ 8.45 (d, J=0.6 Hz, 1H), 7.57 (t, J$_{HF}$=53.6 Hz, 1H), 6.67 (br, exchangeable with D$_2$O, 1H), 6.63 (d, J=0.9 Hz, 1H), 4.11 (m, 2H), 4.02 (s, 3H), 3.97 (m, 2H), 3.88 (m, 2H), 3.82 (m, 2H), 1.52 (s, 9H); Anal. Calcd. for C$_{21}$H$_{24}$ClF$_2$N$_7$O$_4$: C, 49.3; H, 4.7; N, 19.15. Found: C, 49.4; H, 4.8; N, 19.2%.

A mixture of tert-butyl 1-[4-chloro-6-(4-morpholinyl)-1,3,5-triazin-2-yl]-2-(difluoromethyl)-4-methoxy-1H-benzimidazol-6-yl-carbamate (0.333 g, 0.65 mmol), 1-(methylsulfonyl)piperazine (0.32 g, 2 mmol), and DIPEA (0.17 g, 1.3 mmol) in THF (50 mL) was heated under reflux for 3 hrs. The solution was concentrated and then diluted with 100 mL of water containing 1% HOAc to give a solid, which was collected and dried. Chromatography on silica eluting with CH$_2$Cl$_2$/EtOAc (4:1), followed by recrystallization from MeOH, gave 0.33 g (79% yield) of tert-butyl 2-(difluoromethyl)-4-methoxy-1-[4-[4-(methylsulfonyl)-1-piperazinyl]-6-(4-morpholinyl)-1,3,5-triazin-2-yl]-1H-benzimidazol-6-ylcarbamate: mp 223° C. (decomp.); $^1$HNMR (CDCl$_3$) δ 8.63 (br s, 1H), 7.44 (t, J$_{HF}$=53.6 Hz, 1H), 6.62 (br s, exchangeable with D$_2$O, 1H), 6.35 (d, J=1.7 Hz, 1H), 4.09-3.80 (m, 15H), 3.35 (m, 4H), 2.80 (s, 3H), 1.52 (s, 9H); Anal. Calcd. for C$_{26}$H$_{35}$F$_2$N$_9$O$_6$S: C, 48.8; H, 5.5; N, 19.7. Found: C, 48.9; H, 5.6; N, 19.9%.

A mixture of tert-butyl 2-(difluoromethyl)-4-methoxy-1-[4-[4-(methylsulfonyl)-1-piperazinyl]-6-(4-morpholinyl)-1,3,5-triazin-2-yl]-1H-benzimidazol-6-ylcarbamate (0.20 g, 0.31 mmol) and TFA (5 mL) in CH$_2$Cl$_2$ (20 mL) was stirred at room temperature for 2 hrs. The mixture was diluted with CH$_2$Cl$_2$ (100 mL) and water (100 mL), and the aqueous layer was made basic with aqueous NH$_3$. The organic layer was dried and concentrated under vacuum. Recrystallization of the residue from CH$_2$Cl$_2$/MeOH gave 0.145 g (86% yield) of 2-(difluoromethyl)-4-methoxy-1-[4-[4-(methylsulfonyl)-1-piperazinyl]-6-(4-morpholinyl)-1,3,5-triazin-2-yl]-1H-benzimidazol-6-ylamine: mp 280-283° C.; $^1$H NMR (CDCl$_3$) δ 7.59 (t, J$_{HF}$=53.4 Hz, 1H), 7.05 (d, J=1.7 Hz, 1H), 6.26 (d, J=1.7 Hz, 1H), 5.45 (s, exchangeable with D$_2$O, 2H), 3.93 (m, 4H), 3.87 (s, 3H), 3.80 (m, 4H), 3.69 (m, 4H), 3.24 (m, 4H), 2.91 (s, 3H); Anal. Calcd. for C$_{21}$H$_{27}$F$_2$N$_9$O$_4$S: C, 46.75; H, 5.0; N, 23.4. Found: C, 47.0; H, 5.2; N, 23.4%.

Example 10

Synthesis of N-[2-({4-[4-[2-(difluoromethyl)-4-methoxy-1H-benzimidazol-1-yl]-6-(4-morpholinyl)-1,3,5-triazin-2-yl]-1-piperazinyl}sulfonyl)ethyl]-N,N-dimethylamine

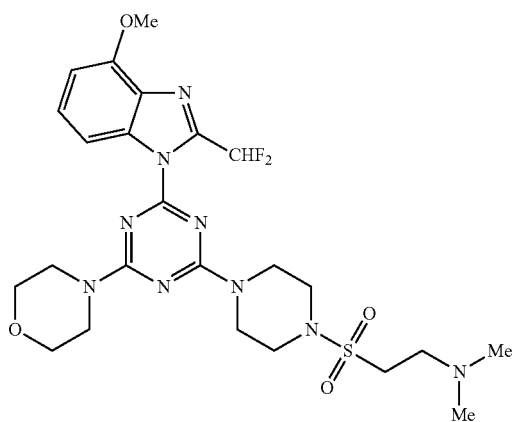 [SMILES: COc1cccc2c1nc(C(F)F)n2-c1nc(N2CCOCC2)nc(N2CCN(S(=O)(=O)CCN(C)C)CC2)n1]

A mixture of 2-(difluoromethyl)-4-methoxy-1-{4-(4-morpholinyl)-6-[4-(vinylsulfonyl)-1-piperazinyl]-1,3,5-triazin-2-yl}-1H-benzimidazole (Example 3) (0.536 g, 1 mmol) and 40% aqueous dimethylamine (10 mL) in THF (200 mL) was warmed gently until a clear solution was obtained. After 15 min, the THF was removed under vacuum and the residue was diluted with water to give N-[2-({4-[4-[2-(difluoromethyl)-4-methoxy-1H-benzimidazol-1-yl]-6-(4-morpholinyl)-1,3,5-triazin-2-yl]-1-piperazinyl}sulfonyl)ethyl]-N,N-dimethylamine: $^1$HNMR (CDCl$_3$) δ 7.86 (dd, J=8.4, 0.6 Hz, 1H), 7.45 (t, J$_{HF}$=53.5 Hz, 1H), 7.36 (t, J=8.2 Hz, 1H), 6.82 (d, J=7.8 Hz, 1H), 4.05 (s, 3H), 4.00 (m, 4H), 3.89 (m, 4H), 3.79 (m, 4H), 3.39 (m, 4H), 3.11 (dd, J=8.1, 6.4 Hz, 2H), 2.78 (dd, J=8.1, 6.4 Hz, 2H), 2.26 (s, 6H).

To a suspension of N-[2-({4-[4-[2-(difluoromethyl)-4-methoxy-1H-benzimidazol-1-yl]-6-(4-morpholinyl)-1,3,5-triazin-2-yl]-1-piperazinyl}sulfonyl)ethyl]-N,N-dimethylamine from the previous step in MeOH (100 mL) was added a slight excess of 1.25 M HCl in MeOH (0.45 mL). The resulting clear solution was concentrated to dryness. The residue was recrystallized from MeOH/EtOAc to give 0.51 g (83% yield for the last two steps) of N-[2-({4-[4-[2-(difluoromethyl)-4-methoxy-1H-benzimidazol-1-yl]-6-(4-morpholinyl)-1,3,5-triazin-2-yl]-1-piperazinyl}sulfonyl)ethyl]-N,N-dimethylamine hydrochloride: mp (MeOH/EtOAc) 222-224° C.; Anal. Calcd. for C$_{24}$H$_{34}$ClF$_2$N$_9$O$_4$S: C, 46.6; H, 5.5; N, 20.4; Cl, 5.7. Found: C, 46.3; H, 5.7; N, 20.0; Cl, 5.7%.

Example 11

Synthesis of 2-(difluoromethyl)-4-methoxy-1-[4-(4-morpholinyl)-6-(4-{[2-(4-morpholinyl)ethyl]sulfonyl}-1-piperazinyl]-1,3,5-triazin-2-yl]-1H-benzimidazole

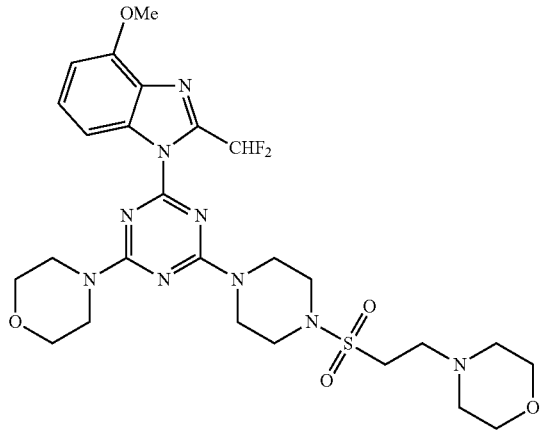 [SMILES: COc1cccc2c1nc(C(F)F)n2-c1nc(N2CCOCC2)nc(N2CCN(S(=O)(=O)CCN3CCOCC3)CC2)n1]

A mixture of 2-(difluoromethyl)-4-methoxy-1-{4-(4-morpholinyl)-6-[4-(vinylsulfonyl)-1-piperazinyl]-1,3,5-triazin-2-yl}-1H-benzimidazole (from Example 3) (0.536 g, 1 mmol) and morpholine (10 mL) in THF (150 mL) was heated under reflux for 2 hrs. The solvent was removed under vacuum and the residue was diluted with water to give 0.605 g (97% yield) of 2-(difluoromethyl)-4-methoxy-1-[4-(4-morpholinyl)-6-(4-{[2-(4-morpholinyl)ethyl]sulfonyl}-1-piperazinyl]-1,3,5-triazin-2-yl]-1H-benzimidazole: $^1$H NMR (CDCl$_3$) δ 7.86 (d, J=7.9 Hz, 1H), 7.44 (t, $J_{HF}$=53.5 Hz, 1H), 7.36 (t, J=8.2 Hz, 1H), 6.83 (d, J=7.8 Hz, 1H), 4.05 (s, 3H), 4.00 (m, 4H), 3.89 (m, 4H), 3.79 (m, 4H), 3.37 (m, 4H) 3.39 (m, 4H), 3.14 (dd, J=8.3, 6.4 Hz, 2H), 2.84 (dd, J=8.3, 6.3 Hz, 2H), 2.48 (m, 4H).

2-(Difluoromethyl)-4-methoxy-1-[4-(4-morpholinyl)-6-(4-{[2-(4-morpholinyl)ethyl]sulfonyl}-1-piperazinyl]-1,3,5-triazin-2-yl]-1H-benzimidazole hydrochloride was prepared according to the procedure as described in Example 10: mp (MeOH/EtOAc) 209-212° C.; Anal. Calcd. for C$_{26}$H$_{36}$ClF$_2$N$_9$O$_5$S.1.2H$_2$O: C, 45.8; H, 5.7; N, 18.5; Cl, 5.2. Found: C, 45.8; H, 5.7; N, 18.3; Cl, 5.2%.

Example 12

Synthesis of 2-(difluoromethyl)-4-methoxy-1-[4-[4-({2-[4-(methylsulfonyl)-1-piperazinyl]ethyl}sulfonyl)-1-piperazinyl]-6-(4-morpholinyl)-1,3,5-triazin-2-yl]-1H-benzimidazole

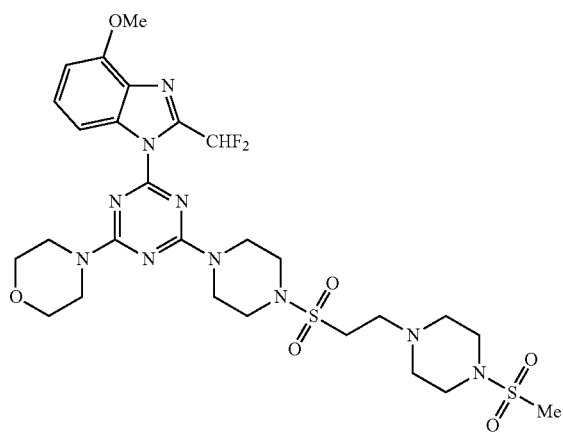 [SMILES: COc1cccc2c1nc(C(F)F)n2-c1nc(N2CCOCC2)nc(N2CCN(S(=O)(=O)CCN3CCN(S(C)(=O)=O)CC3)CC2)n1]

A mixture of 2-(difluoromethyl)-4-methoxy-1-{4-(4-morpholinyl)-6-[4-(vinylsulfonyl)-1-piperazinyl]-1,3,5-triazin-2-yl}-1H-benzimidazole (from Example 3) (0.20 g, 0.37 mmol) and 1-(methylsulfonyl)piperazine (0.31 g, 1.9 mmol) in THF (100 mL) was refluxed for 2 days. The solvent was then removed under vacuum, and the residue was diluted with water to give a white solid, which was collected and dried. Chromatography on alumina eluting with CH$_2$Cl$_2$/EtOAc (9:1) gave 0.22 g (84% yield) of 2-(difluoromethyl)-4-methoxy-1-[4-[4-({2-[4-(methylsulfonyl)-1-piperazinyl]ethyl}sulfonyl)-1-piperazinyl]-6-(4-morpholinyl)-1,3,5-triazin-2-yl]-1H-benzimidazole: $^1$H NMR (CDCl$_3$) δ 7.86 (dd, J=8.4, 0.6 Hz, 1H), 7.43 (t, $J_{HF}$=53.5 Hz, 1H), 7.35 (t, J=8.2 Hz, 1H), 6.82 (d, J=7.7 Hz, 1H), 4.05 (s, 3H), 4.01 (m, 4H), 3.88 (m, 4H), 3.79 (m, 4H), 3.38 (m, 4H) 3.23 (m, 4H), 3.11 (dd, J=8.5, 6.0 Hz, 2H), 2.92 (dd, J=8.4, 6.0 Hz, 2H), 2.75 (s, 3H), 2.60 (m, 4H).

A suspension of 2-(difluoromethyl)-4-methoxy-1-[4-[4-({2-[4-(methylsulfonyl)-1-piperazinyl]ethyl}sulfonyl)-1-piperazinyl]-6-(4-morpholinyl)-1,3,5-triazin-2-yl]-1H-benzimidazole from the previous step in MeOH (50 mL) was treated with methanesulfonic acid (33 mg, 1.1 equiv.) to give a clear solution. The solvent was removed under vacuum and the residue was washed with EtOAc to give 2-(difluoromethyl)-4-methoxy-1-[4-[4-({2-[4-(methylsulfonyl)-1-piperazinyl]ethyl}sulfonyl)-1-piperazinyl]-6-(4-morpholinyl)-1,3,5-triazin-2-yl]-1H-benzimidazole methanesulfonate: mp (MeOH/EtOAc) 232-235° C.; Anal. Calcd. for C$_{28}$H$_{42}$F$_2$N$_{10}$O$_9$S$_3$.0.5H$_2$O: C, 41.7; H, 5.4; N, 17.4. Found: C, 41.7; H, 5.3; N, 17.2%.

Example 13

Synthesis of 2-(difluoromethyl)-4-methoxy-1-[4-[1-(methylsulfonyl)-4-piperidinyl]-6-(4-morpholinyl)-1,3,5-triazin-2-yl]-1H-benzimidazole

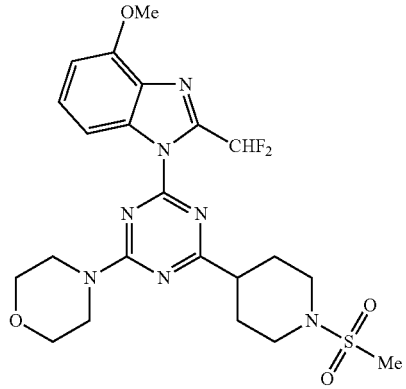 [SMILES: COc1cccc2c1nc(C(F)F)n2-c1nc(C2CCN(S(C)(=O)=O)CC2)nc(N2CCOCC2)n1]

A mixture of 1-[4-chloro-6-(4-morpholinyl)-1,3,5-triazin-2-yl]-2-(difluoromethyl)-4-methoxy-1H-benzimidazole (0.397 g, 1 mmol), tert-butyl 4-(4,4,5,5-tetramethyl-1,3,2-dioxaborolan-2-yl)-3,6-dihydro-1(2H)-pyridinecarboxylate (0.464 g, 1.5 mmol), PdCl$_2$(dppf) (56 mg), and 2 M Na$_2$CO$_3$ solution (8 mL) in dioxane (40 mL) was refluxed under nitrogen for 2 hrs. The dioxane was removed under vacuum and the residue was extracted into CH$_2$Cl$_2$. Chromatography on silica eluting with CH$_2$Cl$_2$/EtOAc (95:5) gave 0.51 g (94% yield) of tert-butyl 4-[4-[2-(difluoromethyl)-4-methoxy-1H-benzimidazol-1-yl]-6-(4-morpholinyl)-1,3,5-triazin-2-yl]-3,6-dihydro-1(2H)-pyridinecarboxylate: mp (MeOH) 223-225° C.; $^1$H NMR (CDCl$_3$) δ 8.00 (dd, J=8.4, 0.6 Hz, 1H), 7.56 (t, $J_{HF}$=53.5 Hz, 1H), 7.39 (t, J=8.2 Hz, 1H), 7.38 (m, 1H), 6.85 (d, J=7.7 Hz, 1H), 4.23 (br d, J=3.0 Hz, 2H), 4.06 (s, 3H), 4.01 (m, 2H), 3.95 (m, 2H), 3.82 (m, 4H), 3.65 (t, J=5.7 Hz, 2H), 2.69 (m, 2H), 1.54-1.45 (m, 2H), 1.50 (s, 9H); Anal. Calcd. for C$_{26}$H$_{31}$F$_2$N$_7$O$_4$: C, 57.45; H, 5.75; N, 18.0. Found: C, 57.4; H, 5.9; N, 18.15%.

A solution of tert-butyl 4-[4-[2-(difluoromethyl)-4-methoxy-1H-benzimidazol-1-yl]-6-(4-morpholinyl)-1,3,5-triazin-2-yl]-3,6-dihydro-1(2H)-pyridinecarboxylate (1.79 g, 3.29 mmol) in a mixture of MeOH (80 mL) and THF (80 mL) was hydrogenated over 10% Pd on carbon (100 mg). After removal of the hydrogen, the mixture was refluxed in air for additional 2 hrs. The catalyst Pd/C was removed by filtration through celite, and the solvents were removed under vacuum. Recrystallization of the residue from methanol gave tert-butyl 4-[4-[2-(difluoromethyl)-4-methoxy-1H-benzimidazol-1-yl]-6-(4-morpholinyl)-1,3,5-triazin-2-yl]-1-piperidine-carboxylate: mp (MeOH) 177-179° C.; $^1$H NMR (CDCl$_3$) δ 8.01 (dd, J=8.4, 0.7 Hz, 1H), 7.58 (t, J$_{HF}$=53.6 Hz, 1H), 7.38 (t, J=8.2 Hz, 1H), 6.84 (d, J=7.8 Hz, 1H), 4.22 (m, 2H), 4.05 (s, 3H), 3.99 (m, 2H), 3.94 (m, 2H), 3.81 (m, 4H), 2.94-2.78 (m, 3H), 2.05 (dd, J=13.0, 1.9 Hz, 2H), 1.81 (qd, J=12.7, 4.4 Hz, 2H), 1.49 (s, 9H); Anal. Calcd. for C$_{26}$H$_{33}$F$_2$N$_7$O$_4$: C, 57.2; H, 6.1; N, 18.0. Found: C, 57.4; H, 6.15; N, 18.1%.

Reaction of tert-butyl 4-[4-[2-(difluoromethyl)-4-methoxy-1H-benzimidazol-1-yl]-6-(4-morpholinyl)-1,3,5-triazin-2-yl]-1-piperidine-carboxylate (0.23 g, 0.37 mmol) with TFA (0.45 mL) in CH$_2$Cl$_2$ (8 mL) gave 2-(difluoromethyl)-4-methoxy-1-[4-(4-morpholinyl)-6-(4-piperidinyl)-1,3,5-triazin-2-yl]-1H-benzimidazole, which was treated subsequently with methanesulfonyl chloride and Et$_3$N in CH$_2$Cl$_2$. The reaction mixture was purified by chromatography on silica eluting first with hexanes/EtOAc (1:1) and then hexanes/EtOAc (3:5) to give 0.13 g (67% yield) of 2-(difluoromethyl)-4-methoxy-1-[4-[1-(methylsulfonyl)-4-piperidinyl]-6-(4-morpholinyl)-1,3,5-triazin-2-yl]-1H-benzimidazole: mp 256-258° C.; $^1$H NMR (CDCl$_3$) δ 7.99 (dd, J=8.4, 0.7 Hz, 1H), 7.55 (t, J$_{HF}$=53.6 Hz, 1H), 7.39 (t, J=8.3 Hz, 1H), 6.85 (d, J=8.1 Hz, 1H), 4.06 (s, 3H), 4.02-3.89 (m, 6H), 3.87-3.76 (m, 4H), 2.92-2.75 (m, 6H), 2.24-2.16 (m, 2H), 2.10-1.97 (m, 2H); Anal. Calcd. for C$_{22}$H$_{27}$F$_2$N$_7$O$_4$S: C, 50.5; H, 5.2; N, 18.7. Found: C, 50.6; H, 5.3; N, 18.6%.

Example 14

Synthesis of N-[2-({4-[4-[2-(difluoromethyl)-4-methoxy-1H-benzimidazol-1-yl]-6-(4-morpholinyl)-1,3,5-triazin-2-yl]-1-piperidinyl}sulfonyl)ethyl]-N,N-dimethylamine

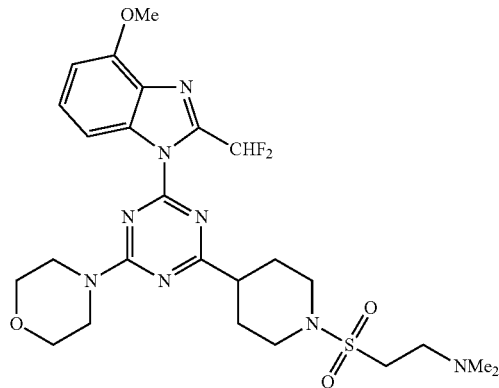 [SMILES: COc1cccc2c1nc(C(F)F)n2-c1nc(C2CCN(S(=O)(=O)CCN(C)C)CC2)nc(N2CCOCC2)n1]

To a mixture of 2-(difluoromethyl)-4-methoxy-1-[4-(4-morpholinyl)-6-(4-piperidinyl)-1,3,5-triazin-2-yl]-1H-benzimidazole (Example 13) (0.891 mg, 2 mmol) and DIPEA (0.77 g, 6 mmol) in CH$_2$Cl$_2$ (100 mL) was added dropwise 2-chloroethanesulfonyl chloride (0.49 g, 3 mmol) at 0° C. After addition, the reaction mixture was stirred at 0° C. for additional 2 hrs. The reaction mixture was quenched with water (100 mL). The organic layer was washed successively with aqueous HOAc (1%, 100 mL) and aqueous NH$_3$, and dried. Chromatography on silica eluting with CH$_2$Cl$_2$/EtOAc (9:1) gave 0.589 g (55% yield) of 2-(difluoromethyl)-4-methoxy-1-{4-(4-morpholinyl)-6-[1-(vinylsulfonyl)-4-piperidinyl]-1,3,5-triazin-2-yl}-1H-benzimidazole: mp (MeOH) 229-232° C.; $^1$H NMR (CDCl$_3$) δ 7.99 (dd, J=8.4, 0.7 Hz, 1H), 7.54 (t, J$_{HF}$=53.6 Hz, 1H), 7.39 (t, J=8.3 Hz, 1H), 6.85 (d, J=7.6 Hz, 1H), 6.47 (dd, J=16.6, 9.9 Hz, 1H), 6.27 (d, J=16.6 Hz, 1H), 6.05 (d, J=9.9 Hz, 1H), 4.06 (s, 3H), 4.00-3.97 (m, 4H), 3.89-3.79 (m, 6H), 2.78 (m, 3H), 2.17 (br dd, J=13.6, 3.0 Hz, 2H), 2.01 (ddd, J=25.2, 11.7, 4.1 Hz, 2H); Anal. Calcd. for C$_{23}$H$_{27}$F$_2$N$_7$O$_4$S: C, 51.6; H, 5.1; N, 18.3. Found: C, 51.7; H, 5.2; N, 18.25%.

A mixture of 2-(difluoromethyl)-4-methoxy-1-{4-(4-morpholinyl)-6-[1-(vinylsulfonyl)-4-piperidinyl]-1,3,5-triazin-2-yl}-1H-benzimidazole (59 mg, 0.11 mmol) and 40% aqueous dimethylamine (5 mL) in THF (25 mL) was stirred at room temperature for 15 min. The solvent was removed under vacuum and the residue was diluted with water to give 63 mg (99% yield) of N-[2-({4-[4-[2-(difluoromethyl)-4-methoxy-1H-benzimidazol-1-yl]-6-(4-morpholinyl)-1,3,5-triazin-2-yl]-1-piperidinyl}sulfonyl)ethyl]-N,N-dimethylamine: $^1$H NMR (CDCl$_3$) δ 7.99 (d, J=7.9 Hz, 1H), 7.55 (t, J$_{HF}$=53.6 Hz, 1H), 7.39 (t, J=8.3 Hz, 1H), 6.85 (d, J=7.9 Hz, 1H), 4.06 (s, 3H), 4.02-3.89 (m, 6H), 3.85-3.78 (m, 4H), 3.14-3.11 (m, 2H), 2.97 (dt, J=12.2, 2.6 Hz, 2H), 2.84-2.77 (m, 3H), 2.28 (s, 6H), 2.17 (br dd, J=13.2, 2.6 Hz, 2H), 2.00 (ddd, J=25.1, 11.8, 4.1 Hz, 2H).

To a suspension of N-[2-({4-[4-[2-(difluoromethyl)-4-methoxy-1H-benzimidazol-1-yl]-6-(4-morpholinyl)-1,3,5-triazin-2-yl]-1-piperidinyl}sulfonyl)ethyl]-N,N-dimethylamine from the previous step in MeOH (50 mL) was added a slight excess of 1.25 M HCl in MeOH (95 μL) to give a clear solution. The solvent was removed under vacuum and the residue was washed with EtOAc to give N-[2-({4-[4-[2-(difluoromethyl)-4-methoxy-1H-benzimidazol-1-yl]-6-(4-morpholinyl)-1,3,5-triazin-2-yl]-1-piperidinyl}sulfonyl)ethyl]-N,N-dimethylamine hydrochloride: mp (MeOH/EtOAc) 243-245° C.; Anal. Calcd. for C$_{25}$H$_{35}$ClF$_2$N$_8$O$_4$S: C, 48.7; H, 5.7; N, 18.2; Cl, 5.7. Found: C, 48.7; H, 5.7; N, 18.0; Cl, 5.7%.

Example 15

Synthesis of 2-(difluoromethyl)-4-methoxy-1-[4-[1-(methylsulfonyl)-3-piperidinyl]-6-(4-morpholinyl)-1,3,5-triazin-2-yl]-1H-benzimidazole

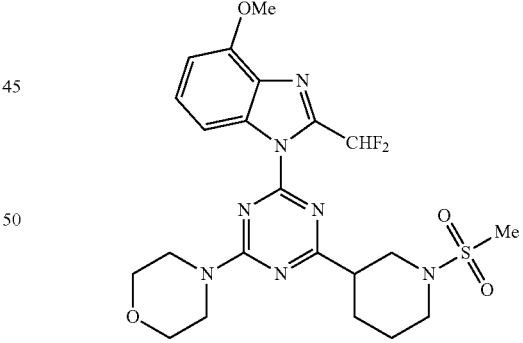

A mixture of 1-[4-chloro-6-(4-morpholinyl)-1,3,5-triazin-2-yl]-2-(difluoromethyl)-4-methoxy-1H-benzimidazole (0.40 g, 1 mmol), tert-butyl 5-(4,4,5,5-tetramethyl-1,3,2-dioxaborolan-2-yl)-3,4-dihydropyridine-1(2H)-carboxylate (0.382 g, 1.24 mmol), PdCl$_2$(dppf) (63 mg), and 2 M aqueous Na$_2$CO$_3$ (8 mL) in dioxane (40 mL) was refluxed under nitrogen for 2 hrs. The dioxane was removed under vacuum and the residue was extracted into CH$_2$Cl$_2$. Chromatography on silica eluting with hexanes/EtOAc (8:2) gave 0.27 g (50% yield) of tert-butyl 5-[4-[2-(difluoromethyl)-4-methoxy-1H-benzimidazol-1-yl]-6-(4-morpholinyl)-1,3,5-triazin-2-yl]-3,4-dihydro-1(2H)-pyridinecarboxylate: $^1$H NMR (CDCl$_3$) δ 8.59 (s, 1H), 7.99 (d, J=8.4 Hz, 1H), 7.60 (t, J$_{HF}$=53.6 Hz, 1H), 7.34 (t, J=8.2 Hz, 1H), 6.81 (d, J=8.1 Hz, 1H), 4.04 (s, 3H), 4.02-3.75 (m, 8H), 3.71-3.64 (m, 2H), 2.56 (t, J=6.1 Hz, 2H), 2.00-1.91 (m, 2H), 1.57 (s, 9H).

A solution of tert-butyl 5-[4-[2-(difluoromethyl)-4-methoxy-1H-benzimidazol-1-yl]-6-(4-morpholinyl)-1,3,5-triazin-2-yl]-3,4-dihydro-1(2H)-pyridinecarboxylate (272 mg, 0.50 mmol) in MeOH (20 mL) and THF (20 mL) was hydrogenated over 10% Pd on carbon (50 mg). After removal of the hydrogen, the mixture was refluxed in air for additional 2 hrs. The catalyst Pd/C was removed by filtration through celite, and the solvents were removed under vacuum. Recrystallization of the residue from methanol gave 0.23 g (81% yield) of tert-butyl 3-[4-[2-(difluoromethyl)-4-methoxy-1H-benzimidazol-1-yl]-6-(4-morpholinyl)-1,3,5-triazin-2-yl]-1-piperidinecarboxylate: mp 200-202° C.; $^{1}$H NMR (CDCl$_{3}$) δ 8.01 (dd, J=8.4, 0.6 Hz, 1H), 7.58 (t, J$_{HF}$=53.6 Hz, 1H), 7.38 (t, J=8.2 Hz, 1H), 6.84 (d, J=8.1 Hz, 1H), 4.47-4.35 (m, 1H), 4.06 (s, 3H), 3.96 (m, 4H), 3.85-3.77 (m, 4H), 3.09 (dd, J=13.1, 10.7 Hz, 1H), 2.89-2.76 (m, 2H), 2.30-2.20 (m, 1H), 1.88-1.57 (m, 4H), 1.48 (s, 9H); Anal. Calcd. for C$_{26}$H$_{33}$F$_{2}$N$_{7}$O$_{4}$: C, 57.2; H, 6.1; N, 18.0. Found: C, 57.1; H, 6.3; N, 17.8%.

Reaction of tert-butyl 3-[4-[2-(difluoromethyl)-4-methoxy-1H-benzimidazol-1-yl]-6-(4-morpholinyl)-1,3,5-triazin-2-yl]-1-piperidinecarboxylate (0.22 g, 0.40 mmol) with TFA (0.5 mL) in CH$_{2}$Cl$_{2}$ (8 mL) gave 2-(difluoromethyl)-4-methoxy-1-[4-(4-morpholinyl)-6-(3-piperidinyl)-1,3,5-triazin-2-yl]-1H-benzimidazole, which was dissolved in a mixture of CH$_{2}$Cl$_{2}$ (4 mL) and NEt$_{3}$ (0.29 mL, 2.1 mmol) and cooled to 0° C. Methanesulfonyl chloride (0.05 mL, 0.65 mmol) was added, and the resulting mixture was allowed to warm to room temperature over 2 hrs. The reaction mixture was then diluted with water, extracted with CH$_{2}$Cl$_{2}$, and dried. Chromatography on silica eluting first with hexanes/EtOAc (4:1), followed by hexanes/EtOAc (1:1), and then CH$_{2}$Cl$_{2}$/MeOH (99:1), gave 0.19 g (91% yield) of 2-(difluoromethyl)-4-methoxy-1-[4-[1-(methylsulfonyl)-3-piperidinyl]-6-(4-morpholinyl)-1,3,5-triazin-2-yl]-1H-benzimidazole: mp 237-239° C.; $^{1}$H NMR (CDCl$_{3}$) δ 7.98 (dd, J=8.4, 0.7 Hz, 1H), 7.54 (t, J$_{HF}$=53.5 Hz, 1H), 7.40 (t, J=8.3 Hz, 1H), 6.85 (d, J=8.1 Hz, 1H), 4.08-3.92 (m, 8H), 3.86-3.72 (m, 5H), 3.14 (dd, J=11.5, 10.2 Hz, 1H), 3.07-2.99 (m, 1H), 2.86-2.77 (m, 4H), 2.30-2.22 (m, 1H), 2.00-1.71 (m, 3H); Anal. Calcd. for C$_{22}$H$_{27}$F$_{2}$N$_{7}$O$_{4}$S.0.5H$_{2}$O: C, 49.6; H, 5.3; N, 18.4. Found: C, 49.7; H, 5.2; N, 18.3%.

Example 16

Synthesis of 2-(difluoromethyl)-4-methoxy-1-[4-{[1-(methylsulfonyl)-4-piperidinyl]oxy}-6-(4-morpholinyl)-1,3,5-triazin-2-yl]-1H-benzimidazole

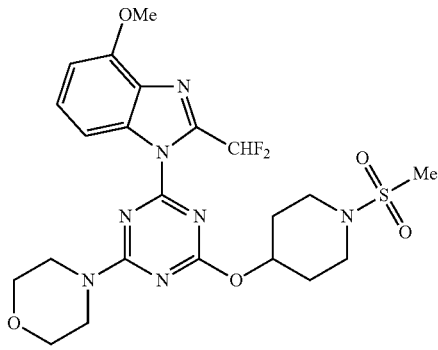 [SMILES: COc1cccc2c1nc(C(F)F)n2-c1nc(OC2CCN(S(C)(=O)=O)CC2)nc(N2CCOCC2)n1]

A mixture of 2,4-dichloro-6-(4-morpholinyl)-1,3,5-triazine (0.47 g, 2 mmol), tert-butyl 4-hydroxy-1-piperidinecarboxylate (0.40 g, 2 mmol), and a small excess of NaH (58 mg, 2.4 mmol) in THF (20 mL) was stirred at room temperature overnight. The reaction was quenched with water, and the mixture was extracted with EtOAc. Chromatography on silica eluting with CH$_{2}$Cl$_{2}$/EtOAc (9:1) gave 0.65 g (81% yield) of tert-butyl 4-(4-chloro-6-morpholino-1,3,5-triazin-2-yloxy)piperidine-1-carboxylate as a white solid: mp (i-Pr$_{2}$O) 150-152° C.; $^{1}$H NMR (CDCl$_{3}$) δ 5.18 (tt, J=7.7, 3.8 Hz, 1H), 3.87 (m, 2H), 3.83 (m, 2H), 3.78-3.71 (m, 6H), 3.30 (ddd, J=13.5, 8.3, 3.8 Hz, 2H), 1.95 (m, 2H), 1.78 (m, 2H), 1.46 (s, 9H); Anal. Calcd. for C$_{17}$H$_{26}$ClN$_{5}$O$_{4}$: C, 51.06; H, 6.55; N, 17.51. Found: C, 51.21; H, 6.28; N, 17.4%.

A mixture of 4-(4-chloro-6-morpholino-1,3,5-triazin-2-yloxy)piperidine-1-carboxylate (175 mg, 0.44 mmol), 2-(difluoromethyl)-4-methoxy-1H-benzimidazole (100 mg, 0.505 mmol), and powdered K$_{2}$CO$_{3}$ (0.28 g, 2 mmol) in DMSO (10 mL) was stirred at room temperature for 3 days, and then diluted with water. The resulting precipitate was collected, washed with water, and dried. Chromatography on silica eluting with CH$_{2}$Cl$_{2}$/EtOAc (4:1) gave 200 mg (81% yield) of tert-butyl 4-(4-(2-(difluoromethyl)-4-methoxy-1H-benzimidazol-1-yl)-6-morpholino-1,3,5-triazin-2-yloxy)piperidine-1-carboxylate: mp (CH$_{2}$Cl$_{2}$-MeOH) 191-193° C.; $^{1}$H NMR (CDCl$_{3}$) δ 7.96 (dd, J=8.4, 0.5 Hz, 1H), 7.49 (t, J$_{HF}$=53.5 Hz, 1H), 7.38 (t, J=8.3 Hz, 1H), 6.85 (d, J=7.8 Hz, 1H), 5.25 (m, 1H), 4.06 (s, 3H), 3.96-3.78 (m, 10H), 3.28 (m, 2H), 2.50 (m, 2H), 1.85 (m, 2H), 1.48 (s, 9H); Anal. Calcd. for C$_{26}$H$_{33}$F$_{2}$N$_{7}$O$_{5}$: C, 55.61; H, 5.92; N, 17.46. Found: C, 55.77; H, 5.92; N, 17.40%.

Treatment of tert-butyl 4-(4-(2-(difluoromethyl)-4-methoxy-1H-benzimidazol-1-yl)-6-morpholino-1,3,5-triazin-2-yloxy)piperidine-1-carboxylate (112 mg, 0.2 mmol) with TFA (5 mL) in CH$_{2}$Cl$_{2}$ (10 mL), followed by quenching with aqueous NH$_{3}$ gave 2-(difluoromethyl)-4-methoxy-1-(4-morpholinyl)-6-(4-piperidinyloxy)-1,3,5-triazin-2-yl]-1H-benzimidazole: $^{1}$H NMR (DMSO-d$_{6}$) δ 7.96 (dd, J=8.4, 0.5 Hz, 1H), 7.71 (t, J$_{HF}$=52.8 Hz, 1H), 7.44 (t, J=8.3 Hz, 1H), 6.98 (d, J=7.7 Hz, 1H), 5.11 (m, 1H), 3.98 (s, 3H), 3.83 (m, 4H), 3.71 (m, 4H), 3.00 (m, 2H), 2.62 (m, 2H), 2.00 (m, 2H), 1.58 (m, 2H).

Reaction of 2-(difluoromethyl)-4-methoxy-1-(4-morpholinyl)-6-(4-piperidinyloxy)-1,3,5-triazin-2-yl]-1H-benzimidazole (245 mg, 0.53 mmol) with methanesulfonyl chloride (0.5 mL, 6.87 mmol) and K$_{2}$CO$_{3}$ (2.0 g, 14.5 mmol) in CH$_{2}$Cl$_{2}$ (10 mL) gave 2-(difluoromethyl)-4-methoxyl-[4-{[1-(methylsulfonyl)-4-piperidinyl]oxy}-6-(4-morpholinyl)-1,3,5-triazin-2-yl]-1H-benzimidazole in 87% yield: mp (CH$_{2}$Cl$_{2}$/MeOH) 285-288° C.; $^{1}$H NMR (DMSO-d$_{6}$) δ 7.96 (d, J=8.0 Hz, 1H), 7.71 (t, J$_{HF}$=52.9 Hz, 1H), 7.45 (t, J=8.2 Hz, 1H), 6.99 (d, J=7.9 Hz, 1H), 5.27-5.21 (m, 1H), 3.98 (s, 3H), 3.84 (br m, 4H), 3.75-3.71 (m, 4H), 3.46-3.38 (m, 2H), 3.20-3.14 (m, 2H), 2.93 (s, 3H), 2.15-2.09 (m, 2H), 1.91-1.82 (m, 2H); Anal. Calcd. for C$_{22}$H$_{27}$F$_{2}$N$_{7}$O$_{5}$S: C, 49.0; H, 5.0; N, 18.2. Found: C, 49.0; H, 5.2; N, 18.3%.

Example 17

Synthesis of N-{1-[4-[2-(difluoromethyl)-4-methoxy-1H-benzimidazol-1-yl]-6-(4-morpholinyl)-1,3,5-triazin-2-yl]-4-piperidinyl}methanesulfonamide

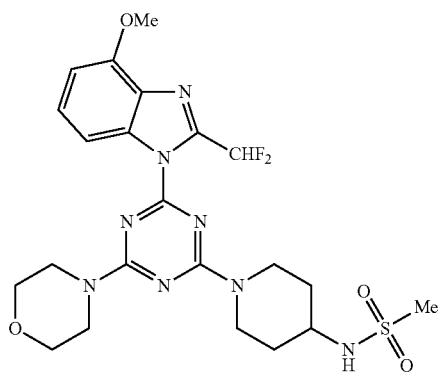 [SMILES: COc1cccc2c1nc(C(F)F)n2-c1nc(N2CCOCC2)nc(N2CCC(NS(C)(=O)=O)CC2)n1]

A mixture of 1-[4-chloro-6-(4-morpholinyl)-1,3,5-triazin-2-yl]-2-(difluoromethyl)-4-methoxy-1H-benzimidazole (0.992 g, 2.5 mmol), tert-butyl 4-piperidinylcarbamate (1.00 g, 5 mmol), and DIPEA (0.65 g, 5 mmol) in THF (100 mL) was stirred at room temperature for 30 min. The solution was then concentrated and diluted with water (100 mL) containing 1 mL of acetic acid. The resulting solid was collected, washed with water, and dried to give 1.38 g (98%) of tert-butyl 1-[4-[2-(difluoromethyl)-4-methoxy-1H-benzimidazol-1-yl]-6-(4-morpholinyl)-1,3,5-triazin-2-yl]-4-piperidinylcarbamate: mp (MeOH) 208-209° C.; $^1$H NMR (CDCl$_3$) δ 7.88 (d, J=8.1 Hz, 1H), 7.48 (t, $J_{HF}$=53.6 Hz, 1H), 7.34 (t, J=8.2 Hz, 1H), 6.81 (d, J=7.9 Hz, 1H), 4.66 (br d, J=13.4 Hz, 2H), 4.46 (m, exchangeable with D$_2$O, 1H), 4.04 (s, 3H), 3.87 (m, 4H), 3.78 (m, 5H), 3.12 (m, 2H), 2.07 (br d, J=14.0 Hz, 2H), 1.46 (s, 9H), 1.45-1.33 (m, 2H); Anal. Calcd. for C$_{26}$H$_{34}$F$_2$N$_8$O$_4$: C, 55.7; H, 6.1; N, 20.0. Found: C, 55.85; H, 6.1; N, 20.1%.

Treatment of tert-butyl 1-[4-[2-(difluoromethyl)-4-methoxy-1H-benzimidazol-1-yl]-6-(4-morpholinyl)-1,3,5-triazin-2-yl]-4-piperidinylcarbamate (0.28 g, 0.5 mmol) with TFA (5 mL) in CH$_2$Cl$_2$ (10 mL) gave 1-[4-[2-(difluoromethyl)-4-methoxy-1H-benzimidazol-1-yl]-6-(4-morpholinyl)-1,3,5-triazin-2-yl]-4-piperidinamine in a quantitative yield: $^1$H NMR (CDCl$_3$) δ 7.90 (d, J=8.4 Hz, 1H), 7.51 (t, $J_{HF}$=53.6 Hz, 1H), 7.34 (t, J=8.2 Hz, 1H), 6.81 (d, J=8.0 Hz, 1H), 4.66 (br d, J=13.1 Hz, 2H), 4.05 (s, 3H), 3.88 (m, 4H), 3.78 (m, 4H), 3.15-2.96 (m, 3H), 1.94 (m, 2H), 1.39-1.25 (m, 2H).

Reaction of 1-[4-[2-(difluoromethyl)-4-methoxy-1H-benzimidazol-1-yl]-6-(4-morpholinyl)-1,3,5-triazin-2-yl]-4-piperidinamine (460 mg, 1.0 mmol) with methanesulfonyl chloride (1 mL, 12.7 mmol) and K$_2$CO$_3$ (2.0 g, 14.5 mmol) in CH$_2$Cl$_2$ (10 mL) gave N-{1-[4-[2-(difluoromethyl)-4-methoxy-1H-benzimidazol-1-yl]-6-(4-morpholinyl)-1,3,5-triazin-2-yl]-4-piperidinyl}methanesulfonamide in 97% yield: mp (CH$_2$Cl$_2$/MeOH) 225-228° C.; $^1$H NMR (DMSO-d$_6$) δ 7.88 (d, J=8.0 Hz, 1H), 7.68 (t, $J_{HF}$=52.9 Hz, 1H), 7.41 (t, J=8.2 Hz, 1H), 7.15 (d, J=5.7 Hz, 1H), 6.95 (d, J=7.8 Hz, 1H), 4.52-4.45 (m, 2H), 3.97 (s, 3H), 3.81-3.79 (m, 4H), 3.70-3.69 (m, 4H), 3.50 (br m, 1H), 3.29-3.21 (m, 2H), 2.96 (s, 3H), 1.96 (br, 2H), 1.44-1.42 (m, 2H); Anal. Calcd. for C$_{22}$H$_{28}$F$_2$N$_8$O$_5$S: C, 49.1; H, 5.2; N, 20.8. Found: C, 49.2; H, 5.2; N, 20.9%.

Example 18

Synthesis of N-{1-[4-[2-(difluoromethyl)-4-methoxy-1H-benzimidazol-1-yl]-6-(4-morpholinyl)-1,3,5-triazin-2-yl]-4-piperidinyl}-N-methylmethanesulfonamide

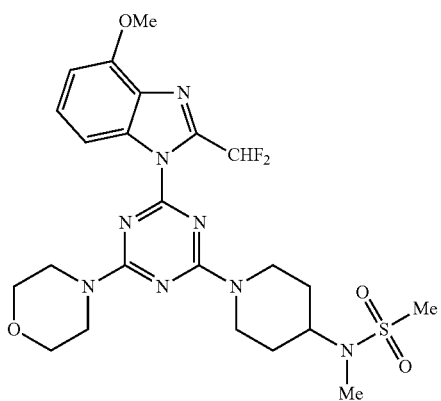 [SMILES: COc1cccc2c1nc(C(F)F)n2-c1nc(N2CCOCC2)nc(N2CCC(N(C)S(C)(=O)=O)CC2)n1]

Reaction of N-{1-[4-[2-(difluoromethyl)-4-methoxy-1H-benzimidazol-1-yl]-6-(4-morpholinyl)-1,3,5-triazin-2-yl]-4-piperidinyl}methanesulfonamide (Example 17) (114 mg, 0.21 mmol) with iodomethane (0.5 mL, 8.1 mmol) and K$_2$CO$_3$ (2 g, 14.5 mmol) in DMF (5 mL) gave N-{1-[4-[2-(difluoromethyl)-4-methoxy-1H-benzimidazol-1-yl]-6-(4-morpholinyl)-1,3,5-triazin-2-yl]-4-piperidinyl}-N-methylmethanesulfonamide (98 mg) in 84% yield: mp (CH$_2$Cl$_2$/MeOH) 231-233° C.; $^1$H NMR (DMSO-d$_6$) δ 7.89 (d, J=8.2 Hz, 1H), 7.69 (t, $J_{HF}$=52.9 Hz, 1H), 7.41 (t, J=8.2 Hz, 1H), 6.95 (d, J=7.9 Hz, 1H), 4.82-4.72 (m, 2H), 3.98 (s, 3H), 3.98-3.90 (m, 2H), 3.82-3.79 (m, 4H), 3.70-3.69 (m, 4H), 3.11-2.98 (m, 2H), 2.94 (s, 3H), 2.68 (s, 3H), 1.77-1.70 (m, 4H); Anal. Calcd. for C$_{23}$H$_{30}$F$_2$N$_8$O$_4$S: C, 50.0; H, 5.5; N, 20.3. Found: C, 49.9; H, 5.6; N, 20.3%.

Example 19

Synthesis of N$^1$-[4-[2-(difluoromethyl)-4-methoxy-1H-benzimidazol-1-yl]-6-(4-morpholinyl)-1,3,5-triazin-2-yl]-N$^3$—N$^3$-dimethyl-N$^1$-[1-methylsulfonyl)-3-piperidinyl]-1,3-propanediamine

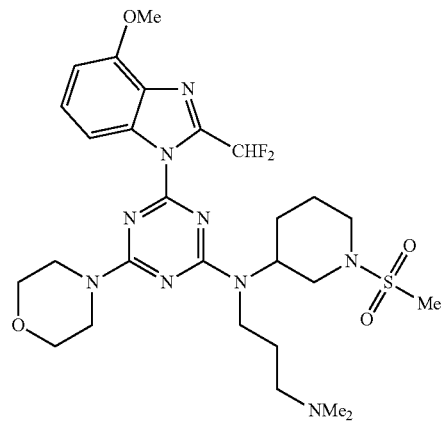 [SMILES: COc1cccc2c1nc(C(F)F)n2-c1nc(N2CCOCC2)nc(N(CCCN(C)C)C2CCCN(S(C)(=O)=O)C2)n1]

A mixture of tert-butyl 3-oxo-1-piperidinecarboxylate (5.0 g, 25.1 mmol) and 3-amino-1-propanol (5.66 mL, 73.8 mmol) in MeOH (75 mL) was hydrogenated over 10% Pd on C (200 mg) for 1 day (Yokoyama et al., Bioorg. Med. Chem. 2008, 16, 7968) to give tert-butyl 3-[(3-hydroxypropyl)amino]-1-piperidinecarboxylate as an oil: $^1$H NMR (CDCl$_3$) (rotamers) δ 3.80 (t, J=5.1 Hz, 2H), 3.80 (br, 1H), 3.65 and 3.67 (2t, J=4.7 Hz, 1H), 3.06-2.86 (m, 4H), 2.62-2.56 (m, 1H), 1.90-1.86 (m, 1H), 1.72-1.62 (m, 3H), 1.50-1.30 (m, 2H), 1.46 (s, 9H).

A mixture of tert-butyl 3-[(3-hydroxypropyl)amino]-1-piperidinecarboxylate (516 mg, 2.00 mmol), 1-[4-chloro-6-(4-morpholinyl)-1,3,5-triazin-2-yl]-2-(difluoromethyl)-4-methoxy-1H-benzimidazole (610 mg, 1.54 mmol), and DIPEA (1.5 mL, excess) in DMF (20 mL) was stirred at room temperature for 2 days. The reaction mixture was diluted with water and extracted with CH$_2$Cl$_2$ (3×30 mL). The combined extracts were washed with water, dried over Na$_2$SO$_4$, and concentrated. Chromatography of the residue on SiO$_2$ eluting with a gradient of CH$_2$Cl$_2$/EtOAc (0-40%) gave tert-butyl 3-[[4-[2-(difluoromethyl)-4-methoxy-1H-benzimidazol-1-yl]-6-(4-morpholinyl)-1,3,5-triazin-2-yl](3-hydroxypropyl)amino]-1-piperidinecarboxylate (854 mg, 90%): mp (CH$_2$Cl$_2$/hexanes) 109-191° C.; $^1$H NMR (DMSO-d$_6$) (rotamers) δ 8.00 and 7.88 (2d, J=8.3, 8.4 Hz, 1H), 7.79 and 7.63 (2t, $J_{HF}$=53.0 Hz, 1H), 7.40-7.33 (m, 1H), 6.94 (dd, J=8.0, 4.13 Hz, 1H), 4.60-4.48 and 4.29 (m, 2H), 3.98 and 3.97 (2s, 3H), 3.97-3.48 (m, 16H), 2.93-2.88 and 2.66-2.64 (2 m, 2H), 1.99-1.69 (m, 3H), 1.52-1.17 (m, 10H); Anal. Calcd. for C$_{29}$H$_{40}$F$_2$N$_8$O$_5$: C, 56.3; H, 6.5; N, 18.1. Found: C, 56.4; H, 6.4; N, 18.1%.

To a solution of tert-butyl 3-[[4-[2-(difluoromethyl)-4-methoxy-1H-benzimidazol-1-yl]-6-(4-morpholinyl)-1,3,5-triazin-2-yl](3-hydroxypropyl)-amino]-1-piperidinecarboxylate (420 mg, 0.72 mmol) in CH$_2$Cl$_2$ (12 mL) at 0° C. was added Et$_3$N (0.2 mL, 1.4 mmol) and methanesulfonyl chloride (0.1 mL, 1.08 mmol). The reaction mixture was stirred at 0° C. for 30 min, and a solution of 40% aqueous dimethylamine (5 mL) was then added. The reaction mixture was stirred at room temperature for 2 days and the solvent was removed under vacuum. The residue was diluted with water and stirred for 30 min to give a precipitate, which was collected by filtration, washed with water, and dried. Chromatography on SiO$_2$ eluting first with CH$_2$Cl$_2$/EtOAc (4:1), and then with CH$_2$Cl$_2$/MeOH (95:5) containing 1% aqueous NH$_3$, gave tert-butyl 3-{[4-[2-(difluoromethyl)-4-methoxy-1H-benzimidazol-1-yl]-6-(4-morpholinyl)-1,3,5-triazin-2-yl][3-(dimethylamino)propyl]amino}-1-piperidinecarboxylate (465 mg; 100%) as a white solid: mp (CH$_2$Cl$_2$/MeOH) 133-136° C.; $^1$H NMR (DMSO-d$_6$) (rotamers) δ 7.96 and 7.88 (2d, J=8.3 Hz, 1H), 7.77 and 7.68 (2t, J$_1$=53.0, 52.9 Hz, 1H), 7.40-7.34 (m, 1H), 6.96-6.93 (m, 1H), 4.56-4.88 and 4.30-4.27 (2 m, 1H), 3.98 and 3.97 (2s, 3H), 3.97-3.49 (m, 13H), 2.93-2.88 and 2.77-2.63 (2m, 2H), 2.35-2.27 (m, 2H), 2.15 and 2.13 (2s, 6H), 1.93-1.71 (m, 4H), 1.48-1.16 (m, 1H), 1.40 (s, 9H); Anal. Calcd. for C$_{31}$H$_{45}$F$_2$N$_9$O$_4$C, 57.7; H, 7.0; N, 19.5. Found: C, 57.7; H, 7.1; N, 19.7%.

To a solution of tert-butyl 3-{[4-[2-(difluoromethyl)-4-methoxy-1H-benzimidazol-1-yl]-6-(4-morpholinyl)-1,3,5-triazin-2-yl][3-(dimethylamino)propyl]amino}-1-piperidinecarboxylate (430 mg, 0.67 mmol) in CH$_2$Cl$_2$ (10 mL), was added TFA (5 mL). The resulting mixture was stirred at room temperature for 30 min. The solvent and excess TFA were removed under vacuum. The residue was diluted with water and neutralized with aqueous NH$_3$. The resulting precipitate was filtered, washed with water, and dried to give N$^1$-[4-[2-(difluoromethyl)-4-methoxy-1H-benzimidazol-1-yl]-6-(4-morpholinyl)-1,3,5-triazin-2-yl]-N$^3$,N$^3$-dimethyl-N$^1$-(3-piperidinyl)-1,3-propanediamine (323 mg, 88%): $^1$H NMR (DMSO-d$_6$) (rotamers) δ 7.95 and 7.93 (2d, J=9.5, 8.8 Hz, 1H), 7.77 and 7.71 (2t, J$_{HF}$=53.1 Hz, 1H), 7.42-7.36 (m, 1H), 6.95 (d, J=1 Hz, 1H), 4.55-4.48 and 4.46-4.39 (2m, 1H), 3.98 (s, 3H), 3.81-3.80 (m, 4H), 3.72-3.70 (m, 4H), 3.55-3.45 (m, 2H), 2.99-2.96 (m, 1H), 2.92-2.89 (m, 1H), 2.77-2.66 (m, 1H), 2.45-2.40 (m, 1H), 2.27 (t, J=6.9 Hz, 2H), 2.16 and 2.12 (2s, 6H), 1.80-1.48 (m, 6H).

To a solution of N$^1$-[4-[2-(difluoromethyl)-4-methoxy-1H-benzimidazol-1-yl]-6-(4-morpholinyl)-1,3,5-triazin-2-yl]-N$^3$,N$^3$-dimethyl-N$^1$-(3-piperidinyl)-1,3-propanediamine (155 mg, 0.28 mmol) and DIPEA (1 mL) in CH$_2$Cl$_2$ (10 mL) was added methanesulfonyl chloride (0.5 mL) at 0° C. The resulting mixture was stirred for 16 hrs at room temperature. After dilution with water, the organic layer was separated, and the aqueous layer was further extracted with CH$_2$Cl$_2$ (3×15 mL). The combined organic fractions were dried over Na$_2$SO$_4$, and the solvent removed under vacuum. The residue was chromatographed on alumina eluting with CH$_2$Cl$_2$/MeOH (97:3) to give partially pure material, which was further purified by chromatography on silica eluting with CH$_2$Cl$_2$/MeOH (97:3) to give N$^1$-[4-[2-(difluoromethyl)-4-methoxy-1H-benzimidazol-1-yl]-6-(4-morpholinyl)-1,3,5-triazin-2-yl]-N$^3$,N$^3$-dimethyl-N$^1$-[1-(methylsulfonyl)-3-piperidinyl]-1,3-propanediamine (125 mg, 72% yield).

To a suspension of N$^1$-[4-[2-(difluoromethyl)-4-methoxy-1H-benzimidazol-1-yl]-6-(4-morpholinyl)-1,3,5-triazin-2-yl]-N$^3$,N$^3$-dimethyl-N$^1$-[1-(methylsulfonyl)-3-piperidinyl]-1,3-propanediamine from the previous step in MeOH (20 mL) was added a slight excess of 1.25 M HCl in MeOH (0.18 mL) to give a clear solution. The solvent was removed under vacuum and the residue was washed with EtOAc to give N$^1$-[4-[2-(Difluoromethyl)-4-methoxy-1H-benzimidazol-1-yl]-6-(4-morpholinyl)-1,3,5-triazin-2-yl]-N$^3$,N$^3$-dimethyl-N$^1$-[1-(methylsulfonyl)-3-piperidinyl]-1,3-propanediamine hydrochloride: mp (MeOH/EtOAc/hexanes) 189° C. (dec.); $^1$H NMR (DMSO-d$_6$) (rotamers) δ 10.11 and 9.98 (2br, 1H), 7.89 (d, J=8.4 Hz, 1H), 7.71 and 7.65 (2t, J$_{HF}$=52.8, 52.9 Hz, 1H), 7.45 and 7.38 (2t, J=8.2, 1H), 6.97 and 6.95 (2d, J=5.7, 5.8 Hz, 1H), 4.73-4.65 and 4.51-4.44 (2m, 1H), 3.97 and 3.96 (2s, 3H), 3.91-3.57 (m, 12H), 3.11-3.03 (m, 2H), 2.93 and 2.92 (2s, 6H), 2.95-2.82 (m, 1H), 2.76-2.66 (m, 6H), 2.05-1.85 (m, 4H); Anal. Calcd. for C$_{27}$H$_{38}$N$_9$O$_4$. 1.25HCl.0.5H$_2$O: C, 47.8; H, 6.1; Cl, 6.5; N, 18.6. Found: C, 47.6; H, 6.1; Cl, 6.6%; N, 17.8%.

Example 20

Synthesis of 4-[2-(difluoromethyl)-4-methoxy-1H-benzimidazol-1-yl]-N-[1-(methylsulfonyl)-3-piperidinyl]-6-(4-morpholinyl)-N-[3-(4-morpholinyl)propyl]-1,3,5-triazin-2-amine

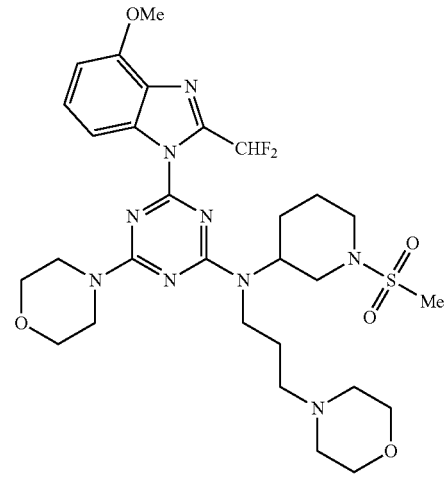 [SMILES: COc1cccc2c1nc(C(F)F)n2-c1nc(N2CCOCC2)nc(N(CCCN2CCOCC2)C2CCCN(S(C)(=O)=O)C2)n1]

The title compound was made according to the procedure as described in Example 19.

Treatment of tert-butyl 4-[[4-[2-(difluoromethyl)-4-methoxy-1H-benzimidazol-1-yl]-6-(4-morpholinyl)-1,3,5-triazin-2-yl](3-hydroxypropyl)amino]-1-piperidinecarboxylate with methanesulfonyl chloride and then morpholine gave tert-butyl 3-{[4-[2-(difluoromethyl)-4-methoxy-1H-benzimidazol-1-yl]-6-(4-morpholinyl)-1,3,5-triazin-2-yl][3-(4-morpholinyl)propyl]amino}-1-piperidinecarboxylate as a sticky oil; $^1$H NMR (DMSO-d$_6$) (rotamers) δ 7.94 and 7.88 (2d, J=8.3, 8.5 Hz, 1H), 7.62 and 7.73 (2t, J$_{HF}$=52.9, 53.5 Hz, 1H) 7.39 and 7.36 (2t, J=8.2 Hz, 1H), 6.95 (t, J=8.0 Hz, 1H), 4.53 and 4.27 (2br, 1H), 4.02-3.93 (m, 2H), 3.98 and 3.98 (2s, 3H), 3.80 and 3.70 (2br, 8H), 3.55-3.53 (m, 4H), 2.94-2.62 (br m, 2H), 2.62-2.55 (m, 3H), 2.41-2.34 (m, 5H), 1.94-1.72 (m, 5H), 1.47-1.40 (m, 1H), 1.40 (s, 9H).

Reaction of tert-butyl 3-{[4-[2-(difluoromethyl)-4-methoxy-1H-benzimidazol-1-yl]-6-(4-morpholinyl)-1,3,5-triazin-2-yl][3-(4-morpholinyl)propyl]amino}-1-piperidinecarboxylate with TFA in $CH_2Cl_2$ gave 4-[2-(difluoromethyl)-4-methoxy-1H-benzimidazol-1-yl]-6-(4-morpholinyl)-N-[3-(4-morpholinyl)propyl]-N-(3-piperidinyl)-1,3,5-triazin-2-amine, which was treated with methanesulfonyl chloride in $CH_2Cl_2$ to give 4-[2-(difluoromethyl)-4-methoxy-1H-benzimidazol-1-yl]-N-[1-(methylsulfonyl)-3-piperidinyl]-6-(4-morpholinyl)-N-[3-(4-morpholinyl)propyl]-1,3,5-triazin-2-amine in 78% yield.

A suspension of 4-[2-(difluoromethyl)-4-methoxy-1H-benzimidazol-1-yl]-N-[1-(methylsulfonyl)-3-piperidinyl]-6-(4-morpholinyl)-N-[3-(4-morpholinyl)propyl]-1,3,5-triazin-2-amine from the previous step in MeOH (20 mL) was treated with a slight excess of 1.25 M HCl in MeOH (1.1 equiv.) to give a clear solution. The solvent was removed under vacuum and the residue was washed with EtOAc to give 4-[2-(difluoromethyl)-4-methoxy-1H-benzimidazol-1-yl]-N-[1-(methylsulfonyl)-3-piperidinyl]-6-(4-morpholinyl)-N-[3-(4-morpholinyl)propyl]-1,3,5-triazin-2-amine hydrochloride: mp (MeOH) 186-190° C.; $^1$H NMR (DMSO-$d_6$) (rotamers) δ 10.65 and 10.43 (2br, 1H), 7.90 and 7.89 (2d, J=8.2, 8.1, Hz, 1H), 7.70 and 7.65 (2t, $J_{HF}$=52.9, Hz, 1H), 7.46 and 7.39 (2t, J=8.3, 8.2 Hz, 1H), 6.96 (m, 1H), 4.75-4.66 and 4.51-4.44 (2m, 1H), 3.98 and 3.97 (2s, 3H), 3.98-3.59 (m, 16H), 3.46-3.24 (m, 2H), 3.18-2.85 (m, 5H), 2.92 (s, 3H), 2.73-2.67 (m, 1H), 2.09-1.89 (m, 6H); Anal. Calcd. for $C_{29}H_{42}ClF_2N_9O_5S \cdot 1.25H_2O$: C, 48.1; H, 6.2; N, 17.4; Cl, 4.9. Found: C, 47.9; H, 6.2; N, 17.3; Cl, 5.2%.

Example 21

Synthesis of $N^1$-[4-[2-(difluoromethyl)-4-methoxy-1H-benzimidazol-1-yl]-6-(4-morpholinyl)-1,3,5-triazin-2-yl]-$N^3$,$N^3$-dimethyl-N-[1-(methylsulfonyl)-4-piperidinyl]-1,3-propanediamine

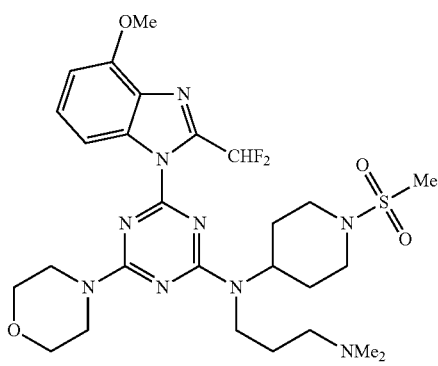 [SMILES: COc1cccc2c1nc(C(F)F)n2-c1nc(N2CCOCC2)nc(N(CCCN(C)C)C2CCN(S(C)(=O)=O)CC2)n1]

The title compound was made according to the procedure as described in Example 19.

Reaction of 1-[4-chloro-6-(4-morpholinyl)-1,3,5-triazin-2-yl]-2-(difluoromethyl)-4-methoxy-1H-benzimidazole with tert-butyl 4-[(3-hydroxypropyl)amino]-piperidine-1-carboxylate (Yokoyama et al., *Bioorg. Med. Chem.* 2008, 16, 7968) in DMF gave tert-butyl 4-[[4-[2-(difluoromethyl)-4-methoxy-1H-benzimidazol-1-yl]-6-(4-morpholinyl)-1,3,5-triazin-2-yl](3-hydroxypropyl)amino]-1-piperidinecarboxylate: $^1$H NMR (DMSO-$d_6$) (rotamers) δ 7.99 and 7.90 (2d, J=8.4, 8.5 Hz, 1H), 7.78 and 7.70 (2t, $J_{HF}$=52.9, 52.3 Hz, 1H), 7.42 and 7.37 (2t, J=8.3 Hz, 1H), 6.95 (d, J=8.0 Hz, 1H), 4.71-4.64 and 4.58-4.47 (2m, 2H), 4.13-4.04 (m, 2H), 3.98 and 3.97 (2s, 3H), 3.79 and 3.69 (2br m, 8H), 3.60-3.46 (m, 4H), 2.82-2.79 (m, 2H), 1.79-1.62 (m, 6H), 1.42 (br s, 9H); Anal. Calcd. for $C_{24}H_{40}F_2N_8O_5$: C, 56.3; H, 6.5; N, 18.1. Found: C, 56.4; H, 6.7; N, 18.0%.

Sequential treatment of tert-butyl 4-[[4-[2-(difluoromethyl)-4-methoxy-1H-benzimidazol-1-yl]-6-(4-morpholinyl)-1,3,5-triazin-2-yl](3-hydroxypropyl)amino]-1-piperidinecarboxylate with methanesulfonyl chloride and aqueous 40% dimethylamine as in Example 19 gave tert-butyl 4-{[4-[2-(difluoromethyl)-4-methoxy-1H-benzimidazol-1-yl]-6-(4-morpholinyl)-1,3,5-triazin-2-yl][3-(dimethylamino)propyl]amino}-1-piperidine-carboxylate in 83% yield: $^1$H NMR (DMSO-$d_6$) (rotamers) δ 7.96 and 7.90 (2d, J=8.3 Hz, 1H), 7.77 and 7.70 (2t, $J_{HF}$=53.1, 53.0 Hz, 1H), 7.42 and 7.38 (t, J=8.3, 8.2 Hz, 1H), 6.95 (d, J=8.2 Hz, 1H), 4.71-4.64 and 4.55-4.45 (2m, 1H), 4.13-4.02 (m, 2H), 3.98 (s, 3H), 3.81-3.77 (m, 4H), 3.66 (br, 4H), 3.54-3.44 (m, 2H), 2.82 (br, 2H), 2.27 (t, J=6.8 Hz, 2H), 2.14 and 2.12 (2s, 6H), 1.73-1.62 (m, 6H), 1.42 (s, 9H).

Reaction of tert-butyl 4-{[4-[2-(difluoromethyl)-4-methoxy-1H-benzimidazol-1-yl]-6-(4-morpholinyl)-1,3,5-triazin-2-yl][3-(dimethylamino)propyl]amino}-1-piperidine-carboxylate from the last step with TFA in $CH_2Cl_2$ gave $N^1$-[4-[2-(difluoromethyl)-4-methoxy-1H-benzimidazol-1-yl]-6-(4-morpholinyl)-1,3,5-triazin-2-yl]-$N^3$,$N^3$-dimethyl-$N^1$-(4-piperidinyl)-1,3-propanediamine in 99% yield: $^1$H NMR (DMSO-$d_6$) (rotamers) δ 7.96 and 7.93 (d, J=8.3 Hz, 1H), 7.77 and 7.70 (t, $J_{HF}$=53.1, 53.0 Hz, 1H), 7.40-7.35 (m, 1H), 6.95 (d, J=8.1 Hz, 1H), 4.63-4.56 and 4.50-4.43 (2m, 1H), 3.98 (s, 3H), 3.82-3.77 (m, 4H), 3.70 (br, 4H), 3.55-3.45 (m, 2H), 3.08-3.05 (m, 2H), 2.59-2.52 (m, 3H), 2.28 (t, J=6.8 Hz, 2H), 2.14 and 2.12 (2s, 6H), 1.76-1.61 (m, 6H).

Reaction of $N^1$-[4-[2-(difluoromethyl)-4-methoxy-1H-benzimidazol-1-yl]-6-(4-morpholinyl)-1,3,5-triazin-2-yl]-$N^3$,$N^3$-dimethyl-$N^1$-(4-piperidinyl)-1,3-propanediamine with methanesulfonyl chloride gave $N^1$-[4-[2-(difluoromethyl)-4-methoxy-1H-benzimidazol-1-yl]-6-(4-morpholinyl)-1,3,5-triazin-2-yl]-$N^3$,$N^3$-dimethyl-$N^1$-[1-(methylsulfonyl)-4-piperidinyl]-1,3-propanediamine in 99% yield.

A suspension of $N^1$-[4-[2-(difluoromethyl)-4-methoxy-1H-benzimidazol-1-yl]-6-(4-morpholinyl)-1,3,5-triazin-2-yl]-$N^3$,$N^3$-dimethyl-$N^1$-[1-(methylsulfonyl)-4-piperidinyl]-1,3-propanediamine from the previous step in MeOH (20 mL) was treated with a slight excess of 1.25 M HCl in MeOH (1.1 equiv.) to give a clear solution. The solvent was removed under vacuum and the residue was washed with EtOAc to give $N^1$-[4-[2-(difluoromethyl)-4-methoxy-1H-benzimidazol-1-yl]-6-(4-morpholinyl)-1,3,5-triazin-2-yl]-$N^3$,$N^3$-dimethyl-$N^1$-[1-(methylsulfonyl)-4-piperidinyl]-1,3-propanediamine hydrochloride: mp ($CH_2Cl_2$/MeOH) 241-243° C.; $^1$H NMR (DMSO-$d_6$) (rotamers) δ 9.95 (br, 1H), 7.90 and 7.89 (2d, J=8.2, 8.3 Hz, 1H), 7.71 and 7.70 (2t, $J_{HF}$=52.9, 53.0 Hz, 1H), 7.45 (t, J=8.2 Hz, 1H), 6.96 (d, J=8.1 Hz, 1H), 4.69-4.55 (m, 1H), 3.98 (s, 3H), 3.82-3.70 (m, 10H), 3.60-3.52 (m, 2H), 3.12-3.05 (m, 2H), 2.94 and 2.92 (2s, 3H), 2.90-2.79 (m, 2H), 2.74 and 2.70 (2s, 6H), 2.02-1.80 (m, 6H); Anal Calcd. for $C_{27}H_{39}F_2N_9O_4S \cdot 1.25HCl \cdot 0.5H_2O$: C, 47.8; H, 6.1; Cl, 6.5; N, 18.6. Found: C, 47.9; H, 6.0; Cl, 6.4; N, 18.6%.

Example 22

Synthesis of 4-[2-(difluoromethyl)-4-methoxy-1H-benzimidazol-1-yl]-N-[1-(methylsulfonyl)-4-piperidinyl]-6-(4-morpholinyl)-N-[3-(4-morpholinyl)propyl]-1,3,5-triazin-2-amine

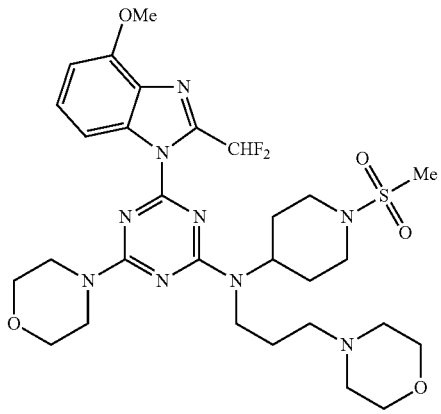 [SMILES: COc1cccc2c1nc(C(F)F)n2-c1nc(N2CCOCC2)nc(N(CCCN2CCOCC2)C2CCN(S(C)(=O)=O)CC2)n1]

The title compound was made according to the procedure as described in Example 21.

Sequential reaction of tert-butyl 4-[[4-[2-(difluoromethyl)-4-methoxy-1H-benzimidazol-1-yl]-6-(4-morpholinyl)-1,3,5-triazin-2-yl](3-hydroxypropyl)amino]-1-piperidinecarboxylate with methanesulfonyl chloride and morpholine gave tert-butyl 4-{[4-[2-(difluoromethyl)-4-methoxy-1H-benzimidazol-1-yl]-6-(4-morpholinyl)-1,3,5-triazin-2-yl][3-(4-morpholinyl)propyl]amino}-1-piperidinecarboxylate: $^1$H NMR (DMSO-$d_6$) (rotamers) δ 7.94 and 7.90 (2d, J=8.3, 8.2 Hz, 1H), 7.73 and 7.70 (2t, $J_{HF}$=53.0 Hz, 1H), 7.42 and 7.38 (2t, J=8.2 Hz, 1H), 6.95 (dd, J=8.0, 2.7 Hz, 1H), 4.72-4.59 and 4.58-4.82 (2m, 1H), 4.17-4.06 (m, 2H), 3.98 (s, 3H), 3.80-3.77 (m, 4H), 3.69 (br, 4H), 3.59-3.45 (m, 6H), 2.82 (br, 2H), 2.35-2.33 (m, 6H), 1.80-1.64 (m, 6H), 1.42 (s, 9H).

Reaction of tert-butyl 4-{[4-[2-(difluoromethyl)-4-methoxy-1H-benzimidazol-1-yl]-6-(4-morpholinyl)-1,3,5-triazin-2-yl][3-(4-morpholinyl)propyl]amino}-1-piperidinecarboxylate with TFA in $CH_2Cl_2$ gave 4-[2-(difluoromethyl)-4-methoxy-1H-benzimidazol-1-yl]-6-(4-morpholinyl)-N-[3-(4-morpholinyl)propyl]-N-(4-piperidinyl)-1,3,5-triazin-2-amine (75% yield over two steps): $^1$H NMR (DMSO-$d_6$) (rotamers) δ 7.94 (t, J=7.6 Hz, 1H), 7.73 and 7.70 (2t, $J_{HF}$=53.1, 53.0 Hz, 1H), 7.42-7.36 (m, 1H), 6.95 (d, J=8.1 Hz, 1H), 4.63-4.55 and 4.50-4.42 (2m, 1H), 3.98 (s, 3H), 3.80-3.77 (m, 4H), 3.70 (br, 4H), 3.59-3.47 (m, 6H), 3.08-3.03 (m, 2H), 2.60-2.53 (m, 2H), 2.36-2.33 (m, 6H), 1.85-1.59 (m, 6H).

Reaction of 4-[2-(difluoromethyl)-4-methoxy-1H-benzimidazol-1-yl]-6-(4-morpholinyl)-N-[3-(4-morpholinyl)propyl]-N-(4-piperidinyl)-1,3,5-triazin-2-amine with methanesulfonyl chloride in $CH_2Cl_2$ gave 4-[2-(difluoromethyl)-4-methoxy-1H-benzimidazo-1-yl]-N-[1-(methylsulfonyl)-4-piperidinyl]-6-(4-morpholinyl)-N-[3-(4-morpholinyl)propyl]-1,3,5-triazin-2-amine in 90% yield.

4-[2-(Difluoromethyl)-4-methoxy-1H-benzimidazol-1-yl]-N-[1-(methylsulfonyl)-4-piperidinyl]-6-(4-morpholinyl)-N-[3-(4-morpholinyl)propyl]-1,3,5-triazin-2-amine hydrochloride: mp (MeOH) 268-271° C., $^1$H NMR (DMSO-$d_6$) (rotamers) δ 10.82 and 10.48 (2br, 1H), 7.89 (d, J=8.2 Hz, 1H), 7.71 and 7.70 (2t, $J_{HF}$=52.9 Hz, 1H), 7.48-7.43 (m, 1H), 6.96 (dd, J=8.0, 2.3 Hz, 1H), 4.69-4.55 (m, 1H), 3.98 (s, 3H), 3.98-3.54 (m, 16H), 3.41-3.33 (m, 2H), 3.19-3.12 (m, 2H), 3.08-2.98 (m, 2H), 2.94 and 2.93 (2s, 3H), 2.89-2.80 (m, 2H), 2.09-1.85 (m, 6H); Anal. Calcd. for $C_{29}H_{42}ClF_2N_9O_5S\cdot0.5H_2O$: C, 49.0; H, 6.1; Cl, 5.0; N, 17.7. Found: C, 48.5; H, 6.0; Cl, 5.1; N, 17.5%.

Example 23

Synthesis of 4-[2-(difluoromethyl)-4-methoxy-1H-benzimidazol-1-yl]-N-{3-[4-(methylsulfonyl)-1-piperazinyl]propyl}-N-[1-(methylsulfonyl)-4-piperidinyl]-6-(4-morpholinyl)-1,3,5-triazin-2-amine

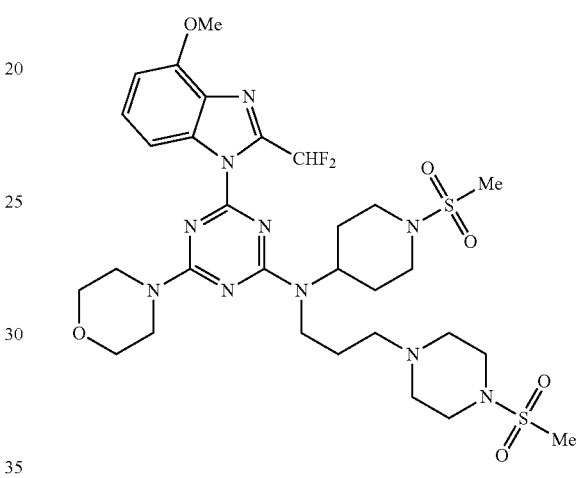

The title compound was made according to the procedure as described in Example 22.

Sequential reaction of tert-butyl 4-[[4-[2-(difluoromethyl)-4-methoxy-1H-benzimidazol-1-yl]-6-(4-morpholinyl)-1,3,5-triazin-2-yl](3-hydroxypropyl)amino]-1-piperidinecarboxylate with methanesulfonyl chloride and tert-butyl 1-piperazinecarboxylate gave tert-butyl 4-(3-{[1-(tert-butoxycarbonyl)-4-piperidinyl][4-[2-(difluoromethyl)-4-methoxy-1H-benzimidazol-1-yl]-6-(4-morpholinyl)-1,3,5-triazin-2-yl]amino}propyl)-1-piperazinecarboxylate, as an oil; $^1$H NMR (DMSO-$d_6$) (rotamers) δ 7.94 and 7.90 (2d, J=8.4, 8.3 Hz, 1H), 7.72 and 7.70 (2t, $J_{HF}$=53.1 53.0 Hz, 1H), 7.42 and 7.38 (2t, J=8.2 Hz, 1H) 6.95 (d, J=8.1 Hz, 1H), 4.75-4.64 and 4.58-4.50 (2m, 1H), 4.14-4.05 (m, 2H), 3.98 and 3.96 (2s, 3H), 3.80-3.77 (m, 4H), 3.69 (br m, 4H), 3.55-3.45 (m, 2H), 2.55-2.50 (m, 4), 2.37-2.28 (m, 9H), 1.67 (br, 5H), 1.42 (s, 9H), 1.39 (s, 9H).

Deprotection of tert-butyl 4-(3-{[1-(tert-butoxycarbonyl)-4-piperidinyl][4-[2-(difluoromethyl)-4-methoxy-1H-benzimidazol-1-yl]-6-(4-morpholinyl)-1,3,5-triazin-2-yl]amino}propyl)-1-piperazinecarboxylate with TFA in $CH_2Cl_2$ gave 4-[2-(difluoromethyl)-4-methoxy-1H-benzimidazol-1-yl]-6-(4-morpholinyl)-N-[3-(1-piperazinyl)propyl]-N-(4-piperidinyl)-1,3,5-triazin-2-amine: $^1$H NMR (DMSO-$d_6$) (rotamers) δ 7.95-7.91 (m, 1H), 7.73 and 7.70 (t, $J_{HF}$=53.0 Hz, 1H), 7.42-7.36 (m, 1H), 6.95 (d, J=8.08 Hz, 1H), 4.70-4.45 (m, 2H), 3.98 (s, 3H), 3.80-3.79 (m, 4H), 3.70 (br m, 4H), 3.56-3.46 (m, 2), 3.13-3.10 (m, 2H), 2.77-2.56 (m, 4H), 2.38-2.29 (m, 8H), 1.78-1.69 (m, 7H).

Reaction of 4-[2-(difluoromethyl)-4-methoxy-1H-benzimidazol-1-yl]-6-(4-morpholinyl)-N-[3-(1-piperazinyl)propyl]-N-(4-piperidinyl)-1,3,5-triazin-2-amine with methanesulfonyl chloride in CH$_2$Cl$_2$ gave 4-[2-(difluoromethyl)-4-methoxy-1H-benzimidazol-1-yl]-N-{3-[4-(methylsulfonyl)-1-piperazinyl]propyl}-N-[1-(methylsulfonyl)-4-piperidinyl]-6-(4-morpholinyl)-1,3,5-triazin-2-amine in 36% yield; mp (CH$_2$Cl$_2$/MeOH) 246-250° C.; $^1$H NMR (DMSO-d$_6$) (rotamers) δ 7.94 and 7.89 (2d, J=8.3 Hz, 1H), 7.73 and 7.70 (2t, J$_{HF}$=53.0, 52.9 Hz, 1H), 7.44 and 7.40 (2t, J=8.4, 8.2 Hz, 1H), 6.97 (dd, J=8.0, 3.3 Hz, 1H), 4.68-4.51 (m, 1H), 3.98 (s, 3H), 3.81-3.69 (m, 10H), 3.59-3.48 (m, 2H), 3.12-3.10 (m, 2H), 3.06-3.02 (m, 2H), 2.94 and 2.92 (2s, 3H), 2.90-2.78 (m, 2H), 2.87 and 2.83 (2s, 3H), 2.55-2.39 (m, 6H), 1.92-1.75 (m, 6H); Anal. Calcd. for C$_{30}$H$_{44}$F$_2$N$_{10}$O$_6$S$_2$.0.25H$_2$O: C, 48.2; H, 6.0; N, 18.7. Found: C, 48.1; H, 6.0; N, 18.7%.

Example 24

Synthesis of 4-[2-(difluoromethyl)-4-methoxy-1H-benzimidazol-1-yl]-N-{3-[4-(methylsulfonyl)-1-piperazinyl]propyl}-N-[1-(methylsulfonyl)-4-piperidinyl]-6-(4-morpholinyl)-1,3,5-triazin-2-amine

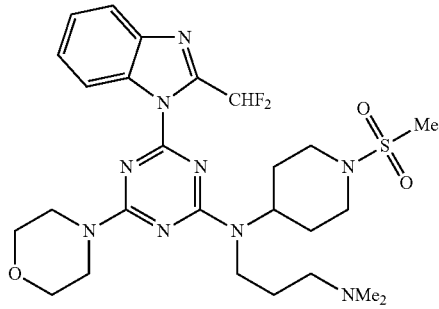 [SMILES: CN(C)CCCN(c1nc(N2CCOCC2)nc(-n2c(C(F)F)nc3ccccc32)n1)C1CCN(S(C)(=O)=O)CC1]

The title compound was made according to the procedure as described in Example 21.

Reaction of 1-[4-chloro-6-(4-morpholinyl)-1,3,5-triazin-2-yl]-2-(difluoromethyl)-1H-benzimidazole (WO 2006/095906) with tert-butyl 4-[(3-hydroxypropyl)amino]-1-piperidinecarboxylate in DMF and DIPEA as in Example 21 gave tert-butyl 4-[[4-[2-(difluoromethyl)-1H-benzimidazol-1-yl]-6-(4-morpholinyl)-1,3,5-triazin-2-yl](3-hydroxypropyl)amino]-1-piperidinecarboxylate in 83% yield: mp (CH$_2$Cl$_2$/hexanes) 188-190° C.; $^1$H NMR (DMSO-d$_6$) (rotamers) δ 8.45 and 8.35 (2d, J=7.9, 8.3 Hz, 1H), 7.83 and 7.75 (2t, J$_{HF}$=52.9 Hz, 1H), 7.85 (2d, J=8.0 Hz, 1H), 7.54-7.41 (m, 2H), 4.72-4.65 and 4.56-4.51 (2m, 1H), 4.58 and 4.48 (2t, J=4.8, 5.0 Hz, 1H), 4.15-4.07 (m, 2H), 3.83-3.78 (m, 4H), 3.70 (m, 4H), 3.62-3.47 (m, 4H), 2.81 (m, 2H), 1.78-1.65 (m, 6H), 1.42 (s, 9H); Anal Calcd. for C$_{28}$H$_{38}$F$_2$N$_8$O$_4$: C, 57.1; H, 6.5; N, 19.0. Found: C, 57.4; H, 6.3; N, 19.1%.

Reaction of the above alcohol with methanesulfonyl chloride and aqueous dimethylamine as in Example 21 gave tert-butyl 4-{[4-[2-(difluoromethyl)-1H-benzimidazol-1-yl]-6-(4-morpholinyl)-1,3,5-triazin-2-yl][3-(dimethylamino)propyl]amino}-1-piperidinecarboxylate in 95% yield: mp (CH$_2$Cl$_2$/hexanes) 190-191° C.; $^1$H NMR (DMSO-d$_6$) (rotamers) δ 8.41 and 8.35 (2d, J=7.6, 8.2 Hz, 1H), 7.85 (d, J=9 Hz, 1H), 7.81 and 7.74 (2t, J$_{HF}$=53.0, 52.9 Hz, 1H), 7.54-7.41 (m, 2H), 4.72-4.63 and 4.56-4.48 (2m, 1H), 4.14-4.07 (m, 2H), 3.83-3.78 (m, 4H), 3.70 (m, 4H), 3.56-3.45 (m, 2H), 2.82 (m, 2H), 2.29-2.25 (m, 2H), 2.14 and 2.12 (2s, 6H), 1.80-1.64 (m, 6H), 1.42 (s, 9H); Anal. Calcd. for C$_{30}$H$_{43}$F$_2$N$_9$O$_3$: C, 58.5; H, 7.0; N, 20.5. Found: C, 58.35; H, 7.3; N, 20.3%.

Reaction of the above carbamate with TFA in CH$_2$Cl$_2$ as in Example 19 gave N$^1$-[4-[2-(difluoromethyl)-1H-benzimidazol-1-yl]-6-(4-morpholinyl)-1,3,5-triazin-2-yl]-N$^3$,N$^3$-dimethyl-N$^1$-(4-piperidinyl)-1,3-propanediamine in 90% yield: $^1$H NMR (DMSO-d$_6$) (rotamers) δ 8.41 and 8.37 (2d, J=7.7, 8.1 Hz, 1H), 7.85 (d, J=7.9 Hz, 1H), 7.81 and 7.74 (2t, J$_{HF}$=53.0, 52.9 Hz, 1H), 7.51-7.41 (m, 2H), 4.64-4.56 and 4.51-4.44 (2m, 1H), 3.83-3.78 (m, 4H), 3.71 (m, 4H), 3.56-3.46 (m, 2H), 3.09-3.04 (m, 2H), 2.60-2.51 (m, 2H), 2.31-2.26 (m, 2H), 2.15 and 2.12 (2s, 6H), 1.75-1.62 (m, 6H).

Reaction of the above amine with methanesulfonyl chloride as in Example 21 gave N$^1$-[4-[2-(difluoromethyl)-1H-benzimidazol-1-yl]-6-(4-morpholinyl)-1,3,5-triazin-2-yl]-N$^3$,N$^3$-dimethyl-N$^1$-[1-(methylsulfonyl)-4-piperidinyl]-1,3-propanediamine in 90% yield. Hydrochloride: $^1$H NMR (DMSO-d$_6$) (rotamers) δ 10.17 and 10.0 (2br, 1H), 8.36 and 8.34 (2d, J=7.0 and 7.9 Hz, 1H), 7.76 and 7.74 (2t, J$_{HF}$=52.8 Hz, 1H), 7.86 (d, J=8.3 Hz, 1H), 7.57-7.53 (m, 1H), 7.46-7.43 (m, 1H), 4.70-4.56 (m, 1H), 3.84-3.71 (m, 10H), 3.62-3.53 (m, 2H), 3.13-3.06 (m, 2H), 2.94 and 2.93 (2s, 3H), 2.90-2.80 (m, 2H), 2.74 and 2.70 (2s, 6H), 1.99-1.87 (m, 6H); Anal. Calcd. for C$_{26}$H$_{38}$ClF$_2$N$_9$O$_3$S.0.5H$_2$O: C, 48.9; H, 6.15; N, 19.7; Cl, 5.6. Found: C, 48.9; H, 6.3; N, 19.8; Cl, 5.7%.

Example 25

Synthesis of 4-[2-(difluoromethyl)-4-methoxy-1H-benzimidazol-1-yl]-N-[1-(methylsulfonyl)-4-piperidinyl]-6-(4-morpholinyl)-1,3,5-triazin-2-amine

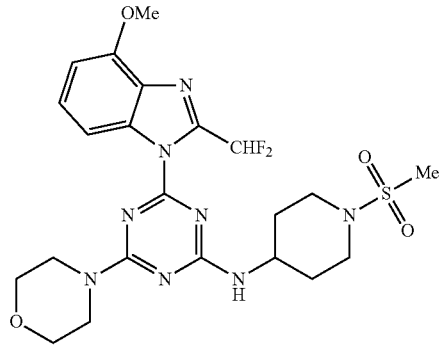 [SMILES: COc1cccc2c1nc(C(F)F)n2-c1nc(NC2CCN(S(C)(=O)=O)CC2)nc(N2CCOCC2)n1]

tert-Butyl 4-{[4-[2-(difluoromethyl)-4-methoxy-1H-benzimidazol-1-yl]-6-(4-morpholinyl)-1,3,5-triazin-2-yl]amino}-1-piperidinecarboxylate (Example 5) was reacted with TFA in CH$_2$Cl$_2$ to give 4-[2-(difluoromethyl)-4-methoxy-1H-benzimidazol-1-yl]-6-(4-morpholinyl)-N-(4-piperidinyl)-1,3,5-triazin-2-amine, which was reacted directly with methanesulfonyl chloride to give 4-[2-(difluoromethyl)-4-methoxy-1H-benzimidazol-1-yl]-N-[1-(methylsulfonyl)-4-piperidinyl]-6-(4-morpholinyl)-1,3,5-triazin-2-amine in 83% yield: mp (CH$_2$Cl$_2$/MeOH) 270-272° C.; $^1$H NMR (DMSO-d$_6$) δ8.11-7.59 (m, 3H), 7.42 and 7.38 (2t, J=8.3. 8.4 Hz, 1H), 6.95 and 6.94 (2m, J=8.0, 7.8 Hz, 1H), 3.98 and 3.97 (2s, 3H), 3.79 (m, 4H), 3.70-3.69 (m, 4H), 3.60-3.56 (m, 2H), 3.56-3.24 (m, 1H), 2.94-2.85 (m, 5H), 2.04-1.97 (m, 2H), 1.65-1.54 (m, 2H); Anal. Calcd. for $C_{22}H_{28}F_2N_8O_4S$: C, 49.1; H, 5.2; N, 20.8. Found: C, 49.3; H, 5.3; N, 20.9%.

Example 26

Synthesis of 3-{4-[2-(difluoromethyl)-4-methoxy-1H-benzimidazol-1-yl]-6-[4-(methylsulfonyl)-1-piperazinyl]-1,3,5-triazin-2-yl}-8-oxa-3-azabicyclo[3.2.1]octane

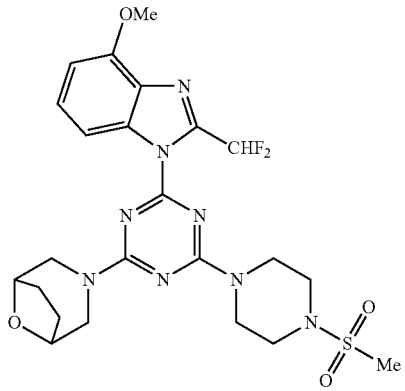 [SMILES: COc1cccc2c1nc(C(F)F)n2-c1nc(N2CCN(S(C)(=O)=O)CC2)nc(N2CC3CCC(C2)O3)n1]

A mixture of 2-(difluoromethyl)-4-methoxy-1H-benzimidazole (0.99 g, 5 mmol), tert-butyl 4-(4,6-dichloro-1,3,5-triazin-2-yl)piperazine-1-carboxylate (Eur. J. Org. Chem. 2001, 2825-2839) (2.0 g, 6 mmol), and 3.5 g (25 mmol) powdered $K_2CO_3$ in 40 mL DMF was stirred at room temperature for 1 hr. Water was added and the product was collected by filtration and washed successively with water and cold ethanol to give 2.14 g (86% yield) of tert-butyl 4-{4-chloro-6-[2-(difluoromethyl)-4-methoxy-1H-benzimidazol-1-yl]-1,3,5-triazin-2-yl}-1-piperazinecarboxylate: mp ($CH_2Cl_2$/EtOH)>300° C.; $^1H$ NMR ($CDCl_3$) δ7.99 (d, J=8.3 Hz, 1H), 7.48 (t, $J_{HF}$=53.4 Hz, 1H), 7.41 (t, J=8.3 Hz, 1H), 6.87 (d, J=8.0 Hz, 1H), 4.06 (s, 3H), 3.95 (m, 4H), 3.58 (m, 4H), 1.50 (s, 9H); Anal. Calcd. for $C_{21}H_{24}ClF_2N_7O_3$: C, 50.9; H, 4.9; N, 19.8. Found: C, 51.1; H, 4.9; N, 19.95%.

A mixture of tert-butyl 4-{4-chloro-6-[2-(difluoromethyl)-4-methoxy-1H-benzimidazol-1-yl]-1,3,5-triazin-2-yl}-1-piperazinecarboxylate (550 mg, 1.11 mmol), 8-oxa-3-azabicyclo[3.2.1]octane hydrochloride (215 mg, 1.44 mmol) and DIPEA (0.77 mL, 4.44 mmol) in THF (20 mL) was stirred at room temperature overnight. The solvent was removed under vacuum and the residue diluted with water. The resulting precipitate was washed with water, dissolved in $CH_2Cl_2$, dried ($Na_2SO_4$) and recrystallized from $CH_2Cl_2$/MeOH to give 540 mg (85% yield) of tert-butyl 4-[4-[2-(difluoromethyl)-4-methoxy-1H-benzimidazol-1-yl]-6-(8-oxa-3-azabicyclo[3.2.1]oct-3-yl)-1,3,5-triazin-2-yl]-1-piperazinecarboxylate: mp ($CH_2Cl_2$/MeOH) 181-183° C.; $^1H$ NMR ($CDCl_3$) δ7.89 (dd, J=8.4, 0.6 Hz, 1H), 7.49 (t, $J_{HF}$=53.6 Hz, 1H), 7.35 (t, J=8.2 Hz, 1H), 6.81 (d, J=7.6 Hz, 1H), 4.48 (d, J=8.0 Hz, 2H), 4.33 (dd, J=12.6, 8.9 Hz, 2H), 4.05 (s, 3H), 3.87 (br s, 4H), 3.53 (br s, 4H), 3.29 (ddd, J=32.8, 13.1, 1.6 Hz, 2H), 1.99 (dd, J=8.3, 4.4 Hz, 2H), 1.79 (m, 2H), 1.50 (s, 9H); Anal. Calcd. for $C_{27}H_{34}F_2N_8O_4 \cdot 0.05H_2O$: C, 56.55; H, 6.0; N, 19.5. Found: C, 56.2; H, 6.0; N, 19.6.

Reaction of tert-butyl 4-[4-[2-(difluoromethyl)-4-methoxy-1H-benzimidazol-1-yl]-6-(8-oxa-3-azabicyclo[3.2.1]oct-3-yl)-1,3,5-triazin-2-yl]-1-piperazinecarboxylate (513 mg, 0.896 mmol) with an excess of TFA (2 mL) in $CH_2Cl_2$ (10 mL) at room temperature for 3 hrs, followed by treatment with aq. $NH_3$ gave 385 mg (91% yield) of 3-[4-[2-(difluoromethyl)-4-methoxy-1H-benzimidazol-1-yl]-6-(1-piperazinyl)-1,3,5-triazin-2-yl]-8-oxa-3-azabicyclo[3.2.1]octane: mp 221-223° C.; $^1H$ NMR ($CDCl_3$) δ7.90 (dd, J=8.4, 0.6 Hz, 1H), 7.51 (t, $J_{HF}$=53.6 Hz, 1H), 7.35 (t, J=8.2 Hz, 1H), 6.81 (d, J=7.7 Hz, 1H), 4.47 (d, J=9.6 Hz, 2H), 4.33 (t, J=12.1 Hz, 2H), 4.05 (s, 3H), 3.86 (br s, 4H), 3.28 (dd, J=32.5, 12.3 Hz, 2H), 2.95 (br s, 4H), 1.98 (dd, J=8.3, 4.5 Hz, 2H), 1.80 (m, 2H).

Methanesulfonyl chloride (0.12 mL, 1.55 mmol) was added dropwise to a stirred suspension of 3-[4-[2-(difluoromethyl)-4-methoxy-1H-benzimidazol-1-yl]-6-(1-piperazinyl)-1,3,5-triazin-2-yl]-8-oxa-3-azabicyclo[3.2.1]octane (165 mg, 0.349 mmol) and powdered $K_2CO_3$ (434 mg, 3.15 mmol) in $CH_2Cl_2$ (5 mL) at 0° C. The reaction mixture was allowed to warm to room temperature and was stirred for 3 days. Water was added, the phases were separated and the aqueous phase was extracted with $CH_2Cl_2$. The combined organic phases were dried ($Na_2SO_4$) and the solvent removed under vacuum. Chromatography on silica, eluting with $CH_2Cl_2$/MeOH (99:1), followed by recrystallization from $CH_2Cl_2$/MeOH gave 170 mg (89% yield) of 3-{4-[2-(difluoromethyl)-4-methoxy-1H-benzimidazol-1-yl]-6-[4-(methylsulfonyl)-1-piperazinyl]-1,3,5-triazin-2-yl}-8-oxa-3-azabicyclo[3.2.1]octane: mp ($CH_2Cl_2$/MeOH) 312-314° C.; $^1H$ NMR ($CDCl_3$) δ7.86 (dd, J=8.4, 0.6 Hz, 1H), 7.45 (t, $J_{HF}$=53.6 Hz, 1H), 7.36 (t, J=8.2 Hz, 1H), 6.82 (d, J=7.8 Hz, 1H), 4.49 (br s, 2H), 4.32 (d, J=13.2 Hz, 2H), 4.05 (s, 3H), 4.02 (br s, 4H), 3.30 (m, 6H), 2.81 (s, 3H), 1.99 (m, 2H), 1.79 (m, 2H); Anal. Calcd. for $C_{23}H_{28}F_2N_8O_4S$: C, 50.2; H, 5.1; N, 20.35. Found: C, 50.3; H, 5.1; N, 20.5.

Example 27

Synthesis of 2-(difluoromethyl)-4-methoxy-1-[4-[4-(methylsulfonyl)-1-piperazinyl]-6-(4-morpholinyl)-2-pyrimidinyl]-1H-benzimidazole

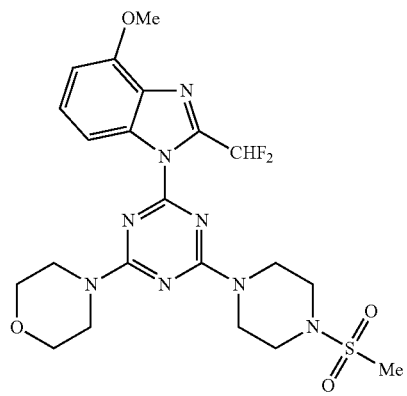 [SMILES: COc1cccc2c1nc(C(F)F)n2-c1nc(N2CCOCC2)nc(N2CCN(S(C)(=O)=O)CC2)n1]

A solution of 0.223 g (0.5 mmol) of 2-(difluoromethyl)-4-methoxy-1-[4-(4-morpholinyl)-6-(1-piperazinyl)-2-pyrimidinyl]-1H-benzimidazole (WO 2008/032064) and 0.345 g (2.5 mmol) of powdered $K_2CO_3$ in 20 mL $CH_2Cl_2$ was cooled to 0° C., and 0.086 g (0.75 mmol) of methanesulfonyl chloride was added. The reaction mixture was allowed to warm to room temperature, and after stirring overnight water was added. The organic layer was separated, washed successively with aqueous acetic acid and aq. ammonia, and dried. Chromatography on silica, eluting with $CH_2Cl_2$/EtOAc (4:1) gave 0.176 g (67% yield) of 2-(difluoromethyl)-4-methoxy-1-[4-[4-(methylsulfonyl)-1-piperazinyl]-6-(4-morpholinyl)-2-pyrimidinyl]-1H-benzimidazole: mp (MeOH) 273-274° C.; $^1$H NMR (CDCl$_3$) δ7.74 (dd, J=8.4, 0.6 Hz, 1H), 7.38 (t, $J_{HF}$=53.5 Hz, 1H), 7.33 (t, J=8.2 Hz, 1H), 6.79 (t, J=7.6 Hz, 1H), 5.54 (s, 1H), 4.05 (s, 3H), 3.83-3.79 (m, 8H), 3.64 (m, 4H), 3.35 (m, 4H), 2.82 (s, 3H); Anal. Calcd. for C$_{22}$H$_{27}$F$_2$N$_7$O$_4$S: C, 50.5; H, 5.2; N, 18.7. Found: C, 50.7; H, 5.3; N, 18.75%.

Example 28

Synthesis of 4-[2-(difluoromethyl)-4-methoxy-1H-benzimidazol-1-yl]-N-[1-(methylsulfonyl)-3-azetidinyl]-6-(4-morpholinyl)-1,3,5-triazin-2-amine

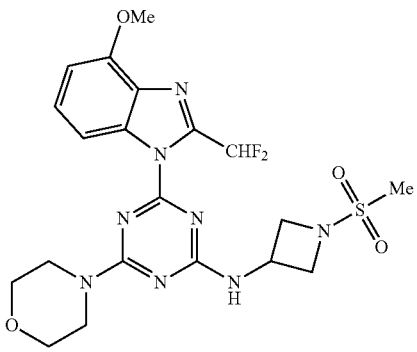 [SMILES: COc1cccc2c1nc(C(F)F)n2-c1nc(NC2CN(S(C)(=O)=O)C2)nc(N2CCOCC2)n1]

Reaction of 1-[4-chloro-6-(4-morpholinyl)-1,3,5-triazin-2-yl]-2-(difluoromethyl)-4-methoxy-1H-benzimidazole with tert-butyl 3-amino-1-azetidinecarboxylate gave tert-butyl 3-{[4-[2-(difluoromethyl)-4-methoxy-1H-benzimidazol-1-yl]-6-(4-morpholinyl)-1,3,5-triazin-2-yl]amino}-1-azetidinecarboxylate in 86% yield: mp (CH$_2$Cl$_2$/hexanes) 201-203° C.; $^1$H NMR (DMSO-d$_6$) (rotamers) δ8.50 and 8.45 (2d, J=6.3, 6.5 Hz, 1H), 8.01 and 7.93 (2d, J=8.2, 8.3 Hz, 1H), 7.83 and 7.44 (2t, $J_{HF}$=53.1, 52.9 Hz, 1H), 7.44-7.37 (m, 1H), 6.96 and 6.95 (2d, J=8.1, 8.0 Hz, 1H), 4.73-4.58 (m, 1H), 4.78 (t, J=7.8 Hz, 2H), 3.97 (s, 3H), 3.87-3.82 (m, 2H), 3.78 (m, 4H), 3.69, (m, 4H), 1 40 and 1.39 (2s, 9H); Anal. Calcd. for C$_{24}$H$_{30}$F$_2$N$_8$O$_4$: C, 54.1; H, 5.7; N, 21.0. Found: C, 54.0; 5.8; N, 21.0%.

Deprotection of the above carbamate with TFA in CH$_2$Cl$_2$ gave N-(3-azetidinyl)-4-[2-(difluoromethyl)-4-methoxy-1H-benzimidazol-1-yl]-6-(4-morpholinyl)-1,3,5-triazin-2-amine in 100% yield: $^1$H NMR (DMSO-d$_6$) (rotamers) δ8.58 and 8.54 (2d, J=5.9, 6.6 Hz, 1H), 8.07 and 7.91 (2d, J=8.4, 8.3 Hz, 1H), 7.82 and 7.70 (2t, $J_{HF}$=51.3 and 52.9 Hz, 1H), 7.44-7.38 (m, 1H), 6.97 and 6.96 (2d, J=7.9, 8.0 Hz, 1H), 4.98-4.88 and 4.88-4.80 (2m, 1H), 4.23-4.16 (m, 2H), 4.06-3.98 (m, 2H), 3.98 (s, 3H), 3.80-3.78 (m, 4H), 3.70 (m, 4H).

A mixture of the above amine (573 mg, 1.32 mmol) and dry powdered K$_2$CO$_3$ (4.0 g, 29.0 mmol) in CH$_2$Cl$_2$ (30 mL) at 0° C. was treated with methanesulfonyl chloride (0.5 mL, 6.5 mmol). The reaction mixture was stirred at 20° C. for 20 hrs, diluted with water (100 mL), and the CH$_2$Cl$_2$ was separated and removed under vacuum. The residue was washed with water and dried. Recrystallization from CH$_2$Cl$_2$/MeOH gave 550 mg (81% yield) of 4-[2-(difluoromethyl)-4-methoxy-1H-benzimidazol-1-yl]-N-[1-(methylsulfonyl)-3-azetidinyl]-6-(4-morpholinyl)-1,3,5-triazin-2-amine: mp (CH$_2$Cl$_2$/MeOH) 240-242° C.; $^1$H NMR (DMSO-d$_6$) δ8.55 and 8.50 (2d, J=6.2 and 6.8 Hz, 1H), 8.09 and 7.93 (2d, J=8.3 and 8.4 Hz, 1H), 7.82 and 7.72 (2t, $J_{HF}$=53.1 and 52.9 Hz, 1H), 7.44 and 7.39 (2t, J=8.3 and 8.2 Hz, 1H), 6.96 and 6.95 (2d, J=8.00 Hz, 1H), 4.82-4.66 (m, 1H), 4.19-4.12 (m, 2H), 3.97 (s, 3H), 3.94-3.88 (m, 2H), 3.79 (m, 4H), 3.69 (m, 4H), 3.04 (s, 3H); Anal. Calcd. for C$_{20}$H$_{24}$F$_2$N$_8$O$_4$S: C, 47.1; H, 4.7; N, 22.0. Found: C, 47.0; H, 4.9; N, 21.7%.

Example 29

Synthesis of 4-[2-(difluoromethyl)-4-methoxy-1H-benzimidazol-1-yl]-N-methyl-N-[1-(methylsulfonyl)-3-azetidinyl]-6-(4-morpholinyl)-1,3,5-triazin-2-amine

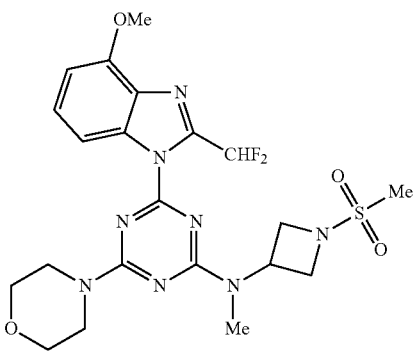 [SMILES: COc1cccc2c1nc(C(F)F)n2-c1nc(N2CCOCC2)nc(N(C)C2CN(S(C)(=O)=O)C2)n1]

To a solution of 4-[2-(difluoromethyl)-4-methoxy-1H-benzimidazol-1-yl]-N-[1-(methylsulfonyl)-3-azetidinyl]-6-(4-morpholinyl)-1,3,5-triazin-2-amine (Example 28) (170 mg, 0.33 mmol) in DMF (4 mL) at 0° C. was added NaH (24 mg, 1.0 mmol). The mixture was stirred for 30 min at this temperature and iodomethane (0.3 mL, excess) was added. The resulting mixture was allowed to warm to 20° C. and stirred for 2 hrs. Water was added and the resulting precipitate was filtered, washed with water, and dried. Recrystallization from CH$_2$Cl$_2$/MeOH gave 4-[2-(difluoromethyl)-4-methoxy-1H-benzimidazol-1-yl]-N-methyl-N-[1-(methylsulfonyl)-3-azetidinyl]-6-(4-morpholinyl)-1,3,5-triazin-2-amine (156 mg, 89% yield): mp (CH$_2$Cl$_2$/MeOH) 242-244° C.; $^1$H NMR (DMSO-d$_6$) δ7.97-7.60 (m, 2H), 7.42 (t, J=8.1 Hz, 1H), 6.96 (d, J=7.9 Hz, 1H), 5.50 and 5.26 (2m, 1H), 4.17-4.12 (m, 4H), 3.98 (s, 3H), 3.81 (m, 4H), 3.71-3.69 (m, 4H), 3.24 (s, 3H), 3.09 (s, 3H); Anal. Calcd. for C$_{21}$H$_{26}$F$_2$N$_8$O$_4$S: C, 48.1; H, 5.0; N, 21.3. Found: C, 48.0; H, 5.0; N, 21.3%.

Example 30

Synthesis of N-{1-[4-[2-(difluoromethyl)-4-methoxy-1H-benzimidazol-1-yl]-6-(4-morpholinyl)-1,3,5-triazin-2-yl]-3-azetidinyl}methanesulfonamide

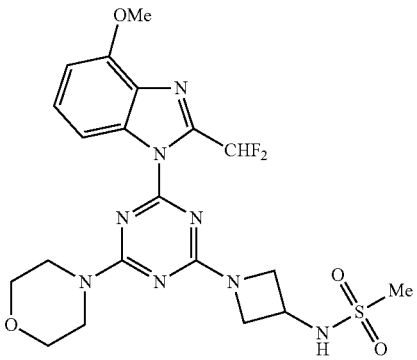 [SMILES: COc1cccc2c1nc(C(F)F)n2-c1nc(N2CCOCC2)nc(N2CC(NS(C)(=O)=O)C2)n1]

Reaction of 1-[4-chloro-6-(4-morpholinyl)-1,3,5-triazin-2-yl]-2-(difluoromethyl)-4-methoxy-1H-benzimidazole and tert-butyl 3-azetidinylcarbamate gave tert-butyl 1-[4-[2-(difluoromethyl)-4-methoxy-1H-benzimidazol-1-yl]-6-(4-morpholinyl)-1,3,5-triazin-2-yl]-3-azetidinylcarbamate in 90% yield: mp (CH$_2$Cl$_2$/hexanes) 217-220° C.; $^1$H NMR (DMSO-d$_6$) δ7.98 (d, J=8.0 Hz, 1H), 7.73 (t, J$_{HF}$=53.0 Hz, 1H), 8.24 (t, J=8.2 Hz, 1H), 6.95 (d, J=7.8 Hz, 1H), 4.42 and 4.36-4.32 (2m, 3H), 4.01-3.98 (m, 2H), 3.79-3.77 (m, 4H), 3.68 (m, 4H), 1.40 (s, 9H). Anal. Calcd. for C$_{24}$H$_{30}$F$_2$N$_8$O$_4$: C, 54.1; H, 5.7; N, 21.0. Found: C, 54.4; H, 5.8; N, 21.2%.

Deprotection of the above carbamate with TFA in CH$_2$Cl$_2$ gave 1-[4-[2-(difluoromethyl)-4-methoxy-1H-benzimidazol-1-yl]-6-(4-morpholinyl)-1,3,5-triazin-2-yl]-3-azetidinamine in 100% yield: $^1$H NMR (DMSO-d$_6$) δ7.99 (d, J=8.4 Hz, 1H), 7.74 (t, J$_{HF}$=53.1 Hz, 1H), 7.40 (t, J=8.2 Hz, 1H), 6.94 (d, J=7.8 Hz, 1H), 4.35-4.32 and 4.27-4.23 (2m, 2H), 3.97 (s, 3H), 3.87-3.68 (m, 10H), 2.21 (br, exchangeable with D$_2$O, 2H).

Reaction of 1-[4-[2-(difluoromethyl)-4-methoxy-1H-benzimidazol-1-yl]-6-(4-morpholinyl)-1,3,5-triazin-2-yl]-3-azetidinamine and methanesulfonyl chloride as in Example 28 gave N-{1-[4-[2-(difluoromethyl)-4-methoxy-1H-benzimidazol-1-yl]-6-(4-morpholinyl)-1,3,5-triazin-2-yl]-3-azetidinyl}methanesulfonamide in 86% yield: mp 307-309° C.; $^1$H NMR (DMSO-d$_6$) δ7.98 (d, J=8.1 Hz, 1H), 7.92 (br s, 1H), 7.73 (t, J$_{HF}$=53.0 Hz, 1H), 7.40 (t, J=8.2 Hz, 1H), 6.95 (d, J=7.7 Hz, 1H), 4.54-4.33 (m, 3H), 4.07-3.97 (m, 2H), 3.97 (s, 3H), 3.80-3.78 (m, 4H), 3.69 (m, 4H), 2.97 (s, 3H); Anal. Calcd. for C$_{20}$H$_{24}$F$_2$N$_8$O$_4$S.0.25H$_2$O: C, 46.6; H, 4.8; N, 21.8. Found: C, 46.7; H, 4.8; N, 22.0%.

Example 31

Synthesis of N-{1-[4-[2-(difluoromethyl)-4-methoxy-1H-benzimidazol-1-yl]-6-(4-morpholinyl)-1,3,5-triazin-2-yl]-3-azetidinyl}-N-methylmethanesulfonamide

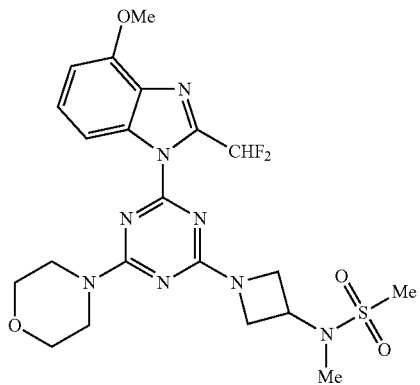 [SMILES: COc1cccc2c1nc(C(F)F)n2-c1nc(N2CCOCC2)nc(N2CC(N(C)S(C)(=O)=O)C2)n1]

To a solution of compound N-{1-[4-[2-(difluoromethyl)-4-methoxy-1H-benzimidazol-1-yl]-6-(4-morpholinyl)-1,3,5-triazin-2-yl]-3-azetidinyl}methanesulfonamide (Example 30) (182 mg, 0.36 mmol) in DMF (4 mL) was added dry powdered K$_2$CO$_3$ (1.0 g, 7.3 mmol) and iodomethane (0.5 mL, excess). The reaction mixture was stirred at 20° C. for 20 hrs and diluted with water. The resulting precipitate was collected by filtration, washed with water, and dried. Recrystallization from CH$_2$Cl$_2$/MeOH gave N-{1-[4-[2-(difluoromethyl)-4-methoxy-1H-benzimidazol-1-yl]-6-(4-morpholinyl)-1,3,5-triazin-2-yl]-3-azetidinyl}-N-methylmethanesulfonamide in 83% yield: mp (CH$_2$Cl$_2$/MeOH) 290-291; $^1$H NMR (DMSO-d$_6$) δ7.99 (d, J=7.8 Hz, 1H), 7.75 (t, J$_{HF}$=53.0 Hz, 1H), 7.40 (t, J=8.2 Hz, 1H), 6.95 (d, J=7.7 Hz, 1H), 4.78-4.71 (m, 1H), 4.46-4.26 (m, 4H), 3.98 (s, 3H), 3.80-3.79 (m, 4H), 3.69 (m, 4H), 2.93 (s, 3H), 2.91 (s, 3H); Anal. Calcd. for C$_{21}$H$_{26}$F$_2$N$_8$O$_4$S: C, 48.1; H, 5.0; N, 21.4. Found: C, 47.9; H, 4.9; N, 21.5%.

Example 32

Synthesis of 4-[2-(difluoromethyl)-4-methoxy-1H-benzimidazol-1-yl]-N-[(3R)-1-(methylsulfonyl)pyrrolidinyl]-6-(4-morpholinyl)-1,3,5-triazin-2-amine

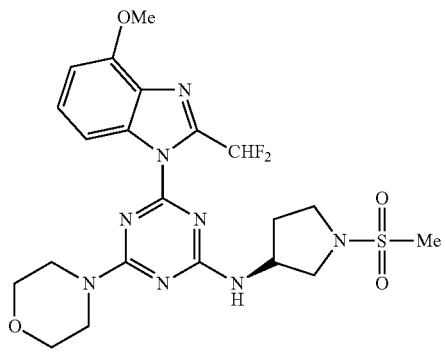

A mixture of 1-[4-chloro-6-(4-morpholinyl)-1,3,5-triazin-2-yl]-2-(difluoromethyl)-4-methoxy-1H-benzimidazole (420 mg, 1.06 mmol), tert-butyl (3R)-pyrrolidinylcarbamate (0.24 g, 1.27 mmol), and DIPEA (0.3 mL, 1.6 mmol) in THF (25 mL) was stirred at 20° C. for 20 hrs. The reaction mixture was diluted with water (100 mL), and the resulting precipitate was filtered, washed with water, and dried. Recrystallization from CH$_2$Cl$_2$/hexanes gave 554 mg (96% yield) of tert-butyl (3R)-1-[4-[2-(difluoromethyl)-4-methoxy-1H-benzimidazol-1-yl]-6-(4-morpholinyl)-1,3,5-triazin-2-yl]pyrrolidinylcarbamate: mp 151-153° C.; $^1$H NMR (DMSO-d$_6$) δ8.01 and 7.98 (2d, J=8.3, 8.9 Hz, 1H), 7.77 and 7.74 (2t, J$_{HF}$=53.0 Hz, 1H) 7.40 and 7.39 (2t, J=8.2 Hz, 1H), 7.20 (br s, exchangeable with D$_2$O, 1H), 6.94 (d, J=8.1 Hz, 1H), 4.13 (br, 1H), 3.92 (s, 3H), 3.79 (m, 4H), 3.78-3.37 (m, 2H), 3.68 (m, 4H), 3.28 (m, 2H), 2.20-2.08 and 1.95-1.84 (2m, 2H), 1.40 (s, 9H).

A solution of tert-butyl (3R)-1-[4-[2-(difluoromethyl)-4-methoxy-1H-benzimidazol-1-yl]-6-(4-morpholinyl)-1,3,5-triazin-2-yl]pyrrolidinylcarbamate (200 mg, 0.36 mmol) in CH$_2$Cl$_2$ (10 mL) was treated with TFA (5 mL) and stirred for 3 hrs. The solvent and excess TFA were removed under vacuum, and the resulting residue was diluted with H$_2$O (50 mL), and basified with aq. NH$_3$. The resulting precipitate was filtered, washed with water, and dried to give 143 mg (89% yield) of (3R)-1-[4-[2-(difluoromethyl)-4-methoxy-1H-benzimidazol-1-yl]-6-(4-morpholinyl)-1,3,5-triazin-2-yl]-3-pyrrolidinamine.

Reaction of 4-[2-(difluoromethyl)-4-methoxy-1H-benzimidazol-1-yl]-6-(4-morpholinyl)-N-[(3R)-pyrrolidinyl]-1,3,5-triazin-2-amine and methanesulfonyl chloride as in Example 28 gave 4-[2-(difluoromethyl)-4-methoxy-1H-benzimidazol-1-yl]-N-[(3R)-1-(methylsulfonyl)pyrrolidinyl]-6-(4-morpholinyl)-1,3,5-triazin-2-amine in 44% yield: mp (CH$_2$Cl$_2$/MeOH) 260-261° C.; $^1$H NMR (DMSO-d$_6$) δ8.19 and 8.13 (2d, J=6.3, 6.7 Hz, 1H), 8.10 and 7.96 (2d, J=8.3, 8.4 Hz, 1H), 7.86 and 7.73 (2t, J$_{HF}$=53.0, 52.9 Hz, 1H), 7.43-7.36 (m, 1H), 6.96 and 6.94 (2d, J=8.0 Hz, 1H), 4.61-4.48 9 (m, 1H), 3.97 (s, 3H), 3.79 (m, 4H), 3.70 (m, 4H), 3.61-3.57 and 3.50-3.44 (2m, 2H), 3.38-3.32 and 3.24-3.21 (2m, 2H), 2.924 and 2.918 (2s, 3H), 2.29-2.19 and 2.04-1.96 (2m, 2H); Anal. Calcd. for $C_{21}H_{26}F_2N_8O_4S$: C, 48.1; H, 5.0; N, 21.4. Found: C, 48.3; H, 5.2; N, 21.5%.

Example 33

Synthesis of 4-[2-(difluoromethyl)-4-methoxy-1H-benzimidazol-1-yl]-N-methyl-N-[(3R)-1-(methylsulfonyl)pyrrolidinyl]-6-(4-morpholinyl)-1,3,5-triazin-2-amine

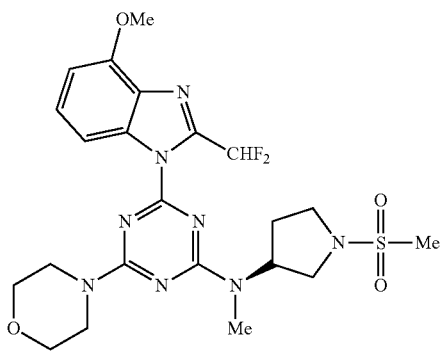

Methylation of 4-[2-(difluoromethyl)-4-methoxy-1H-benzimidazol-1-yl]-N-[(3R)-1-(methylsulfonyl)pyrrolidinyl]-6-(4-morpholinyl)-1,3,5-triazin-2-amine (Example 33) with NaH and iodomethane in DMF as in Example 29 gave 4-[2-(difluoromethyl)-4-methoxy-1H-benzimidazol-1-yl]-N-methyl-N-[(3R)-1-(methylsulfonyl)pyrrolidinyl]-6-(4-morpholinyl)-1,3,5-triazin-2-amine in 87% yield: mp ($CH_2Cl_2$/MeOH) 238-240° C.; $^1$H NMR (DMSO-$d_6$) δ7.95-7.95 (m, 2H), 7.40 (t, J=8.2 Hz, 1H), 6.95 (d, J=7.8 Hz, 1H), 5.42-5.35 (m, 1H), 3.98 (s, 3H), 3.82 (m, 4H), 3.71-3.70 (m, 4H), 3.55-3.44 (m, 2H), 3.35-3.25 (m, 2H), 3.14 (br s, 3H), 2.97 (s, 3H), 2.21-2.09 (m, 2H); Anal. Calcd. for $C_{22}H_{28}F_2N_8O_4S$: C, 49.1; H, 5.2; N, 20.8. Found: C, 49.3; H, 5.2; 21.0%.

Example 34

Synthesis of 4-[2-(difluoromethyl)-4-methoxy-1H-benzimidazol-1-yl]-N-[(3S)-1-(methylsulfonyl)pyrrolidinyl]-6-(4-morpholinyl)-1,3,5-triazin-2-amine

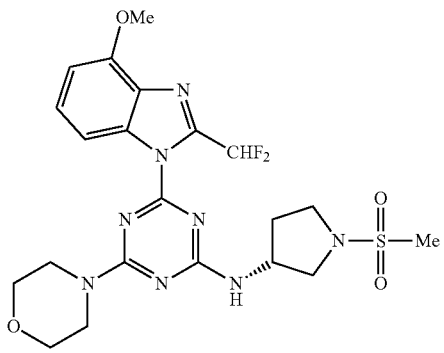

Reaction of 1-[4-chloro-6-(4-morpholinyl)-1,3,5-triazin-2-yl]-2-(difluoromethyl)-4-methoxy-1H-benzimidazole with tert-butyl (3S)-pyrrolidinylcarbamate as in Example 32 gave tert-butyl (3S)-1-[4-[2-(difluoromethyl)-4-methoxy-1H-benzimidazol-1-yl]-6-(4-morpholinyl)-1,3,5-triazin-2-yl]pyrrolidinylcarbamate in 91% yield as a white solid: mp ($CH_2Cl_2$/MeOH) 292° C. dec.; $^1$H NMR (DMSO-$d_6$) δ8.01 and 7.98 (2d, J=8.2, 8.4 Hz, 1H), 7.77 and 7.75 (2t, J=53.0 Hz, 1H), 7.40 (2t, J=8.2 Hz, 1H), 7.21 (br, exchangeable with $D_2O$, 1H), 6.95 (d, J=8.0 Hz, 1H), 4.15-411 (m, 1H), 3.97 (s, 3H), 3.79-3.37 (m, 12H), 3.00-2.08 and 1.95-1.05 (2m, 2H), 1.40 (s, 9H).

Deprotection of the carbamate with TFA in $CH_2Cl_2$ gave (3S)-1-[4-[2-(difluoromethyl)-4-methoxy-1H-benzimidazol-1-yl]-6-(4-morpholinyl)-1,3,5-triazin-2-yl]-3-pyrrolidinamine in 95% yield.

Reaction of 4-[2-(difluoromethyl)-4-methoxy-1H-benzimidazol-1-yl]-6-(4-morpholinyl)-N-[(3S)-pyrrolidinyl]-1,3,5-triazin-2-amine and methanesulfonyl chloride as in Example 28 gave 4-[2-(difluoromethyl)-4-methoxy-1H-benzimidazol-1-yl]-N-[(3S)-1-(methylsulfonyl)pyrrolidinyl]-6-(4-morpholinyl)-1,3,5-triazin-2-amine in 42% yield: mp ($CH_2Cl_2$/MeOH) 260-261° C.; $^1$H NMR (DMSO-$d_6$) δ8.19 and 8.13 (2d, J=6.4, 6.8 Hz, 1H), 8.10 and 7.96 (2d, J=8.3, 8.4 Hz, 1H), 7.86 and 7.73 (2t, $J_{HF}$=53.1, 52.9 Hz, 1H), 7.43-7.36 (m, 1H), 6.96 and 6.94 (2d, J=8.0, 7.9 Hz, 1H), 4.59-4.48 (m, 1H), 3.97 (s, 3H), 3.79 (m, 4H), 3.70 (m, 4H), 3.61-3.57 and 3.50-3.44 (2m, 2H), 3.39-3.32 and 3.24-3.21 (2 m, 2H), 2.923 and 2.917 (2s, 3H), 2.29-2.19 and 2.04-1.96 (2m, 2H); Anal. Calcd. for $C_{21}H_{26}F_2N_8O_4S$: C, 48.1; H, 5.0; N, 21.4. Found: C, 48.2; H, 5.0; N, 21.5%.

Example 35

Synthesis of 4-[2-(difluoromethyl)-4-methoxy-1H-benzimidazol-1-yl]-N-methyl-N-[(3S)-1-(methylsulfonyl)pyrrolidinyl]-6-(4-morpholinyl)-1,3,5-triazin-2-amine

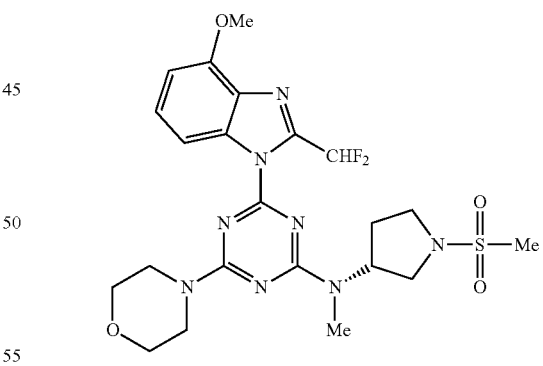

Methylation of 4-[2-(difluoromethyl)-4-methoxy-1H-benzimidazol-1-yl]-N-[(3S)-1-(methylsulfonyl)pyrrolidinyl]-6-(4-morpholinyl)-1,3,5-triazin-2-amine (Example 34) with iodomethane in the presence of NaH in DMF as in Example 29 gave 4-[2-(difluoromethyl)-4-methoxy-1H-benzimidazol-1-yl]-N-methyl-N-[(3S)-1-(methylsulfonyl)pyrrolidinyl]-6-(4-morpholinyl)-1,3,5-triazin-2-amine in 90% yield: mp ($CH_2Cl_2$/MeOH) 238-240° C.; $^1$H NMR (DMSO-$d_6$) δ7.97-7.59 (m, 2H), 7.41 (t, J=8.2 Hz, 1H), 6.9 (d, J=7.8 Hz, 1H), 5.42-5.35 (m, 1H), 3.98 (s, 3H), 3.82 (m, 4H), 3.71-3.70 (m, 4H), 3.54-3.44 (m, 2H), 3.35-3.24 (m, 2H), 3.14 (br s, 3H), 2.97 (s, 3H), 2.21-2.09 (m, 2H); Anal. Calcd. for $C_{22}H_{28}F_2N_8O_4S$: C, 49.1; H, 5.2; N, 20.8. Found: C, 49.3; H, 5.2; 21.0%.

Example 36

Synthesis of N-{(3R)-1-[4-[2-(difluoromethyl)-4-methoxy-1H-benzimidazol-1-yl]-6-(4-morpholinyl)-1,3,5-triazin-2-yl]pyrrolidinyl}methanesulfonamide

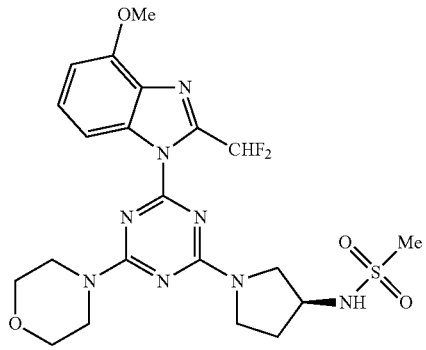 [SMILES: COc1cccc2c1nc(C(F)F)n2-c1nc(N2CCOCC2)nc(N2CC[C@H](NS(C)(=O)=O)C2)n1]

A mixture of 1-[4-chloro-6-(4-morpholinyl)-1,3,5-triazin-2-yl]-2-(difluoromethyl)-4-methoxy-1H-benzimidazole (420 mg, 1.06 mmol), tert-butyl (3R)-pyrrolidinylcarbamate (0.24 g, 1.27 mmol), and DIPEA (0.3 mL, 1.6 mmol) in THF (25 mL) was stirred at 20° C. for 20 hrs. The reaction mixture was diluted with water (100 mL), and the resulting precipitate was filtered, washed with water, and recrystallized from $CH_2Cl_2$/hexanes to give 554 mg (96% yield) of tert-butyl (3R)-1-[4-[2-(difluoromethyl)-4-methoxy-1H-benzimidazol-1-yl]-6-(4-morpholinyl)-1,3,5-triazin-2-yl]pyrrolidinylcarbamate: mp 151-153° C.; $^1$H NMR (DMSO-d$_6$) δ8.01 and 7.98 (2d, J=8.3, 8.9 Hz, 1H), 7.77 and 7.74 (2t, $J_{HF}$=53.0 Hz, 1H) 7.40 and 7.39 (2t, J=8.2 Hz, 1H), 7.20 (br s, exchangeable with D$_2$O, 1H), 6.94 (d, J=8.1 Hz, 1H), 4.13 (br, 1H), 3.92 (s, 3H), 3.79 (m, 4H), 3.78-3.37 (m, 2H), 3.68 (m, 4H), 3.28 (m, 2H), 2.20-2.08 and 1.95-1.84 (2m, 2H), 1.40 (s, 9H).

A solution of tert-butyl (3R)-1-[4-[2-(difluoromethyl)-4-methoxy-1H-benzimidazol-1-yl]-6-(4-morpholinyl)-1,3,5-triazin-2-yl]pyrrolidinylcarbamate (200 mg, 0.36 mmol) in CH$_2$Cl$_2$ (10 mL) was treated with TFA (5 mL) and stirred for 3 hrs. The solvent and excess TFA was evaporated at 20° C. under vacuum, and the resulting residue was diluted with H$_2$O (50 mL), and basified with aq. NH$_3$. The resulting precipitate was filtered, washed with water and dried to give 143 mg (89% yield) of (3R)-1-[4-[2-(difluoromethyl)-4-methoxy-1H-benzimidazol-1-yl]-6-(4-morpholinyl)-1,3,5-triazin-2-yl]-3-pyrrolidinamine.

Reaction of (3R)-1-[4-[2-(difluoromethyl)-4-methoxy-1H-benzimidazol-1-yl]-6-(4-morpholinyl)-1,3,5-triazin-2-yl]-3-pyrrolidinamine with methanesulfonyl chloride as in Example 28 gave N-{(3R)-1-[4-[2-(difluoromethyl)-4-methoxy-1H-benzimidazol-1-yl]-6-(4-morpholinyl)-1,3,5-triazin-2-yl]pyrrolidinyl}methanesulfonamide in 90% yield: mp (CH$_2$Cl$_2$/MeOH) 290-292° C.; $^1$H NMR (DMSO-d$_6$) δ8.00 (t, J=8.7 Hz, 1H), 7.77 and 7.75 (2t, $J_{HF}$=53.0 Hz, 1H), 7.43 (br s, 1H), 7.40 (dt, J=8.3, 2.5 Hz, 1H), 6.95 (d, J=8.0 Hz, 1H), 4.11-4.02 (m, 1H), 3.98 (s, 3H), 3.90-3.45 (m, 12H), 3.00 and 2.59 (2s, 3H), 2.30-2.19 and (2m, 2H); Anal. Calcd. for $C_{21}H_{26}F_2N_8O_4S$: C, 48.1; H, 5.0; N, 21.4. Found: C, 48.2; H, 5.1; N, 21.6%.

Example 37

Synthesis of N-{(3R)-1-[4-[2-(difluoromethyl)-4-methoxy-1H-benzimidazol-1-yl]-6-(4-morpholinyl)-1,3,5-triazin-2-yl]pyrrolidinyl}-N-methylmethanesulfonamide

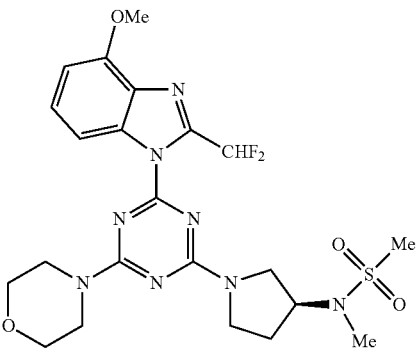 [SMILES: COc1cccc2c1nc(C(F)F)n2-c1nc(N2CCOCC2)nc(N2CC[C@H](N(C)S(C)(=O)=O)C2)n1]

Methylation of N-{(3R)-1-[4-[2-(difluoromethyl)-4-methoxy-1H-benzimidazol-1-yl]-6-(4-morpholinyl)-1,3,5-triazin-2-yl]pyrrolidinyl}methanesulfonamide (Example 36) with iodomethane in the presence of K$_2$CO$_3$ in DMF as in Example 31 gave N-{(3R)-1-[4-[2-(difluoromethyl)-4-methoxy-1H-benzimidazol-1-yl]-6-(4-morpholinyl)-1,3,5-triazin-2-yl]pyrrolidinyl}-N-methylmethanesulfonamide in 94% yield: mp (CH$_2$Cl$_2$/MeOH) 242-244° C.; $^1$H NMR (DMSO-d$_6$) δ 8.01 (d, J=8.10 Hz, 1H), 7.78 and 7.77 (2t, $J_{HF}$=53.0, Hz, 1H), 7.41 (dt, J=8.3, 2.2 Hz, 1H), 6.95 (d, J=8.0 Hz, 1H), 4.57-4.46 (m, 1H)' 3.98 (s, 3H), 3.92-3.82 (m, 6H), 3.70-3.69 (m, 4H), 3.62-3.45 (m, 2H), 2.99 (s, 3H), 2.79 (s, 3H), 2.25-2.10 (m, 2H); Anal. Calcd. for $C_{22}H_{28}F_2N_8O_4S$: C, 49.1; H, 5.2; N, 20.8. Found: C, 49.2; H, 5.3; 20.8%.

Example 38

Synthesis of N-{(3S)-1-[4-[2-(difluoromethyl)-4-methoxy-1H-benzimidazol-1-yl]-6-(4-morpholinyl)-1,3,5-triazin-2-yl]pyrrolidinyl}methanesulfonamide

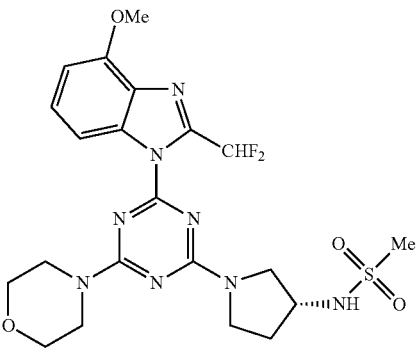 [SMILES: COc1cccc2c1nc(C(F)F)n2-c1nc(N2CCOCC2)nc(N2CC[C@@H](NS(C)(=O)=O)C2)n1]

Reaction of 1-[4-chloro-6-(4-morpholinyl)-1,3,5-triazin-2-yl]-2-(difluoromethyl)-4-methoxy-1H-benzimidazole with tert-butyl (3S)-pyrrolidinylcarbamate as in Example 36 gave tert-butyl (3S)-1-[4-[2-(difluoromethyl)-4-methoxy-1H-benzimidazol-1-yl]-6-(4-morpholinyl)-1,3,5-triazin-2-yl]pyrrolidinylcarbamate in 91% yield as a white solid: mp (CH$_2$Cl$_2$/MeOH) 292° C. dec.; $^1$H NMR (DMSO-d$_6$) δ8.01 and 7.98 (2d, J=8.2, 8.4 Hz, 1H), 7.77 and 7.75 (2t, J=53.0 Hz, 1H), 7.40 (2t, J=8.2 Hz, 1H), 7.21 (br, exchangeable with D$_2$O, 1H), 6.95 (d, J=8.0 Hz, 1H), 4.15-411 (m, 1H), 3.97 (s, 3H), 3.79-3.37 (m, 12H), 3.00-2.08 and 1.95-1.05 (2m, 2H), 1.40 (s, 9H).

Deprotection of the carbamate with TFA in CH$_2$Cl$_2$ gave (3S)-1-[4-[2-(difluoromethyl)-4-methoxy-1H-benzimidazol-1-yl]-6-(4-morpholinyl)-1,3,5-triazin-2-yl]-3-pyrrolidinamine in 95% yield.

Reaction of (3S)-1-[4-[2-(difluoromethyl)-4-methoxy-1H-benzimidazol-1-yl]-6-(4-morpholinyl)-1,3,5-triazin-2-yl]-3-pyrrolidinamine with methanesulfonyl chloride as in Example 28 gave N-{(3S)-1-[4-[2-(difluoromethyl)-4-methoxy-1H-benzimidazol-1-yl]-6-(4-morpholinyl)-1,3,5-triazin-2-yl]pyrrolidinyl}methanesulfonamide in 87% yield: mp (CH$_2$Cl$_2$/MeOH) 290-292° C.; $^1$H NMR (DMSO-d$_6$) δ8.00 (t, J=8.7 Hz, 1H), 7.77 and 7.76 (2t, J$_{HF}$=53.0 Hz, 1H), 7.44 (br s, 1H), 7.40 (dt, J=8.3, 2.5 Hz, 1H), 6.95 (d, J=8.0 Hz, 1H), 4.12-4.02 (m, 1H), 3.98 (s, 3H), 3.90-3.45 (m, 12H), 3.00 and 2.99 (2s, 3H), 2.30-2.19 and 2.03-1.93 (m, 2H); Anal. Calcd. for C$_{21}$H$_{26}$F$_2$N$_8$O$_4$S: C, 48.1; H, 5.0; N, 21.4. Found: C, 48.2; H, 5.0; N, 21.3%.

Example 39

Synthesis of N-{(3S)-1-[4-[2-(difluoromethyl)-4-methoxy-1H-benzimidazol-1-yl]-6-(4-morpholinyl)-1,3,5-triazin-2-yl]pyrrolidinyl}-N-methylmethanesulfonamide

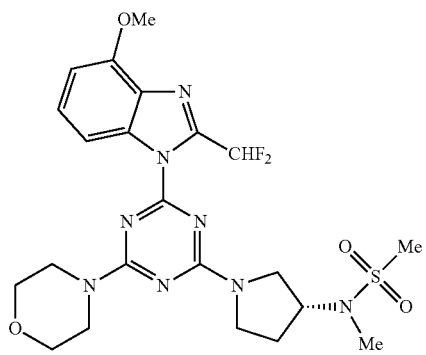 [SMILES: COc1cccc2c1nc(C(F)F)n2-c1nc(N2CCOCC2)nc(N2CC[C@@H](N(C)S(C)(=O)=O)C2)n1]

Methylation of N-{(3S)-1-[4-[2-(difluoromethyl)-4-methoxy-1H-benzimidazol-1-yl]-6-(4-morpholinyl)-1,3,5-triazin-2-yl]pyrrolidinyl}methanesulfonamide (Example 38) with iodomethane in the presence of K$_2$CO$_3$ in DMF as in Example 31 gave N-{(3S)-1-[4-[2-(difluoromethyl)-4-methoxy-1H-benzimidazol-1-yl]-6-(4-morpholinyl)-1,3,5-triazin-2-yl]pyrrolidinyl}-N-methylmethanesulfonamide in 98% yield: mp (CH$_2$Cl$_2$/MeOH) 244-247° C.; $^1$H NMR (DMSO-d$_6$) δ8.01 and 8.00 (2d, J=8.2 Hz, 1H), 7.78 and 7.77 (2t, J=53.0 Hz, 1H), 7.41 (dt, J=8.3, 2.2 Hz, 1H), 6.95 (d, J=8.0 Hz, 1H), 4.57-4.46 (m, 1H), 3.98 (s, 3H), 3.92-3.82 (m, 6H), 3.70-3.69 (m, 4H), 3.62-3.45 (m, 2H), 2.99 (s, 3H), 2.79 (s, 3H), 2.25-2.10 (m, 2H); Anal. Calcd. for C$_{22}$H$_{28}$F$_2$N$_8$O$_4$S: C, 49.1; H, 5.2; N, 20.8. Found: C, 49.3; H, 5.3; 20.8%.

Example 40

Synthesis of 4-[2-(difluoromethyl)-4-methoxy-1H-benzimidazol-1-yl]-N-[(3R)-1-(methylsulfonyl)piperidinyl]-6-(4-morpholinyl)-1,3,5-triazin-2-amine

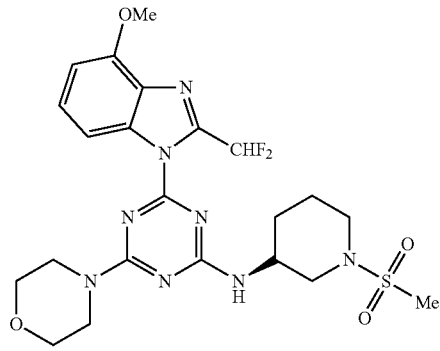

Reaction of 1-[4-chloro-6-(4-morpholinyl)-1,3,5-triazin-2-yl]-2-(difluoromethyl)-4-methoxy-1H-benzimidazole with tert-butyl (3R)-3-amino-1-piperidinecarboxylate as in Example 28 gave tert-butyl (3R)-3-{[4-[2-(difluoromethyl)-4-methoxy-1H-benzimidazol-1-yl]-6-(4-morpholinyl)-1,3,5-triazin-2-yl]amino}-1-piperidinecarboxylate in 88% yield: $^1$H NMR (DMSO-d$_6$) (rotamers) δ8.11 and 8.00 (2d, J=8.1, 8.2 Hz, 1H), 7.89 and 7.71 (2t, J$_{HF}$=53.1 Hz, 1H), 7.38 (t, J=8.2 Hz, 1H), 6.95 and 6.94 (2d, J=8.0, 7.8 Hz, 1H), 3.97 (s, 3H), 3.79-3.69 (m, 10H), 3.02-2.80 (m, 2H), 1.97-1.93 (m, 1H), 1.76 (m, 1H), 1.59-1.20 (m, 2H), 1.35 (s, 9H). Anal. Calcd. for C$_{26}$H$_{34}$F$_2$N$_8$O$_4$: C, 55.7; H, 6.1; N, 20.0. Found: C, 55.9; H, 6.1; N, 20.1%.

Deprotection of the above carbamate with TFA in CH$_2$Cl$_2$ gave 4-[2-(difluoromethyl)-4-methoxy-1H-benzimidazol-1-yl]-6-(4-morpholinyl)-N-[(3R)-piperidinyl]-1,3,5-triazin-2-amine in 98% yield: $^1$H NMR (DMSO-d$_6$) (rotamers) δ8.10 and 7.93 (2d, J=8.3 Hz, 1H), 7.88 and 7.73 (2t, J$_{HF}$=53.0 Hz, 1H), 7.84 and 7.91 (2d, J=7.7, 7.9 Hz, 1H), 7.43-7.36 (m, 1H), 6.95 and 6.94 (2d, J=7.9 Hz, 1H), 3.98 and 3.97 (2s, 3H), 3.93-3.91 (m, 1H), 3.79 (m, 4H), 3.69 (m, 4H), 3.18-3.09 (m, 1H), 2.93-2.89 (m, 1H), 2.60-2.52 (m, 2H), 1.96-1.94 and 1.73-1.70 (2m, 2H), 1.56-1.42 (m, 2H).

Reaction of 4-[2-(difluoromethyl)-4-methoxy-1H-benzimidazol-1-yl]-6-(4-morpholinyl)-N-[(3R)-piperidinyl]-1,3,5-triazin-2-amine with methanesulfonyl chloride as in Example 28 gave 4-[2-(difluoromethyl)-4-methoxy-1H-benzimidazol-1-yl]-N-[(3R)-1-(methylsulfonyl)piperidinyl]-6-(4-morpholinyl)-1,3,5-triazin-2-amine in 76% yield: mp (CH$_2$Cl$_2$/MeOH) 241-243° C.; $^1$H NMR (DMSO-d$_6$) δ8.11-7.90 (m, 2H), 7.88 and 7.38 (2t, J$_{HF}$=53.1, 53.0 Hz, 1H), 7.38 (t, J=8.2 Hz, 1H), 6.94 (d, J=8.1 Hz, 1H), 4.04-3.68 (m, 10H), 3.97 (s, 3H), 3.48 (m, 1H), 2.88 (s, 3H), 2.82-2.75 (m, 1H), 2.70-2.52 (m, 1H), 1.97-1.87 (m, 2H), 1.68-1.47 (m, 2H); Anal. Calcd. for C$_{22}$H$_{28}$F$_2$N$_8$O$_4$S: C, 49.1; H, 5.2; N, 20.8. Found: C, 49.3; H, 5.3; N, 20.8%.

Example 41

Synthesis of 4-[2-(difluoromethyl)-4-methoxy-1H-benzimidazol-1-yl]-N-methyl-N-[(3R)-1-(methylsulfonyl)piperidinyl]-6-(4-morpholinyl)-1,3,5-triazin-2-amine

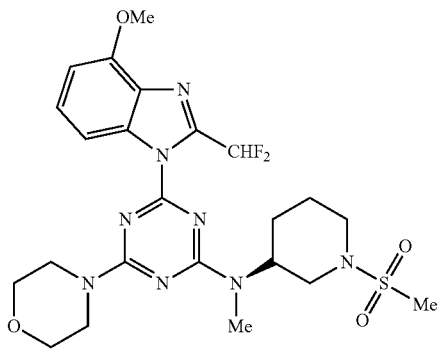

Methylation of 4-[2-(difluoromethyl)-4-methoxy-1H-benzimidazol-1-yl]-N-[(3R)-1-(methylsulfonyl)piperidinyl]-6-(4-morpholinyl)-1,3,5-triazin-2-amine (Example 40) with iodomethane in the presence of NaH in DMF as in Example 29 gave 4-[2-(difluoromethyl)-4-methoxy-1H-benzimidazol-1-yl]-N-methyl-N-[(3R)-1-(methylsulfonyl)piperidinyl]-6-(4-morpholinyl)-1,3,5-triazin-2-amine in 87% yield: mp CH$_2$Cl$_2$/MeOH) 219-221° C.; $^1$H NMR (DMSO-d$_6$) δ7.96 and 7.89 (2d, J=8.3, 8.4 Hz, 1H), 7.73 and 7.65 (2t, J$_{HF}$=52.9, 53.0 Hz, 1H), 7.41 and 7.38 (2t, J=8.2, 8.3 Hz, 1H), 6.95 (dd, J=8.1, 1.8 Hz, 1H), 4.71-4.66 and 4.60-4.53 (2m, 1H), 3.98 (s, 3H), 3.81-3.56 (m, 10H), 3.14 and 3.10 (2s, 3H), 2.98-2.80 (m, 1H), 2.90 (s, 3H), 2.73-2.68 (m, 1H), 1.93-1.55 (m, 4H); Anal. Calcd. for C$_{23}$H$_{30}$F$_2$N$_8$O$_4$S: C, 50.0; H, 5.5; N, 20.3. Found: C, 50.0; H, 5.5; N, 20.5%.

Example 42

Synthesis of 4-[2-(difluoromethyl)-4-methoxy-1H-benzimidazol-1-yl]-N-[(3S)-1-(methylsulfonyl)piperidinyl]-6-(4-morpholinyl)-1,3,5-triazin-2-amine

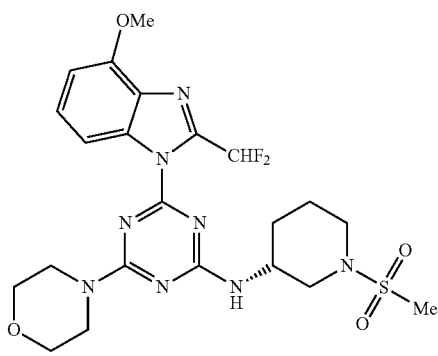

Reaction of 1-[4-chloro-6-(4-morpholinyl)-1,3,5-triazin-2-yl]-2-(difluoromethyl)-4-methoxy-1H-benzimidazole with tert-butyl (3S)-3-amino-1-piperidinecarboxylate as in Example 28 gave tert-butyl (3S)-3-{[4-[2-(difluoromethyl)-4-methoxy-1H-benzimidazol-1-yl]-6-(4-morpholinyl)-1,3,5-triazin-2-yl]amino}-1-piperidinecarboxylate in 90% yield: $^1$H NMR (DMSO-d$_6$) (rotamers) δ8.12-7.58 (m, 3H), 7.38 and 7.38 (2t, J=8.2 Hz, 1H), 6.95 and 6.94 (2d, J=7.8 Hz, 1H), 3.97 (s, 3H), 3.78-3.69 (m, 10H), 2.99-2.94 and 2.85-2.83 (2m, 2H), 1.97-1.93 and 1.78-1.76 (2m, 2H), 1.58-1.19 (m, 11H).

Deprotection of the carbamate with TFA in CH$_2$Cl$_2$ gave 4-[2-(difluoromethyl)-4-methoxy-1H-benzimidazol-1-yl]-6-(4-morpholinyl)-N-[(3S)-piperidinyl]-1,3,5-triazin-2-amine in 100% yield: $^1$H NMR (DMSO-d$_6$) (rotamers) δ8.78 (m, 2H), 8.11-7.59 (m, 3H), 7.43-7.37 (m, 1H), 6.98-6.94 (m, 1H), 4.20-4.15 (m, 1H), 3.99 and 3.97 (2s, 3H), 3.80 (m, 4H), 3.70 (m, 4H), 3.44-3.22 (m, 2H), 2.90-2.76 (m, 2H), 2.04-1.91 (m, 2H), 1.77-1.53 (m, 2H).

Reaction of 4-[2-(difluoromethyl)-4-methoxy-1H-benzimidazol-1-yl]-6-(4-morpholinyl)-N-[(3S)-piperidinyl]-1,3,5-triazin-2-amine with methanesulfonyl chloride as in Example 28 gave 4-[2-(difluoromethyl)-4-methoxy-1H-benzimidazol-1-yl]-N-[(3S)-1-(methylsulfonyl)piperidinyl]-6-(4-morpholinyl)-1,3,5-triazin-2-amine in 87% yield: mp (CH$_2$Cl$_2$/MeOH) 239-241° C.; $^1$H NMR (DMSO-d$_6$) δ8.11-7.90 (m, 2H), 7.88 and 7.69 (2t, J$_{HF}$=53.1, 53.0 Hz, 1H), 7.38 (t, J=8.2 Hz, 1H), 6.94 (d, J=8.1 Hz, 1H), 3.97 (s, 3H), 3.94-3.68 (m, 10H), 3.52-3.44 (m, 1H), 2.88 (s, 3H), 2.82-2.75 and 2.70-2.55 (2m, 2H), 1.97-1.86 (m, 2H), 1.68-1.47 (m, 2H); Anal. Calcd. for C$_{22}$H$_{28}$F$_2$N$_8$O$_4$S: C, 49.1; H, 5.2; N, 20.8. Found: C, 49.2; H, 5.4; N, 20.8%.

Example 43

Synthesis of 4-[2-(difluoromethyl)-4-methoxy-1H-benzimidazol-1-yl]-N-methyl-N-[(3S)-1-(methylsulfonyl)piperidinyl]-6-(4-morpholinyl)-1,3,5-triazin-2-amine

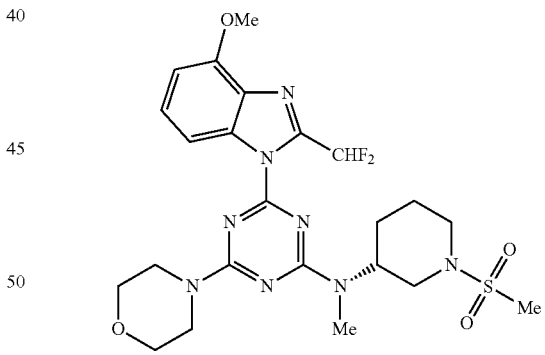

Methylation of 4-[2-(difluoromethyl)-4-methoxy-1H-benzimidazol-1-yl]-N-[(3S)-1-(methylsulfonyl)piperidinyl]-6-(4-morpholinyl)-1,3,5-triazin-2-amine with iodomethane in the presence of NaH in DMF as in Example 29 gave 4-[2-(difluoromethyl)-4-methoxy-1H-benzimidazol-1-yl]-N-methyl-N-[(3S)-1-(methylsulfonyl)piperidinyl]-6-(4-morpholinyl)-1,3,5-triazin-2-amine in 61% yield: mp (CH$_2$Cl$_2$/MeOH) 201-203° C.; $^1$H NMR (DMSO-d$_6$) δ7.96 and 7.89 (2d, J=8.3, 8.4 Hz, 1H), 7.74 and 7.65 (2t, J$_{HF}$=52.9 Hz, 1H), 7.41 and 7.38 (t, J=8.21, 8.3 Hz, 1H), 6.95 (dd, J=8.1, 1.9 Hz, 1H), 4.72-4.65 and 4.60-4.53 (2m, 1H), 3.98 (s, 3H), 3.82-3.56 (m, 10H), 3.14 and 3.10 (2s, 3H), 3.00-2.80 and 2.73-2.67 (2m, 2H), 2.90 (s, 3H), 1.93-1.55 (m, 4H); Anal. Calcd. for $C_{23}H_{30}F_2N_8O_4S$: C, 50.0; H, 5.5; N, 20.3. Found: C, 50.0; H, 5.5; N, 20.6%.

Example 44

Synthesis of N-{(3R)-1-[4-[2-(difluoromethyl)-4-methoxy-1H-benzimidazol-1-yl]-6-(4-morpholinyl)-1,3,5-triazin-2-yl]piperidinyl}methanesulfonamide

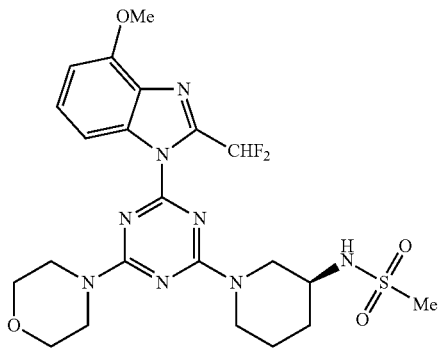 [SMILES: COc1cccc2c1nc(C(F)F)n2-c1nc(N2CCOCC2)nc(N2CCC[C@H](NS(C)(=O)=O)C2)n1]

Reaction of 1-[4-chloro-6-(4-morpholinyl)-1,3,5-triazin-2-yl]-2-(difluoromethyl)-4-methoxy-1H-benzimidazole with tert-butyl (3R)-piperidinylcarbamate gave tert-butyl (3R)-1-[4-[2-(difluoromethyl)-4-methoxy-1H-benzimidazol-1-yl]-6-(4-morpholinyl)-1,3,5-triazin-2-yl]piperidinylcarbamate in 94% yield: mp (CH$_2$Cl$_2$/hexanes) 115-118° C.; $^1$H NMR (DMSO-d$_6$) (rotamers) δ8.00 and 7.89 (2d, J=8.1, 8.4 Hz, 1H), 7.72 and 7.69 (t, $J_{HF}$=52.6, 52.7 Hz, 1H), 7.43-7.36 (m, 1H), 6.95 (d, J=7.9 Hz, 1H), 6.95 (br, exchangeable with D$_2$O, 1H), 4.53-4.43, 4.37-4.31 and 4.21-4.13 (3m, 1H), 3.97 (s, 3H), 3.79 (m, 4H), 3.69 (m, 4H), 3.42-3.36 (m, 2H), 3.16-3.10 and 3.02-2.96 (2m, 2H) 1.88-1.79 (m, 2H), 1.55-1.40 (m, 2H), 1.40 and 1.38 (2s, 9H).

Deprotection of the above carbamate with TFA in CH$_2$Cl$_2$ gave (3R)-1-[4-[2-(difluoromethyl)-4-methoxy-1H-benzimidazol-1-yl]-6-(4-morpholinyl)-1,3,5-triazin-2-yl]-3-piperidinamine in 96% yield: $^1$H NMR (DMSO-d$_6$) δ7.88 (d, J=8.2 Hz, 1H), 7.72 and 7.68 (t, $J_{HF}$=53.4, 53.0 Hz, 1H), 7.41 (t, J=8.2 Hz, 1H), 7.41 (br, exchangeable with D$_2$O, 2H), 6.96 (d, J=8.2 Hz, 1H), 4.49-4.38 (m, 1H), 4.22-4.14 and 3.90 (2m, 2H), 3.98 (s, 3H), 3.81 (m, 4H), 3.70 (m, 4H), 3.94-3.40 (m, 2H), 2.03-2.00 and 1.81 (2m, 2H), 1.66-1.54 (m, 2H).

Reaction of (3R)-1-[4-[2-(difluoromethyl)-4-methoxy-1H-benzimidazol-1-yl]-6-(4-morpholinyl)-1,3,5-triazin-2-yl]-3-piperidinamine with methanesulfonyl chloride as in Example 28 gave N-{(3R)-1-[4-[2-(difluoromethyl)-4-methoxy-1H-benzimidazol-1-yl]-6-(4-morpholinyl)-1,3,5-triazin-2-yl]piperidinyl}methanesulfonamide in 90% yield: mp (CH$_2$Cl$_2$/MeOH) 220-221° C.; $^1$H NMR (DMSO-d$_6$) δ7.98 and 7.88 (2d, J=8.4 Hz, 1H), 7.70 and 7.68 (2t, $J_{HF}$=52.9 Hz, 1H), 7.41 and 7.37 (2t, J=8.2, 8.1 Hz, 1H), 7.30-7.27 (m, 1H), 6.96 (d, J=8.1 Hz, 1H), 4.55 and 4.52 (2d, J=3.3 Hz, 1H), 4.36-4.33 and 4.26-4.23 (2m, 1H), 3.97 (s, 3H), 3.80 (m, 4H), 3.69 (m, 4H), 3.39-3.10 (m, 2H), 2.95 (s, 3H), 1.98 and 1.80-1.78 ((2m, 2H), 1.69-1.49 (m, 2H); Anal. Calcd. for $C_{22}H_{28}F_2N_8O_4S$: C, 49.1; H, 5.2; N, 20.8. Found: C, 49.0; H, 5.3; N, 20.8%.

Example 45

Synthesis of N-{(3R)-1-[4-[2-(difluoromethyl)-4-methoxy-1H-benzimidazol-1-yl]-6-(4-morpholinyl)-1,3,5-triazin-2-yl]piperidinyl}-N-methylmethanesulfonamide

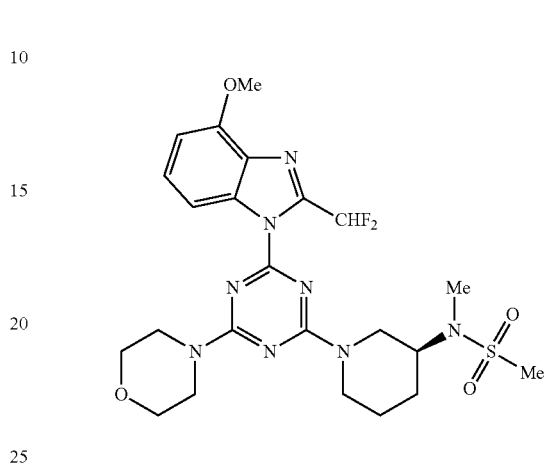

Methylation of N-{(3R)-1-[4-[2-(difluoromethyl)-4-methoxy-1H-benzimidazol-1-yl]-6-(4-morpholinyl)-1,3,5-triazin-2-yl]piperidinyl}methanesulfonamide (Example 44) with iodomethane in the presence of K$_2$CO$_3$ in DMF as in Example 31 gave N-{(3R)-1-[4-[2-(difluoromethyl)-4-methoxy-1H-benzimidazol-1-yl]-6-(4-morpholinyl)-1,3,5-triazin-2-yl]piperidinyl}-N-methylmethanesulfonamide in 93% yield: mp (CH$_2$Cl$_2$/MeOH) 224-226° C.; $^1$H NMR (DMSO-d$_6$) δ7.92 and 7.88 (2d, J=8.3 Hz, 1H), 7.68 and 7.67 (2t, $J_{HF}$=52.8 Hz, 1H), 7.43-7.35 (m, 1H), 6.95 (d, J=8.0 Hz, 1H), 4.69-4.54 (m, 2H), 3.97 (s. 3H), 3.80-3.59 (m, 9H), 3.18-3.08 (m, 1H), 2.96 and 2.93 (2s, 3H), 2.90-2.87 (m, 1H), 2.83 and 2.82 (2s, 3H), 1.86-1.57 (m, 4H); Anal. Calcd. for $C_{23}H_{30}F_2N_8O_4S$: C, 50.0; H, 5.5; N, 20.3. Found: C, 49.8; H, 5.4; N, 20.4%.

Example 46

Synthesis of N-{(3S)-1-[4-[2-(difluoromethyl)-4-methoxy-1H-benzimidazol-1-yl]-6-(4-morpholinyl)-1,3,5-triazin-2-yl]piperidinyl}methanesulfonamide

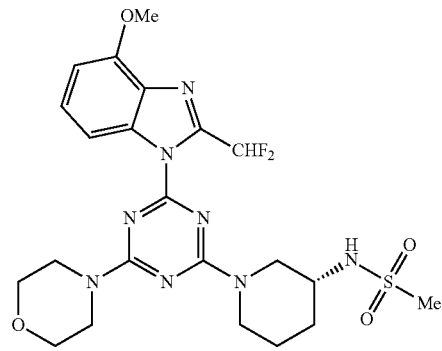 [SMILES: COc1cccc2c1nc(C(F)F)n2-c1nc(N2CCOCC2)nc(N2CCC[C@@H](NS(C)(=O)=O)C2)n1]

Reaction of 1-[4-chloro-6-(4-morpholinyl)-1,3,5-triazin-2-yl]-2-(difluoromethyl)-4-methoxy-1H-benzimidazole and tert-butyl (3S)-piperidinylcarbamate gave tert-butyl (3S)-1-[4-[2-(difluoromethyl)-4-methoxy-1H-benzimidazol-1-yl]-6-(4-morpholinyl)-1,3,5-triazin-2-yl]piperidinylcarbamate in 100% yield: mp (CH$_2$Cl$_2$/hexanes) 119-122° C.; $^1$H NMR (DMSO-d$_6$) (rotamers) δ8.00 and 7.89 (2d, J=8.4, 8.3 Hz, 1H), 7.72 and 7.69 (2t, J$_{HF}$=52.9 Hz, 1H), 7.43-7.36 (m, 1H), 6.95 (d, J=7.9 Hz, 1H), 6.96 (br, exchangeable with D$_2$O, 1H), 4.51-4.80, 4.37-4.34, and 4.21-4.14 (3m, 1H), 3.97 (s, 3H), 3.79 (m, 4H), 3.69 (m, 4H), 3.42-3.39 and 3.28 (2m, 2H), 3.17-3.10 and 3.02-2.96 (2m, 2H), 1.88-1.74 (m, 2H), 1.53-1.44 (m, 2H), 1.40 and 1.38 (2s, 9H).

Deprotection of the above carbamate with TFA in CH$_2$Cl$_2$ gave (3S)-1-[4-[2-(difluoromethyl)-4-methoxy-1H-benzimidazol-1-yl]-6-(4-morpholinyl)-1,3,5-triazin-2-yl]-3-piperidinamine in 100% yield: $^1$H NMR (DMSO-d$_6$) (rotamers) δ7.88 (d, J=8.3 Hz, 1H), 7.72 and 7.68 (2t, J$_{HF}$=53.0 Hz, 1H), 7.41 (t, J=8.2 Hz, 1H), 6.96 (d, J=8.1 Hz, 1H), 6.71 (br, exchangeable with D$_2$O, 2H), 4.52-4.35 (m, 1H), 4.25-4.16 and 3.10 (2m, 2H), 3.98 (s, 3H), 3.81 (m, 4H), 3.70 (m, 4H), 3.28 (m, 2H), 1.99 and 1.81 (2m, 2H), 1.55 (m, 2H).

Reaction of (3S)-1-[4-[2-(difluoromethyl)-4-methoxy-1H-benzimidazol-1-yl]-6-(4-morpholinyl)-1,3,5-triazin-2-yl]-3-piperidinamine with methanesulfonyl chloride as in Example 28 gave N-{(3S)-1-[4-[2-(difluoromethyl)-4-methoxy-1H-benzimidazol-1-yl]-6-(4-morpholinyl)-1,3,5-triazin-2-yl]piperidinyl}methanesulfonamide in 79% yield: mp (CH$_2$Cl$_2$/MeOH) 220-221° C.; $^1$H NMR (DMSO-d$_6$) δ7.98 and 7.88 (2d, 1H), 7.70 and 7.68 (2t, J$_{HF}$=52.8, 53.0 Hz, 1H), 7.41 and 7.37 (2t, J=8.0, 8.2 Hz, 1H), 7.30-7.26 (m, 1H), 6.94 (d, J=8.1 Hz, 1H), 4.55 and 4.52 2 (d, J=3.6, 3.3 Hz, 1H), 4.36-4.33 and 4.26-4.23 (2m, 2H), 3.97 (s, 3H), 3.80 (m, 4H), 3.69 (m, 4H), 3.39-3.10 (m, 2H), 2.95 (s, 3H), 1.98 and 1.81-1.78 (2m, 2H), 1.60-1.51 (m, 2H); Anal. Calcd. for C$_{22}$H$_{28}$F$_2$N$_8$O$_4$S: C, 49.1; H, 5.2; N, 20.8. Found: C, 49.2; H, 5.2; N, 20.8%.

Example 47

Synthesis of N-{(3S)-1-[4-[2-(difluoromethyl)-4-methoxy-1H-benzimidazol-1-yl]-6-(4-morpholinyl)-1,3,5-triazin-2-yl]piperidinyl}-N-methylmethanesulfonamide

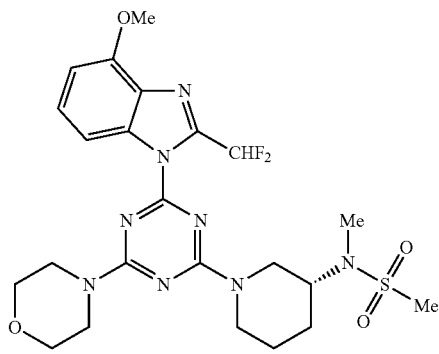 [SMILES: COc1cccc2c1nc(C(F)F)n2-c1nc(N2CCOCC2)nc(N2CCC[C@@H](N(C)S(C)(=O)=O)C2)n1]

Methylation of N-{(3S)-1-[4-[2-(difluoromethyl)-4-methoxy-1H-benzimidazol-1-yl]-6-(4-morpholinyl)-1,3,5-triazin-2-yl]piperidinyl}methanesulfonamide (Example 46) with iodomethane in the presence of K$_2$CO$_3$ in DMF as in Example 31 gave N-{(3S)-1-[4-[2-(difluoromethyl)-4-methoxy-1H-benzimidazol-1-yl]-6-(4-morpholinyl)-1,3,5-triazin-2-yl]piperidinyl}-N-methylmethanesulfonamide in 91% yield: mp (CH$_2$Cl$_2$/MeOH) 221-223° C.; $^1$H NMR (DMSO-d$_6$) δ7.92 and 7.88 (2d, J=8.3, 8.4 Hz, 1H), 7.68 and 7.67 (2t, J$_{HF}$=52.9, 52.7 Hz, 1H), 7.43-7.35 (m, 1H), 6.95 (d, J=8.1 Hz, 1H), 4.69-4.55 (m, 2H), 3.97 (s, 3H), 3.80-3.60 (m, 9H), 3.18-3.08 (m, 1H), 2.96 and 2.94 (2s, 3H), 2.90-2.87 (m, 1H), 2.83-2.82 (2s, 3H), 1.88-1.83 and 1.60-1.53 (2m, 4H); Anal. Calcd. for C$_{23}$H$_{30}$F$_2$N$_8$O$_4$S: C, 50.0; H, 5.5; N, 20.3. Found: C, 49.9; H, 5.5; N, 20.5%.

Example 48

Synthesis of 2-(difluoromethyl)-4-methoxy-1-[4-(4-morpholinyl)-6-(4-{[2-(1-oxido-4-thiomorpholinyl)ethyl]sulfonyl}-1-piperazinyl)-1,3,5-triazin-2-yl]-1H-benzimidazole

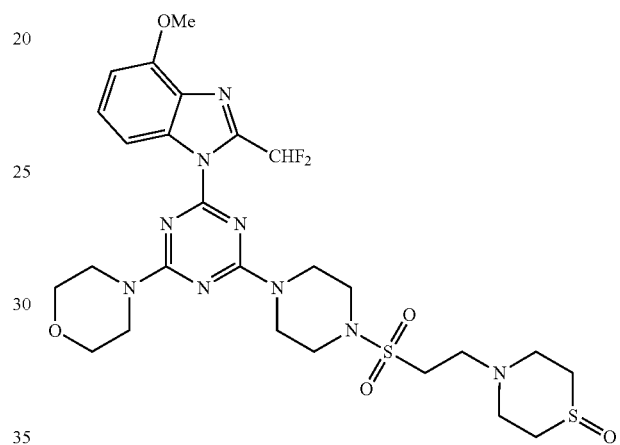

A mixture of 2-(difluoromethyl)-4-methoxy-1-{4-(4-morpholinyl)-6-[4-(vinylsulfonyl)-1-piperazinyl]-1,3,5-triazin-2-yl}-1H-benzimidazole (Example 3) (200 mg, 0.373 mmol), thiomorpholine 1-oxide trifluoroacetate (U.S. Pat. No. 6,372,773) (242 mg, 1.12 mmol), and DIPEA (0.45 mL, 2.61 mmol) was refluxed in THF (60 mL) for 4 days. The THF was removed under vacuum and the residue was dissolved in dioxane (60 mL). Additional thiomorpholine 1-oxide trifluoroacetate (161 mg, 0.745 mmol) and DIPEA (0.45 mL, 2.61 mmol) were added and the mixture was refluxed for 2 days. The solvent was removed under vacuum and the residue was diluted with water. The resulting precipitate was filtered, washed with water, and dissolved in CH$_2$Cl$_2$. The solution was dried (Na$_2$SO$_4$) and the solvent was removed under vacuum. Chromatography on silica, eluting with CH$_2$Cl$_2$/MeOH (95:5), followed by recrystallization from CH$_2$Cl$_2$/hexane gave 138 mg (56% yield) of 2-(difluoromethyl)-4-methoxy-1-[4-(4-morpholinyl)-6-(4-{[2-(1-oxido-4-thiomorpholinyl)ethyl]sulfonyl}-1-piperazinyl)-1,3,5-triazin-2-yl]-1H-benzimidazole: mp (CH$_2$Cl$_2$/hexane) 229-231° C.; $^1$H NMR (CDCl$_3$) δ7.85 (d, J=8.0 Hz, 1H), 7.43 (t, J$_{HF}$=53.5 Hz, 1H), 7.36 (t, J=8.2 Hz, 1H), 6.82 (d, J=7.9 Hz, 1H), 4.05 (s, 3H), 4.01 (br s, 4H), 3.89 (br s, 4H), 3.79 (m, 4H), 3.38 (t, J=5.0 Hz, 4H), 3.15 (m, 4H), 2.99 (dd, J=8.8, 5.4, 2H), 2.79 (m, 6H); Anal. Calcd. for C$_{26}$H$_{35}$F$_2$N$_9$O$_5$S$_2$.0.2H$_2$O: C, 47.4; H, 5.4; N, 19.1. Found: C, 47.3; H, 5.5; N, 18.7.

Example 49

Synthesis of 2-(difluoromethyl)-1-[4-(4-{[2-(1,1-dioxido-4-thiomorpholinyl)ethyl]sulfonyl}-1-piperazinyl)-6-(4-morpholinyl)-1,3,5-triazin-2-yl]-4-methoxy-1H-benzimidazole

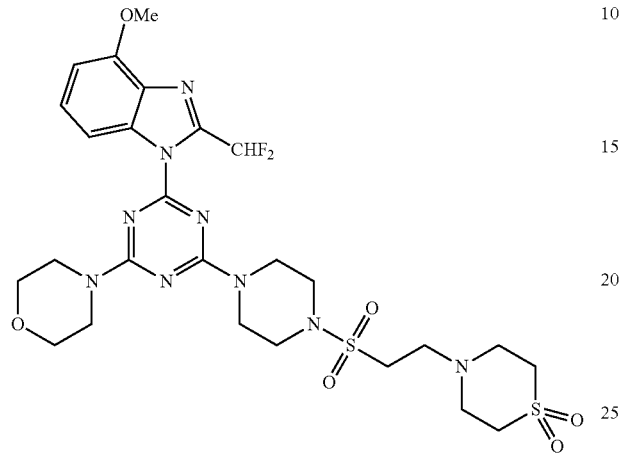

A mixture of 2-(difluoromethyl)-4-methoxy-1-{4-(4-morpholinyl)-6-[4-(vinylsulfonyl)-1-piperazinyl]-1,3,5-triazin-2-yl}-1H-benzimidazole (Example 3) (180 mg, 0.335 mmol), thiomorpholine (0.17 mL, 1.68 mmol) in THF (50 mL) was stirred at room temperature for 3 days and then at reflux for 3 hrs. The solvent was removed under vacuum and the residue was dissolved in dioxane (30 mL) and additional thiomorpholine (0.17 mL, 1.68 mmol) was added. The reaction mixture was refluxed for 2 days. The solvent was removed under vacuum and the residue diluted with water. The resulting precipitate was filtered, washed with water and dissolved in $CH_2Cl_2$. The solution was dried ($Na_2SO_4$) and solvent removed under vacuum. Chromatography on silica, eluting with $CH_2Cl_2$/MeOH (98:2), followed by recrystallization from $CH_2Cl_2$/hexane gave 180 mg (84% yield) of 2-(difluoromethyl)-4-methoxy-1-[4-(4-morpholinyl)-6-(4-{[2-(4-thiomorpholinyl)ethyl]sulfonyl}-1-piperazinyl)-1,3,5-triazin-2-yl]-1H-benzimidazole: mp ($CH_2Cl_2$/hexane) 210-212° C.; $^1$H NMR (CDCl$_3$) δ7.86 (dd, J=8.3, 0.5 Hz, 1H), 7.43 (t, $J_{HF}$=53.5 Hz, 1H), 7.36 (t, J=8.2 Hz, 1H), 6.82 (d, J=7.7 Hz, 1H), 4.05 (s, 3H), 4.00 (br s, 4H), 3.89 (br s, 4H), 3.79 (m, 4H), 3.38 (t, J=5.1 Hz, 4H), 3.11 (dd, J=8.3, 6.1 Hz, 2H), 2.87 (dd, J=8.3, 6.1 Hz, 2H), 2.73 (dd, J=6.1, 3.8 Hz, 4H), 2.63 (m, 4H); Anal. Calcd. for $C_{26}H_{35}F_2N_9O_4S_2 \cdot 0.5H_2O$: C, 48.1; H, 5.6; N, 19.4. Found: C, 48.2; H, 5.4; N, 19.3%.

A solution of $KMnO_4$ (88 mg, 0.559 mmol) in water (6 mL) was added dropwise to a stirred solution of 2-(difluoromethyl)-4-methoxy-1-[4-(4-morpholinyl)-6-(4-{[2-(4-thiomorpholinyl)ethyl]sulfonyl}-1-piperazinyl)-1,3,5-triazin-2-yl]-1H-benzimidazole (170 mg, 0.266 mmol) in acetone (50 mL) and acetic acid (7.5 mL) at room temperature. After 2.5 hrs the reaction was diluted with water, decolourized with $Na_2SO_3$ and the acetone removed under vacuum. The mixture was neutralized with conc. aq. $NH_3$ to give a precipitate, which was dissolved in $CH_2Cl_2$ and dried ($Na_2SO_4$). The solvent was then removed under vacuum. Chromatography on silica, eluting with $CH_2Cl_2$/MeOH (98.5:1.5) gave 117 mg (65% yield) of 2-(difluoromethyl)-1-[4-(4-{[2-(1,1-dioxido-4-thiomorpholinyl)ethyl]sulfonyl}-1-piperazinyl)-6-(4-morpholinyl)-1,3,5-triazin-2-yl]-4-methoxy-1H-benzimidazole: mp 258-261° C.; $^1$H NMR (CDCl$_3$) δ7.85 (d, J=8.3 Hz, 1H), 7.42 (t, $J_{HF}$=53.5 Hz, 1H), 7.35 (t, J=8.2 Hz, 1H), 6.82 (d, J=8.0 Hz, 1H), 4.05 (s, 3H), 4.01 (br s, 4H), 3.88 (br s, 4H), 3.79 (m, 4H), 3.37 (t, J=5.0 Hz, 4H), 3.07 (m, 4H), 3.05 (s, 8H); HRMS Calcd. for $C_{26}H_{36}F_2N_9O_6S_2$: MH$^+$ m/z 672.2198. Found: m/z 672.2184.

Example 50

Synthesis of N-{2-[(4-{[4-[2-(difluoromethyl)-4-methoxy-1H-benzimidazol-1-yl]-6-(4-morpholinyl)-1,3,5-triazin-2-yl]oxy}-1-piperidinyl)sulfonyl]ethyl}-N,N-dimethylamine

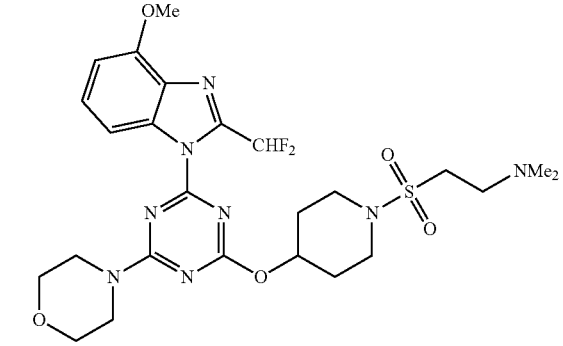 [SMILES: COc1cccc2c1nc(C(F)F)n2-c1nc(OC2CCN(S(=O)(=O)CCN(C)C)CC2)nc(N2CCOCC2)n1]

To a solution of 2-(difluoromethyl)-4-methoxy-1-[4-(4-morpholinyl)-6-(4-piperidinyloxy)-1,3,5-triazin-2-yl]-1H-benzimidazole (Example 16) (1.52 g, 3.29 mmol) and DIPEA (2.3 ml, 4 eq.) in $CH_2Cl_2$ (30 mL) at 0° C. was added 2-chloroethanesulfonyl chloride (1 mL, excess). The reaction mixture was stirred at 20° C. for 20 hrs and diluted with water (50 mL). The $CH_2Cl_2$ layer was separated and the aqueous layer was further extracted with $CH_2Cl_2$ (3×20 mL). The combined organic fractions were washed successively with aq. HOAc, aq. $K_2CO_3$, and water, and dried ($MgSO_4$). Evaporation of the solvent and chromatography of the residue on silica, eluting with $CH_2Cl_2$/EtOAc (9:1) gave 2-(difluoromethyl)-4-methoxy-1-(4-(4-morpholinyl)-6-{[1-(vinylsulfonyl)-4-piperidinyl]oxy}-1,3,5-triazin-2-yl)-1H-benzimidazole (1.17 g, 65% yield): mp ($CH_2Cl_2$/MeOH) 266-269° C.; $^1$H NMR (DMSO-d$_6$) δ7.95 (d, J=7.9 Hz, 1H), 7.70 (t, $J_{HF}$=52.8 Hz, 1H), 7.44 (t, J=8.2 Hz, 1H), 6.98 (d, J=7.8 Hz, 1H), 6.88 (dd, J=16.5, 10.0 Hz, 1H), 6.19 (d, J=10.0 Hz, 1H), 6.15 (d, J=16.5 Hz, 1H), 5.26-5.20 (m, 1H), 3.98 (s, 3H), 3.84 (m, 4H), 3.74-3.32 (m, 4H), 3.39-3.32 (m, 2H), 3.14-3.08 (m, 2H), 2.14-2.09 (m, 2H), 1.90-1.18 (m, 2H); Anal. Calcd. for $C_{23}H_{27}F_2N_7O_5S \cdot 0.5CH_2Cl_2$: C, 47.7; H, 4.7; N, 16.5. Found: C, 47.8; H, 4.7; N, 16.8%.

To a suspension of the above vinylsulfone (207 mg, 0.38 mmol) in THF (25 mL) was added 40% aq. dimethylamine (5 mL, excess) and the reaction mixture was stirred at 20° C. for 20 hrs. The solvent was evaporated and the residue was diluted with $H_2O$ (50 mL). The resulting precipitate was filtered, washed with water and dried. Chromatography on silica, eluting with $CH_2Cl_2$/MeOH (97:3) gave N-{2-[(4-{[4-[2-(difluoromethyl)-4-methoxy-1H-benzimidazol-1-yl]-6-(4-morpholinyl)-1,3,5-triazin-2-yl]oxy}-1-piperidinyl)sulfonyl]ethyl}-N,N-dimethylamine (210 mg, 97% yield). The amine was converted to the hydrochloride salt by combining with 1.25 M HCl in MeOH: mp (MeOH), 264-268° C.; $^1$H NMR (DMSO-d$_6$) δ10.20 (br s, 1H), 7.96 (d, J=7.9 Hz, 1H), 7.72 (t, J$_{HF}$=52.8 Hz, 1H), 7.45 (t, J=8.3 Hz, 1H), 6.99 (d, J=7.8 Hz, 1H), 5.30-5.24 (m, 1H), 3.90 (s, 3H), 3.86-3.83 (m, 4H), 3.74-3.71 (m, 4H), 3.64-3.60 (m, 2H), 3.54-3.49 (m, 2H), 3.42-3.39 (m, 2H), 3.32-3.24 (m, 2H), 2.80 (s, 6H), 2.16-2.09 (m, 2H), 1.92-1.84 (m, 2H); Anal. Calcd. for C$_{25}$H$_{35}$ClF$_2$N$_8$O$_5$S: C, 47.3; H, 5.6; N, 17.7; Cl, 5.6. Found: C, 47.4; H, 5.7; N, 17.8; Cl, 5.7%.

Example 51

Synthesis of 2-(difluoromethyl)-4-methoxy-1-{4-(4-morpholinyl)-6-[(1-{[2-(4-morpholinyl)ethyl]sulfonyl}-4-piperidinyl)oxy]-1,3,5-triazin-2-yl}-1H-benzimidazole

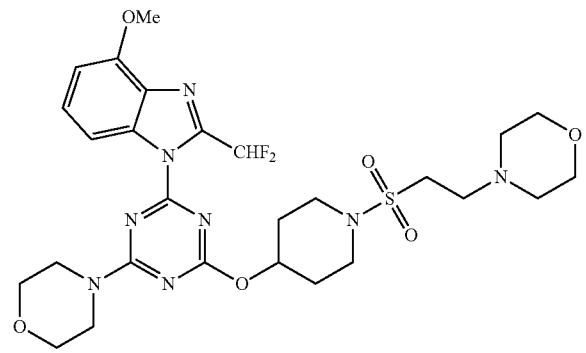 [SMILES: COc1cccc2c1nc(C(F)F)n2-c1nc(OC2CCN(S(=O)(=O)CCN3CCOCC3)CC2)nc(N2CCOCC2)n1]

The title compound was made according to the procedure as described in Example 50.

Reaction of 2-(difluoromethyl)-4-methoxy-1-(4-(4-morpholinyl)-6-{[1-(vinylsulfonyl)-4-piperidinyl]oxy}-1,3,5-triazin-2-yl)-1H-benzimidazole (Example 50) with morpholine as in Example 11 gave 2-(difluoromethyl)-4-methoxy-1-{4-(4-morpholinyl)-6-[(1-{[2-(4-morpholinyl)ethyl]sulfonyl}-4-piperidinyl)oxy]-1,3,5-triazin-2-yl}-1H-benzimidazole in 81% yield. Hydrochloride: mp (MeOH) 255-259° C.; $^1$H NMR (DMSO-d$_6$) δ10.87 (br s, 1H), 7.96 (d, J=8.3 Hz, 1H), 7.72 (t, J$_{HF}$=52.8 Hz, 1H), 7.45 (t, J=8.3 Hz, 1H), 6.99 (d, J=7.8 Hz, 1H), 5.30-5.25 (m, 1H), 4.06-3.95 (m, 2H), 3.98 (s, 3H), 3.86-3.84 (m, 4H), 3.74-3.71 (m, 8H), 3.53-3.49 (m, 6H), 3.37-3.27 (m, 2H), 3.15 (m, 2H), 2.16-2.15 (m, 2H), 2.19-1.87 (m, 2H); Anal. Calcd. for C$_{27}$H$_{37}$ClF$_2$N$_8$O$_6$S.0.1H$_2$O: C, 47.9; H, 5.5; N, 16.6; Cl, 5.2. Found: C, 47.9; H, 5.6; N, 16.6; Cl, 5.5%.

Example 52

Synthesis of 2-(difluoromethyl)-4-methoxy-1-[4-{[1-({2-[4-(methylsulfonyl)-1-piperazinyl]ethyl}sulfonyl)-4-piperidinyl]oxy}-6-(4-morpholinyl)-1,3,5-triazin-2-yl]-1H-benzimidazole

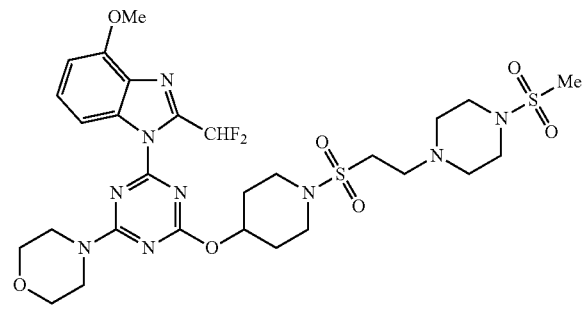 [SMILES: COc1cccc2c1nc(C(F)F)n2-c1nc(OC2CCN(S(=O)(=O)CCN3CCN(S(C)(=O)=O)CC3)CC2)nc(N2CCOCC2)n1]

The title compound was made according to the procedure as described in Example 50.

Reaction of 2-(difluoromethyl)-4-methoxy-1-(4-(4-morpholinyl)-6-{[1-(vinylsulfonyl)-4-piperidinyl]oxy}-1,3,5-triazin-2-yl)-1H-benzimidazole with 1-(methylsulfonyl)piperazine as in Example 12 gave 2-(difluoromethyl)-4-methoxy-1-[4-{[1-({2-[4-(methylsulfonyl)-1-piperazinyl]ethyl}sulfonyl)-4-piperidinyl]oxy}-6-(4-morpholinyl)-1,3,5-triazin-2-yl]-1H-benzimidazole in 28% yield: mp (MeOH) 251-254° C.; $^1$H NMR (DMSO-d$_6$) δ7.96 (d, J=8.3 Hz, 1H), 7.71 (t, J$_{HF}$=52.8 Hz, 1H), 7.45 (t, J=8.3 Hz, 1H), 6.99 (d, J=7.9 Hz, 1H), 5.28-5.22 (m, 1H), 3.98 (s, 3H), 3.85-3.84 (m, 4H), 3.74-3.70 (m, 4H), 3.52-3.46 (m, 2H), 3.34-3.20 (m, 4H), 3.13-3.11 (m, 4H), 2.86 (s, 3H), 2.78-2.74 (m, 2H), 2.56-2.54 (m, 4H), 2.13-2.08 (m, 2H), 1.88-1.80 (m, 2H); Anal. Calcd. for C$_{28}$H$_{39}$F$_2$N$_9$O$_7$S$_2$: C, 47.0; H, 5.5; N, 17.6. Found: C, 47.2; H, 5.4; N, 17.4%.

Example 53

Synthesis of N-{1-[4-[2-(difluoromethyl)-4-methoxy-1H-benzimidazol-1-yl]-6-(4-morpholinyl)-1,3,5-triazin-2-yl]-4-piperidinyl}-N-[3-(dimethylamino)propyl]-methanesulfonamide

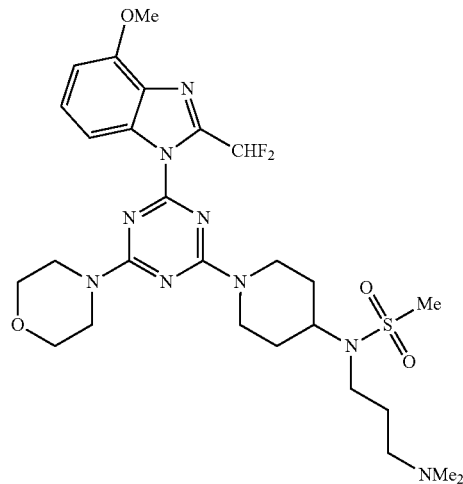 [SMILES: COc1cccc2c1nc(C(F)F)n2-c1nc(N2CCOCC2)nc(N2CCC(N(CCCN(C)C)S(C)(=O)=O)CC2)n1]

To a mixture of N-{1-[4-[2-(difluoromethyl)-4-methoxy-1H-benzimidazol-1-yl]-6-(4-morpholinyl)-1,3,5-triazin-2-yl]-4-piperidinyl}methanesulfonamide (Example 17) (1.95 g, 3.62 mmol) and K$_2$CO$_3$ (6 g, excess) in DMF (20 mL) was added 3-bromo-1-propanol (4 mL, excess). The reaction mixture was stirred at 20° C. for 7 days and diluted with water. The resulting sticky material was extracted into CH$_2$Cl$_2$ (4×30 mL) and dried (Na$_2$SO$_4$). Evaporation of the solvent and the chromatography of the residue on silica, eluting with a gradient of CH$_2$Cl$_2$ and EtOAc (0-20%) followed by CH$_2$Cl$_2$/MeOH (97:3) gave N-{1-[4-[2-(difluoromethyl)-4-methoxy-1H-benzimidazol-1-yl]-6-(4-morpholinyl)-1,3,5-triazin-2-yl]-4-piperidinyl}-N-(3-hydroxypropyl)methanesulfonamide (1.04 g, 49%): mp (CH$_2$Cl$_2$/MeOH) 219-221° C.; $^1$H NMR (DMSO-d$_6$) δ7.89 (d, J=8.2 Hz, 1H), 7.69 (t, J$_{HF}$=52.9 Hz, 1H), 7.41 (t, J=8.2 Hz, 1H), 6.95 (d, J=7.9 Hz, 1H), 4.73 (d, J=12.8 Hz, 1H), 4.82 (d, J=12.3 Hz, 1H), 4.44 (t, J=5.1 Hz, 1H), 3.97 (S, 3H), 3.92-3.83 (m, 1H), 3.80-3.79 (m, 4H), 3.69 (m, 4H), 3.40-3.32 (m, 2H), 3.14-2.96 (m, 4H), 3.96

(s, 3H), 1.87-1.80 (m, 2H), 1.74-1.64 (m, 4H); Anal Calcd. for $C_{25}H_{34}F_2N_8O_5S$: C, 50.33; H, 5.74; N, 18.78. Found: C, 50.2; H, 5.9; N, 18.5%.

The above alcohol (305 mg, 0.51 mmol) in $CH_2Cl_2$ (15 mL) was treated with $Et_3N$ (0.3 mL) and methanesulfonyl chloride (0.2 mL, 2.5 mmol) at 0° C. The reaction mixture was stirred at this temp for 45 min and 40% aqueous solution of dimethylamine (5 mL) was then added. Stirring was continued for 2 days at 20° C., and the $CH_2Cl_2$ was evaporated. The residue was diluted with water, and the resulting precipitate was washed with water and dried. Chromatography on neutral alumina, eluting with $CH_2Cl_2$/MeOH (98:2), followed by chromatography on silica, eluting with $CH_2Cl_2$/MeOH/aq. $NH_3$ (96:3:1) gave N-{1-[4-[2-(difluoromethyl)-4-methoxy-1H-benzimidazol-1-yl]-6-(4-morpholinyl)-1,3,5-triazin-2-yl]-4-piperidinyl}-N-[3-(dimethylamino)propyl]methanesulfonamide (200 mg, 63%). The amine was converted to the hydrochloride salt by combining with 1.25 M HCl in MeOH. Recrystallization from MeOH/isopropanol gave N-{1-[4-[2-(difluoromethyl)-4-methoxy-1H-benzimidazol-1-yl]-6-(4-morpholinyl)-1,3,5-triazin-2-yl]-4-piperidinyl}-N-[3-(dimethylamino)propyl]methanesulfonamide hydrochloride: mp 187-191° C.; $^1$H NMR (DMSO-$d_6$) δ9.83 (br s, 1H), 7.89 (d, J=8.0 Hz, 1H), 7.70 (t, $J_{HF}$=52.9 Hz, 1H), 7.41 (t, J=8.2 Hz, 1H), 6.95 (d, J=7.9 Hz, 1H), 4.84-4.73 (m, 2H), 3.98 (s, 3H), 3.92-3.85 (m, 1H), 3.80 (m, 4H), 3.70 (m, 4H), 3.16 (t, J=7.4 Hz, 2H), 3.11-2.96 (m, 7H), 2.71 (s, 6H), 1.91-1.83 (m, 4H), 1.73-1.68 (m, 2H); Anal. Calcd. for $C_{27}H_{40}ClF_2N_9O_4S.H_2O$: C, 47.8; H, 6.2; N, 18.6; Cl, 5.2. Found: C, 47.9; H, 6.2; N, 18.6; Cl, 5.0%.

Example 54

Synthesis of N-{1-[4-[2-(difluoromethyl)-4-methoxy-1H-benzimidazol-1-yl]-6-(4-morpholinyl)-1,3,5-triazin-2-yl]-4-piperidinyl}-N-[3-(4-morpholinyl)propyl]-methanesulfonamide

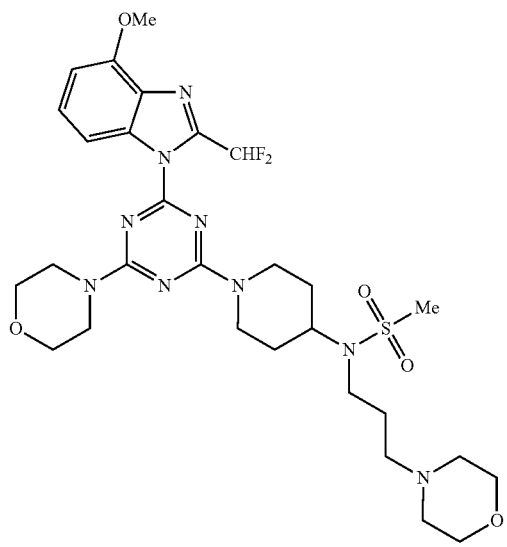 [SMILES: COc1cccc2c1nc(C(F)F)n2-c1nc(N2CCOCC2)nc(N2CCC(N(CCCN3CCOCC3)S(C)(=O)=O)CC2)n1]

Reaction of N-{1-[4-[2-(difluoromethyl)-4-methoxy-1H-benzimidazol-1-yl]-6-(4-morpholinyl)-1,3,5-triazin-2-yl]-4-piperidinyl}-N-(3-hydroxypropyl)methanesulfonamide with methanesulfonyl chloride as in Example 53, followed by reaction with morpholine for 10 days at room temperature, gave N-{1-[4-[2-(difluoromethyl)-4-methoxy-1H-benzimidazol-1-yl]-6-(4-morpholinyl)-1,3,5-triazin-2-yl]-4-piperidinyl}-N-[3-(4-morpholinyl)propyl]methanesulfonamide in 58% yield. Hydrochloride: mp (MeOH) 229-231° C.; $^1$H NMR (DMSO-$d_6$) δ10.23 (br s, 1H), 7.89 (d, J=8.0 Hz, 1H), 7.70 (t, $J_{HF}$=52.9 Hz, 1H), 7.41 (t, J=8.2 Hz, 1H), 6.95 (d, J=7.8 Hz, 1H), 4.84-4.74 (m, 2H), 3.98 (s, 3H), 3.95-3.85 (m, 3H), 3.80 (m, 4H), 3.73-3.67 (m, 6H), 3.39-3.29 (m, 2H), 3.17 (t, J=7.2 Hz, 2H), 3.11-2.99 (m, 9H), 1.94-1.84 (m, 4H), 1.72-1.70 (m, 2H); Anal. Calcd. for $C_{29}H_{42}ClF_2N_9O_5S.0.75H_2O$: C, 48.7; H, 6.1; N, 17.6; Cl, 5.0. Found: C, 48.7; H, 6.2; N, 17.6; Cl, 4.9%.

Example 55

Synthesis of 2-(difluoromethyl)-4-methoxy-1-[4-(4-morpholinyl)-6-(4-{[2-(1-pyrrolidinyl)ethyl]sulfonyl}-1-piperazinyl)-1,3,5-triazin-2-yl]-1H-benzimidazole

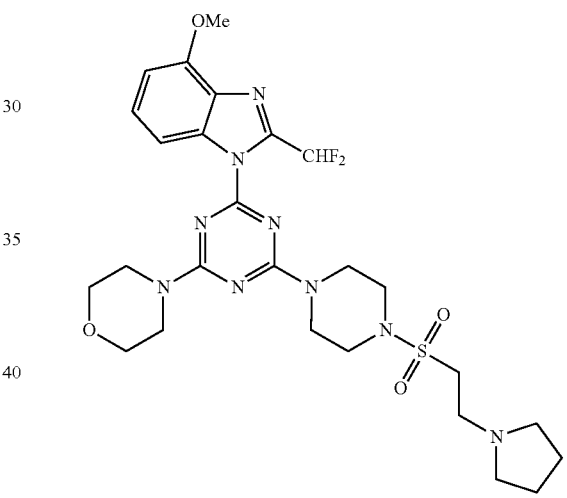

A mixture of 2-(difluoromethyl)-4-methoxy-1-{4-(4-morpholinyl)-6-[4-(vinylsulfonyl)-1-piperazinyl]-1,3,5-triazin-2-yl}-1H-benzimidazole (Example 3) (150 mg, 0.280 mmol) and pyrrolidine (0.23 mL, 2.80 mmol) in 1,4-dioxane (20 mL) was stirred at room temperature for 16 hrs and then refluxed for 3 hrs. The solvent was removed under vacuum, the residue was diluted with water and the resulting precipitate was dissolved in $CH_2Cl_2$. The organic layer was separated and dried ($Na_2SO_4$), and solvent was removed under vacuum. Chromatography on silica eluting with $CH_2Cl_2$/MeOH (98:2), followed by recrystallization from $CH_2Cl_2$/hexanes gave 2-(difluoromethyl)-4-methoxy-1-[4-(4-morpholinyl)-6-(4-{[2-(1-pyrrolidinyl)ethyl]sulfonyl}-1-piperazinyl)-1,3,5-triazin-2-yl]-1H-benzimidazole (137 mg, 81%): mp 186-188° C.; $^1$H NMR (CDCl$_3$) δ7.86 (dd, J=8.4, 0.6 Hz, 1H), 7.44 (t, $J_{HF}$=53.5 Hz, 1H), 7.35 (t, J=8.2 Hz, 1H), 6.82 (d, J=7.6 Hz, 1H), 4.05 (s, 3H), 3.99 (br s, 4H), 3.88 (br s, 4H), 3.79 (m, 4H), 3.39 (t, J=5.0 Hz, 4H), 3.16 (m, 2H), 2.93 (m, 2H), 2.53 (m, 4H), 1.76 (m, 4H); Anal. Calcd. for $C_{26}H_{35}F_2N_9O_4S$: C, 51.4; H, 5.8; N, 20.7. Found: C, 51.3; H, 5.9; N, 20.5%.

Example 56

Synthesis of 3-[2-({4-[4-[2-(Difluoromethyl)-4-methoxy-1H-benzimidazol-1-yl]-6-(4-morpholinyl)-1,3,5-triazin-2-yl]-1-piperazinyl}sulfonyl)ethyl]-8-oxa-3-azabicyclo[3.2.1]octane

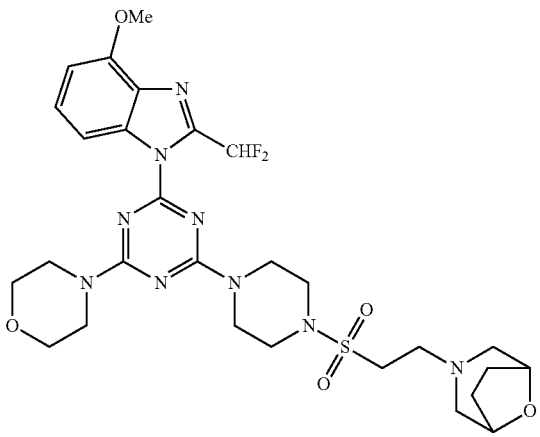 [SMILES: COc1cccc2c1nc(C(F)F)n2-c1nc(N2CCOCC2)nc(N2CCN(S(=O)(=O)CCN3CC4CCC(C3)O4)CC2)n1]

A mixture of 2-(difluoromethyl)-4-methoxy-1-{4-(4-morpholinyl)-6-[4-(vinylsulfonyl)-1-piperazinyl]-1,3,5-triazin-2-yl}-1H-benzimidazole (Example 3) (150 mg, 0.280 mmol), 8-oxa-3-azoniabicyclo[3.2.1]octane hydrochloride (209 mg, 1.40 mmol), and DIPEA (0.49 mL, 2.80 mmol) in 1,4-dioxane was stirred at room temperature for 2.5 days. Additional 8-oxa-3-azoniabicyclo[3.2.1]octane hydrochloride (84 mg, 0.561 mmol) was added and the mixture refluxed for 1 hr. The solvent was removed under vacuum, and the residue was diluted with water. The resulting precipitate was dissolved in CH$_2$Cl$_2$ and dried (Na$_2$SO$_4$). The solvent was removed under vacuum. Chromatography on silica eluting with CH$_2$Cl$_2$/MeOH (98:2), followed by recrystallization from CH$_2$Cl$_2$/hexanes gave 3-[2-({4-[4-[2-(difluoromethyl)-4-methoxy-1H-benzimidazol-1-yl]-6-(4-morpholinyl)-1,3,5-triazin-2-yl]-1-piperazinyl}sulfonyl)ethyl]-8-oxa-3-azabicyclo[3.2.1]octane (118 mg, 87%): mp 219-221° C.; $^1$H NMR (CDCl$_3$) δ7.85 (dd, J=8.4, 0.5 Hz, 1H), 7.43 (t, J$_{HF}$=53.5 Hz, 1H), 7.36 (t, J=8.2 Hz, 1H), 6.82 (d, J=7.7 Hz, 1H), 4.26 (m, 2H), 4.05 (s, 3H), 4.01 (br s, 4H), 3.88 (br s, 4H), 3.79 (m, 4H), 3.38 (t, J=5.0 Hz, 4H), 3.07 (dd, J=8.1, 6.3 Hz, 2H), 2.79 (dd, J=8.1, 6.3 Hz, 2H), 2.55 (d, J=10.6 Hz, 2H), 2.38 (dd, J=10.9, 2.0 Hz, 2H), 1.83 (m, 4H); Anal. Calcd. for C$_{28}$H$_{37}$F$_2$N$_9$O$_5$S: C, 51.8; H, 5.7; N, 19.4. Found: C, 51.8; H, 5.9; N, 19.3%.

Example 57

Synthesis of N-[3-({4-[4-[2-(difluoromethyl)-4-methoxy-1H-benzimidazol-1-yl]-6-(4-morpholinyl)-1,3,5-triazin-2-yl]-1-piperazinyl}sulfonyl)propyl]-N,N-dimethylamine

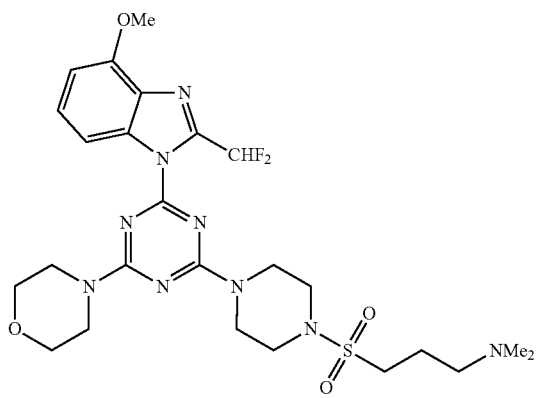 [SMILES: COc1cccc2c1nc(C(F)F)n2-c1nc(N2CCOCC2)nc(N2CCN(S(=O)(=O)CCCN(C)C)CC2)n1]

A mixture of 2-(difluoromethyl)-4-methoxy-1-[4-(4-morpholinyl)-6-(1-piperazinyl)-1,3,5-triazin-2-yl]-1H-benzimidazole (Example 2) (150 mg, 0.378 mmol), N,N-dimethyl-3-(1-piperazinylsulfonyl)-1-propanamine dihydrochloride (WO 2006/046040) (151 mg, 0.491 mmol), and DIPEA (0.40 mL, 2.27 mmol) in DMSO was stirred at room temperature for 30 minutes. The reaction mixture was diluted with water; and the resulting precipitate was collected by filtration, washed with water, and dissolved in CH$_2$Cl$_2$. The solution was dried (Na$_2$SO$_4$) and the solvent removed under vacuum. Chromatography on silica eluting with CH$_2$Cl$_2$/MeOH (95:5), followed by additional chromatography on silica eluting with CH$_2$Cl$_2$/MeOH (96:4) gave N-[3-({4-[4-[2-(difluoromethyl)-4-methoxy-1H-benzimidazol-1-yl]-6-(4-morpholinyl)-1,3,5-triazin-2-yl]-1-piperazinyl}sulfonyl)propyl]-N,N-dimethylamine (91 mg, 40%). Treatment with 1.25 M HCl solution in MeOH and recrystallization from MeOH/EtOAc gave the hydrochloride salt: mp 209-211° C.; $^1$H NMR (DMSO-d$_6$) δ10.16 (br s, 1H), 7.89 (d, J=8.4 Hz, 1H), 7.69 (t, J$_{HF}$=52.9 Hz, 1H), 7.41 (t, J=8.2 Hz, 1H), 6.96 (d, J=7.8 Hz, 1H), 3.98 (s, 3H), 3.94 (m, 4H), 3.82 (m, 4H), 3.70 (br s, 4H), 3.33 (m, 4H), 3.23 (dd, J=9.3, 5.8 Hz, 2H), 3.12 (m, 2H), 2.75 (s, 6H), 2.08 (td, J=15.4, 7.8 Hz, 2H); Anal. Calcd. for C$_{25}$H$_{36}$ClF$_2$N$_9$O$_4$S.0.5H$_2$O: C, 46.8; H, 5.8; N, 19.7. Found: C, 46.9; H, 5.8; N, 19.4%.

Example 58

Synthesis of 2-(difluoromethyl)-4-methoxy-1-[4-(4-morpholinyl)-6-(4-{[3-(4-morpholinyl)propyl]sulfonyl}-1-piperazinyl)-1,3,5-triazin-2-yl]-1H-benzimidazole

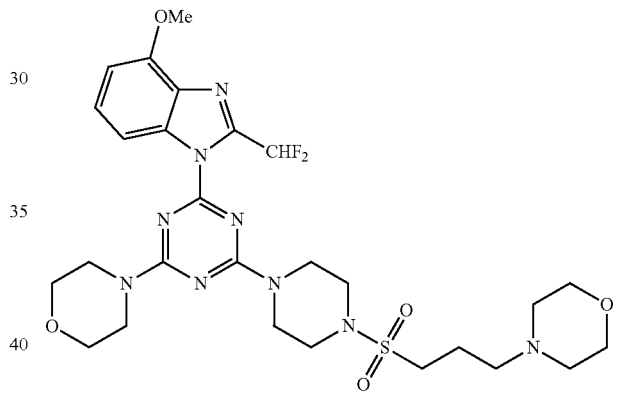

A mixture of 2-(difluoromethyl)-4-methoxy-1-[4-(4-morpholinyl)-6-(1-piperazinyl)-1,3,5-triazin-2-yl]-1H-benzimidazole (Example 2) (150 mg, 0.378 mmol), 4-[3-(1-piperazinylsulfonyl)propyl]morpholine dihydrochloride (WO 2006/046040) (172 mg, 0.491 mmol) and DIPEA (0.40 mL, 2.27 mmol) in THF was stirred at room temperature for 17 hrs. The solvent was removed under vacuum, and the residue was diluted with water and extracted with CH$_2$Cl$_2$. The CH$_2$Cl$_2$ was dried (Na$_2$SO$_4$) and removed under vacuum. Chromatography on silica, eluting with CH$_2$Cl$_2$/MeOH (98:2) followed by recrystallization from CH$_2$Cl$_2$/hexanes gave 2-(difluoromethyl)-4-methoxy-1-[4-(4-morpholinyl)-6-(4-{[3-(4-morpholinyl)propyl]sulfonyl}-1-piperazinyl)-1,3,5-triazin-2-yl]-1H-benzimidazole (188 mg, 78%). Treatment with methanesulfonic acid in CH$_2$Cl$_2$/MeOH and recrystallization from MeOH/EtOAc gave 2-(difluoromethyl)-4-methoxy-1-[4-(4-morpholinyl)-6-(4-{[3-(4-morpholinyl)propyl]sulfonyl}-1-piperazinyl)-1,3,5-triazin-2-yl]-1H-benzimidazole methanesulfonate: mp 216-218° C.; $^1$H NMR (DMSO-d$_6$) δ9.50 (br s, 1H), 7.89 (d, J=8.2 Hz, 1H), 7.69 (t, J$_{HF}$=52.9 Hz, 1H), 7.41 (t, J=8.2 Hz, 1H), 6.96 (d, J=7.8 Hz, 1H), 4.01-3.93 (m, 6H), 3.98 (s, 3H), 3.82 (m, 4H), 3.70 (br s, 4H), 3.63 (t, J=12.1 Hz, 2H), 3.45 (d, J=12.6 Hz, 2H), 3.32 (m, 4H), 3.21 (t, J=7.1 Hz, 4H), 3.09 (dd, J=21.2, 11.8 Hz, 2H), 2.30 (s, 3H), 2.09 (m, 2H); Anal. Calcd for C$_{28}$H$_{41}$F$_2$N$_9$O$_8$S$_2$: C, 45.8; H, 5.6; N, 17.2. Found: C, 45.7; H, 5.6; N, 17.2%.

Example 59

Synthesis of N¹-{1-[(chloromethyl)sulfonyl]-4-piperidinyl}-N¹-[4-[2-(difluoromethyl)-4-methoxy-1H-benzimidazol-1-yl]-6-(4-morpholinyl)-1,3,5-triazin-2-yl]-N³,N³-dimethyl-1,3-propanediamine

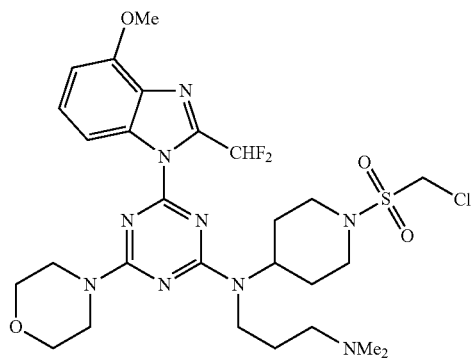 [SMILES: COc1cccc2c1nc(C(F)F)n2-c1nc(N2CCOCC2)nc(N(CCCN(C)C)C2CCN(S(=O)(=O)CCl)CC2)n1]

Reaction of N¹-[4-[2-(difluoromethyl)-4-methoxy-1H-benzimidazol-1-yl]-6-(4-morpholinyl)-1,3,5-triazin-2-yl]-N³,N³-dimethyl-N¹-(4-piperidinyl)-1,3-propanediamine (Example 21) with chloromethanesulfonyl chloride and $K_2CO_3$ in $CH_2Cl_2$, followed by conversion to the hydrochloride salt with 1.25 M HCl in methanol gave N¹-{1-[(chloromethyl) sulfonyl]-4-piperidinyl}-N¹-[4-[2-(difluoromethyl)-4-methoxy-1H-benzimidazol-1-yl]-6-(4-morpholinyl)-1,3,5-triazin-2-yl]-N³,N³-dimethyl-1,3-propanediamine hydrochloride in 44% yield: mp (MeOH) 222-225° C.; ¹H NMR (DMSO-d₆) δ 9.89 (br, 1H), 7.90 (d, J=8.4 Hz, 1H), 7.71 (t, $J_{HF}$=53.0 Hz, 1H), 7.47-7.41 (m, 1H), 7.00 (d, J=8.2 Hz, 1H), 5.17 and 5.11 (2s, 2H), 4.74-4.71 and 4.66-4.53 (2m, 1H), 3.98 (s, 3H), 3.92-3.82 (m, 6H), 3.71 (m, 4H), 3.60-3.51 (m, 2H), 3.16-3.04 (m, 4H), 2.75 and 2.70 (2s, 6H), 2.02-1.80 (m, 6H); Anal. Calcd. for $C_{27}H_{39}Cl_2F_2N_9O_4S \cdot 0.5H_2O$: C, 46.1; H, 5.7; N, 17.9; Cl, 10.1. Found: C, 46.1; H, 5.8; N, 17.9; Cl, 9.7%.

Example 60

Synthesis of chloro-N-{1-[4-[2-(difluoromethyl)-4-methoxy-1H-benzimidazol-1-yl]-6-(4-morpholinyl)-1,3,5-triazin-2-yl]-4-piperidinyl}-N-[3-(dimethylamino)propyl]methanesulfonamide

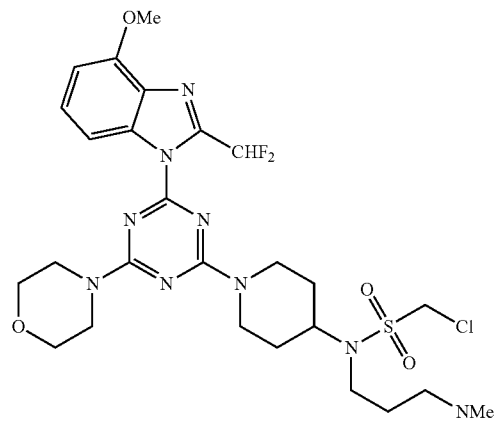

To a mixture of tert-butyl 4-[(3-hydroxypropyl)amino]piperidine-1-carboxylate (Yokoyama et al., *Bioorg. Med. Chem.* 2008, 16, 7968) (710 mg, 2.75 mmol) and dry powdered $K_2CO_3$ (5.0 g, 36.0 mmol) in $CH_2Cl_2$ (20 mL) at 0° C. was added chloromethanesulfonyl chloride (1 mL, excess). The reaction mixture was stirred at 20° C. for 4 hrs, a solution of 40% aqueous dimethylamine (5 mL) was then added, and stirring was continued for a further 20 hrs. The organic layer was separated and the aqueous layer was further extracted with $CH_2Cl_2$ (2×20 mL). The combined organic fractions were washed with water (50 mL) and dried ($Na_2SO_4$). The solvent was removed to give an oily product. Chromatography on neutral alumina eluting with $CH_2Cl_2$/MeOH (98:2) gave tert-butyl 4-{[(chloromethyl)sulfonyl][3-(dimethylamino)propyl]amino}-1-piperidinecarboxylate, as an oil (946 mg, 87%): ¹H NMR (CDCl₃) δ 4.47 (s, 2H), 4.22 (br, 2H), 3.82-3.75 (m, 1H), 3.31-3.27 (m, 2H), 2.28-2.46 (m, 2H), 2.76-2.70 (m, 2H), 2.26 (t, J=6.9 Hz, 2H), 2.23 (s, 6H), 1.87-1.64 (m, 6H), 1.46 (s, 9H).

To a solution of the above carbamate (940 mg, 2.36 mmol) in $CH_2Cl_2$ (10 mL) was added TFA (5 mL). The reaction mixture was stirred for 1 hr. After being diluted with $CH_2Cl_2$ (10 mL) and $H_2O$ (10 mL), the mixture was made alkaline with aqueous $NH_3$. The organic layer was separated and the aqueous layer was further extracted with $CH_2Cl_2$ (2×15 mL). The combined organic fractions were washed with $H_2O$ (2×20 mL) and dried ($Na_2SO_4$). Evaporation of the solvent gave chloro-N-[3-(dimethylamino)propyl]-N-(4-piperidinyl)methanesulfonamide (571 mg, 81%): ¹H NMR (CDCl₃) δ 4.46 (s, 2H), 3.76-3.68 (m, 1H), 3.35-3.31 (m, 2H), 3.16-3.14 (m, 2H), 2.70-2.63 (m, 2H), 2.28 (t, J=6.9 Hz, 2H), 2.22 (s, 6H), 1.88-1.68 (m, 7H).

A mixture of the above amine (82 mg, 0.28 mmol), 2-(difluoromethyl)-4-methoxy-1-[4-(4-morpholinyl)-6-(1-piperazinyl)-1,3,5-triazin-2-yl]-1H-benzimidazole (Example 2) (98 mg, 0.25 mmol), and DIPEA (0.3 mL) in THF (5 mL) was stirred at 20° C. for 4 hrs. Most of the THF was removed under vacuum and the residue was diluted with water (20 mL). The resulting precipitate was collected by filtration, washed with water, and chromatographed on silica eluting initially with $CH_2Cl_2$/EtOAc (4:1), then with $CH_2Cl_2$/MeOH/aqueous $NH_3$ (95:4:1) to give chloro-N-{1-[4-[2-(difluoromethyl)-4-methoxy-1H-benzimidazol-1-yl]-6-(4-morpholinyl)-1,3,5-triazin-2-yl]-4-piperidinyl}-N-[3-(dimethylamino)propyl]methanesulfonamide (120 mg 74% yield), which treated with 1.25 M HCl in MeOH to give the hydrochloride salt: mp (MeOH/EtOAc) 260-263° C.; ¹H NMR (DMSO-d₆) δ 10.0 (br s, 1H), 7.89 (d, J=8.2 Hz, 1H), 7.70 (t, $J_{HF}$=52.9 Hz, 1H), 7.41 (t, J=8.2 Hz, 1H), 6.95 (d, J=7.9 Hz, 1H), 5.10 (s, 2H), 4.86-4.74 (m, 2H), 3.98-3.90 (m, 1H), 3.98 (s, 3H), 3.81 (m, 4H), 3.79 (m, 4H), 3.24-3.25 (m, 2H), 3.11-2.96 (m, 4H), 2.70 (s, 6H), 1.93-1.75 (m, 6H); Calcd. for $C_{27}H_{39}Cl_2F_2N_9O_4S \cdot 0.5H_2O$: C, 46.1; H, 5.7; N, 17.9; Cl, 10.1. Found: C, 46.1; H, 5.8; N, 17.9; Cl, 9.7%.

Example 61

Synthesis of chloro-N-{1-[4-[2-(difluoromethyl)-4-methoxy-1H-benzimidazol-1-yl]-6-(4-morpholinyl)-1,3,5-triazin-2-yl]-4-piperidinyl}methanesulfonamide

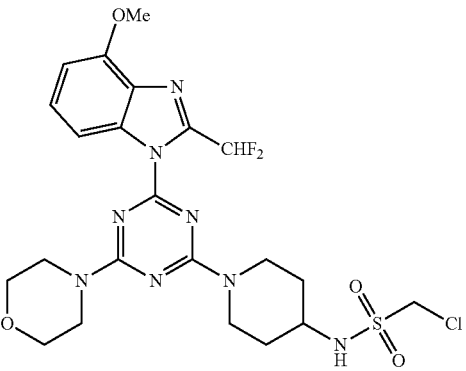 [SMILES: COc1cccc2c1nc(C(F)F)n2-c1nc(N2CCOCC2)nc(N2CCC(NS(=O)(=O)CCl)CC2)n1]

Reaction of 1-[4-[2-(difluoromethyl)-4-methoxy-1H-benzimidazol-1-yl]-6-(4-morpholinyl)-1,3,5-triazin-2-yl]-4-piperidinamine (Example 17) with chloromethanesulfonyl chloride and K$_2$CO$_3$ in CH$_2$Cl$_2$ gave chloro-N-{1-[4-[2-(difluoromethyl)-4-methoxy-1H-benzimidazol-1-yl]-6-(4-morpholinyl)-1,3,5-triazin-2-yl]-4-piperidinyl}methanesulfonamide in 56% yield: mp (CH$_2$Cl$_2$/MeOH) 230-232° C.; $^1$H NMR (DMSO-d$_6$) δ7.88 (d, J=8.0 Hz, 1H), 7.87 (br, 1H), 7.69 (t, J$_{HF}$=52.9 Hz, 1H), 7.41 (t, J=8.2 Hz, 1H), 6.95 (d, J=7.9 Hz, 1H), 4.95 (s, 2H), 4.59-4.49 (m, 2H), 3.98 (s, 3H), 3.81-3.79 (m, 4H), 3.70-3.69 (m, 4H), 3.55 (br, 1H), 3.22-3.12 (m, 2H), 1.96 (br, 2H), 1.46-1.41 (m, 2H); Anal. Calcd. for C$_{22}$H$_{27}$ClF$_2$N$_8$O$_4$S: C, 46.1; H, 4.75; N, 19.6. Found: C, 46.4; H, 4.8; N, 19.6%.

Example 62

Synthesis of chloro-N-{(3S)-1-[4-[2-(difluoromethyl)-4-methoxy-1H-benzimidazol-1-yl]-6-(4-morpholinyl)-1,3,5-triazin-2-yl]-3-piperidinyl}methanesulfonamide

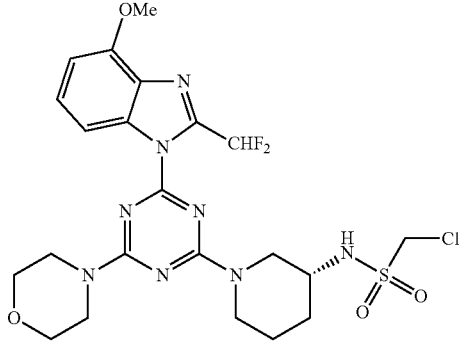 [SMILES: COc1cccc2c1nc(C(F)F)n2-c1nc(N2CCOCC2)nc(N2CCC[C@@H](NS(=O)(=O)CCl)C2)n1]

Reaction of (3S)-1-[4-[2-(difluoromethyl)-4-methoxy-1H-benzimidazol-1-yl]-6-(4-morpholinyl)-1,3,5-triazin-2-yl]-3-piperidinamine (Example 46) with chloromethanesulfonyl chloride and K$_2$CO$_3$ in CH$_2$Cl$_2$ gave chloro-N-{(3S)-1-[4-[2-(difluoromethyl)-4-methoxy-1H-benzimidazol-1-yl]-6-(4-morpholinyl)-1,3,5-triazin-2-yl]-3-piperidinyl}methanesulfonamide in 57% yield: mp (MeOH) 166-168° C.; $^1$H NMR (DMSO-d$_6$) (rotamers) δ7.99 (br, 1H), 7.98 and 7.88 (2d, J=8.5, 8.4 Hz, 1H), 7.69 and 7.68 (2t, J$_{HF}$=52.9 Hz, 1H), 7.41 and 7.37 (2t, J=8.1, 8.2 Hz, 1H), 6.95 (d, J=7.9 Hz, 1H), 4.98-4.88 (m, 2H), 4.55-4.52 and 4.37-4.23 (2m, 2H), 3.97 (s, 3H), 3.80 (m, 4H), 3.69 (m, 4H), 3.45-3.11 (m, 3H), 1.99 (br, 1H), 1.83-1.80 (m, 1H), 1.64-1.48 (m, 2H); Anal. Calcd. for C$_{22}$H$_{27}$ClF$_2$N$_8$O$_4$S.0.5H$_2$O: C, 45.4; H, 4.85; N, 19.25. Found: C, 45.4; H, 4.8; N, 19.2%.

Example 63

Synthesis of N-{(3S)-1-[4-[2-(difluoromethyl)-4-methoxy-1H-benzimidazol-1-yl]-6-(4-morpholinyl)-1,3,5-triazin-2-yl]piperidinyl}-N-[3-(dimethylamino)propyl]methanesulfonamide

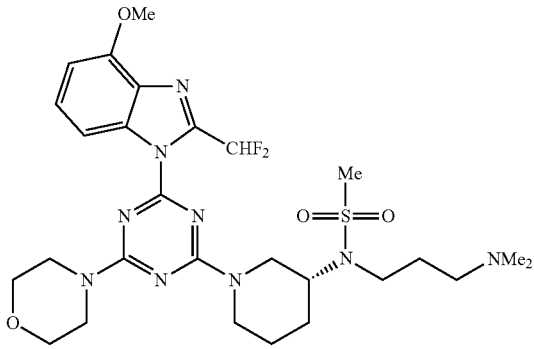 [SMILES: COc1cccc2c1nc(C(F)F)n2-c1nc(N2CCOCC2)nc(N2CCC[C@@H](N(CCCN(C)C)S(C)(=O)=O)C2)n1]

A mixture of N-{(3S)-1-[4-[2-(difluoromethyl)-4-methoxy-1H-benzimidazol-1-yl]-6-(4-morpholinyl)-1,3,5-triazin-2-yl]piperidinyl}methanesulfonamide (Example 46) (678 mg, 1.26 mmol), dry powdered K$_2$CO$_3$ (0.6 g, 4.3 mmol), and 3-bromopropanol (1.0 mL) in DMF (5 mL) was stirred at 20° C. for 3 days. The reaction mixture was diluted with H$_2$O (50 mL). The resulting precipitate was collected by filtration, washed with water, and dried. Chromatography on silica, eluting with CH$_2$Cl$_2$/EtOAc (4:1) gave partially purified material, which was further purified by chromatography on neutral alumina, eluting first with CH$_2$Cl$_2$/EtOAc (4:1) and then with CH$_2$Cl$_2$/MeOH (96:4) to give N-{(3S)-1-[4-[2-(difluoromethyl)-4-methoxy-1H-benzimidazol-1-yl]-6-(4-morpholinyl)-1,3,5-triazin-2-yl]piperidinyl}-N-(3-hydroxypropyl)methanesulfonamide (602 mg, 80%): mp 122-124° C.; $^1$H NMR (DMSO-d$_6$) δ 7.90 and 7.88 (2d, J=8.4, 8.3 Hz 1H), 7.68 (t, J$_{HF}$=52.8 Hz, 1H), 7.43-7.35 (m, 1H), 6.95 (d, J=8.1 Hz, 1H), 4.75-4.68 and 4.59-4.56 (2m, 2H), 4.46 (q, J=5.0 Hz, 1H), 3.98 (s, 3H), 3.80 (m, 4H), 3.69 (m, 4H), 3.64-3.24 (m, 5H), 3.16-3.07 (m, 1H), 2.99-2.79 (m, 1H), 2.97 and 2.96 (2s, 3H), 1.93-1.54 (m, 6H); Anal. Calcd. for C$_{25}$H$_{34}$F$_2$N$_8$O$_5$S.0.4H$_2$O: C, 49.7; H, 5.8; N, 18.6. Found: C, 49.7; H, 6.0; N, 18.6%.

To a solution of the above alcohol (326 mg, 0.55 mmol) and Et$_3$N (0.3 mL, 2 mmol) in CH$_2$Cl$_2$ (10 mL) at 0° C. was added methanesulfonyl chloride (0.08 mL, 2 eq.). The mixture was stirred for additional 1 hr, with the temperature being allowed to rise to room temperature. A solution of 40% aqueous dimethylamine (5 mL, excess) was added and the resulting mixture was stirred for 20 hrs before the CH$_2$Cl$_2$ was removed under vacuum. The residue was diluted with water, and the resulting precipitate was collected by filtration, washed with water, and dried. Chromatography on silica, eluting first with CH$_2$Cl$_2$/EtOAc (4:1) and then with CH$_2$Cl$_2$/MeOH (94:6) gave 281 mg (82% yield) of N-{(3S)-1-[4-[2-(difluoromethyl)-4-methoxy-1H-benzimidazol-1-yl]-6-(4-morpholinyl)-1,3,5-triazin-2-yl]piperidinyl}-N-[3-(dimethylamino)propyl]methanesulfonamide.

Hydrochloride: mp (MeOH/EtOAc) 213-216° C.; $^1$H NMR (DMSO-d$_6$) δ 9.93 (br s, 1H), 7.94 and 7.88 (2d, J=8.4, 8.3 Hz, 1H), 7.69 (t, J$_{HF}$=52.9 Hz, 1H), 7.43-7.36 (m, 1H), 6.95 (dd, J=8.1, 2.3 Hz, 1H), 4.76-7.58 (m, 2H), 3.98 (s, 3H), 3.80 (m, 4H), 3.69 (m, 4H), 3.58 (br, 1H), 3.20-2.81 (m, 6H), 3.02 and 3.00 (2s, 3H), 2.77 and 2.73 (2s, 6H), 1.95-1.85 (m, 5H), 1.57 (m, 1H); Anal. Calcd. for C$_{27}$H$_{40}$ClF$_2$N$_9$O$_4$S.H$_2$O: C, 47.8; H, 6.2; C, 5.2; N, 18.6. Found: C, 47.8; H, 6.3; Cl, 5.2; N, 18.6%.

Example 64

Synthesis of N-[2-({4-[4-[2-(difluoromethyl)-4-methoxy-1H-benzimidazol-1-yl]-6-(4-morpholinyl)-1,3,5-triazin-2-yl]-1-piperazinyl}sulfonyl)ethyl]-N,N-diethylamine

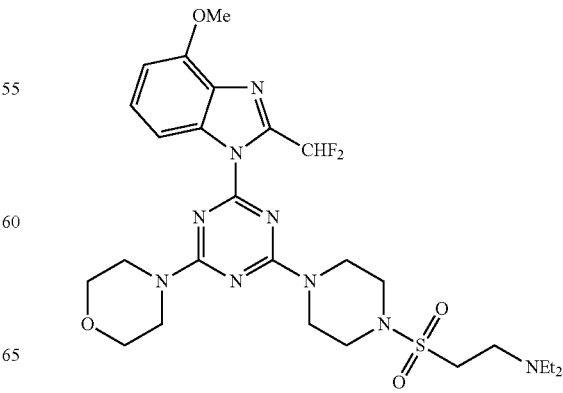

A mixture of 2-(difluoromethyl)-4-methoxy-1-{4-(4-morpholinyl)-6-[4-(vinylsulfonyl)-1-piperazinyl]-1,3,5-triazin-2-yl}-1H-benzimidazole (Example 3) (150 mg, 0.280 mmol) and N,N-diethylamine (0.14 mL, 1.35 mmol) in THF (20 mL) was stirred at room temperature for 17 hrs, refluxed for 1 hr, and then stirred at room temperature for 4 hrs. 1,4-Dioxane (20 mL) was added and the mixture was refluxed for 21 hrs. Additional N,N-diethylamine (0.14 mL, 1.35 mmol) was then added and the mixture was refluxed for another 4.5 hrs. The reaction mixture was cooled to room temperature and the solvents were removed under vacuum. The residue was diluted with water and extracted with $CH_2Cl_2$ (2×). The organic layers were combined, dried ($Na_2SO_4$), and concentrated under vacuum. Chromatography on silica, eluting with $CH_2Cl_2$/MeOH (100:0 to 98:2), gave N-[2-({4-[4-[2-(difluoromethyl)-4-methoxy-1H-benzimidazol-1-yl]-6-(4-morpholinyl)-1,3,5-triazin-2-yl]-1-piperazinyl}sulfonyl)ethyl]-N,N-diethylamine (54 mg, 53%).

Treatment with methanesulfonic acid in $CH_2Cl_2$/MeOH and recrystallization from EtOAc/hexanes gave a methanesulfonate salt: mp 148-151° C.; $^1$H NMR (DMSO-$d_6$) δ 9.32 (br s, 1H), 7.89 (d, J=8.1 Hz, 1H), 7.70 (t, $J_{HF}$=52.9 Hz, 1H), 7.41 (t, J=8.2 Hz, 1H), 6.96 (d, J=7.8 Hz, 1H), 3.98 (s, 3H), 3.96 (m, 4H), 3.83 (m, 4H), 3.70 (br s, 4H), 3.59 (dd, J=10.0, 5.5 Hz, 2H), 3.44 (m, 2H), 3.36 (br s, 4H), 3.19 (m, 4H), 2.31 (s, 3H), 1.19 (t, J=7.2 Hz, 6H); Anal. Calcd. for $C_{27}H_{41}F_2N_9O_7S_2 \cdot 0.4H_2O$: C, 45.5; H, 5.9; N, 17.7. Found: C, 45.5; H, 5.9; N, 17.6%.

Example 65

Synthesis of 2-(difluoromethyl)-4-methoxy-1-[4-(4-morpholinyl)-6-(4-{[2-(1-piperidinyl)ethyl]sulfonyl}-1-piperazinyl)-1,3,5-triazin-2-yl]-1H-benzimidazole

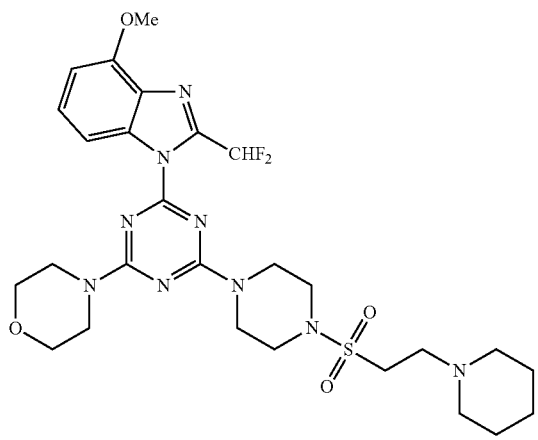 [SMILES: COc1cccc2c1nc(C(F)F)n2-c1nc(N2CCOCC2)nc(N2CCN(S(=O)(=O)CCN3CCCCC3)CC2)n1]

A mixture of 2-(difluoromethyl)-4-methoxy-1-{4-(4-morpholinyl)-6-[4-(vinylsulfonyl)-1-piperazinyl]-1,3,5-triazin-2-yl}-1H-benzimidazole (Example 3) (150 mg, 0.280 mmol) and piperidine (0.14 mL, 1.42 mmol) in THF (20 mL) was stirred at room temperature for 4 hrs. 1,4-Dioxane (20 mL) was added and the mixture was refluxed for 18 hrs. After cooled to room temperature, the solvents were removed under vacuum. The residue was partitioned between $CH_2Cl_2$ and $H_2O$. The layers were separated and the aqueous phase extracted with $CH_2Cl_2$ (1×). The combined organic extracts were dried ($Na_2SO_4$) and the solvent removed under vacuum. Chromatography on silica, eluting with $CH_2Cl_2$/MeOH (100:0 to 98:2) gave 2-(difluoromethyl)-4-methoxy-1-[4-(4-morpholinyl)-6-(4-{[2-(1-piperidinyl)ethyl]sulfonyl}-1-piperazinyl)-1,3,5-triazin-2-yl]-1H-benzimidazole (147 mg, 84%).

Treatment with methanesulfonic acid in $CH_2Cl_2$/MeOH and recrystallization from MeOH/EtOAc gave a methanesulfonate salt: mp 250-252° C.; $^1$H NMR (DMSO-$d_6$) δ 9.21 (br s, 1H), 7.89 (d, J=7.9, 1H), 7.70 (t, $J_{HF}$=52.9 Hz, 1H), 7.41 (t, J=8.2 Hz, 1H), 6.96 (d, J=7.8, 1H), 3.98 (s, 3H), 3.96 (m, 4H), 3.83 (m, 4H), 3.70 (br s, 4H), 3.59 (m, 2H), 3.47 (m, 4H), 3.35 (m, 4H), 2.93 (m, 2H), 2.31 (s, 3H), 1.83 (m, 2H), 1.70-1.54 (m, 3H), 1.34 (m, 1H); Anal. Calcd. for $C_{28}H_{41}F_2N_9O_7S_2$: C, 46.85; H, 5.8; N, 17.6. Found: C, 46.85; H, 5.9; N, 17.3%.

Example 66

Synthesis of 2-(difluoromethyl)-4-methoxy-1-[4-(4-{[2-(4-methyl-1-piperazinyl)ethyl]sulfonyl}-1-piperazinyl)-6-(4-morpholinyl)-1,3,5-triazin-2-yl]-1H-benzimidazole

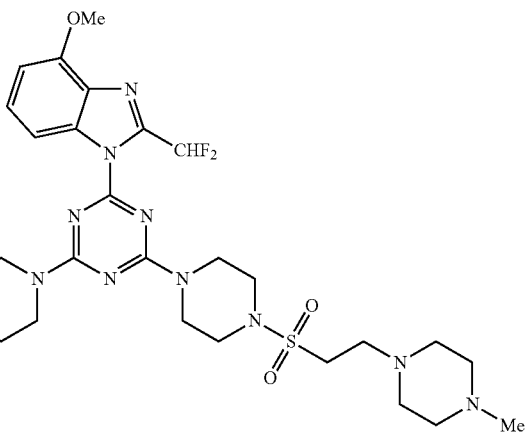

A mixture of 2-(difluoromethyl)-4-methoxy-1-{4-(4-morpholinyl)-6-[4-(vinylsulfonyl)-1-piperazinyl]-1,3,5-triazin-2-yl}-1H-benzimidazole (Example 3) (150 mg, 0.280 mmol) and 1-methylpiperazine (0.16 mL, 1.44 mmol) in THF (20 mL) was refluxed for 5 hrs and then stirred at room temperature for 3 days. Additional 1-methylpiperazine (0.16 mL, 1.44 mmol) and 1,4-dioxane (20 mL) were added and the reaction mixture was refluxed for 20 hrs. The mixture was cooled to room temperature and the solvents were removed under vacuum. The residue was partitioned between $CH_2Cl_2$ and $H_2O$. The layers were separated and the aqueous layer was extracted with $CH_2Cl_2$ (1×). The combined organic extracts were dried ($Na_2SO_4$) and the solvent was removed under vacuum. Chromatography on silica eluting with $CH_2Cl_2$/MeOH (100:0 to 95:5) followed by recrystallization from $CH_2Cl_2$/hexanes gave 2-(difluoromethyl)-4-methoxy-1-[4-(4-{[2-(4-methyl-1-piperazinyl)ethyl]sulfonyl}-1-piperazinyl)-6-(4-morpholinyl)-1,3,5-triazin-2-yl]-1H-benzimidazole (116 mg, 65%).

Treatment with methanesulfonic acid in $CH_2Cl_2$/MeOH and recrystallization from MeOH/EtOAc gave a dimethanesulfonate salt: mp 198-201° C.; $^1$H NMR (DMSO-$d_6$) δ 9.52 (br s, 1H), 7.89 (d, J=8.1 Hz, 1H), 7.69 (t, $J_{HF}$=52.9 Hz, 1H), 7.41 (t, J=8.2 Hz, 1H), 6.96 (d, J=7.9 Hz, 1H), 3.98 (s, 3H), 3.93 (m, 4H), 3.82 (m, 4H), 3.70 (br s, 4H), 3.44-3.18 (m, 12H), 3.00 (m, 4H), 2.79 (s, 3H), 2.35 (s, 6H); Anal. Calcd. for $C_{29}H_{46}F_2N_{10}O_{10}S_3$: C, 42.0; H, 5.6; N, 16.9. Found: C, 42.3; H, 5.6; N, 16.6%.

Example 67

Synthesis of 2-{4-[2-({4-[4-[2-(difluoromethyl)-4-methoxy-1H-benzimidazol-1-yl]-6-(4-morpholinyl)-1,3,5-triazin-2-yl]-1-piperazinyl}sulfonyl)ethyl]-1-piperazinyl}ethanol

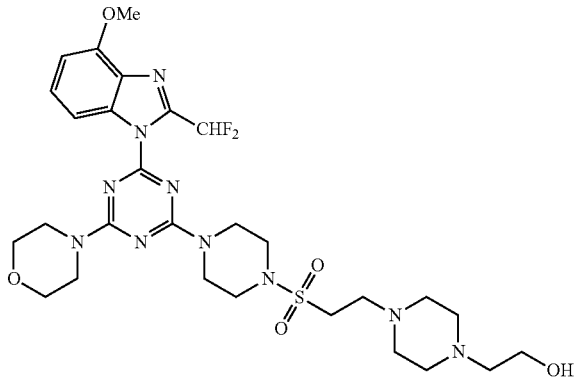 [SMILES: COc1cccc2c1nc(C(F)F)n2-c1nc(N2CCOCC2)nc(N2CCN(S(=O)(=O)CCN3CCN(CCO)CC3)CC2)n1]

A mixture of 2-(difluoromethyl)-4-methoxy-1-{4-(4-morpholinyl)-6-[4-(vinylsulfonyl)-1-piperazinyl]-1,3,5-triazin-2-yl}-1H-benzimidazole (Example 3) (150 mg, 0.280 mmol) and N-(2-hydroxyethyl)piperazine (360 mg, 2.77 mmol) in 1,4-dioxane (15 mL) was refluxed for 3 hrs. The reaction mixture was then cooled to room temperature and the solvent was removed under vacuum. The residue was partitioned between $CH_2Cl_2$ and $H_2O$. The phases were separated, the organic phase was dried ($Na_2SO_4$), and the solvent was removed under vacuum. Recrystallization from $CH_2Cl_2$/hexanes gave 2-{4-[2-({4-[4-[2-(difluoromethyl)-4-methoxy-1H-benzimidazol-1-yl]-6-(4-morpholinyl)-1,3,5-triazin-2-yl]-1-piperazinyl}sulfonyl)ethyl]-1-piperazinyl}ethanol (134 mg, 72%).

Treatment with methanesulfonic acid in $CH_2Cl_2$/MeOH and recrystallization from MeOH/EtOAc gave a dimethanesulfonate salt: mp 236-238° C.; $^1$H NMR (DMSO-$d_6$) δ 9.46 (br s, 1H), 7.89 (d, J=8.1 Hz, 1H), 7.69 (t, $J_{HF}$=52.9 Hz, 1H), 7.41 (t, J=8.2 Hz, 1H), 6.96 (d, J=7.9 Hz, 1H), 3.98 (s, 3H), 3.93 (m, 4H), 3.82 (m, 4H), 3.71 (m 4H), 3.70-3.66 (m, 4H), 3.40-3.32 (m, 6H), 3.18 (t, J=4.9 Hz, 4H), 3.08-2.99 (m, 4H), 2.67 (m, 2H), 2.34 (s, 6H); Anal. Calcd. for $C_{30}H_{48}F_2N_{10}O_{11}S_3$·1.5$H_2O$: C, 40.7; H, 5.8; N, 15.8. Found: C, 40.3; H, 5.6; N, 15.8%.

Example 68

Synthesis of 2-(difluoromethyl)-1-[4-(4-{[2-(1H-imidazol-1-yl)ethyl]sulfonyl}-1-piperazinyl)-6-(4-morpholinyl)-1,3,5-triazin-2-yl]-4-methoxy-1H-benzimidazole

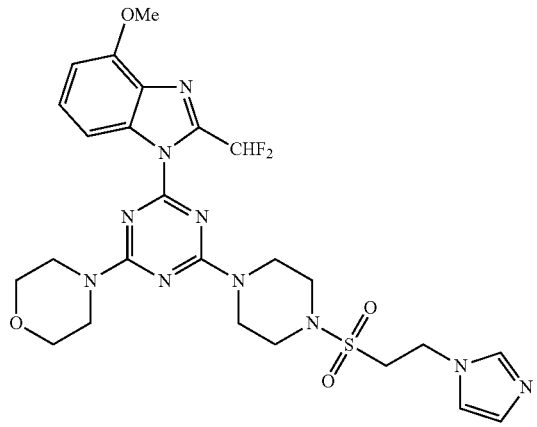 [SMILES: COc1cccc2c1nc(C(F)F)n2-c1nc(N2CCOCC2)nc(N2CCN(S(=O)(=O)CCn3ccnc3)CC2)n1]

A mixture of 2-(difluoromethyl)-4-methoxy-1-{4-(4-morpholinyl)-6-[4-(vinylsulfonyl)-1-piperazinyl]-1,3,5-triazin-2-yl}-1H-benzimidazole (Example 3) (150 mg, 0.280 mmol), imidazole (38 mg, 0.558 mmol), and pyridine (2 drops) in DMSO (5 mL) was heated at 135-140° C. for 5 days. The mixture was then poured over ice and extracted with $CH_2Cl_2$ (3×). The combined organic extracts were washed with $H_2O$ (1×), dried ($Na_2SO_4$) and concentrated. Chromatography on silica, eluting with $CH_2Cl_2$/MeOH (100:0 to 95:5), followed by recrystallization from $CH_2Cl_2$/hexanes gave 2-(difluoromethyl)-1-[4-(4-{[2-(1H-imidazol-1-yl)ethyl]sulfonyl}-1-piperazinyl)-6-(4-morpholinyl)-1,3,5-triazin-2-yl]-4-methoxy-1H-benzimidazole (45 mg, 27%): mp 188-191° C.; $^1$H NMR (CDCl$_3$) δ 7.84 (dd, J=8.4, 0.6 Hz, 1H), 7.55 (s, 1H), 7.41 (t, $J_{HF}$=53.5 Hz, 1H), 7.35 (t, J=8.2 Hz, 1H), 7.10 (t, J=1.0 Hz, 1H), 6.96 (t, J=1.3 Hz, 1H), 6.82 (d, J=7.7 Hz, 1H), 4.46 (t, J=7.0 Hz, 2H), 4.05 (s, 3H), 3.94 (br s, 4H), 3.87 (br s, 4H), 3.78 (m, 4H), 3.35 (t, J=7.1 Hz, 2H), 3.29 (br s, 4H); Anal. Calcd. for $C_{25}H_{30}F_2N_{10}O_4S$: C, 49.7; H, 5.0; N, 23.2. Found: C, 49.3; H, 4.9; N, 23.2%.

Example 69

Synthesis of 2-(difluoromethyl)-4-methoxy-1-[4-(4-morpholinyl)-6-(4-{[2-(2-pyridinyl)ethyl]sulfonyl}-1-piperazinyl)-1,3,5-triazin-2-yl]-1H-benzimidazole

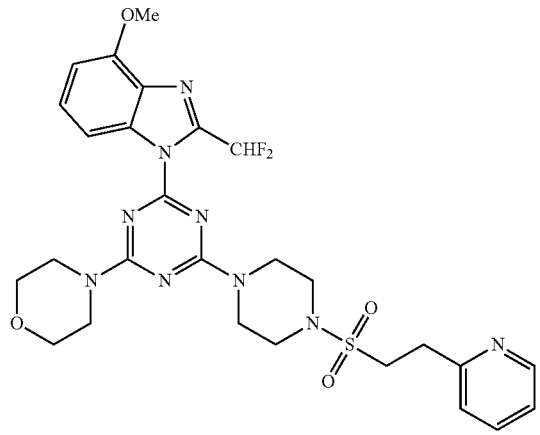 [SMILES: COc1cccc2c1nc(C(F)F)n2-c1nc(N2CCOCC2)nc(N2CCN(S(=O)(=O)CCc3ccccn3)CC2)n1]

DIPEA (0.29 mL, 1.66 mmol) was added to a suspension of 2-(difluoromethyl)-4-methoxy-1-[4-(4-morpholinyl)-6-(1-piperazinyl)-1,3,5-triazin-2-yl]-1H-benzimidazole (Example 2) (150 mg, 0.336 mmol) and 2-[2-(chlorosulfonyl)ethyl]pyridinium chloride (122 mg, 0.504 mmol) in $CH_2Cl_2$ (10 mL) at room temperature under nitrogen, and the mixture was stirred for 4 hrs. Additional 2-[2-(chlorosulfonyl)ethyl]pyridinium chloride (41 mg, 0.169 mmol) was added and the reaction mixture was stirred for another 20 hrs. Water was added and the phases were separated. The aqueous phase was extracted with $CH_2Cl_2$, the combined organic extracts were dried ($Na_2SO_4$), and the solvent was removed under vacuum. Chromatography on silica, eluting with $CH_2Cl_2$/MeOH (100:0 to 98.5:1.5), gave 2-(difluoromethyl)-4-methoxy-1-[4-(4-morpholinyl)-6-(4-{[2-(2-pyridinyl)ethyl]sulfonyl}-1-piperazinyl)-1,3,5-triazin-2-yl]-1H-benzimidazole (148 mg, 71%).

Treatment with methanesulfonic acid in $CH_2Cl_2$/MeOH and recrystallization from MeOH/EtOAc gave a methanesulfonate salt: mp 154-157° C.; $^1$H NMR (DMSO-$d_6$) δ 8.64 (d, J=4.8 Hz, 1H), 8.07 (t, J=6.9 Hz, 1H), 7.88 (d, J=8.0 Hz, 1H), 7.69 (t, $J_{HF}$=52.9 Hz, 1H), 7.67-7.52 (m, 2H), 7.41 (t, J=8.2 Hz, 1H), 6.96 (d, J=7.8 Hz, 1H), 3.98 (s, 3H), 3.91 (m, 4H), 3.82 (m, 4H), 3.70 (br s, 4H), 3.59 (dd, J=9.0, 6.7 Hz, 2H), 3.30-3.27 (m, 6H), 2.31 (s, 3H); Anal. Calcd. for $C_{28}H_{35}F_2N_9O_7S_2$·0.7$H_2O$: C, 46.4; H, 5.1; N, 17.4. Found: C, 46.4; H, 5.2; N, 17.6%.

Example 70

Synthesis of 2-(difluoromethyl)-4-methoxy-1-[4-(4-morpholinyl)-6-(4-{[2-(4-pyridinyl)ethyl]sulfonyl}-1-piperazinyl)-1,3,5-triazin-2-yl]-1H-benzimidazole

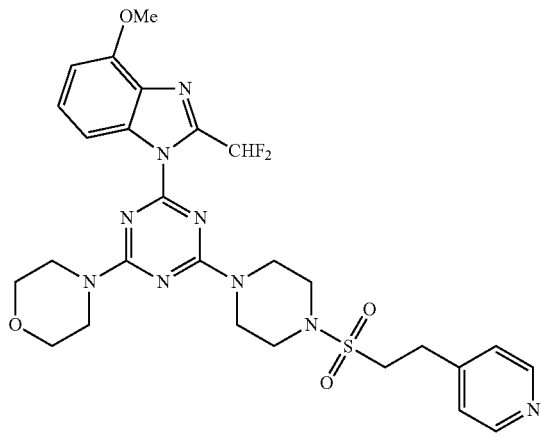 [SMILES: COc1cccc2c1nc(C(F)F)n2-c1nc(N2CCOCC2)nc(N2CCN(S(=O)(=O)CCc3ccncc3)CC2)n1]

DIPEA (0.29 mL, 1.66 mmol) was added to a suspension of 2-(difluoromethyl)-4-methoxy-1-[4-(4-morpholinyl)-6-(1-piperazinyl)-1,3,5-triazin-2-yl]-1H-benzimidazole (Example 2) (150 mg, 0.336 mmol) and 4-[2-(chlorosulfonyl)ethyl]pyridinium chloride (122 mg, 0.504 mmol) in $CH_2Cl_2$ (10 mL) at room temperature under nitrogen, and the mixture was stirred for 3 hrs. Additional 4-[2-(chlorosulfonyl)ethyl]pyridinium chloride (41 mg, 0.169 mmol) was added and the mixture stirred for another 21 hrs. Water was added and the phases were separated. The aqueous phase was extracted with $CH_2Cl_2$ (1×), the combined organic extracts were dried ($Na_2SO_4$), and the solvent was removed under vacuum. Chromatography on silica eluting with $CH_2Cl_2$/MeOH (100:0 to 98:2) followed by recrystallization from $CH_2Cl_2$/MeOH gave 2-(difluoromethyl)-4-methoxy-1-[4-(4-morpholinyl)-6-(4-{[2-(4-pyridinyl)ethyl]sulfonyl}-1-piperazinyl)-1,3,5-triazin-2-yl]-1H-benzimidazole (134 mg, 65%).

Treatment with methanesulfonic acid in $CH_2Cl_2$/MeOH and recrystallization from MeOH/EtOAc gave a methanesulfonate salt: mp 290-293° C.; $^1$H NMR (DMSO-$d_6$) δ 8.76 (dd, J=5.4, 1.1 Hz, 2H), 7.89-7.87 (m, 3H), 7.69 (t, $J_{HF}$=52.9 Hz, 1H), 7.41 (t, J=8.2 Hz, 1H), 6.96 (d, J=7.8 Hz, 1H), 3.98 (s, 3H), 3.93 (m, 4H), 3.82 (m, 4H), 3.70 (br s, 4H), 3.59 (dd, J=8.8, 6.8 Hz, 2H), 3.30-3.23 (m, 6H), 2.31 (s, 3H); Anal. Calcd. for $C_{28}H_{35}F_2N_9O_7S_2$: C, 47.25; H, 5.0; N, 17.7. Found: C, 47.1; H, 5.0; N, 17.6%.

Example 71

Synthesis of 2-(difluoromethyl)-4-methoxy-1-{4-(4-morpholinyl)-6-[4-(3-pyridinylsulfonyl)-1-piperazinyl]-1,3,5-triazin-2-yl}-1-1H-benzimidazole

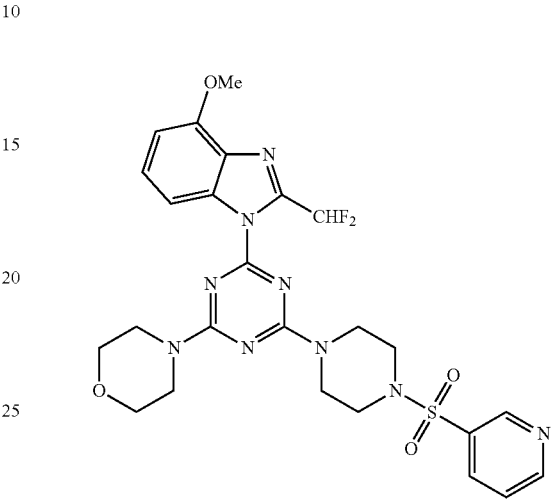

DIPEA (0.78 mL, 4.48 mmol) was added to a mixture of 2-(difluoromethyl)-4-methoxy-1-[4-(4-morpholinyl)-6-(1-piperazinyl)-1,3,5-triazin-2-yl]-1H-benzimidazole (Example 2) (200 mg, 0.449 mmol) and 3-pyridinesulfonyl chloride (159 mg, 0.859 mmol) at room temperature under nitrogen. The reaction mixture was stirred at room temperature for 18.5 hrs. Water was added and the phases were separated. The organic phase was dried ($Na_2SO_4$) and the solvent was removed under vacuum. Chromatography on silica, eluting with $CH_2Cl_2$/MeOH (99:1), gave 2-(difluoromethyl)-4-methoxy-1-{4-(4-morpholinyl)-6-[4-(3-pyridinylsulfonyl)-1-piperazinyl]-1,3,5-triazin-2-yl}-1H-benzimidazole (227 mg, 86%).

Treatment with methanesulfonic acid in $CH_2Cl_2$/MeOH and recrystallization from MeOH/EtOAc gave a methanesulfonate salt: mp 243-246° C.; $^1$H NMR (DMSO-$d_6$) δ 8.94 (dd, J=2.2, 0.5 Hz, 1H), 8.88 (dd, J=4.8, 1.6 Hz, 1H), 8.19 (ddd, J=8.1, 2.3, 1.7 Hz, 1H), 7.84 (dd, J=8.4, 0.4 Hz, 1H), 7.68 (ddd, J=8.1, 4.8, 0.7 Hz, 1H), 7.63 (t, $J_{HF}$=52.8 Hz, 1H), 7.39 (t, J=8.2 Hz, 1H), 6.94 (d, J=7.8 Hz, 1H), 3.96 (s, 3H), 3.93 (m, 4H), 3.77 (m, 4H), 3.66 (br s, 4H), 3.11 (br s, 4H), 2.33 (s, 3H); Anal. Calcd. for $C_{26}H_{31}F_2N_9O_7S_2$: C, 45.7; H, 4.6; N, 18.4. Found: C, 45.6; H, 4.6; N, 18.3%.

Example 72

Synthesis of N-{1-[4-[2-(difluoromethyl)-4-methoxy-1H-benzimidazol-1-yl]-6-(4-morpholinyl)-1,3,5-triazin-2-yl]-4-piperidinyl}-2-(dimethylamino)ethanesulfonamide

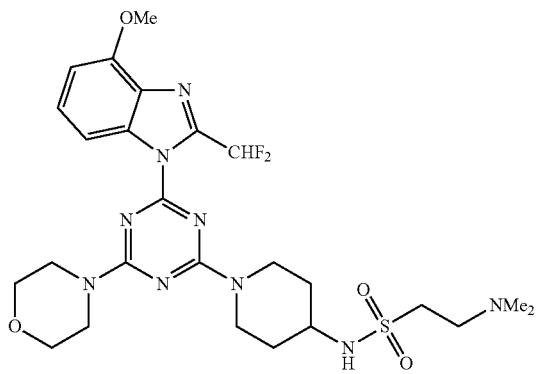 [SMILES: COc1cccc2c1nc(C(F)F)n2-c1nc(N2CCOCC2)nc(N2CCC(NS(=O)(=O)CCN(C)C)CC2)n1]

Reaction of 1-[4-[2-(difluoromethyl)-4-methoxy-1H-benzimidazol-1-yl]-6-(4-morpholinyl)-1,3,5-triazin-2-yl]-4-piperidinamine (Example 17) with 2-chloroethanesulfonyl chloride, as in previous examples, gave N-{1-[4-[2-(difluoromethyl)-4-methoxy-1H-benzimidazol-1-yl]-6-(4-morpholinyl)-1,3,5-triazin-2-yl]-4-piperidinyl}ethylenesulfonamide in 42% yield: mp (CH$_2$Cl$_2$/MeOH) 221-224° C.; $^1$H NMR (DMSO-d$_6$) δ 7.87 (dd, J=7.9, 0.6 Hz, 1H), 7.68 (t, J$_{HF}$=52.9 Hz, 1H), 7.45 (br s, 1H), 7.41 (t, J=8.2 Hz, 1H), 6.95 (d, J=7.8 Hz, 1H), 6.79 (dd, J=16.5, 9.9 Hz, 1H), 6.07 (d, J=16.5 Hz, 1H), 5.96 (d, J=9.9 Hz, 1H), 4.46 (t, J=17.0 Hz, 1H), 9.98 (s, 3H), 3.81-3.78 (m, 4H), 3.70-3.69 (m, 4H), 3.41-3.32 (m, 4H), 1.92 (br s, 2H), 1.44-1.42 (m, 2H); Anal. Calcd. for C$_{23}$H$_{28}$F$_2$N$_8$O$_4$S: C, 50.2; H, 5.1; N, 20.3. Found: C, 50.3; H, 5.1; N, 20.5%.

Reaction of the above vinylsulfonamide with 40% aqueous dimethylamine gave N-{1-[4-[2-(difluoromethyl)-4-methoxy-1H-benzimidazol-1-yl]-6-(4-morpholinyl)-1,3,5-triazin-2-yl]-4-piperidinyl}-2-(dimethylamino)ethanesulfonamide in 65% yield: Hydrochloride: mp (MeOH) 236-239° C.; $^1$H NMR (DMSO-d$_6$) δ 10.31 (br s, 1H), 7.88 (dd, J=8.4, 0.4 Hz, 1H), 7.69 (t, J$_{HF}$=52.9 Hz, 1H), 7.65 (d, J=7.5 Hz, 1H), 7.41 (t, J=8.2 Hz, 1H), 6.95 (d, J=7.8 Hz, 1H), 4.52 (t, J=16.8 Hz, 2H), 3.98 (s, 3H), 3.82-3.79 (m, 4H), 3.71-3.69 (m, 4H), 3.62-3.49 (m, 3H), 3.40-3.36 (m, 2H), 3.25-3.24 (m, 2H), 2.81 (s, 6H), 2.00 (br, 2H), 1.50-1.45 (m, 2H); Anal. Calcd. for C$_{21}$H$_{36}$ClF$_2$N$_9$O$_4$S: C, 47.5; H, 5.7; N, 19.9; Cl, 5.6. Found: C, 47.6; H, 5.8; N, 20.1; Cl, 5.9%.

Example 73

Synthesis of N-{1-[4-[2-(difluoromethyl)-4-methoxy-1H-benzimidazol-1-yl]-6-(4-morpholinyl)-1,3,5-triazin-2-yl]-4-piperidinyl}-2-(dimethylamino)-N-methylethanesulfonamide

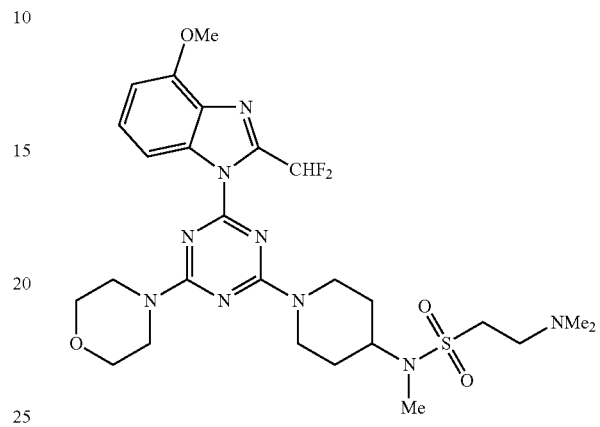

Reaction of 1-[4-chloro-6-(4-morpholinyl)-1,3,5-triazin-2-yl]-2-(difluoromethyl)-4-methoxy-1H-benzimidazole (Example 2) and tert-butyl methyl(4-piperidinyl)carbamate as in previous examples gave tert-butyl 1-[4-[2-(difluoromethyl)-4-methoxy-1H-benzimidazol-1-yl]-6-(4-morpholinyl)-1,3,5-triazin-2-yl]-4-piperidinyl(methyl)carbamate in 93% yield: mp (CH$_2$Cl$_2$/MeOH) 182-184° C.; $^1$H NMR (DMSO-d$_6$) δ 7.89 (d, J=7.9 Hz, 1H), 7.69 (t, J$_{HF}$=52.9 Hz, 1H), 7.41 (t, J=8.2 Hz, 1H), 6.95 (d, J=7.8 Hz, 1H), 4.83-4.72 (m, 2H), 4.09 (br, 1H), 3.98 (s, 3H), 3.81-3.79 (m, 4H), 3.70-3.69 (m, 4H), 3.07-2.93 (m, 2H), 2.66 (s, 3H), 1.66 (m, 4H), 1.41 (s, 9H); Anal. Calcd. for C$_{27}$H$_{36}$F$_2$N$_8$O$_4$: C, 56.4; H, 6.3; N, 19.7. Found: C, 56.6; H, 6.3; N, 19.8%.

Deprotection of the above carbamate with TFA in CH$_2$Cl$_2$ gave 1-[4-[2-(difluoromethyl)-4-methoxy-1H-benzimidazol-1-yl]-6-(4-morpholinyl)-1,3,5-triazin-2-yl]-N-methyl-4-piperidinamine in 96% yield: $^1$H NMR (DMSO-d$_6$) δ 7.89 (dd, J=8.3, 0.5 Hz, 1H), 7.68 (t, J$_{HF}$=52.9 Hz, 1H), 7.40 (t, J=8.2 Hz, 1H), 6.94 (d, J=7.7 Hz, 1H), 4.42 (t, J=14.2 Hz, 1H), 3.98 (s, 3H), 3.80-3.78 (m, 4H), 3.70-3.69 (m, 4H), 3.36-3.18 (m, 2H), 2.62-2.54 (m, 1H), 2.30 (s, 3H), 1.89 (br, 2H), 1.64 (br, 1H), 1.24 (br, 2H).

Reaction of the above amine with chloroethanesulfonyl chloride gave N-{1-[4-[2-(difluoromethyl)-4-methoxy-1H-benzimidazol-1-yl]-6-(4-morpholinyl)-1,3,5-triazin-2-yl]-4-piperidinyl}-N-methylethylenesulfonamide in 65% yield: mp (CH$_2$Cl$_2$/MeOH) 223-225° C.; $^1$H NMR (DMSO-d$_6$) δ 7.88 (d, J=8.0 Hz, 1H), 7.68 (t, J$_{HF}$=52.9 Hz, 1H), 7.41 (t, J=8.2 Hz, 1H), 6.95 (d, J=7.9 Hz, 1H), 6.85 (dd, J=16.4, 10.0 Hz, 1H), 6.07 (dd, J=15.2, 13.2 Hz, 2H), 4.82-4.70 (m, 2H), 3.98 (s, 3H), 3.95-3.88 (m, 1H), 3.81-3.79 (m, 4H), 3.70-3.69 (m, 4H), 3.10-2.97 (m, 2H), 2.62 (s, 3H), 1.72 (m, 4H); Anal. Calcd. for C$_{24}$H$_{30}$F$_2$N$_8$O$_4$S: C, 51.1; H, 5.4; N, 19.9. Found: C, 50.8; H, 5.3; N, 19.9%.

Reaction of the above vinylsulfonamide with 40% aqueous dimethylamine gave N-{1-[4-[2-(difluoromethyl)-4-methoxy-1H-benzimidazol-1-yl]-6-(4-morpholinyl)-1,3,5-triazin-2-yl]-4-piperidinyl}-2-(dimethylamino)-N-methylethanesulfonamide in 86% yield.

Hydrochloride: mp (MeOH) 242-245° C.; $^1$H NMR (DMSO-d$_6$) δ 10.47 (br, 1H, N$^+$H), 7.89 (d, J=8.0 Hz, 1H), 7.69 (t, J$_{HF}$=52.9 Hz, 1H), 7.41 (t, J=8.2 Hz, 1H), 6.95 (d, J=7.8 Hz, 1H), 4.84-4.74 (m, 2H), 3.98 (s, 3H), 3.98-3.91 (m, 1H), 3.82-3.80 (m, 4H), 3.70-3.63 (m, 6H), 3.40-3.36 (m, 2H), 3.14-3.00 (m, 2H), 2.81 (s. 6H), 2.75 (s, 3H), 1.78 (m, 4H); Anal. Calcd. for C$_{26}$H$_{38}$ClF$_2$N$_9$O$_4$S.0.25H$_2$O: C, 48.0; H, 6.0; Cl, 5.5; N, 19.4. Found: C, 48.0; H, 6.1; Cl, 5.7; N, 19.5%.

Example 74

Synthesis of N-{4-[4-[2-(difluoromethyl)-4-methoxy-1H-benzimidazol-1-yl]-6-(4-morpholinyl)-1,3,5-triazin-2-yl]phenyl}-2-(dimethylamino)ethanesulfonamide

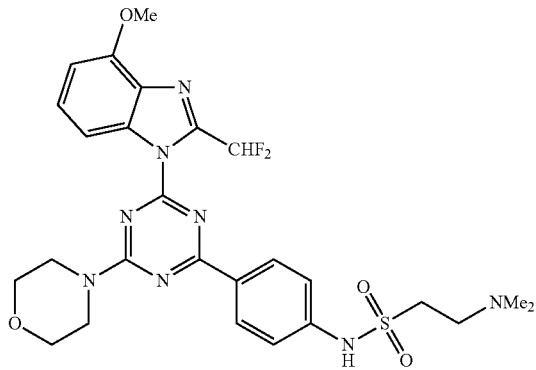 [SMILES: COc1cccc2c1nc(C(F)F)n2-c1nc(-c2ccc(NS(=O)(=O)CCN(C)C)cc2)nc(N2CCOCC2)n1]

A mixture of 1-[4-chloro-6-(4-morpholinyl)-1,3,5-triazin-2-yl]-2-(difluoromethyl)-4-methoxy-1H-benzimidazole (Example 2), 4-[(tert-butoxycarbonyl)amino]phenylboronic acid (90 mg, 0.380 mmol), PdCl$_2$(dppf) (10.3 mg, 0.0126 mmol) and aq. K$_2$CO$_3$ (2M, 2 mL) in 1,4-dioxane (10 mL) was refluxed under nitrogen for 1 hr. The mixture was cooled to room temperature and diluted with H$_2$O, and the aqueous phase was extracted with CH$_2$Cl$_2$ (3×). The combined organic extracts were dried (Na$_2$SO$_4$) and the solvent was removed under vacuum. Chromatography on alumina, eluting with CH$_2$Cl$_2$, followed by recrystallization from CH$_2$Cl$_2$/MeOH/hexanes gave tert-butyl 4-[4-[2-(difluoromethyl)-4-methoxy-1H-benzimidazol-1-yl]-6-(4-morpholinyl)-1,3,5-triazin-2-yl]phenylcarbamate (99 mg, 71%): mp (CH$_2$Cl$_2$/MeOH/hexanes) 188-190° C.; $^1$H NMR (CDCl$_3$) δ 8.41 (d, J=8.8 Hz, 2H), 8.08 (dd, J=8.4, 0.6 Hz, 1H), 7.62 (t, J$_{HF}$=53.4 Hz, 1H), 7.52 (d, J=8.8 Hz, 2H), 7.41 (t, J=8.2 Hz, 1H), 6.86 (d, J=7.7 Hz, 1H), 6.69 (s, 1H), 4.12 (m, 2H), 4.07 (s, 3H), 3.99 (m, 2H), 3.85 (m, 4H), 1.55 (s, 9H); Anal. Calcd. for C$_{27}$H$_{29}$F$_2$N$_7$O$_4$: C, 58.6; H, 5.3; N, 17.2. Found: C, 58.5; H, 5.0; N, 17.7%.

Reaction of the above carbamate (300 mg, 0.542 mmol) with an excess of TFA (2 mL) in CH$_2$Cl$_2$ (10 mL) at room temperature for 3 hrs, followed by treatment with aq. NH$_3$ gave 4-[4-[2-(difluoromethyl)-4-methoxy-1H-benzimidazol-1-yl]-6-(4-morpholinyl)-1,3,5-triazin-2-yl]aniline (217 mg, 88%), which was used in the next step without further purification: $^1$H NMR (DMSO-d$_6$) δ 8.17 (d, J=8.7 Hz, 2H), 8.05 (dd, J=8.3, 0.4 Hz, 1H), 7.80 (t, J$_{HF}$=52.9 Hz, 1H), 7.47 (t, J=8.2 Hz, 1H), 6.99 (d, J=7.8 Hz, 1H), 6.68 (d, J=8.8 Hz, 2H), 6.05 (s, 2H), 4.01 (br s, 2H), 3.99 (s, 3H), 3.88 (br s, 2H), 3.75 (m, 4H).

2-Chloroethanesulfonyl chloride (0.090 mL, 0.861 mmol) was added drop-wise to a suspension of the above amine (190 mg, 0.419 mmol) in pyridine (4 mL) at 0° C. The mixture was stirred at 0° C. for 2.5 hrs, then diluted with H$_2$O, and warmed to room temperature. The resulting precipitate was collected by filtration and dried to give N-{4-[4-[2-(difluoromethyl)-4-methoxy-1H-benzimidazol-1-yl]-6-(4-morpholinyl)-1,3,5-triazin-2-yl]phenyl}ethylenesulfonamide, which was used in the next step without further purification.

Excess dimethylamine (2 mL; 40% solution in H$_2$O) was added to a suspension of the above vinylsulfonamide in THF (10 mL) at room temperature. The mixture was stirred at room temperature for 21 hrs and then at reflux for 2 hrs. After cooled to room temperature, the solvent was removed under vacuum. The residue was partitioned between H$_2$O and CH$_2$Cl$_2$. The aqueous layer was extracted with CH$_2$Cl$_2$ (1×), the combined organic extracts were dried (Na$_2$SO$_4$), and the solvent was removed under vacuum. Chromatography on silica, eluting with CH$_2$Cl$_2$/MeOH (100:0 to 95:5), gave N-{4-[4-[2-(difluoromethyl)-4-methoxy-1H-benzimidazol-1-yl]-6-(4-morpholinyl)-1,3,5-triazin-2-yl]phenyl}-2-(dimethylamino)ethanesulfonamide (169 mg, 68% over 2 steps).

Treatment with methanesulfonic acid in CH$_2$Cl$_2$/MeOH and recrystallization from MeOH/EtOAc gave a methanesulfonate salt: mp (MeOH/EtOAc) 218-220° C.; $^1$H NMR (DMSO-d$_6$) δ 10.68 (br s, 1H), 9.47 (br s, 1H), 8.45 (d, J=8.8 Hz, 2H), 8.07 (d, J=8.1 Hz, 1H), 7.82 (t, J$_{HF}$=52.8 Hz, 1H), 7.49 (t, J=8.2 Hz, 1H), 7.43 (d, J=8.9 Hz, 2H), 7.01 (d, J=7.9 Hz, 1H), 4.06 (m, 2H), 4.00 (s, 3H), 3.92 (m, 2H), 3.79-3.74 (m, 6H), 3.50 (dd, J=9.4, 6.3 Hz, 2H), 2.82 (s, 6H), 2.31 (s, 3H); Anal. Calcd. for C$_{27}$H$_{34}$F$_2$N$_8$O$_7$S$_2$: C, 47.4; H, 5.0; N, 16.4. Found: 47.1; H, 5.1; N, 16.2%.

Example 75

Synthesis of N-{4-[4-[2-(difluoromethyl)-4-methoxy-1H-benzimidazol-1-yl]-6-(4-morpholinyl)-1,3,5-triazin-2-yl]phenyl}-2-(dimethylamino)-N-methyl-ethanesulfonamide

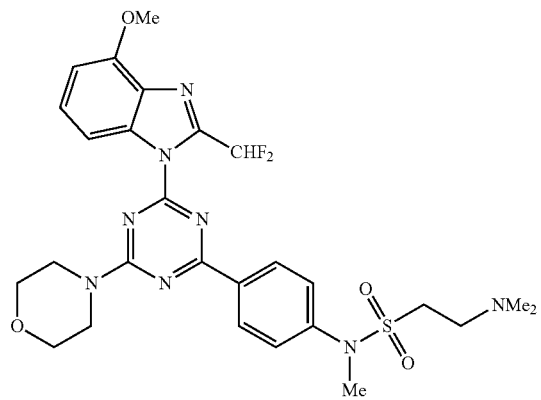 [SMILES: COc1cccc2c1nc(C(F)F)n2-c1nc(-c2ccc(N(C)S(=O)(=O)CCN(C)C)cc2)nc(N2CCOCC2)n1]

NaH (95%, 11 mg, 0.435 mmol) was added to a suspension of tert-butyl 4-[4-[2-(difluoromethyl)-4-methoxy-1H-benzimidazol-1-yl]-6-(4-morpholinyl)-1,3,5-triazin-2-yl]phenylcarbamate (Example 74) (120 mg, 0.217 mmol) in DMF (3 mL) at 0° C. After stirring at 0° C. for 15 min, iodomethane (0.020 mL, 0.321 mmol) was added. The reaction mixture was warmed to room temperature, stirred for additional 17 hrs, and then diluted with $H_2O$. The resulting precipitate was collected by filtration and dried to give tert-butyl 4-[4-[2-(difluoromethyl)-4-methoxy-1H-benzimidazol-1-yl]-6-(4-morpholinyl)-1,3,5-triazin-2-yl]phenyl(methyl)carbamate (104 mg, 85%): mp ($CH_2Cl_2$/MeOH) 205-208° C.; $^1$H NMR ($CDCl_3$) δ 8.42 (d, J=8.8 Hz, 2H), 8.09 (dd, J=8.4, 0.6 Hz, 1H), 7.63 (t, $J_{HF}$=53.5 Hz, 1H), 7.45-7.40 (m, 3H), 6.86 (d, J=7.8 Hz, 1H), 4.13 (m, 2H), 4.07 (s, 3H), 4.00 (m, 2H), 3.86 (m, 4H), 3.35 (s, 3H), 1.50 (s, 9H); Anal. Calcd. for $C_{28}H_{31}F_2N_7O_4$: C, 59.25; H, 5.5; N, 17.3. Found: C, 59.0; H, 5.3; N, 17.2%.

Reaction of the above carbamate (235 mg, 0.414 mmol) with an excess of TFA (1.2 mL) in $CH_2Cl_2$ (6 mL) at room temperature for 2 hrs, followed by treatment with aq. $NH_3$ gave 4-[4-[2-(difluoromethyl)-4-methoxy-1H-benzimidazol-1-yl]-6-(4-morpholinyl)-1,3,5-triazin-2-yl]-N-methylaniline (168 mg, 87%): $^1$H NMR (DMSO-$d_6$) δ 8.23 (d, J=8.9 Hz, 2H), 8.06 (d, J=8.0 Hz, 1H), 7.80 (t, $J_{HF}$=52.9 Hz, 1H), 7.47 (t, J=8.2 Hz, 1H), 6.99 (d, J=7.8 Hz, 1H), 6.67 (d, J=8.9 Hz, 2H), 6.63 (q, J=4.8 Hz, 1H), 4.01 (br s, 2H), 3.99 (s, 3H), 3.88 (br s, 2H), 3.76 (t, J=4.8 Hz, 4H), 2.79 (d, J=4.9 Hz, 3H).

2-Chloroethanesulfonyl chloride (0.060 mL, 0.574 mmol) was added dropwise to a mixture of the above amine (160 mg, 0.342 mmol) and DIPEA (0.18 mL, 1.03 mmol) in $CH_2Cl_2$ (20 mL) at 0° C. The mixture was stirred at 0° C. for 3.5 hrs, when additional DIPEA (0.18 mL, 1.03 mmol) and 2-chloroethanesulfonyl chloride (0.030 mL, 0.287 mmol) were added. The mixture was stirred for another 2 hrs at 0° C. The reaction mixture was then quenched with $H_2O$ and the organic layer was washed successively with HOAc (1%) and aq. $NH_3$. The aqueous layer was extracted with $CH_2Cl_2$ (5×), the combined organic extracts were dried ($Na_2SO_4$), and the solvent was removed under vacuum to give N-{4-[4-[2-(difluoromethyl)-4-methoxy-1H-benzimidazol-1-yl]-6-(4-morpholinyl)-1,3,5-triazin-2-yl]phenyl}-N-methylethylenesulfonamide which was used in the next step without further purification.

Excess dimethylamine (1.0 mL, 40% solution in $H_2O$) was added to a solution of the above vinylsulfonamide in THF (10 mL) at room temperature and the mixture was stirred for 3 days. The solvent was removed under vacuum and the residue was partitioned between $H_2O$ and $CH_2Cl_2$. The aqueous phase was extracted with $CH_2Cl_2$ (2×), the combined organic extracts were dried ($Na_2SO_4$), and the solvent was removed under vacuum. Chromatography on silica, eluting with $CH_2Cl_2$/MeOH (100:0 to 98:2), followed by recrystallization from $CH_2Cl_2$/MeOH/hexanes, gave N-{4-[4-[2-(difluoromethyl)-4-methoxy-1H-benzimidazol-1-yl]-6-(4-morpholinyl)-1,3,5-triazin-2-yl]phenyl}-2-(dimethylamino)-N-methylethanesulfonamide (104 mg, 50% yield over 2 steps).

Treatment with methanesulfonic acid in $CH_2Cl_2$/MeOH and recrystallization from MeOH/EtOAc gave a methanesulfonate salt: mp (MeOH/EtOAc) 218-220° C.; $^1$H NMR (DMSO-$d_6$) δ 9.45 (br s, 1H), 8.50 (d, J=8.8 Hz, 2H), 8.07 (d, J=7.9 Hz, 1H), 7.83 (t, $J_{HF}$=52.8 Hz, 1H), 7.68 (d, J=8.8 Hz, 2H), 7.49 (t, J=8.2 Hz, 1H), 7.02 (d, J=7.9 Hz, 1H), 4.08 (m, 2H), 4.00 (s, 3H), 3.94 (m, 2H), 3.79 (m, 4H), 3.72 (dd, J=9.7, 6.2 Hz, 2H), 3.47 (m, 2H), 3.41 (s, 3H), 2.82 (s, 6H), 2.30 (s, 3H); Anal. Calcd. for $C_{28}H_{36}F_2N_8O_7S_2$.0.35$H_2O$: C, 47.7; H, 5.25; N, 15.9. Found: C, 47.7; H, 4.9; N, 15.8%.

Example 76

Synthesis of N-{1-[4-[2-(difluoromethyl)-4-methoxy-1H-benzimidazol-1-yl]-6-(4-morpholinyl)-1,3,5-triazin-2-yl]-3-azetidinyl}-2-(dimethylamino)ethanesulfonamide

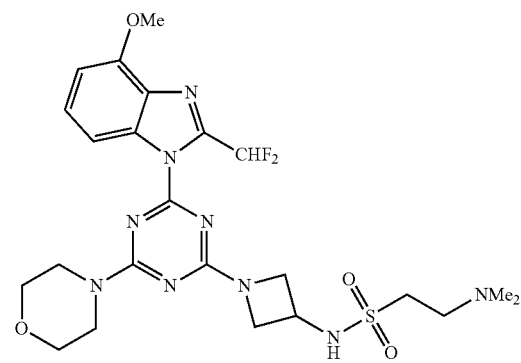 [SMILES: COc1cccc2c1nc(C(F)F)n2-c1nc(N2CCOCC2)nc(N2CC(NS(=O)(=O)CCN(C)C)C2)n1]

Reaction of 1-[4-[2-(difluoromethyl)-4-methoxy-1H-benzimidazol-1-yl]-6-(4-morpholinyl)-1,3,5-triazin-2-yl]-3-azetidinamine (Example 30) with 2-chloroethanesulfonyl chloride as in previous examples gave N-{1-[4-[2-(difluoromethyl)-4-methoxy-1H-benzimidazol-1-yl]-6-(4-morpholinyl)-1,3,5-triazin-2-yl]-3-azetidinyl}ethylenesulfonamide in 9.7% yield: mp ($CH_2Cl_2$/MeOH) 250-252° C.; $^1$H NMR (DMSO-$d_6$) δ 8.20 (br, 1H), 7.96 (dd, J=7.9, 0.6 Hz, 1H), 7.72 (t, $J_{HF}$=53.0 Hz, 1H), 7.40 (t, J=8.2 Hz, 1H), 6.95 (d, J=7.8 Hz, 1H), 6.82 (dd, J=16.5, 10.0 Hz, 1H), 6.08 (dd, J=26.8, 13.2 Hz, 2H), 4.47 (t, J=7.6 Hz, 1H), 4.37 (t, J=8.1 Hz, 1H), 4.26-4.20 (m, 1H), 4.04-3.97 (m, 2H), 3.97 (s, 3H), 3.80-3.77 (m, 4H), 3.68 (m, 4H); Anal. Calcd. for $C_{21}H_{24}F_2N_8O_4S$; C, 48.3; H, 4.6; N, 21.4. Found: C, 48.4; H, 4.7; N, 21.6%.

Reaction of the above vinylsulfonamide with 40% aqueous dimethylamine gave N-{1-[4-[2-(difluoromethyl)-4-methoxy-1H-benzimidazol-1-yl]-6-(4-morpholinyl)-1,3,5-triazin-2-yl]-3-azetidinyl}-2-(dimethylamino)ethanesulfonamide in 74% yield.

Hydrochloride: mp (MeOH) 214-216° C.; $^1$H NMR (DMSO-$d_6$) δ 10.25 (br s, 1H, exchangeable with $D_2O$), 8.45 (d, J=7.40 Hz, 1H), 7.98 (d, J=8.41 Hz, 1H), 7.74 (t, $J_{HF}$=53.0 Hz, 1H), 7.40 (t, J=8.2 Hz, 1H), 6.95 (d, J=7.7 Hz, 1H), 4.55-4.36 (m, 3H), 4.15-4.00 (m, 2H), 3.97 (s, 3H), 3.97-3.98 (m, 4H), 3.69 (m, 4H), 3.62-3.59 (m, 2H), 3.41-3.38 (m, 2H), 2.80 (s, 6H); Anal. Calcd. for $C_{23}H_{32}ClF_2N_9O_4S$.0.25$H_2O$: C, 45.4; H, 5.4; Cl, 6.2; N, 20.7. Found: C, 45.4; H, 5.2; Cl; 6.0; N, 20.8%.

Example 77

Synthesis of N-{1-[4-[2-(difluoromethyl)-4-methoxy-1H-benzimidazol-1-yl]-6-(4-morpholinyl)-1,3,5-triazin-2-yl]-3-azetidinyl}-2-(dimethylamino)-N-methylethanesulfonamide

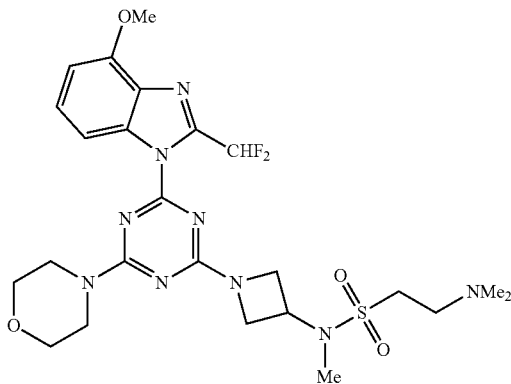 [SMILES: COc1cccc2c1nc(C(F)F)n2-c1nc(N2CCOCC2)nc(N2CC(N(C)S(=O)(=O)CCN(C)C)C2)n1]

Reaction of tert-butyl 1-[4-[2-(difluoromethyl)-4-methoxy-1H-benzimidazol-1-yl]-6-(4-morpholinyl)-1,3,5-triazin-2-yl]-3-azetidinylcarbamate (Example 30) with NaH/MeI in THF as in previous examples gave tert-butyl 1-[4-[2-(difluoromethyl)-4-methoxy-1H-benzimidazol-1-yl]-6-(4-morpholinyl)-1,3,5-triazin-2-yl]-3-azetidinyl(methyl)-carbamate in 95% yield: mp (CH$_2$Cl$_2$/MeOH) 186-188° C.; $^1$H NMR (DMSO-d$_6$) δ 8.00 (d, J=8.3 Hz, 1H), 7.75 (t, J$_{HF}$=53.0 Hz, 1H), 7.39 (t, J=8.2 Hz, 1H), 6.95 (d, J=8.0 Hz, 1H), 4.88 (br, 1H), 4.40-4.15 (m, 4H), 3.97 (s, 3H), 3.80-3.78 (m, 4H), 3.69 (m, 4H), 2.89 (s, 3H), 1.41 (s, 9H); Anal. Calcd. for C$_{25}$H$_{32}$F$_2$N$_8$O$_4$: C, 54.9; H, 5.9; N, 20.5. Found: C, 55.1; H, 5.9; N, 20.6%.

Deprotection of the above carbamate with TFA in CH$_2$Cl$_2$ as in previous examples gave 1-[4-[2-(difluoromethyl)-4-methoxy-1H-benzimidazol-1-yl]-6-(4-morpholinyl)-1,3,5-triazin-2-yl]-N-methyl-3-azetidinamine in 96% yield: mp (CH$_2$Cl$_2$/hexanes) 199-201° C.; $^1$H NMR (DMSO-d$_6$) δ 7.99 (dd, J=8.4, 0.5 Hz, 1H), 7.75 (t, J$_{HF}$=53.1 Hz, 1H), 7.40 (t, J=8.2 Hz, 1H), 6.95 (d, J=7.8 Hz, 1H), 4.30-4.20 (m, 2H), 3.97 (s, 3H), 3.89-3.85 (m, 1H), 3.80-3.77 (m, 5H), 3.70-3.68 (m, 4H), 3.64-3.58 (m, 1H), 2.26 (s, 3H).

Reaction of the above amine with 2-chloroethanesulfonyl chloride as in previous examples gave N-{1-[4-[2-(difluoromethyl)-4-methoxy-1H-benzimidazol-1-yl]-6-(4-morpholinyl)-1,3,5-triazin-2-yl]-3-azetidinyl}-N-methylethenesulfonamide in 44% yield: mp (CH$_2$Cl$_2$/MeOH) 244-246° C.; $^1$H NMR (DMSO-d$_6$) δ 7.98 (d, J=8.4 Hz, 1H), 7.74 (t, J$_{HF}$=53.0 Hz, 1H), 7.40 (t, J=8.2 Hz, 1H), 6.95 (d, J=7.8 Hz, 1H), 6.86 (dd, J=16.5, 10.0 Hz, 1H), 6.17 (dd, J=13.2, 7.7 Hz, 2H), 4.74-4.67 (m, 1H), 4.22-4.20 (m, 4H), 3.98 (s, 3H), 3.80-3.78 (m, 4H), 3.68 (m, 4H), 2.86 (s, 3H); Anal. Calcd. for C$_{22}$H$_{26}$F$_2$N$_8$O$_4$S: C, 49.3; H, 4.9; N, 20.9. Found: C, 49.3; H, 4.9; 20.9%.

Reaction of the above vinylsulfonamide with 40% aqueous dimethylamine gave N-{1-[4-[2-(difluoromethyl)-4-methoxy-1H-benzimidazol-1-yl]-6-(4-morpholinyl)-1,3,5-triazin-2-yl]-3-azetidinyl}-2-(dimethylamino)-N-methyl-ethanesulfonamide in 88% yield.

Methanesulfonate: mp (CH$_2$Cl$_2$/MeOH/EtOAc) 239-242° C.; $^1$H NMR (DMSO-d$_6$) δ 9.44 (br, 1H, exchangeable with D$_2$O), 7.99 (dd, J=8.4, 0.5 Hz, 1H), 7.75 (t, J$_{HF}$=53.0 Hz, 1H), 7.40 (t, J=8.2 Hz, 1H), 6.96 (d, J=7.7 Hz, 1H), 4.88-4.81 (m, 1H), 4.49-4.29 (m, 4H), 3.98 (s, 3H), 3.82-3.79 (m, 4H), 3.69 (m, 4H), 3.60-3.56 (m, 2H), 3.46-3.43 (m, 2H), 3.01 (s, 3H), 2.86 (s, 6H), 2.30 (s, 3H); Anal. Calcd. for C$_{25}$H$_{37}$F$_2$N$_9$O$_7$S$_2$.0.75H$_2$O: C, 43.4; H, 5.6; N, 18.2. Found: C, 43.4; H, 5.5; N, 17.9%.

Example 78

Synthesis of trans-N-(4-{[4-[2-(difluoromethyl)-4-methoxy-1H-benzimidazol-1-yl]-6-(4-morpholinyl)-1,3,5-triazin-2-yl]amino}cyclohexyl)methanesulfonamide

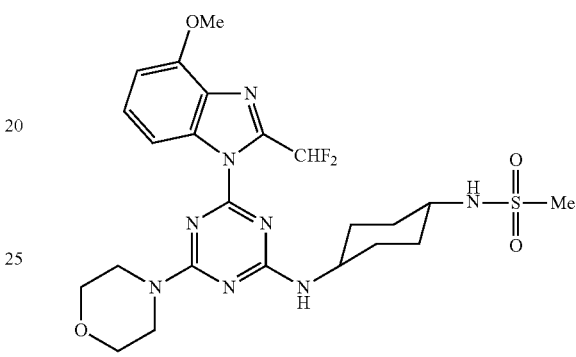

Reaction of 1-[4-chloro-6-(4-morpholinyl)-1,3,5-triazin-2-yl]-2-(difluoromethyl)-4-methoxy-1H-benzimidazole (Example 2) with tert-butyl trans-4-aminocyclohexylcarbamate as in previous examples gave tert-butyl trans-4-{[4-[2-(difluoromethyl)-4-methoxy-1H-benzimidazol-1-yl]-6-(4-morpholinyl)-1,3,5-triazin-2-yl]amino}cyclohexylcarbamate in 88% yield: mp (CH$_2$Cl$_2$/hexanes) 218-221° C.; $^1$H NMR (DMSO-d$_6$) δ 8.10 and 7.97 (2d, J=8.3, 8.1 Hz, 1H), 7.87 and 7.72 (2t, J$_{HF}$=53.1, 53.0 Hz, 1H) 7.83 and 7.77 (2d, J=7.7, 8.10 Hz, 1H), 7.38 (q, J=8.3 Hz, 1H), 6.94 (t, J=8.0 Hz, 1H), 6.75-6.70 (m, 1H), 3.98 and 3.97 (2s, 3H), 3.97 (m, 4H), 3.71-3.69 (m, 4H), 1.98-1.91 (m, 2H), 1.85-1.82 (m, 2H), 1.40-1.22 (m, 4H), 1.38 (s, 9H); Anal. Calcd. for C$_{27}$H$_{36}$F$_2$N$_8$O$_4$: C, 56.4; H, 6.3; N, 19.5. Found: C, 56.6; H, 6.5; N, 19.3%.

Deprotection of the above carbamate with TFA in CH$_2$Cl$_2$ as in previous examples gave trans-N$^1$-[4-[2-(difluoromethyl)-4-methoxy-1H-benzimidazol-1-yl]-6-(4-morpholinyl)-1,3,5-triazin-2-yl]-1,4-cyclohexanediamine in 100% yield: mp (CH$_2$Cl$_2$/hexanes) 220-222° C.; $^1$H NMR (DMSO-d$_6$) δ 8.10 and 7.98 (2d, J=7.9, 8.1 Hz, 1H), 7.88 and 7.73 (t, J$_{HF}$=53.2 Hz, 1H), 7.81 and 7.74 (2d, J=7.9, 9.8 Hz, 1H), 7.42-7.35 (m, 1H), 6.94 (t, J=7.6 Hz, 1H), 3.98 and 3.97 (2s, 3H), 3.78-3.77 (m, 4H), 3.74-3.72 (m, 4H), 3.71-3.69 (m, 4H), 2.55-2.53 (m, 1H), 1.93-1.87 (m, 2H), 1.83-1.76 (m, 2H), 1.40-1.28 (m, 2H), 1.19-1.09 (m, 2H).

Reaction of the above amine with methanesulfonyl chloride as in previous examples gave trans-N-(4-{[4-[2-(difluoromethyl)-4-methoxy-1H-benzimidazol-1-yl]-6-(4-morpholinyl)-1,3,5-triazin-2-yl]amino}cyclohexyl)methanesulfonamide in 90% yield: mp (CH$_2$Cl$_2$/MeOH) 269-272° C.; $^1$H NMR (DMSO-d$_6$) δ 8.10 and 7.97 (d, J=8.3 Hz, 1H), 7.88 and 7.73 (2t, J$_{HF}$=53.2, 53.9 Hz, 1H) 7.86 and 7.80 (d, J=7.6, 8.0 Hz, 1H), 7.38 (q, J=8.1 Hz, 1H), 7.02-6.92 (m, 2H), 3.98 and 3.97 (2s, 3H), 3.77-3.69 (m, 9H), 3.13 (br, 1H), 2.93 and 2.92 (2s, 3H), 1.98-1.96 (m, 4H), 1.42-1.32 (m, 4H); Anal. Calcd. for C$_{23}$H$_{30}$F$_2$N$_8$O$_4$S: C, 50.0; H, 5.5; N, 20.3. Found: C, 50.0; H, 5.4; N, 20.5%.

Example 79

Synthesis of cis-N-(4-{[4-[2-(difluoromethyl)-4-methoxy-1H-benzimidazol-1-yl]-6-(4-morpholinyl)-1,3,5-triazin-2-yl]amino}cyclohexyl)methanesulfonamide

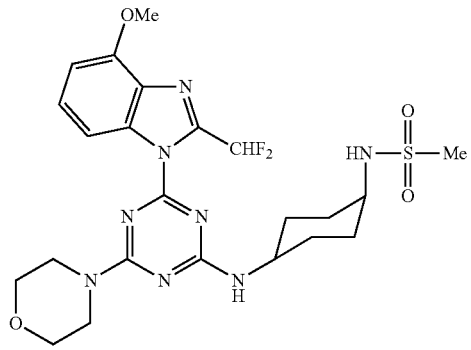 [SMILES: COc1cccc2c1nc(C(F)F)n2-c1nc(NC2CCC(NS(C)(=O)=O)CC2)nc(N2CCOCC2)n1]

Similar to the previous Example, coupling of 1-[4-chloro-6-(4-morpholinyl)-1,3,5-triazin-2-yl]-2-(difluoromethyl)-4-methoxy-1H-benzimidazole (Example 2) and tert-butyl cis-4-aminocyclohexylcarbamate gave tert-butyl cis-4-{[4-[2-(difluoromethyl)-4-methoxy-1H-benzimidazol-1-yl]-6-(4-morpholinyl)-1,3,5-triazin-2-yl]amino}-cyclohexylcarbamate in 90% yield: mp (CH$_2$Cl$_2$/hexanes) 192-195° C.; $^1$H NMR (DMSO-d$_6$) δ 8.13 and 7.97 (2d, J=8.1, 8.3 Hz, 1H), 7.94 and 7.72 (2t, J$_{HF}$=53.1 Hz, 1H), 7.71 and 7.64 (2d, J=6.8, 7.1 Hz, 1H), 7.39 (q, J=8.3 Hz, 1H), 6.94 (dd, J=8.0, 2.4 Hz, 1H), 3.97 (s, 3H), 3.88 (br, 1H), 3.78-3.77 (m, 4H), 3.70-3.69 (m, 4H), 3.46-3.39 (m, 1H), 1.80-1.55 (m, 8H), 1.39 (s, 9H): Anal. Calcd. for C$_{27}$H$_{36}$F$_2$N$_8$O$_4$: C, 56.4; H, 6.3; N, 19.5. Found: C, 56.6; H, 6.5; N, 19.7%.

Deprotection of the above carbamate with TFA in CH$_2$Cl$_2$ as in previous examples gave cis-N$^1$-[4-[2-(difluoromethyl)-4-methoxy-1H-benzimidazol-1-yl]-6-(4-morpholinyl)-1,3,5-triazin-2-yl]-1,4-cyclohexanediamine in 99% yield: mp (CH$_2$Cl$_2$/hexanes) 171-173° C.; $^1$H NMR (DMSO-d$_6$) δ 8.13 and 7.98 (2d, J=8.0, 8.3 Hz, 1H), 7.95 and 7.73 (2t, J$_{HF}$=53.1 Hz, 1H), 7.76 and 7.69 (2d, J=7.4, 7.6 Hz, 1H), 7.41-7.36 (m, 1H), 6.94 (dd, J=8.1, 1.7 Hz, 1H), 3.97 (s, 3H), 3.92-3.85 (m, 1H), 3.78-3.77 (m, 4H), 3.69 (m, 4H), 2.93-2.85 (m, 1H), 1.85-1.72 (m, 2H), 1.62-1.49 (m, 7H).

Reaction of the above amine with methanesulfonyl chloride as in previous examples gave cis-N-(4-{[4-[2-(difluoromethyl)-4-methoxy-1H-benzimidazol-1-yl]-6-(4-morpholinyl)-1,3,5-triazin-2-yl]amino}cyclohexyl) methanesulfonamide in 88% yield: $^1$H NMR (DMSO-d$_6$) δ 8.13 and 7.97 (2d, J=8.3 Hz, 1H), 7.94 and 7.73 (2 t, J$_{HF}$=53.3, 53.1 Hz, 1H), 7.81 and 7.77 (2d, J=6.5, 7.3 Hz, 1H), 7.42-7.36 (m, 1H), 6.96-6.89 (m, 2H), 3.97 (s, 3H), 3.88-3.86 (m, 1H), 3.79-3.78 (m, 4H), 3.70-3.69 (m, 4H), 3.35-3.34 (m, 1H), 2.92 and 2.91 (2s, 3H), 1.84-1.63 (m, 8H); Anal. Calcd. for C$_{23}$H$_{30}$F$_2$N$_8$O$_4$S: C, 50.0; H, 5.5; N, 20.3. Found: C, 50.0; H, 5.4; N, 20.5%.

Example 80

Synthesis of N-({1-[4-[2-(difluoromethyl)-4-methoxy-1H-benzimidazol-1-yl]-6-(4-morpholinyl)-1,3,5-triazin-2-yl]-4-piperidinyl}methyl)methanesulfonamide

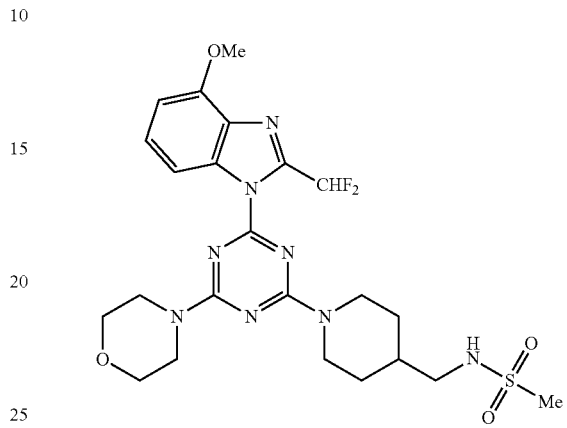

Reaction of 1-[4-chloro-6-(4-morpholinyl)-1,3,5-triazin-2-yl]-2-(difluoromethyl)-4-methoxy-1H-benzimidazole (Example 2) and tert-butyl 4-piperidinylmethylcarbamate as in previous examples gave tert-butyl {1-[4-[2-(difluoromethyl)-4-methoxy-1H-benzimidazol-1-yl]-6-(4-morpholinyl)-1,3,5-triazin-2-yl]-4-piperidinyl}methylcarbamate in 94% yield: mp (CH$_2$Cl$_2$/MeOH) 210-212° C.; $^1$H NMR (DMSO-d$_6$) δ 7.88 (d, J=8.1 Hz, 1H), 7.68 (t, J$_{HF}$=52.9 Hz, 1H), 7.40 (t, J=8.2 Hz, 1H), 6.94 (d, J=7.9 Hz, 1H), 6.87 (t, J=5.5 Hz, 1H), 4.68-4.59 (m, 2H), 3.98 (s, 3H), 3.80-3.78 (m, 4H), 3.70-3.69 (m, 4H), 3.05-2.87 (m, 2H), 2.90 (t, J=5.9 Hz, 2H), 1.72 (br, 3H), 1.38 (s, 9H), 1.09 (br, 2H); Anal. Calcd. for C$_{27}$H$_{36}$F$_2$N$_8$O$_4$: C, 56.4; H, 6.3; N, 19.5. Found: C, 56.7; H, 6.3; N, 19.6%.

Deprotection of the above carbamate with TFA in CH$_2$Cl$_2$ as in previous examples gave {1-[4-[2-(difluoromethyl)-4-methoxy-1H-benzimidazol-1-yl]-6-(4-morpholinyl)-1,3,5-triazin-2-yl]-4-piperidinyl}methylamine in 93% yield: $^1$H NMR (DMSO-d$_6$) δ 7.89 (d, J=8.3 Hz, 1H), 7.68 (t, J$_{HF}$=52.9 Hz, 1H), 7.40 (t, J=8.2 Hz, 1H), 6.94 (d, J=7.8 Hz, 1H), 4.71-4.62 (m, 2H), 3.98 (s, 3H), 3.80-3.78 (m, 4H), 3.70-3.69 (m, 4H), 3.03-2.91 (m, 2H), 2.45 (d, J=6.4 Hz, 2H), 1.81 (br, 2H), 1.58-1.39 (m, 3H), 1.10-1.05 (m, 2H).

Reaction of the above amine with methanesulfonyl chloride as in previous examples gave N-({1-[4-[2-(difluoromethyl)-4-methoxy-1H-benzimidazol-1-yl]-6-(4-morpholinyl)-1,3,5-triazin-2-yl]-4-piperidinyl}methyl)methanesulfonamide in 91% yield: mp (CH$_2$Cl$_2$/MeOH) 238-240° C.; $^1$H NMR (DMSO-d$_6$) δ 7.89 (d, J=8.0 Hz, 1H), 7.69 (t, J$_{HF}$=52.9 Hz, 1H), 7.41 (t, J=8.2 Hz, 1H), 7.03 (t, J=5.2 Hz, 1H), 6.95 (d, J=7.8 Hz, 1H), 4.71-4.61 (m, 2H), 3.98 (s, 3H), 3.81-3.79 (m, 4H), 3.70-3.69 (m, 4H), 3.05-2.93 (m, 2H), 2.88 (s, 3H), 2.88-2.85 (m, 2H), 1.82-1.76 (m, 3H), 1.19-1.12 (m, 2H); Anal. Calcd. for C$_{23}$H$_{30}$F$_2$N$_8$O$_4$S: C, 50.0; H, 5.5; N, 20.3. Found: C, 49.8; H, 5.4; N, 20.3%.

Example 81

Synthesis of N-({1-[4-[2-(difluoromethyl)-4-methoxy-1H-benzimidazol-1-yl]-6-(4-morpholinyl)-1,3,5-triazin-2-yl]-3-piperidinyl}methyl)methanesulfonamide

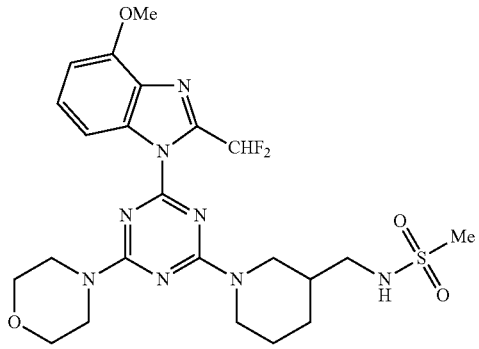 [SMILES: COc1cccc2c1nc(C(F)F)n2-c1nc(N2CCOCC2)nc(N2CCCC(CNS(C)(=O)=O)C2)n1]

Reaction of 1-[4-chloro-6-(4-morpholinyl)-1,3,5-triazin-2-yl]-2-(difluoromethyl)-4-methoxy-1H-benzimidazole (Example 2) with tert-butyl 3-piperidinylmethylcarbamate as in previous examples gave tert-butyl {1-[4-[2-(difluoromethyl)-4-methoxy-1H-benzimidazol-1-yl]-6-(4-morpholinyl)-1,3,5-triazin-2-yl]-3-piperidinyl}methylcarbamate in 83% yield: mp (CH$_2$Cl$_2$/MeOH) 131-133° C.; $^1$H NMR (DMSO-d$_6$) δ 7.93 and 7.89 (2d, J=8.6, 8.4 Hz, 1H), 7.68 (t, J$_{HF}$=53.0 Hz, 1H), 7.46-7.38 (m, 1H), 6.95 (d, J=8.1 Hz, 1H), 6.91 (br, 1H), 4.54-4.41 (m, 2H), 3.97 (s, 3H), 3.79 (br s, 4H), 3.69 (br s, 4H), 3.14-3.05 (m, 1H), 2.94-2.76 (m, 2H), 1.78-1.57 (m, 3H), 1.44-1.24 (m, 2H), 1.39 and 1.32 (2s, 9H); Anal. Calcd. for C$_{27}$H$_{36}$F$_2$N$_8$O$_4$: C, 56.4; H, 6.3; N, 19.5. Found: C, 56.6; H, 6.5; N, 19.5%.

Deprotection of the above carbamate with TFA in CH$_2$Cl$_2$ as in previous examples gave {1-[4-[2-(difluoromethyl)-4-methoxy-1H-benzimidazol-1-yl]-6-(4-morpholinyl)-1,3,5-triazin-2-yl]-3-piperidinyl}methanamine in 93% yield: mp (CH$_2$Cl$_2$/hexanes) 202-204° C.; $^1$H NMR (DMSO-d$_6$) δ 7.97 and 7.89 (d, J=8.3, 8.2 Hz, 1H), 7.75 and 7.69 (2t, J$_{HF}$=52.8 Hz, 1H), 7.42-7.36 (m, 1H), 6.94 (d, J=7.9 Hz, 1H), 4.58-4.34 (m, 2H), 3.97 (s, 3H), 3.79-3.78 (m, 4H), 3.70-3.69 (m, 4H), 3.24-3.22 (m, 2H), 2.94-2.86 (m, 1H), 2.54-2.44 (m, 1H), 1.84-1.71 (m, 2H), 1.45 (m, 4H), 1.31-1.23 (m, 1H).

Reaction of the above amine with methanesulfonyl chloride as in previous examples gave N-({1-[4-[2-(difluoromethyl)-4-methoxy-1H-benzimidazol-1-yl]-6-(4-morpholinyl)-1,3,5-triazin-2-yl]-3-piperidinyl}methyl)methanesulfonamide in 70% yield: mp (CH$_2$Cl$_2$/MeOH) 179-181° C.; $^1$H NMR (DMSO-d$_6$) δ 7.97 and 7.89 (2d, J=8.2 Hz, 1H), 7.71 and 7.69 (2t, J$_{HF}$=52.94, 53.2 Hz, 1H), 7.47 and 7.41 (2t, J=8.2 Hz, 1H), 7.10 (br, 1H), 6.95 (d, J=8.00 Hz, 1H), 4.64-4.38 (m, 2H), 3.98 (s, 3H), 3.79 (m, 4H), 3.70-3.69 (m, 4H), 3.19-3.04 (m, 1H), 2.90-2.89 (m, 6H), 1.86-1.68 (m, 3H), 1.50-1.40 (m, 1H), 1.36-1.26 (m, 1H); Anal. Calcd. for C$_{23}$H$_{30}$F$_2$N$_8$O$_4$S: C, 50.0; H, 5.5; N, 20.3. Found: C, 49.9; H, 5.5; N, 20.4%.

Example 82

Synthesis of 4-[2-(difluoromethyl)-4-methoxy-1H-benzimidazol-1-yl]-N-{[1-(methylsulfonyl)-4-piperidinyl]methyl}-6-(4-morpholinyl)-1,3,5-triazin-2-amine

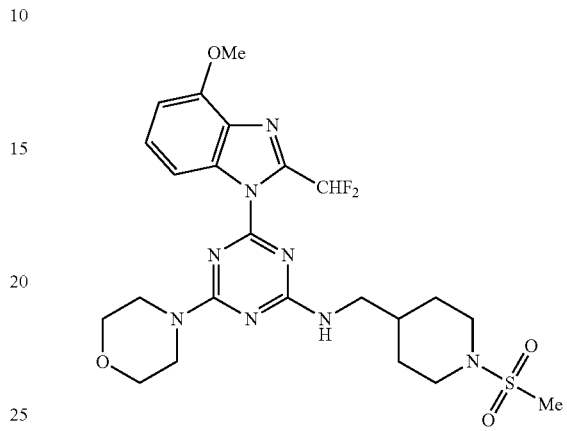

Reaction of 1-[4-chloro-6-(4-morpholinyl)-1,3,5-triazin-2-yl]-2-(difluoromethyl)-4-methoxy-1H-benzimidazole (Example 2) with tert-butyl 4-(aminomethyl)-1-piperidinecarboxylate as in previous examples gave tert-butyl 4-({[4-[2-(difluoromethyl)-4-methoxy-1H-benzimidazol-1-yl]-6-(4-morpholinyl)-1,3,5-triazin-2-yl]amino}methyl)-1-piperidinecarboxylate in 91% yield: mp (CH$_2$Cl$_2$/MeOH) 203-205° C.; $^1$H NMR (DMSO-d$_6$) δ 8.10-7.60 (m, 3H), 7.41-7.36 (m, 1H), 6.94 (dd, J=7.8, 3.8 Hz, 1H), 3.974 and 3.970 (2s, 3H), 3.95-3.92 (m, 2H), 3.78-3.77 (m, 4H), 3.69 (m, 4H), 3.34-3.24 (m, 2H), 2.69 (m, 2H), 1.77-1.67 (m, 3H), 1.389 and 1.381 (2s, 9H), 1.12-1.00 (m, 2H); Anal. Calcd. for C$_{27}$H$_{36}$F$_2$N$_8$O$_4$: C, 56.4; H, 6.3; N, 19.5. Found: C, 56.1; H, 6.3; N, 19.6%.

Deprotection of the above carbamate with TFA in CH$_2$Cl$_2$ as in previous examples gave 4-[2-(difluoromethyl)-4-methoxy-1H-benzimidazol-1-yl]-6-(4-morpholinyl)-N-(4-piperidinylmethyl)-1,3,5-triazin-2-amine in 92% yield: mp (CH$_2$Cl$_2$/hexanes) 154-157° C.; $^1$H NMR (DMSO-d$_6$) δ 8.10-7.60 (m, 3H), 7.42-7.36 (m, 1H), 6.94 (dd, J=7.8, 5.4 Hz, 1H) 3.98 and 3.97 (2s, 3H), 3.78-3.77 (m, 4H), 3.69 (m, 4H), 3.06-3.03 (m, 2H), 2.94-2.92 and 2.81-2.78 (2m, 1H), 2.59-2.44 (m, 2H), 1.87-1.58 (m, 4H), 1.25-1.09 (m, 2H).

Treatment of the above amine with methanesulfonyl chloride as in previous examples gave 4-[2-(difluoromethyl)-4-methoxy-1H-benzimidazol-1-yl]-N-{[1-(methylsulfonyl)-4-piperidinyl]methyl}-6-(4-morpholinyl)-1,3,5-triazin-2-amine in 100% yield: mp (CH$_2$Cl$_2$/MeOH) 213-216° C.; $^1$H NMR (DMSO-d$_6$) δ 8.10-7.61 (m, 3H), 7.43-7.36 (m, 1H), 6.94 (dd, J=7.9, 4.4 Hz, 1H), 3.98, 3.97 (2s, 3H), 3.79-3.76 (m, 4H), 3.69 (m, 4H), 2.59-3.56 (m, 2H), 2.84 and 2.81 (2s, 3H), 2.71-2.62 (m, 2H), 1.83-1.69 (m, 3H), 1.31-1.18 (m, 2H); Anal. Calcd. for C$_{23}$H$_{30}$F$_2$N$_8$O$_4$S: C, 50.0; H, 5.5; N, 20.2. Found: C, 49.9; H, 5.47; N, 20.3%.

Example 83

Synthesis of N-[2-({4-[4-[2-(difluoromethyl)-1H-benzimidazol-1-yl]-6-(4-morpholinyl)-1,3,5-triazin-2-yl]-1-piperazinyl}sulfonyl)ethyl]-N,N-dimethylamine

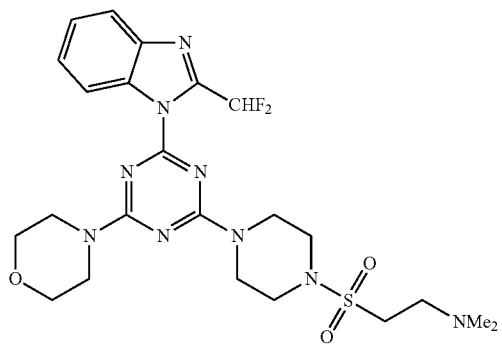 [SMILES: CN(C)CCS(=O)(=O)N1CCN(c2nc(N3CCOCC3)nc(-n3c(C(F)F)nc4ccccc43)n2)CC1]

A mixture of 11 g (50 mmol) of benzyl 1-piperazinecarboxylate and 16.1 g (125 mmol) of DIPEA in 200 mL CH$_2$Cl$_2$ was cooled to −15° C. and 6.3 mL (9.8 g, 60 mmol) of 2-chloroethanesulfonyl chloride was added slowly over 15 min. The mixture was allowed to warm to 0° C. over 30 min and water was then added. The organic layer was separated and washed successively with dil. HCl and aq. NaHCO$_3$. After drying, the solvent was removed and the residue was chromatographed on silica, eluting with CH$_2$Cl$_2$/EtOAc 95:5, to give an oil, which was recrystallized from CH$_2$Cl$_2$/hexanes to give 6.64 g (43% yield) of benzyl 4-(vinylsulfonyl)-1-piperazinecarboxylate: mp (CH$_2$Cl$_2$/hexanes) 85-87° C.; $^1$H NMR (CDCl$_3$) δ 7.39-7.30 (m, 5H), 6.40 (dd, J=16.6, 9.8 Hz, 1H), 6.25 (d, J=16.6 Hz, 1H), 6.06 (d, J=9.8 Hz, 1H), 5.14 (s, 2H), 3.61 (m, 4H), 3.14 (m, 4H); Anal. Calcd. for C$_{14}$H$_{18}$N$_2$O$_4$S: C, 54.2; H, 5.85; N, 9.0. Found: C, 54.1; H, 5.7; N, 9.1%.

A solution of the above vinylsulfonamide (3.10 g, 10 mmol) in 20 mL of THF was treated with an excess (10 mL, 80 mmol) of 40% aqueous dimethylamine. After 5 min, the mixture was diluted with water to give 3.09 g (87% yield) of benzyl 4-{[2-(dimethyl-amino)ethyl]sulfonyl}-1-piperazinecarboxylate as a white solid.: mp (aq. MeOH) 101-103° C.; $^1$H NMR (CDCl$_3$) δ 7.40-7.30 (m, 5H), 5.15 (s, 2H), 3.59 (m, 4H), 3.26 (m, 4H), 3.07 (dd J=8.1, 6.4 Hz, 2H), 2.74 (dd, J=8.0, 6.4 Hz, 2H), 2.25 (s, 6H); Anal. Calcd. for C$_{16}$H$_{25}$N$_3$O$_4$S: C, 54.1; H, 7.1; N, 11.8. Found: C, 53.8; H, 6.9; N, 11.8%.

Hydrogenation of the above carbamate in MeOH with 10% Pd on C gave a quantitative yield of N,N-dimethyl-2-(1-piperazinylsulfonyl)ethanamine, as an oil: $^1$H NMR (CDCl$_3$) δ 3.26 (m, 4H), 3.08 (m, 2H), 2.94 (m, 3.5H), 2.78 (m, 2H), 2.58 (m, 0.5H), 2.28 (s, 6H).

A mixture of the above amine (1.35 g, 6 mmol) and 1-[4-chloro-6-(4-morpholinyl)-1,3,5-triazin-2-yl]-2-(difluoromethyl)-1H-benzimidazole (International Publ. No. WO 2002/088112, the disclosure of which is incorporated herein by reference in its entirety) (1.83 g, 5 mmol) and Et$_3$N (1.4 mL, 10 mmol) in 50 mL THF was stirred at room temperature for 5 hrs and then diluted with water. The white solid was collected and dried. Chromatography on alumina, eluting with CH$_2$Cl$_2$ gave 1.42 g (43% yield) of N-[2-({4-[4-[2-(difluoromethyl)-1H-benzimidazol-1-yl]-6-(4-morpholinyl)-1,3,5-triazin-2-yl]-1-piperazinyl}sulfonyl)ethyl]-N,N-dimethylamine: $^1$H NMR (CDCl$_3$) δ 7.86 (br dd, J=7.1, 1.2 Hz, 1H), 7.89 (br dd, J=6.8, 1.2 Hz, 1H), 7.53 (t, J$_{HF}$=53.5 Hz, 1H), 7.46-7.38 (m, 2H), 4.00 (m, 4H), 3.89 (m, 4H), 3.79 (m, 4H), 3.40 (m, 4H), 3.21 (dd, J=8.1, 6.4 Hz, 2H), 2.78 (dd, J=8.1, 6.4 Hz, 2H), 2.27 (s, 6H).

Hydrochloride: mp (MeOH/EtOAc) 244-246° C.; Anal. Calcd. for C$_{23}$H$_{32}$ClF$_2$N$_9$O$_3$S: C, 47.0; H, 5.5; N, 21.4; Cl, 6.0. Found: C, 47.1; H, 5.5; N, 21.3; Cl, 6.3%.

Example 84

Synthesis of N-[2-({4-[4-[6-amino-2-(difluoromethyl)-4-methoxy-1H-benzimidazol-1-yl]-6-(4-morpholinyl)-1,3,5-triazin-2-yl]-1-piperazinyl}sulfonyl)ethyl]-N,N-dimethylamine

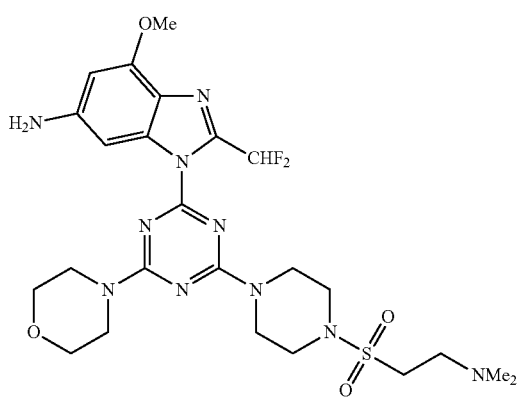 [SMILES: COc1cc(N)cc2c1nc(C(F)F)n2-c1nc(N2CCOCC2)nc(N2CCN(S(=O)(=O)CCN(C)C)CC2)n1]

A mixture of 293 mg (0.57 mmol) of tert-butyl 1-[4-chloro-6-(4-morpholinyl)-1,3,5-triazin-2-yl]-2-(difluoromethyl)-4-methoxy-1H-benzimidazol-6-yl-carbamate (Example 9), 152 mg (0.69 mmol) of N,N-dimethyl-2-(1-piperazinylsulfonyl)ethanamine (Example 83), and 87 mg (0.86 mmol) of Et$_3$N in 20 mL THF was stirred at room temperature for 2 hrs. The solvent was removed under vacuum. After dilution with water, the residue was extracted into CH$_2$Cl$_2$ and dried. Removal of the solvent gave a white solid which was recrystallized from methanol to give 0.27 g, (68% yield) of tert-butyl 2-(difluoromethyl)-1-[4-(4-{[2-(dimethylamino)ethyl]sulfonyl}-1-piperazinyl)-6-(4-morpholinyl)-1,3,5-triazin-2-yl]-4-methoxy-1H-benzimidazol-6-ylcarbamate: mp 200-202° C.; $^1$H NMR (CDCl$_3$) δ 8.63 (br s, 1H), 7.44 (t, J$_{HF}$=53.6 Hz, 1H), 6.62 (br s, 1H), 6.36 (d, J=1.6 Hz, 1H), 4.12-3.77 (m, 15H), 3.40 (m, 4H), 3.10 (dd, J=8.2, 6.4 Hz, 2H), 2.77 (dd, J=8.2, 6.4 Hz, 2H), (s, 6H), 1.52 (s, 9H); Anal. Calcd. for C$_{29}$H$_{42}$F$_2$N$_{10}$O$_6$S: C, 50.0; H, 6.1; N, 20.1. Found: C, 50.3; H, 6.15; N, 20.1%.

A solution of the above carbamate (0.244 g, 0.035 mmol) in a mixture of 10 mL CH$_2$Cl$_2$ and 5 mL TFA was stirred at room temperature for 2 hrs. The mixture was diluted with CH$_2$Cl$_2$ and then made basic with dil. aq. NH$_3$. The organic layer was dried and concentrated to give a quantitative yield of N-[2-({4-[4-[6-amino-2-(difluoromethyl)-4-methoxy-1H-benzimidazol-1-yl]-6-(4-morpholinyl)-1,3,5-triazin-2-yl]-1-piperazinyl}sulfonyl)ethyl]-N,N-dimethylamine: $^1$H NMR (CDCl$_3$) δ 7.35 (t, J$_{HF}$=53.8 Hz, 1H), 7.15 (d, J=1.9 Hz, 1H), 6.22 (d, J=1.9 Hz, 1H), 3.98 (m, 7H), 3.90-3.75 (m, 10H), 3.38 (m, 4H), 3.11 (dd, J=8.1, 6.5 Hz, 2H), 2.78 (dd, J=8.1, 6.4 Hz, 2H), 2.26 (s, 6H).

Dimethanesulfonate: mp (MeOH/EtOAc) 238° C. dec.; Anal. Calcd. for $C_{26}H_{42}F_2N_{10}O_{10}S_3 \cdot 1.5H_2O$: C, 38.3; H, 5.6; N, 17.2. Found: C, 38.1; H, 5.6; N, 17.1%.

Example 85

Synthesis of 2-(difluoromethyl)-4-methoxy-1-{4-[4-(methylsulfonyl)-1-piperazinyl]-6-tetrahydro-2H-pyran-4-yl-1,3,5-triazin-2-yl}-1H-benzimidazole

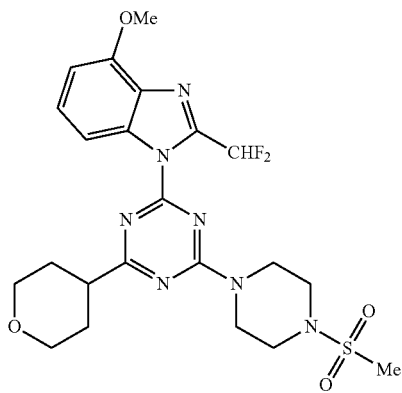 [SMILES: COc1cccc2c1nc(C(F)F)n2-c1nc(C2CCOCC2)nc(N2CCN(S(C)(=O)=O)CC2)n1]

A mixture of 2-(difluoromethyl)-4-methoxy-1H-benzimidazole (Example 2) (0.99 g, 5 mmol), tert-butyl 4-(4,6-dichloro-1,3,5-triazin-2-yl)piperazine-1-carboxylate (Lowik et al, *Eur. J. Org. Chem.*, 2001, 2825) (2.0 g, 6 mmol), and 3.5 g (25 mmol) powdered $K_2CO_3$ in 40 mL DMF was stirred at room temperature for 1 hr. Water was added, and the product was collected by filtration and washed with water and cold ethanol to give 2.14 g (86% yield) of tert-butyl 4-(4-chloro-6-(2-(difluoromethyl)-4-methoxy-1H-benzimidazol-1-yl)-1,3,5-triazin-2-yl)piperazine-1-carboxylate: mp ($CH_2Cl_2$/EtOH)>300° C.; $^1H$ NMR ($CDCl_3$) δ7.99 (d, J=8.3 Hz, 1H), 7.48 (t, $J_{HF}$=53.4 Hz, 1H), 7.41 (t, J=8.3 Hz, 1H), 6.87 (d, J=8.0 Hz, 1H), 4.06 (s, 3H), 3.95 (m, 4H), 3.58 (m, 4H), 1.50 (s, 9H); Anal. Calcd. for $C_{21}H_{24}ClF_2N_7O_3$: C, 50.9; H, 4.9; N, 19.8. Found: C, 51.1; H, 4.9; N, 19.95%.

A mixture of the above chloro compound (800 mg, 1.61 mmol), 4-(4,4,5,5-tetramethyl-1,3,2-dioxaborolan-2-yl)-3,6-dihydro-2H-pyran (400 mg, 1.90 mmol), $PdCl_2(dppf)$ (66 mg, 0.081 mmol), and $K_2CO_3$ (445 mg, 3.22 mmol) in 1,4-dioxane/$H_2O$ (60 mL/15 mL) was refluxed under nitrogen for 1 hr. The mixture was cooled to room temperature and diluted with water. The aqueous phase was extracted with $CH_2Cl_2$ (3×). The combined organic extracts were dried ($Na_2SO_4$) and the solvent was removed under vacuum. Chromatography on silica eluting with $CH_2Cl_2$/MeOH (100:0 to 98:2) gave tert-butyl 4-[4-[2-(difluoromethyl)-4-methoxy-1H-benzimidazol-1-yl]-6-(3,6-dihydro-2H-pyran-4-yl)-1,3,5-triazin-2-yl]-1-piperazinecarboxylate (371 mg, 42%): $^1H$ NMR ($CDCl_3$) δ 8.00 (d, J=8.1 Hz, 1H), 7.56 (t, $J_{HF}$=53.5 Hz, 1H), 7.44 (m, 1H), 7.39 (t, J=8.2 Hz, 1H), 6.85 (d, J=7.9 Hz, 1H), 4.44 (q, J=2.8 Hz, 2H), 4.06 (s, 3H), 4.01 (m, 2H), 3.94 (t, J=5.4 Hz, 4H), 3.58 (br s, 4H), 2.68 (m, 2H), 1.51 (s, 9H).

A mixture of the above dihydro compound (371 mg, 0.683 mmol) and 10% Pd/C in THF/MeOH (90 mL: 10 mL) was hydrogenated for 27 hrs. The reaction mixture was filtered through celite and the solvents were removed under vacuum. Chromatography on silica eluting with $CH_2Cl_2$/MeOH (100:0 to 99:1) followed by chromatography on silica eluting with $CH_2Cl_2$/MeOH (99.75:0.25 to 99.25:0.75) gave tert-butyl 4-{4-[2-(difluoromethyl)-4-methoxy-1H-benzimidazol-1-yl]-6-tetrahydro-2H-pyran-4-yl-1,3,5-triazin-2-yl}-1-piperazinecarboxylate (154 mg, 41%): mp ($CH_2Cl_2$/MeOH) 203-204° C.; $^1H$ NMR ($CDCl_3$) δ 8.03 (d, J=8.1 Hz, 1H), 7.59 (t, J=53.6 Hz, 1H), 7.39 (t, J=8.2 Hz, 1H), 6.85 (d, J=8.2 Hz, 1H), 4.11 (dt, J=11.4, 3.3 Hz, 2H), 4.06 (s, 3H), 3.99 (m, 2H), 3.92 (m, 2H), 3.59-3.53 (m, 6H), 2.93 (ddd, J=18.0, 8.9, 7.0 Hz, 1H), 1.99 (m, 4H), 1.50 (s, 9H).

Reaction of the above carbamate (144 mg, 0.264 mmol) with an excess of TFA (0.6 mL) in $CH_2Cl_2$ (3 mL) at room temperature for 30 minutes, followed by treatment with aq. $NH_3$ gave 2-(difluoromethyl)-4-methoxy-1-[4-(1-piperazinyl)-6-tetrahydro-2H-pyran-4-yl-1,3,5-triazin-2-yl]-1H-benzimidazole (113 mg, 96%): $^1H$ NMR ($CDCl_3$) δ 8.04 (dd, J=8.4, 0.6 Hz, 1H), 7.62 (t, $J_{HF}$=53.6 Hz, 1H), 7.38 (t, J=8.2 Hz, 1H), 6.84 (d, J=7.7 Hz, 1H), 4.10 (dt, J=11.4, 3.4 Hz, 2H), 4.05 (s, 3H), 3.98 (t, J=4.8 Hz, 2H), 3.92 (t, J=4.8 Hz, 2H), 3.56 (m, 2H), 2.98 (m, 4H), 2.91 (m, 1H), 1.99 (m, 4H).

Methanesulfonyl chloride (0.07 mL, 0.904 mmol) was added drop-wise to a mixture of the above amine (102 mg, 0.229 mmol) and powdered $K_2CO_3$ (253 mg, 1.83 mmol) in $CH_2Cl_2$ (5 mL) at 0° C. The reaction mixture was stirred at 0° C. for 5 min and allowed to warm to room temperature. After 5 hrs, additional $K_2CO_3$ (127 mg, 0.919 mmol) and methanesulfonyl chloride (0.04 mL, 0.517 mmol) were added and the mixture stirred at room temperature for another 16 hrs. Water was added and the layers were separated. The organic layer was dried ($Na_2SO_4$) and the solvent was removed under vacuum. Recrystallization from $CH_2Cl_2$/MeOH gave 2-(difluoromethyl)-4-methoxy-1-{4-[4-(methylsulfonyl)-1-piperazinyl]-6-tetrahydro-2H-pyran-4-yl-1,3,5-triazin-2-yl}-1H-benzimidazole (73 mg, 61%): mp ($CH_2Cl_2$/MeOH) 242-244° C.; $^1H$ NMR ($CDCl_3$) δ 8.00 (dd, J=8.4, 0.6 Hz, 1H), 7.55 (t, $J_{HF}$=53.5, 1H), 7.40 (t, J=7.9 Hz, 1H), 6.86 (d, J=7.7 Hz, 1H), 4.14-4.09 (m, 6H), 4.06 (s, 3H), 3.56 (m, 2H), 3.37 (br s, 4H), 2.96 (m, 1H), 2.83 (s, 3H), 1.99 (ddd, J=12.1, 7.9, 4.0, 4H); Anal. Calcd. for $C_{22}H_{27}F_2N_7O_4S$: C, 50.5; H, 5.2; N, 18.7. Found: C, 50.6; H, 5.4; N, 18.6%.

Example 86

Synthesis of 2-(difluoromethyl)-4-methoxy-1-(4-(4-morpholinyl)-6-{4-[(trifluoromethyl)-sulfonyl]-1-piperazinyl}-1,3,5-triazin-2-yl)-1H-benzimidazole

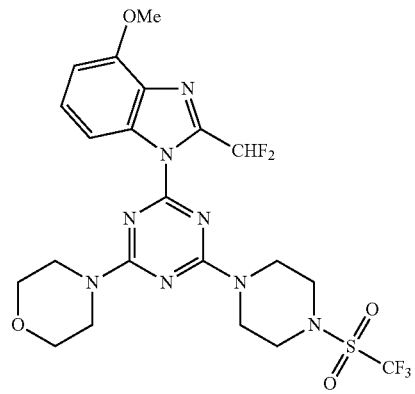 [SMILES: COc1cccc2c1nc(C(F)F)n2-c1nc(N2CCOCC2)nc(N2CCN(S(=O)(=O)C(F)(F)F)CC2)n1]

To a mixture of 223 mg (0.5 mmol) of 2-(difluoromethyl)-4-methoxy-1-[4-(4-morpholinyl)-6-(1-piperazinyl)-1,3,5-triazin-2-yl]-1H-benzimidazole (Example 2) and 126 mg (1.25 mmol) of $Et_3N$ in 10 mL $CH_2Cl_2$ at −78° C. was added 126 μL (211 mg, 0.75 mmol) of trifluoromethanesulfonic anhydride. The mixture was allowed to warm slowly to 0° C. After 30 min, water was added. The organic layer was separated, dried, and concentrated under vacuum. Recrystallization of the residue from CH$_2$Cl$_2$/MeOH gave 240 mg (83% yield) of 2-(difluoromethyl)-4-methoxy-1-(4-(4-morpholinyl)-6-{4-[(trifluoromethyl)-sulfonyl]-1-piperazinyl}-1,3,5-triazin-2-yl)-1H-benzimidazole: mp 272-273° C.; $^1$H NMR (CDCl$_3$) δ 7.84 (dd, J=8.4, 0.6 Hz, 1H), 7.40 (t, J$_{HF}$=53.5 Hz, 1H), 7.36 (t, J=8.2 Hz, 1H), 6.83 (d, J=7.7 Hz, 1H), 4.15-3.93 (m, 7H), 3.89 (m, 4H), 3.79 (m, 4H), 3.61 (m, 4H); $^{19}$F NMR (CDCl$_3$) δ −75.5 (s), −116.6 (d, J=0.11 Hz); Anal. Calcd. for C$_{21}$H$_{23}$F$_5$N$_8$O$_4$S: C, 43.6; H, 4.0; N, 19.4. Found: C, 44.1; H, 4.0; N, 19.7%.

Example 87

Synthesis of N-{1-[4-[2-(difluoromethyl)-4-methoxy-1H-benzimidazol-1-yl]-6-(4-morpholinyl)-1,3,5-triazin-2-yl]-4-piperidinyl}trifluoromethanesulfonamide

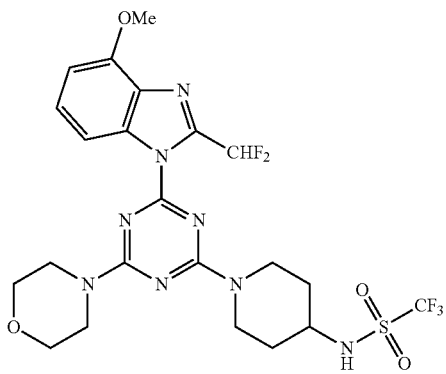 [SMILES: COc1cccc2c1nc(C(F)F)n2-c1nc(N2CCOCC2)nc(N2CCC(NS(=O)(=O)C(F)(F)F)CC2)n1]

To a mixture of 0.76 g (1.55 mmol) of 1-[4-[2-(difluoromethyl)-4-methoxy-1H-benzimidazol-1-yl]-6-(4-morpholinyl)-1,3,5-triazin-2-yl]-4-piperidinamine (Example 17) and 0.4 g (4.0 mmol) of Et$_3$N in 40 mL CH$_2$Cl$_2$ at −78° C. was added 0.42 mL (0.7 g, 2.5 mmol) of trifluoromethanesulfonic anhydride. The mixture was allowed to warm slowly to 0° C. After 30 min water was added. After acidification with dil. HCl, the organic layer was separated, dried, and concentrated under vacuum. Recrystallization of the residue from CH$_2$Cl$_2$/MeOH gave 0.87 g (89% yield of N-{1-[4-[2-(difluoromethyl)-4-methoxy-1H-benzimidazol-1-yl]-6-(4-morpholinyl)-1,3,5-triazin-2-yl]-4-piperidinyl}(trifluoro)methanesulfonamide: mp 282-285° C.; $^1$H NMR (DMSO-d$_6$) δ 9.51 (br s, 1H), 7.88 (d, J=8.1 Hz, 1H), 7.68 (t, J$_{HF}$=52.9 Hz, 1H), 7.41 (t, J=8.2 Hz, 1H), 6.95 (d, J=7.9 Hz, 1H), 4.57 (m, 2H), 3.98 (s, 3H), 3.80 (m, 4H), 3.69 (m, 5H), 3.22 (m, 2H), 1.95 (m, 2H), 1.51 (br dd, J=20.5, 10.1 Hz, 2H); $^{19}$F NMR (DMSO-d$_6$) δ −78.1 (s), −116.6 (dd, J=0.15, 0.03 Hz); Anal. Calcd. for C$_{22}$H$_{25}$F$_5$N$_8$O$_4$S: C, 44.6; H, 4.25; N, 18.9. Found: C, 44.5; H, 4.2; N, 19.2%.

Example 88

Synthesis of N-{1-[4-[2-(difluoromethyl)-4-methoxy-1H-benzimidazol-1-yl]-6-(4-morpholinyl)-1,3,5-triazin-2-yl]-3-azetidinyl}(trifluoro)methanesulfonamide

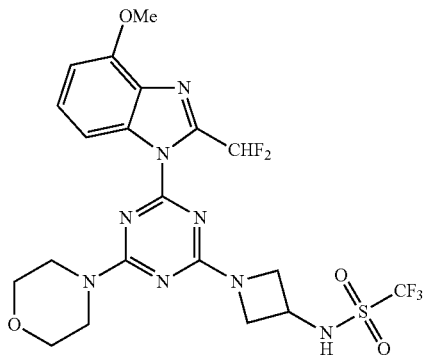 [SMILES: COc1cccc2c1nc(C(F)F)n2-c1nc(N2CCOCC2)nc(N2CC(NS(=O)(=O)C(F)(F)F)C2)n1]

To a suspension of 1-[4-[2-(difluoromethyl)-4-methoxy-1H-benzimidazol-1-yl]-6-(4-morpholinyl)-1,3,5-triazin-2-yl]-3-azetidinamine (Example 30) (303 mg, 0.7 mmol) and Et$_3$N (0.4 ml, 4 eq.) in CH$_2$Cl$_2$ (15 mL) at −78° C. was added trifluoromethanesulfonic anhydride (2 eq.) and the resulting mixture was stirred at −78° C. for 1 hr. The reaction mixture was quenched with MeOH and diluted with aqueous K$_2$CO$_3$ (10 mL) and stirred overnight at room temperature. After neutralization with dil. HCl, the MeOH was evaporated under vacuum and the resulting precipitate was filtered, washed with water and recrystallized from (CH$_2$Cl$_2$/MeOH) to give N-{1-[4-[2-(difluoromethyl)-4-methoxy-1H-benzimidazol-1-yl]-6-(4-morpholinyl)-1,3,5-triazin-2-yl]-3-azetidinyl}(trifluoro)methanesulfonamide (288 mg, 73%): mp (CH$_2$Cl$_2$/MeOH); $^1$H NMR (DMSO-d$_6$) δ 10.42 (br 1H), 7.97 (d, J=8.0 Hz, 1H), 7.73 (t, J$_{HF}$=53.0 Hz, 1H), 7.41 (t, J=8.2 Hz, 1H), 6.95 (d, J=7.9 Hz, 1H), 4.52-4.44 (m, 3H), 4.07-3.97 (m, 2H), 3.97 (s, 3H), 3.80-3.78 (m, 4H), 3.68 (m, 4H); Anal. Calcd. for C$_{20}$H$_{21}$F$_5$N$_8$O$_4$S: C, 42.6; H, 3.6; N, 19.9. Found: C, 42.6; H, 3.7; N, 20.0%.

Example 89

Synthesis of 4-[4-[2-(difluoromethyl)-4-methoxy-1H-benzimidazol-1-yl]-6-(4-morpholinyl)-1,3,5-triazin-2-yl]-N,N-dimethyl-1-piperazinesulfonamide

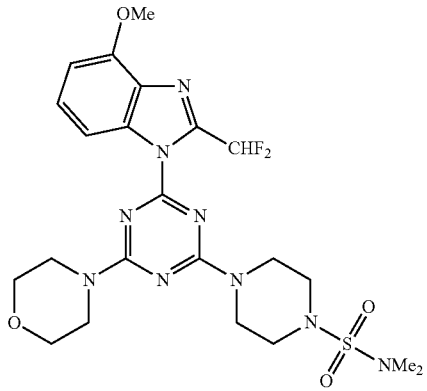 [SMILES: COc1cccc2c1nc(C(F)F)n2-c1nc(N2CCOCC2)nc(N2CCN(S(=O)(=O)N(C)C)CC2)n1]

A solution of 224 mg (0.5 mmol) of 2-(difluoromethyl)-4-methoxy-1-[4-(4-morpholinyl)-6-(1-piperazinyl)-1,3,5-triazin-2-yl]-1H-benzimidazole (Example 2) and 130 mg (1 mmol) of DIPEA in 10 mL of $CH_2Cl_2$ was treated with 150 mg (1 mmol) of dimethylsulfamoyl chloride and the mixture was stirred at room temperature overnight. Water was added, and the organic layer was separated and dried. Chromatography on silica, eluting with $CH_2Cl_2$/EtOAc (9:1), gave 217 mg (78% yield) of 4-[4-[2-(difluoromethyl)-4-methoxy-1H-benzimidazol-1-yl]-6-(4-morpholinyl)-1,3,5-triazin-2-yl]-N,N-dimethyl-1-piperazinesulfonamide: mp (MeOH) 286-288° C.; $^1$H NMR ($CDCl_3$) δ 7.86 (dd, J=8.4, 0.7 Hz, 1H), 7.44 (t, $J_{HF}$=53.5 Hz, 1H), 7.35 (t, J=8.2 Hz, 1H), 6.82 (d, J=7.7 Hz, 1H), 4.05 (s, 3H), 3.96 (m, 4H), 3.89 (m, 4H), 3.78 (m, 4H), 3.34 (m, 4H), 2.87 (s, 6H); Anal. Calcd. for $C_{22}H_{29}F_2N_9O_4S$: C, 47.7; H, 5.3; N, 22.8. Found: C, 47.95; H, 5.3; N, 22.9%.

Example 90

Synthesis of 1-[4-[2-(difluoromethyl)-4-methoxy-1H-benzimidazol-1-yl]-6-(4-morpholinyl)-1,3,5-triazin-2-yl]-N,N-dimethyl-4-piperidinesulfonamide

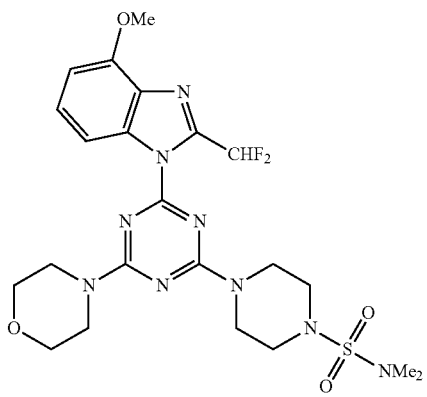 [SMILES: COc1cccc2c1nc(C(F)F)n2-c1nc(N2CCOCC2)nc(N2CCN(S(=O)(=O)N(C)C)CC2)n1]

A solution of 190 mg (0.6 mmol) of benzyl 4-(chlorosulfonyl)-1-piperidinecarboxylate in 10 mL THF was treated with a 10-fold excess of 40% aq. dimethylamine and the mixture was stirred at room temperature for 2 hrs. The THF was removed under vacuum. The residue was diluted with water, extracted with $CH_2Cl_2$, and dried. Chromatography on alumina, eluting with $CH_2Cl_2$, gave 175 mg (89% yield) of benzyl 4-[(dimethylamino)sulfonyl]-1-piperidinecarboxylate as an oil: $^1$H NMR ($CDCl_3$) δ 7.40-7.30 (m, 5H), 5.13 (s, 2H), 4.31 (m, 2H), 3.10 (tt, J=12.0, 3.7 Hz, 1H), 2.92 (s, 6H), 2.85-2.75 (m, 2H), 2.04 (br d, J=13.7 Hz, 2H), 1.76 (dq, J=12.6, 4.5 Hz, 2H).

The above carbamate was hydrogenated over 5% Pd on carbon in MeOH. After removal of the solvent, the residue was combined with 0.19 g (0.48 mmol) 1-[4-chloro-6-(4-morpholinyl)-1,3,5-triazin-2-yl]-2-(difluoromethyl)-4-methoxy-1H-benzimidazole (Example 2) and DIPEA in THF. The mixture was heated under reflux for 30 min and the solvent was removed. After dilution with water, the resulting solid was collected and dried. Chromatography on silica, eluting with $CH_2Cl_2$/EtOAc (93:7), gave 0.227 g (86% yield) of 1-[4-[2-(difluoromethyl)-4-methoxy-1H-benzimidazol-1-yl]-6-(4-morpholinyl)-1,3,5-triazin-2-yl]-N,N-dimethyl-4-piperidinesulfonamide: mp (MeOH) 260-264° C.; $^1$H NMR ($CDCl_3$) δ 7.88 (dd, J=8.4, 0.6 Hz, 1H), 7.46 (t, $J_{HF}$=53.5 Hz, 1H), 7.35 (t, J=7.7 Hz, 1H), 6.81 (d, J=7.7 Hz, 1H), 4.91 (br d, J=13.5 Hz, 2H), 4.05 (s, 3H), 3.88 (m, 4H), 3.78 (m, 4H), 3.27 (tt, J=11.8, 3.8 Hz, 1H), 2.95 (s, 6H), 2.17 (dd, J=12.7, 2.2 Hz, 2H), 1.85 (dq, J=12.6, 4.2 Hz, 2H); Anal. Calcd. for $C_{23}H_{30}F_2N_8O_4S$: C, 50.0; H, 5.5; N, 20.3. Found: C, 49.9; H, 5.5; N, 20.4%.

Example 91

Synthesis of 1-[4-[2-(difluoromethyl)-4-methoxy-1H-benzimidazol-1-yl]-6-(4-morpholinyl)-1,3,5-triazin-2-yl]-N-methyl-4-piperidinesulfonamide

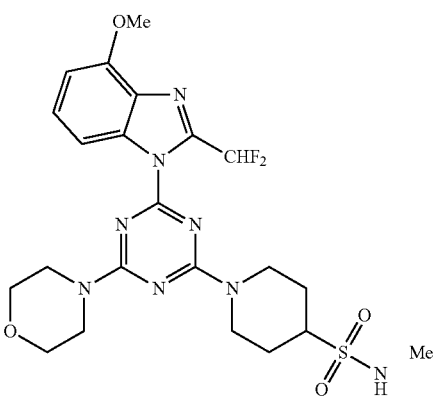 [SMILES: COc1cccc2c1nc(C(F)F)n2-c1nc(N2CCOCC2)nc(N2CCC(S(N)(=O)=O)CC2)n1 ; "Me"]

A solution of 190 mg (0.6 mmol) of benzyl 4-(chlorosulfonyl)-1-piperidinecarboxylate in 10 mL THF was treated with a 10-fold excess of 40% aq. methylamine and the mixture was stirred at room temperature for 2 hrs. The THF was removed under vacuum. After dilution with water, the resulting solid was collected and dried to give 260 mg (83% yield) of benzyl 4-[(methylamino)sulfonyl]-1-piperidinecarboxylate: mp (aq. MeOH) 124-126° C.; $^1$H NMR ($CDCl_3$) δ 7.40-7.30 (m, 5H), 5.13 (s, 2H), 4.34 (m, 2H), 4.01 (dd, J=10.2, 5.0 Hz, 1H), 3.05 (tt, J=11.9, 3.7 Hz, 1H), 2.87-2.77 (m, 5H), 2.11 (br d, J=12.9 Hz, 2H), 1.75 (dq, J=12.6, 4.5 Hz, 2H). Anal. Calcd. for $C_{14}H_{20}N_2O_4S$: C, 53.8; H, 6.45; N, 9.0. Found: C, 53.75; H, 6.5; N, 9.0%.

The above carbamate was hydrogenated over 5% Pd on carbon in MeOH. After removal of the solvent, the residue was combined with 0.19 g (0.48 mmol) 1-[4-chloro-6-(4-morpholinyl)-1,3,5-triazin-2-yl]-2-(difluoromethyl)-4-methoxy-1H-benzimidazole (Example 2) and DIPEA in THF. The mixture was heated under reflux for 30 min and the solvent was concentrated. After dilution with water, the resulting solid was collected and dried. Chromatography on alumina, eluting with $CH_2Cl_2$/EtOAc (9:1), gave 0.127 g (39% yield) of 1-[4-[2-(difluoromethyl)-4-methoxy-1H-benzimidazol-1-yl]-6-(4-morpholinyl)-1,3,5-triazin-2-yl]-N-methyl-4-piperidinesulfonamide: mp (MeOH) 261-263° C.; $^1$H NMR ($CDCl_3$) δ 7.87 (dd, J=8.4, 0.6 Hz, 1H), 7.46 (t, $J_{HF}$=53.6 Hz, 1H), 7.35 (t, J=8.0 Hz, 1H), 6.82 (d, J=7.7 Hz, 1H), 4.93 (br d, J=13.5 Hz, 2H), 4.05 (s, 3H), 4.02 (q, J=5.3 Hz, 1H), 3.88 (m, 4H), 3.78 (m, 4H), 3.22 (tt, J=11.8, 3.7 Hz, 1H), 3.00 (m, 2H), 2.86 (d, J=5.3 Hz, 3H), 2.24 (br d, J=12.0 Hz, 2H), 1.85 (dq, J=12.5, 4.4 Hz, 2H); Anal. Calcd. for $C_{22}H_{28}F_2N_8O_4S$: C, 49.1; H, 5.2; N, 20.8. Found: C, 49.2; H, 5.3; N, 21.0%.

Example 92

Synthesis of 1-[4-[2-(difluoromethyl)-4-methoxy-1H-benzimidazol-1-yl]-6-(4-morpholinyl)-1,3,5-triazin-2-yl]-N-[2-(dimethylamino)ethyl]-4-piperidinesulfonamide

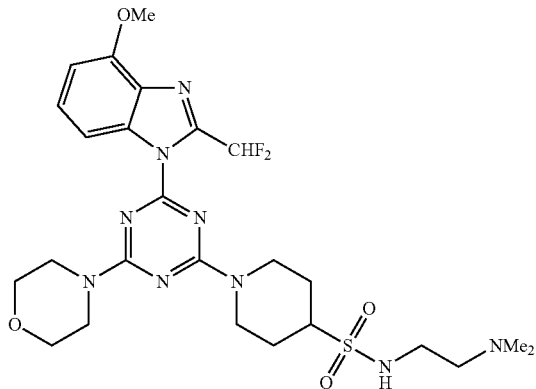 [SMILES: COc1cccc2c1nc(C(F)F)n2-c1nc(N2CCOCC2)nc(N2CCC(S(=O)(=O)NCCN(C)C)CC2)n1]

A solution of 430 mg (1.35 mmol) of benzyl 4-(chlorosulfonyl)-1-piperidinecarboxylate in 10 mL THF was treated with a 5-fold excess of N,N-dimethylethylenediamine and the mixture was stirred at room temperature for 2 hrs. The THF was removed under vacuum. After dilution with water, the product was extracted with $CH_2Cl_2$ and dried. Chromatography on alumina, eluting with EtOAc, gave 450 mg (90% yield) of benzyl 4-({[2-(dimethylamino)ethyl]amino}sulfonyl)-1-piperidinecarboxylate as an oil: $^1$H NMR ($CDCl_3$) δ 7.40-7.30 (m, 5H), 5.13 (s, 2H), 4.33 (m, exchangeable with $D_2O$, 1H), 3.16 (m, 2H), 3.04 (tt, J=11.9, 3.7 Hz, 1H), 2.81 (br t, J=11.9 Hz, 1H), 2.43 (m, 2H), 2.22 (s, 6H), 2.12 (br d, J=12.8 Hz, 2H), 1.74 (ddd, J=25.0, 12.6, 4.5 Hz, 2H).

The above carbamate was hydrogenated over 5% Pd on carbon in MeOH. After removal of the solvent, the residue was combined with 0.48 g (1.2 mmol) 1-[4-chloro-6-(4-morpholinyl)-1,3,5-triazin-2-yl]-2-(difluoromethyl)-4-methoxy-1H-benzimidazole (Example 2) and 0.35 g (2.7 mmol) DIPEA in THF. The mixture was heated under reflux for 1 hr and the solvent was concentrated. After dilution with water, the resulting solid was collected and dried. Chromatography on alumina, eluting with EtOAc, gave 1-[4-[2-(difluoromethyl)-4-methoxy-1H-benzimidazol-1-yl]-6-(4-morpholinyl)-1,3,5-triazin-2-yl]-N-[2-(dimethylamino)ethyl]-4-piperidinesulfonamide: mp (MeOH) 231-234° C.; $^1$H NMR ($CDCl_3$) δ 7.87 (dd, J=8.4, 0.6 Hz, 1H), 7.47 (t, $J_{HF}$=53.5 Hz, 1H), 7.35 (t, J=8.2 Hz, 1H), 6.81 (d, J=7.8 Hz, 1H), 4.91 (br d, J=13.3 Hz, 2H), 4.04 (s, 3H), 3.88 (m, 4H), 3.78 (m, 4H), 3.25-3.17 (m, 3H), 3.00 (m, 2H), 2.45 (br t, J=5.7 Hz, 2H), 2.27 (m, 2H), 2.23 (s, 6H), 1.83 (dq, J=12.5, 4.4 Hz, 2H); Anal. Calcd. for $C_{25}H_{35}F_2N_9O_4S$: C, 50.4; H, 5.9; N, 21.2. Found: C, 50.2; H, 5.7; N, 21.3%.

Example 93

Synthesis of 1-[4-[2-(difluoromethyl)-4-methoxy-1H-benzimidazol-1-yl]-6-(4-morpholinyl)-1,3,5-triazin-2-yl]-N-methyl-3-pyrrolidinesulfonamide

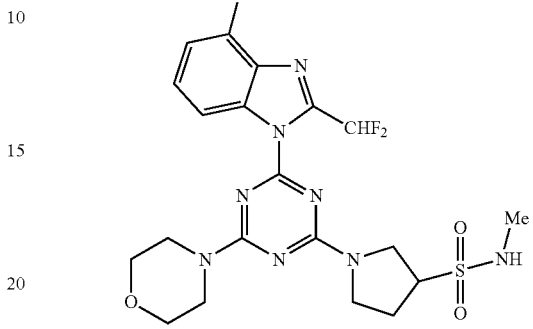

Methylamine (40 wt % in $H_2O$, 1 mL) was added to a solution of 3-chlorosulfonyl-pyrrolidine-1-carboxylic acid benzyl ester (256 mg, 0.843 mmol) in THF (1 mL) at 0° C. The mixture was stirred at 0° C. for 10 min, and then warmed to room temperature and stirred for 2 hrs. Water was added and the phases were separated. The aqueous phase was extracted with $CH_2Cl_2$ (2×), the combined organic extracts were dried ($Na_2SO_4$), and the solvent was removed under vacuum. Chromatography on neutral alumina, eluting with $CH_2Cl_2$/MeOH (99:1 to 95:5), gave benzyl 3-[(methylamino)sulfonyl]-1-pyrrolidinecarboxylate (173 mg, 69%): $^1$H NMR ($CDCl_3$) δ 7.36-7.29 (m, 5H), 5.14 (d, J=1.9 Hz, 2H), 4.27 (d, J=42.6 Hz, 1H), 3.80-3.70 (m, 4H), 3.50 (m, 1H), 2.82 (d, J=4.9 Hz, 3H), 2.35 (m, 2H).

A mixture of the above benzyl carbamate (173 mg, 0.580 mmol) and 10% Pd on carbon in MeOH (15 mL) was hydrogenated for 24 hrs. The reaction mixture was filtered through celite, the celite pad was washed with MeOH, and the solvent was removed under vacuum to give N-methyl-3-pyrrolidinesulfonamide (92 mg, 97%) which was used in the next step without further purification. $^1$H NMR (DMSO-$d_6$) δ 6.89 (br s, 1H), 3.62 (qd, J=8.9, 6.3 Hz, 1H), 2.99 (m, 2H), 2.82 (m, 1H), 2.72 (m, 1H), 2.59 (s, 3H), 1.95 (m, 2H).

DIPEA (0.15 mL, 0.861 mmol) was added to a stirred suspension of 1-[4-chloro-6-(4-morpholinyl)-1,3,5-triazin-2-yl]-2-(difluoromethyl)-4-methoxy-1H-benzimidazole (Example 2) (174 mg, 0.438 mmol) and the above amine (90 mg, 0.548 mmol) in THF (15 mL) at room temperature, and the mixture was stirred for 19 hrs. The solvent was removed under vacuum and the residue was partitioned between $H_2O$ and $CH_2Cl_2$. The aqueous phase was extracted with $CH_2Cl_2$ (2×), the combined organic extracts were dried ($Na_2SO_4$), and the solvent was removed under vacuum. Chromatography on silica, eluting with $CH_2Cl_2$/MeOH (100:0 to 98:2), gave 1-[4-[2-(difluoromethyl)-4-methoxy-1H-benzimidazol-1-yl]-6-(4-morpholinyl)-1,3,5-triazin-2-yl]-N-methyl-3-pyrrolidinesulfonamide (201 mg, 87%): mp ($CH_2Cl_2$/MeOH) 260-261° C.; $^1$H NMR (DMSO-$d_6$) δ 8.00 (dd, J=8.3, 3.2 Hz, 1H), 7.76 (t, $J_{HF}$=53.0 Hz, 1H), 7.41 (dt, J=8.3, 1.3 Hz, 1H), 7.25 (br s, 1H), 6.95 (dd, J=8.1, 1.4 Hz, 1H), 4.07 (m, 1H), 3.98 (s, 3H), 3.98-3.95 (m, 1H), 3.88 (d, J=6.5 Hz, 1H), 3.86-3.63 (m, 10H), 2.65 (s, 3H), 2.35 (m, 2H); Anal. Calcd. for $C_{21}H_{26}F_2N_8O_4S$: C, 48.1; H, 5.0; N, 21.4. Found: C, 48.4; H, 5.1; N, 21.1%.

Example 94

Synthesis of 1-[4-[2-(difluoromethyl)-4-methoxy-1H-benzimidazol-1-yl]-6-(4-morpholinyl)-1,3,5-triazin-2-yl]-N-[2-(dimethylamino)ethyl]-3-pyrrolidinesulfonamide

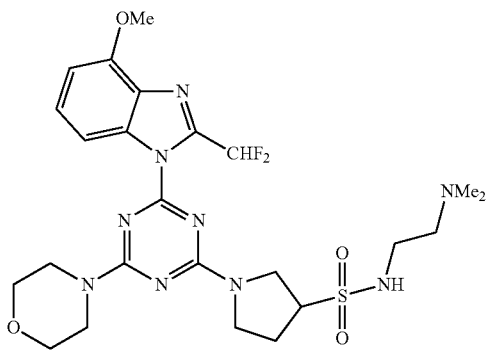 [SMILES: COc1cccc2c1nc(C(F)F)n2-c1nc(N2CCOCC2)nc(N2CCC(S(=O)(=O)NCCN(C)C)C2)n1]

A solution of 3-chlorosulfonyl-pyrrolidine-1-carboxylic acid benzyl ester (110 mg, 0.362 mmol) in $CH_2Cl_2$ (1.5 mL) was added to a solution of N,N-dimethylethylenediamine (0.20 mL, 1.83 mmol) in $CH_2Cl_2$ (1 mL) at 0° C. The mixture was stirred at 0° C. for 10 min, and then warmed to room temperature and stirred for 1 hr. Water was added and the phases were separated. The aqueous phase was extracted with $CH_2Cl_2$ (2×), the combined organic extracts were dried ($Na_2SO_4$), and the solvent was removed under vacuum to give benzyl 3-({[2-(dimethylamino)ethyl]amino}sulfonyl)-1-pyrrolidinecarboxylate (102 mg, 88%), which was used in the next step without further purification: $^1H$ NMR ($CDCl_3$) δ 7.36-7.29 (m, 5H), 5.14 (d, J=1.8 Hz, 2H), 3.80-3.72 (m, 4H), 3.50 (m, 1H), 3.16 (br s, 2H), 2.42 (t, J=5.7 Hz, 2H), 2.31 (m, 2H), 2.21 (s, 6H).

A mixture of the above benzyl carbamate (171 mg, 0.481 mmol) and 10% Pd on carbon in MeOH (15 mL) was hydrogenated for 29 hrs. The reaction mixture was filtered through celite, the celite pad was washed with MeOH, and the solvent was removed under vacuum to give N-[2-(dimethylamino)ethyl]-3-pyrrolidinesulfonamide (94 mg, 89%), which was used in the next step without further purification: $^1H$ NMR ($DMSO-d_6$) δ 6.93 (br s, 1H), 3.62 (m, 1H), 3.04-2.99 (m 4H), 2.83 (m, 1H), 2.72 (m, 1H), 2.31 (t, J=6.8 Hz, 2H), 2.14 (s, 6H), 1.92 (m, 2H).

DIPEA (0.11 mL, 0.632 mmol) was added to a stirred suspension of 1-[4-chloro-6-(4-morpholinyl)-1,3,5-triazin-2-yl]-2-(difluoromethyl)-4-methoxy-1H-benzimidazole (Example 2) (127 mg, 0.320 mmol) and the above amine (92 mg, 0.416 mmol) in THF (10 mL) at room temperature and the mixture stirred for 2.5 days. The solvent was removed under vacuum, and the residue was partitioned between $H_2O$ and $CH_2Cl_2$. The aqueous phase was extracted with $CH_2Cl_2$ (1×), the combined organic fractions were dried ($Na_2SO_4$), and the solvent was removed under vacuum. Recrystallization from $CH_2Cl_2$/hexanes, followed by chromatography on silica, eluting with $CH_2Cl_2$/MeOH (100:0 to 95:5), gave 1-[4-[2-(difluoromethyl)-4-methoxy-1H-benzimidazol-1-yl]-6-(4-morpholinyl)-1,3,5-triazin-2-yl]-N-[2-(dimethylamino)ethyl]-3-pyrrolidinesulfonamide (92 mg, 49%).

Treatment with methanesulfonic acid in $CH_2Cl_2$/MeOH and recrystallization from MeOH/EtOAc gave a methanesulfonate salt: mp 196-199° C.; $^1H$ NMR ($DMSO-d_6$) δ 9.34 (br s, 1H), 8.00 (dd, J=8.2, 5.4 Hz, 1H), 7.77 (m, 1H), 7.77 (t, $J_{HF}$=53.1 Hz, 1H), 7.41 (t, J=8.2 Hz, 1H), 6.96 (d, J=8.2 Hz, 1H), 4.16 (m, 1H), 3.40-3.95 (m, 1H), 3.98 (s, 3H), 3.91 (d, J=6.6 Hz, 1H), 3.87-3.66 (m, 10H), 3.38 (q, J=6.1 Hz, 2H), 3.19 (t, J=6.3 Hz, 2H), 2.82 (d, J=1.8 Hz, 6H), 2.39 (m, 2H), 2.31 (s, 3H); Anal. Calcd. for $C_{25}H_{37}F_2N_9O_7S_2 \cdot 0.6H_2O$: C, 43.6; H, 5.6; N, 18.3. Found: C, 43.4; H, 5.6; N, 18.3%.

Example 95

Synthesis of 2-(difluoromethyl)-4-methoxy-1-[4-{4-[(4-methyl-1-piperazinyl)sulfonyl]phenyl}-6-(4-morpholinyl)-1,3,5-triazin-2-yl]-1H-benzimidazole

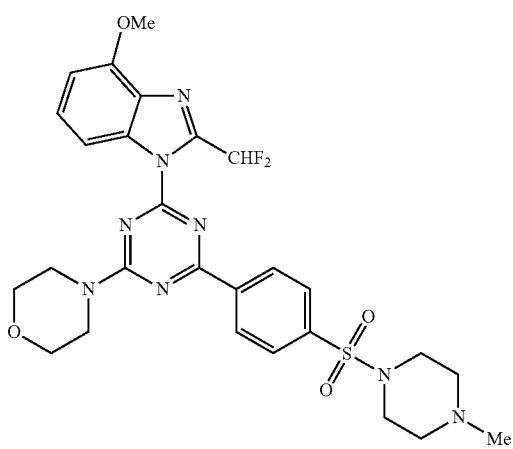 [SMILES: COc1cccc2c1nc(C(F)F)n2-c1nc(-c2ccc(S(=O)(=O)N3CCN(C)CC3)cc2)nc(N2CCOCC2)n1]

A mixture of 1-[4-chloro-6-(4-morpholinyl)-1,3,5-triazin-2-yl]-2-(difluoromethyl)-4-methoxy-1H-benzimidazole (Example 2) (200 mg, 0.504 mmol), 4-[(4-methyl-1-piperazinyl)sulfonyl]phenylboronic acid (186 mg, 0.655 mmol), $PdCl_2$ (dppf) (29 mg, 0.0355 mmol), and aq. $K_2CO_3$ (2M, 3 mL) in 1,4-dioxane (20 mL) was refluxed under nitrogen for 1 hr. The mixture was cooled to room temperature and diluted with $H_2O$, and the aqueous phase extracted with $CH_2Cl_2$ (9×). The combined organic extracts were dried ($Na_2SO_4$), and the solvent was removed under vacuum. Chromatography on alumina, eluting with $CH_2Cl_2$/MeOH (100:0 to 99.75:0.25), followed by chromatography on silica, eluting with $CH_2Cl_2$/MeOH (100:0 to 98:2), and recrystallization from $CH_2Cl_2$/MeOH/hexanes gave 2-(difluoromethyl)-4-methoxy-1-[4-{4-[(4-methyl-1-piperazinyl)sulfonyl]phenyl}-6-(4-morpholinyl)-1,3,5-triazin-2-yl]-1H-benzimidazole (93 mg, 31%).

Treatment with methanesulfonic acid in $CH_2Cl_2$/MeOH and recrystallization from MeOH/EtOAc gave a methanesulfonate salt: mp 289-292° C.; $^1H$ NMR ($DMSO-d_6$) δ 9.36 (br s, 1H), 8.71 (d, J=8.6 Hz, 2H), 8.08 (d, J=8.0 Hz, 1H), 8.03 (d, J=8.6 Hz, 2H), 7.83 (t, $J_{HF}$=52.7 Hz, 1H), 7.50 (t, J=8.2 Hz, 1H), 7.03 (d, J=8.0 Hz, 1H), 4.09 (m 2H), 4.00 (s, 3H), 3.96 (m, 2H), 3.81-3.79 (m, 6H), 3.47 (br s, 2H), 3.19 (br s, 2H), 2.79 (br s, 3H), 2.65 (br s, 2H), 2.29 (s, 3H); Anal. Calcd. for $C_{28}H_{34}F_2N_8O_7S_2$: C, 48.3; H, 4.9; N, 16.1. Found: C, 48.1; H, 5.1; N, 15.9%.

Example 96

Synthesis of 2-[2-(difluoromethyl)-4-methoxy-1H-benzimidazol-1-yl]-9-[1-(methylsulfonyl)-4-piperidinyl]-6-(4-morpholinyl)-7,9-dihydro-8H-purin-8-one

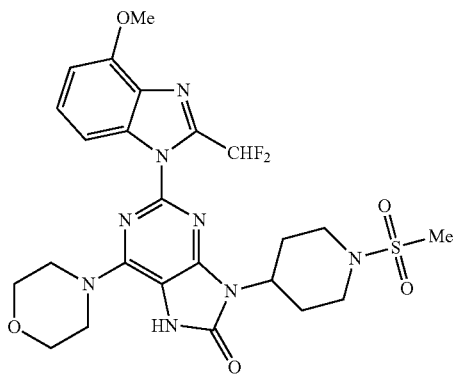 [SMILES: COc1cccc2c1nc(C(F)F)n2-c1nc(N2CCOCC2)c2[nH]c(=O)n(C3CCN(S(C)(=O)=O)CC3)c2n1]

Powdered $K_2CO_3$ (1.305 g, 9.44 mmol) was added to a stirred suspension of tert-butyl 4-{[2-chloro-6-(4-morpholinyl)-5-nitro-4-pyrimidinyl]amino}-1-piperidinecarboxylate (U.S. Pat. Appl. Publ. No. 2009/0181963, the disclosure of which is incorporated herein by reference in its entirety) (1.047 g, 2.36 mmol) and 2-difluoromethyl-4-methoxy-1H-benzimidazole (Example 2) (608 mg, 3.07 mmol) in DMF (70 mL) at room temperature, and the mixture was stirred for 2.5 days. The reaction mixture was diluted with water, and the resulting precipitate was collected by filtration and dried. Recrystallization from $CH_2Cl_2$/MeOH gave tert-butyl 4-{[2-[2-(difluoromethyl)-4-methoxy-1H-benzimidazol-1-yl]-6-(4-morpholinyl)-5-nitro-4-pyrimidinyl]amino}-1-piperidinecarboxylate (1.27 g, 89%): mp 229-231° C.; $^1$H NMR ($CDCl_3$) δ 8.64 (d, J=7.7 Hz, 1H), 7.81 (dd, J=8.4, 0.6 Hz, 1H), 7.36 (t, $J_{HF}$=53.5 Hz, 1H), 7.36 (t, J=8.2 Hz, 1H), 6.84 (d, J=7.7 Hz, 1H), 4.36 (m, 1H), 4.11 (m, 2H), 4.06 (s, 3H), 3.85 (t, J=4.9 Hz, 4H), 3.65 (t, J=4.6 Hz, 4H), 3.01 (t, J=11.5 Hz, 2H), 2.08 (m, 2H), 1.64-1.51 (m, 2H), 1.48 (s, 9H); Anal. Calcd. for $C_{27}H_{34}F_2N_8O_6$: C, 53.6; H, 5.7; N, 18.5. Found: C, 53.35; H, 5.7; N, 18.8%.

A mixture of the above nitro compound (700 mg, 1.16 mmol) and 10% Pd on carbon in MeOH/THF (70 mL: 15 mL) was hydrogenated for 5 hrs. The reaction mixture was filtered through celite, the celite pad was washed with MeOH and $CH_2Cl_2$, and the solvents were removed under vacuum. Recrystallization from $CH_2Cl_2$/MeOH gave tert-butyl 4-{[5-amino-2-[2-(difluoromethyl)-4-methoxy-1H-benzimidazol-1-yl]-6-(4-morpholinyl)-4-pyrimidinyl]amino}-1-piperidinecarboxylate (622 mg, 94%): mp 223-225° C.; $^1$H NMR ($CDCl_3$) δ 7.92 (dd, J=8.4, 0.6 Hz, 1H), 7.54 (t, $J_{HF}$=53.7 Hz, 1H), 7.32 (t, J=8.2 Hz, 1H), 6.79 (d, J=7.6 Hz, 1H), 4.68 (d, J=7.6 Hz, 1H), 4.23-4.10 (m, 3H), 4.05 (s, 3H), 3.89 (m, 4H), 3.25 (m, 4H), 3.06 (br s, 2H), 2.96 (t, J=12.0 Hz, 2H), 2.11 (m, 2H), 1.47 (s, 9H), 1.50-1.40 (m, 2H); Anal. Calcd. for $C_{27}H_{36}F_2N_8O_4$: C, 56.4. H, 6.3; N, 19.5. Found: C, 56.3; H, 6.4; N, 19.7%.

1,1'-Carbonyldiimidazole (689 mg, 4.25 mmol) was added to a solution of the above amine (244 mg, 0.425 mmol) in 1,4-dioxane (25 mL) and the mixture was refluxed under nitrogen for 4.5 hrs. Additional 1,1'-carbonyldiimidazole (689 mg, 4.25 mmol) was added, and the mixture refluxed for additional 17.5 hrs. The mixture was cooled to room temperature and diluted with water. The resulting precipitate was collected by filtration, washed with $H_2O$, and dried. Chromatography on silica, eluting with $CH_2Cl_2$/MeOH (100:0 to 97:3), gave tert-butyl 4-[2-[2-(difluoromethyl)-4-methoxy-1H-benzimidazol-1-yl]-6-(4-morpholinyl)-8-oxo-7,8-dihydro-9H-purin-9-yl]-1-piperidinecarboxylate (176 mg, 69%): mp ($CH_2Cl_2$/i-$Pr_2O$) 269-272° C.; $^1$H NMR ($CDCl_3$) δ 10.94 (br s, 1H), 7.73 (dd, J=8.3, 0.3 Hz, 1H), 7.36 (t, J=8.2 Hz, 1H), 7.36 (t, $J_{HF}$=53.6 Hz, 1H), 6.81 (d, J=7.8 Hz, 1H), 4.49 (tt, J=12.1, 4.1 Hz, 1H), 4.38 (br s, 2H), 4.06 (s, 3H), 3.89 (dd, J=5.6, 3.6 Hz, 4H), 3.82 (dd, J=5.6, 3.7 Hz, 4H), 2.85 (m, 2H), 2.56 (m, 2H), 1.83 (d, J=11.0 Hz, 2H), 1.48 (s, 9H); Anal. Calcd. for $C_{28}H_{34}F_2N_8O_5$.0.1 i-$Pr_2O$: C, 56.2; H, 5.8; N, 18.3. Found: C, 56.2; H, 5.90; N, 18.0%.

Reaction of the above carbamate (150 mg, 0.250 mmol) with an excess of TFA (4 mL) in $CH_2Cl_2$ (40 mL) at room temperature for 2 hrs, followed by treatment with aq. $NH_3$ gave 2-[2-(difluoromethyl)-4-methoxy-1H-benzimidazol-1-yl]-6-(4-morpholinyl)-9-(4-piperidinyl)-7,9-dihydro-8H-purin-8-one (96 mg, 77%), which was used in the next step without further purification.

Powdered $K_2CO_3$ (217 mg, 1.57 mmol) was added to a sonicated suspension of the above amine (87 mg, 0.174 mmol) in $CH_2Cl_2$ (50 mL). The mixture was cooled to 0° C. and methanesulfonyl chloride (0.06 mL, 0.775 mmol) added dropwise. The reaction mixture was allowed to warm to room temperature and stirred for 5 hrs. Water was added, the phases were separated, and the aqueous phase was extracted with $CH_2Cl_2$ (1×). MeOH was added to the combined organic extracts to dissolve the precipitate, the solution was dried ($Na_2SO_4$), and the solvents were removed. Recrystallization from $CH_2Cl_2$/MeOH gave 2-[2-(difluoromethyl)-4-methoxy-1H-benzimidazol-1-yl]-9-[1-(methylsulfonyl)-4-piperidinyl]-6-(4-morpholinyl)-7,9-dihydro-8H-purin-8-one (48 mg, 48%): mp 268-271° C.; $^1$H NMR ($CDCl_3$) δ 11.08 (br s, 1H), 7.76 (dd, J=8.4, 0.3 Hz, 1H), 7.40 (t, J=8.2 Hz, 1H), 7.37 (t, $J_{HF}$=53.6 Hz, 1H), 6.83 (d, J=7.9 Hz, 1H), 4.50 (tt, J=11.8, 4.1 Hz, 1H), 4.08-4.05 (m, 2H), 4.06 (s, 3H), 3.92 (m, 4H), 3.84 (m, 4H), 2.92-2.87 (m, 2H), 2.88 (s, 3H), 2.79 (ddd, J=16.5, 12.3, 3.8 Hz, 2H), 1.96 (dd, J=11.7, 2.4 Hz, 2H); Anal. Calcd. for $C_{24}H_{28}F_2N_8O_5S$.0.48$H_2O$: C, 49.1; H, 5.0; N, 19.1. Found: C, 49.1; H, 4.9; N, 19.0%.

Example 97

Synthesis of 2-[2-(difluoromethyl)-4-methoxy-1H-benzimidazol-1-yl]-9-[1-(methylsulfonyl)-4-piperidinyl]-6-(4-morpholinyl)-9H-purine

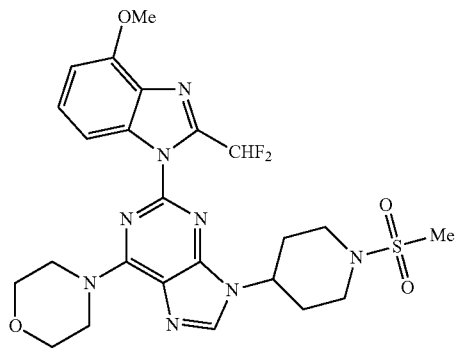 [SMILES: COc1cccc2c1nc(C(F)F)n2-c1nc(N2CCOCC2)c2ncn(C3CCN(S(C)(=O)=O)CC3)c2n1]

A mixture of tert-butyl 4-{[5-amino-2-[2-(difluoromethyl)-4-methoxy-1H-benzimidazol-1-yl]-6-(4-morpholinyl)-4-pyrimidinyl]amino}-1-piperidinecarboxylate (Example 96) (250 mg, 0.435 mmol), trimethylorthoformate (5 mL), and p-TSOH.$H_2O$ (8.3 mg, 0.0436 mmol) was heated at 95-100° C. for 3 hrs. The mixture was cooled to room temperature and the solvent was removed under vacuum. Chromatography on silica, eluting with $CH_2Cl_2$/MeOH (100:0 to 99:1), gave tert-butyl 4-[2-[2-(difluoromethyl)-4-methoxy-1H-benzimidazol-1-yl]-6-(4-morpholinyl)-9H-purin-9-yl]-1-piperidinecarboxylate (193 mg, 76%): mp ($CH_2Cl_2$/

MeOH) 213-215° C.; $^1$H NMR (CDCl$_3$) δ 7.82 (s, 1H), 7.79 (d, J=8.3 Hz, 1H), 7.44 (t, J$_{HF}$=53.6 Hz, 1H), 7.35 (t, J=8.2 Hz, 1H), 6.81 (d, J=7.9 Hz, 1H), 4.57 (tt, J=12.0, 4.0 Hz, 1H), 4.38 (m, 6H), 4.06 (s, 3H), 3.88 (t, J=4.9 Hz, 4H), 2.95 (t, J=12.6 Hz, 2H), 2.19 (dd, J=12.1, 2.0 Hz, 2H), 2.05 (dq, J=12.3, 4.2 Hz, 2H), 1.49 (s, 9H); Anal. Calcd. for C$_{28}$H$_{34}$F$_2$N$_8$O$_4$: C, 57.5; H, 5.9; N, 19.2. Found: C, 57.3; H, 5.8; N, 19.1%.

Reaction of the above carbamate (165 mg, 0.282 mmol) with an excess of TFA (2 mL) in CH$_2$Cl$_2$ (10 mL) at room temperature for 1.5 hrs, followed by treatment with aq. NH$_3$ gave 2-[2-(difluoromethyl)-4-methoxy-1H-benzimidazol-1-yl]-6-(4-morpholinyl)-9-(4-piperidinyl)-9H-purine (121 mg, 88%), which was used in the next step without further purification: $^1$H NMR (CDCl$_3$) δ 7.87 (s, 1H), 7.81 (dd, J=8.4, 0.5 Hz, 1H), 7.48 (t, J=53.6 Hz, 1H), 7.35 (t, J=8.2 Hz, 1H), 6.81 (d, J=7.8 Hz, 1H), 4.54 (tt, J=12.0, 4.1 Hz, 1H), 4.38 (br s, 4H), 4.07 (s, 3H), 3.88 (t, J=4.8 Hz, 4H), 3.30 (d, J=12.4 Hz, 2H), 2.86 (dt, J=12.4, 2.3 Hz, 2H), 2.20 (dd, J=11.8, 2.2 Hz, 2H), 2.04 (dq, J=12.3, 4.1 Hz, 2H).

Methanesulfonyl chloride (0.08 mL, 1.03 mmol) was added dropwise to a mixture of the above amine (102 mg, 0.211 mmol) and powdered K$_2$CO$_3$ (263 mg, 1.90 mmol) in CH$_2$Cl$_2$ (10 mL) at 0° C. The mixture was allowed to warm to room temperature and was stirred for 5 hrs. Water was added, the phases were separated, and the aqueous phase was extracted with CH$_2$Cl$_2$. The combined organic extracts were dried (Na$_2$SO$_4$) and the solvent was removed under vacuum. Recrystallization from CH$_2$Cl$_2$/MeOH gave 2-[2-(difluoromethyl)-4-methoxy-1H-benzimidazol-1-yl]-9-[1-(methylsulfonyl)-4-piperidinyl]-6-(4-morpholinyl)-9H-purine (105 mg, 88%): mp 236-239° C.; $^1$H NMR (CDCl$_3$) δ 7.84 (s, 1H), 7.76 (dd, J=8.4, 0.5 Hz, 1H), 7.42 (t, J$_{HF}$=53.6 Hz, 1H), 7.36 (t, J=8.2 Hz, 1H), 6.81 (d, J=7.8 Hz, 1H), 4.57 (tt, J=11.7, 4.4 Hz, 1H), 4.38 (br s, 4H), 4.09 (m, 2H), 4.06 (s, 3H), 3.88 (t, J=4.8 Hz, 4H), 2.96 (dt, J=12.5, 2.8 Hz, 2H), 2.88 (s, 3H), 2.35-2.20 (m, 4H); Anal. Calcd. for C$_{24}$H$_{28}$F$_2$N$_8$O$_4$S: C, 51.2; H, 5.0; N, 19.9. Found: C, 51.0; H, 4.9; N, 19.7%.

Example 98

Synthesis of 5-[2-(difluoromethyl)-4-methoxy-1H-benzimidazol-1-yl]-3-[1-(methylsulfonyl)-4-piperidinyl]-7-(4-morpholinyl)-3H-[1,2,3]triazolo[4,5-d]pyrimidine

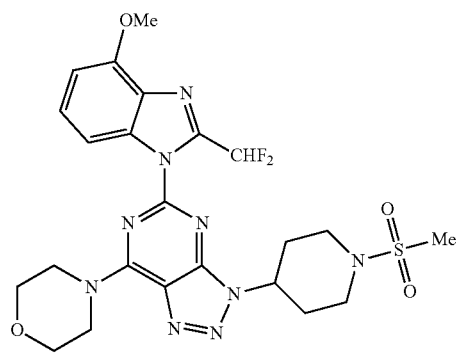 [SMILES: COc1cccc2c1nc(C(F)F)n2-c1nc(N2CCOCC2)c2nnn(C3CCN(S(C)(=O)=O)CC3)c2n1]

Aqueous NaNO$_2$ solution (0.5 M, 1.7 mL) was added dropwise to a stirred suspension of tert-butyl 4-{[5-amino-2-[2-(difluoromethyl)-4-methoxy-1H-benzimidazol-1-yl]-6-(4-morpholinyl)-4-pyrimidinyl]amino}-1-piperidinecarboxylate (Example 96) (250 mg, 0.435 mmol) in HOAc/H$_2$O (2:1, 12 mL) at 0° C. The reaction mixture was stirred at 0° C. for 1.5 hrs and then diluted with H$_2$O. The resulting precipitate was collected by filtration, washed sequentially with H$_2$O and aqueous NH$_3$, and dried to give tert-butyl 4-[5-[2-(difluoromethyl)-4-methoxy-1H-benzimidazol-1-yl]-7-(4-morpholinyl)-3H-[1,2,3]triazolo[4,5-d]pyrimidin-3-yl]-1-piperidinecarboxylate (192 mg, 75%): mp (CH$_2$Cl$_2$/hexanes) 220-222° C.; $^1$H NMR (CDCl$_3$) δ 7.81 (dd, J=8.4, 0.6 Hz, 1H), 7.42 (t, J$_{HF}$=53.6 Hz, 1H), 7.38 (t, J=8.2 Hz, 1H), 6.83 (d, J=7.71 Hz, 1H), 4.92 (tt, J=11.3, 4.1 Hz, 1H), 4.79 (br s, 2H), 4.33 (m, 2H), 4.15 (br s, 2H), 3.92 (dd, J=13.4, 3.0 Hz, 4H), 3.05 (t, J=12.0 Hz, 2H), 2.40 (dq, J=12.0, 4.4 Hz, 2H), 2.18 (dd, J=12.9, 2.5 Hz, 2H), 1.50 (s, 9H); Anal. Calcd. for C$_{27}$H$_{33}$F$_2$N$_9$O$_4$: C, 55.4; H, 5.7; N, 21.5. Found: C, 55.5; H, 5.7; N, 21.3%.

Reaction of the above carbamate (158 mg, 0.270 mmol) with an excess of TFA (2 mL) in CH$_2$Cl$_2$ (10 mL) at room temperature for 2 hrs, followed by treatment with aq. NH$_3$ gave 5-[2-(difluoromethyl)-4-methoxy-1H-benzimidazol-1-yl]-7-(4-morpholinyl)-3-(4-piperidinyl)-3H-[1,2,3]triazolo[4,5-d]pyrimidine (112 mg, 85%), which was used in the next step without further purification: $^1$H NMR (CDCl$_3$) δ 7.83 (dd, J=8.4, 0.4 Hz, 1H), 7.46 (t, J$_{HF}$=53.6 Hz, 1H), 7.38 (t, J=8.2 Hz, 1H), 6.83 (d, J=7.9 Hz, 1H), 4.87 (tt, J=11.7, 4.2 Hz, 1H), 4.80 (br s, 2H), 4.15 (br s, 2H), 4.07 (s, 3H), 3.92 (d, J=15.0 Hz, 4H), 3.34 (m, 2H), 2.88 (dt, J=12.7, 2.5 Hz, 2H), 2.38 (dq, J=12.0, 4.2 Hz, 2H), 2.18 (m, 2H).

Methanesulfonyl chloride (0.09 mL, 1.16 mmol) was added dropwise to a mixture of the above amine (107 mg, 0.220 mmol) and powdered K$_2$CO$_3$ (274 mg, 1.98 mmol) in CH$_2$Cl$_2$ (10 mL) at 0° C. The mixture was allowed to warm to room temperature and was stirred for 16.5 hrs. Water was added, the phases were separated, and the aqueous phase was extracted with CH$_2$Cl$_2$ (1×). The combined organic extracts were dried (Na$_2$SO$_4$) and the solvent removed under vacuum. Recrystallization from CH$_2$Cl$_2$/MeOH gave 5-[2-(difluoromethyl)-4-methoxy-1H-benzimidazol-1-yl]-3-[1-(methylsulfonyl)-4-piperidinyl]-7-(4-morpholinyl)-3H-[1,2,3]triazolo[4,5-d]pyrimidine (108 mg, 87%): mp 258-259° C.; $^1$H NMR (CDCl$_3$) δ 7.81 (dd, J=8.4, 0.5 Hz, 1H), 7.41 (t, J$_{HF}$=53.5 Hz, 1H), 7.39 (t, J=8.2 Hz, 1H), 6.84 (d, J=7.7 Hz, 1H), 4.93 (tt, J=10.5, 4.2 Hz, 1H), 4.79 (br s, 2H), 4.16 (br s, 2H), 4.07 (s, 3H), 4.01-3.90 (m, 6H), 3.14 (m, 2H), 2.89 (s, 3H), 2.60 (m, 2H), 2.35 (m, 2H); Anal. Calcd. for C$_{23}$H$_{27}$F$_2$N$_9$O$_4$S: C, 49.0; H, 4.8; N, 22.4. Found: C, 48.9; H, 4.8; N, 22.2%.

Example 99

Synthesis of N-[2-({4-[6-[2-(difluoromethyl)-4-methoxy-1H-benzimidazol-1-yl]-4-(4-morpholinyl)-1H-pyrazolo[3,4-d]pyrimidin-1-yl]-1-piperidinyl}sulfonyl)ethyl]-N,N-dimethylamine

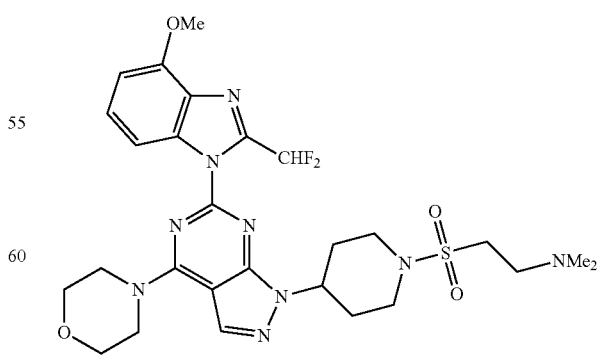

A mixture of 0.41 g (0.84 mmol) of 6-[2-(difluoromethyl)-4-methoxy-1H-benzimidazol-1-yl]-4-(4-morpholinyl)-1-(4-piperidinyl)-1H-pyrazolo[3,4-d]pyrimidine (Example 8) and 0.27 g (2 mmol) DIPEA in CH$_2$Cl$_2$ was cooled to −15° C., and 200 mg (1.2 mmol) of 2-chloroethanesulfonyl chloride was added. The mixture was allowed to warm to 0° C. over 1 hr, and water was added. The organic layer was dried and concentrated. Chromatography on silica, eluting with CH$_2$Cl$_2$/EtOAc (1:1), gave 216 mg (45% yield) of 6-[2-(difluoromethyl)-4-methoxy-1H-benzimidazol-1-yl]-4-(4-morpholinyl)-1-[1-(vinylsulfonyl)-4-piperidinyl]-1H-pyrazolo[3,4-d]pyrimidine: mp (CH$_2$Cl$_2$-MeOH) 243-246° C.; $^1$H NMR (CDCl$_3$) δ 8.00 (s, 1H), 7.81 (dd, J=8.4, 0.7 Hz, 1H), 7.44 (t, J$_{HF}$=53.5 Hz, 1H), 7.37 (t, J=8.2 Hz, 1H), 6.82 (d, J=7.7 Hz, 1H), 6.51 (dd, J=16.6, 9.9 Hz, 1H), 6.29 (d, J=16.6 Hz, 1H), 6.07 (d, J=9.9 Hz, 1H), 4.81 (tt, J=11.2, 4.1 Hz, 1H), 4.07 (s, 3H), 4.06 (m, 4H), 3.96 (m, 1H), 3.91 (m, 4H), 3.88 (m, 1H), 2.95 (dt J=12.4, 2.6 Hz, 2H), 2.43 (ddd, J=24.5, 11.8, 4.2 Hz, 2H), 2.14 (dd, J=11.8, 4.2 Hz, 2H); Anal. Calcd. for C$_{25}$H$_{28}$F$_2$N$_8$O$_4$S: C, 52.3; H, 4.9; N, 19.5. Found: C, 52.3; H, 4.7; N, 19.8%.

A suspension of the above vinylsulfonamide (140 mg, 0.243 mmol) in 100 mL THF was treated with 10 mL of 40% aq. dimethylamine to give a clear solution. After 10 min, the mixture was diluted with water and the THF was removed under vacuum to give 140 mg (93% yield) of N-[2-({4-[6-[2-(difluoromethyl)-4-methoxy-1H-benzimidazol-1-yl]-4-(4-morpholinyl)-1H-pyrazolo[3,4-d]pyrimidin-1-yl]-1-piperidinyl}sulfonyl)ethyl]-N,N-dimethylamine as a white solid: $^1$H NMR (CDCl$_3$) δ 7.99 (s, 1H), 7.82 (dd, J=8.4, 0.6 Hz, 1H), 7.45 (t, J$_{HF}$=53.6 Hz, 1H), 7.37 (t, J=8.2 Hz, 1H), 6.83 (d, J=7.8 Hz, 1H), 4.85 (tt, J=11.1, 4.1 Hz, 1H), 4.07 (s, 3H), 4.06 (m, 4H), 4.02 (m, 1H), 3.98 (m, 1H), 3.91 (m, 4H), 3.18-3.07 (m, 4H), 2.80 (dd, J=8.3, 6.4 Hz, 2H), 2.41 (dq, J=11.7, 4.2 Hz, 2H), 2.29 (s, 6H), 2.14 (dd, J=12.5, 2.5 Hz, 2H).

Dimethanesulfonate: mp (MeOH-EtOAc) 191-193° C.; $^1$H NMR (DMSO-d$_6$) δ 9.53 (br, 1H, exchangeable with D$_2$O), 8.46 (s, 1H), 7.88 (d, J=7.9 Hz, 1H), 7.78 (t, J$_{HF}$=52.9 Hz, 1H), 7.40 (t, J=8.2 Hz, 1H), 6.95 (d, J=7.7 Hz, 1H), 4.91 (ddd, J=15.5, 10.9, 4.5 Hz, 1H), 4.01 (m, 4H), 4.00 (s, 3H), 3.83 (m, 6H), 3.64 (dd, J=10.0, 5.5 Hz, 2H), 3.49 (m, 1H), 3.21 (dt, J=12.3, 2.7 Hz, 2H), 2.87 (d, J=4.1 Hz, 6H), 2.25-2.09 (m, 4H); Anal. Calcd. for C$_{29}$H$_{43}$F$_2$N$_9$O$_{10}$S$_3$: C, 42.9; H, 5.3; N, 15.5. Found: C, 42.8; H, 5.55; N, 15.5%.

Example 100

Synthesis of N-(5-{[4-[2-(difluoromethyl)-4-methoxy-1H-benzimidazol-1-yl]-6-(4-morpholinyl)-1,3,5-triazin-2-yl]amino}-2-pyridinyl)methanesulfonamide

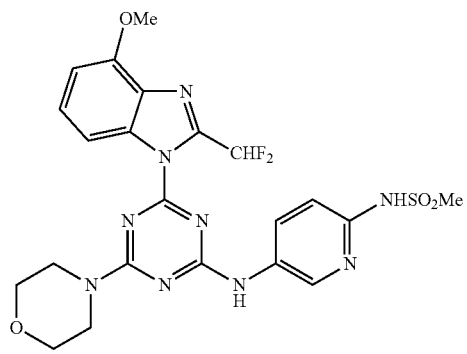

To 0.652 g (4.69 mmol) of 2-amino-5-nitropyridine in THF (5 mL) was added 3.5 mL of NaHMDS (2M solution in THF) at 0° C. After 20 min a solution of 1.085 g (4.97 mmol) of di-tert-butyl dicarbonate in THF (6 mL) was added and the mixture was slowly warmed to room temperature overnight. Water was added, and the mixture was extracted with EtOAc (×4). The organic layer was washed with brine, dried (Na$_2$SO$_4$), and concentrated. Chromatography on, silica with hexanes-EtOAc (7:3), gave 0.695 g (62% yield) of tert-butyl-5-nitropyridin-2-ylcarbamate as an orange powder: $^1$H NMR (CDCl$_3$) δ 9.19 (dd, J=2.8, 0.5 Hz, 1H), 8.93 (br s, 1H), 8.46 (ddd, J=9.4, 2.8, 0.5 Hz, 1H), 8.20 (dd, J=9.5, 0.5 Hz, 1H), 1.59 (s, 9H); LCMS (APCI$^-$) m/z: 238 (MH$^+$, 100%).

To 0.314 g (1.31 mmol) of the above nitro compound in THF-MeOH (16 mL, 1:1) was added 0.460 g of 10% Pd/C and the mixture was stirred under hydrogen (40 in/Hg) for 4 hrs. The reaction mixture was filtered through celite, washed with MeOH and concentrated to give 0.277 g (99% yield) of tert-butyl 5-aminopyridin-2-yl-carbamate as a white powder: $^1$H NMR (DMSO-d$_6$) δ9.00 (br s, 1H), 7.62 (dd, J=2.7, 0.4 Hz, 1H), 7.39 (d, J=8.7 Hz, 1H), 6.94 (dd, J=8.7, 2.8 Hz, 1H), 4.92 (s, 2H), 1.44 (s, 9H).

To 0.277 g (1.33 mmol) of the above amino compound in THF (3 mL) was added 0.61 mL of n-butyllithium (2.5 M solution in hexanes) and the mixture was stirred for 10 min. A solution of 0.176 g (0.44 mmol) of 1-[4-chloro-6-(4-morpholinyl)-1,3,5-triazin-2-yl]-2-(difluoromethyl)-4-methoxy-1H-benzimidazole in THF (5 mL) was added and the resulting mixture was stirred for 1 hr at room temperature. The reaction mixture was neutralized with acetic acid, diluted with water, and extracted with EtOAc. The organic layer was washed with water and aq. NH$_3$, dried, and concentrated. Chromatography on silica, eluting with hexanes-EtOAc (7:3), then with CH$_2$Cl$_2$-EtOAc (3:1), gave 0.033 g (13% yield) of tert-butyl 5-{[4-[2-(difluoromethyl)-4-methoxy-1H-benzimidazol-1-yl]-6-(4-morpholinyl)-1,3,5-triazin-2-yl]amino}-2-pyridinylcarbamate: $^1$H NMR (DMSO-d$_6$) δ10.02 (s, 1H), 9.66 (s, 1H), 8.54 (s, 1H), 8.17-7.80 (m, 4H), 7.39 (d, J=8.7 Hz, 1H), 6.97-6.93 (m, 1H), 3.98 (s, 3H), 3.82 (s, 4H), 3.74-3.72 (m, 4H), 1.48 (s, 9H).

To 0.033 g (0.06 mmol) of the above carbamate in CH$_2$Cl$_2$ (3 mL) was added 0.1 mL (1.30 mmol) of trifluoroacetic acid, and the mixture was stirred for 5 hrs. The reaction mixture was diluted with CH$_2$Cl$_2$ and aq. NH$_4$OH, and the organic layer was washed with brine, dried (Na$_2$SO$_4$), and concentrated. The residue was recrystallized from EtOH/CH$_2$Cl$_2$ to give 0.0133 g (49% yield) of N$^5$-[4-[2-(difluoromethyl)-4-methoxy-1H-benzimidazol-1-yl]-6-(4-morpholinyl)-1,3,5-triazin-2-yl]-2,5-pyridinediamine, as a brown powder: mp 267-270° C.; $^1$H NMR (DMSO-d$_6$) δ9.67-9.49 (m, 1H), 8.18-7.27 (m, 5H), 6.96 (d, J=7.6 Hz, 1H), 6.48 (d, J=8.4 Hz, 1H), 5.87-5.75 (m, 2H), 3.98 (s, 3H), 3.81 (s, 4H), 3.71 (s, 4H); HRMS (ESI) M+H$^+$ Calcd. for C$_{21}$H$_{22}$F$_2$N$_9$O$_2$: m/z 470.1859. Found: m/z 470.1867.

To 86 mg (0.18 mmol) of the above amine in pyridine (1 mL) was added 17 μL (0.22 mmol) of methanesulfonyl chloride, and the mixture was heated at 50° C. for 18 hrs. The mixture was cooled to room temperature, sat. NaHCO$_3$ solution was added, and the resulting mixture was extracted with EtOAc (×4). The combined organic layers were dried, and the solvent removed. Chromatography on silica, eluting with CH$_2$CH$_2$/EtOAc (1:1) gave 50 mg (51% yield) of N-(5-{[4-[2-(difluoromethyl)-4-methoxy-1H-benzimidazol-1-yl]-6-(4-morpholinyl)-1,3,5-triazin-2-yl]amino}-2-pyridinyl)methanesulfonamide, as a yellow powder: mp 302-306° C.; $^1$H NMR (DMSO-d$_6$) δ10.49 (s, 1H), 10.04 (s, 1H), 8.56 (s, 1H), 8.16-7.41 (m, 4H), 7.05 (d, J=8.8 Hz, 1H), 6.96 (d, J=8.0 Hz, 1H), 3.98 (s, 3H), 3.82 (s, 4H), 3.74-3.72 (m, 4H), 3.29 (s, 3H); HRMS (ESI) M+Na+ Calcd. for $C_{23}H_{23}F_2N_9NaO_4S$: m/z 570.1454. Found: m/z 570.1442.

Example 101

Synthesis of N-(5-{[4-[2-(difluoromethyl)-4-methoxy-1H-benzimidazol-1-yl]-6-(4-morpholinyl)-1,3,5-triazin-2-yl]amino}-2-pyridinyl)-N-methylmethanesulfonamide

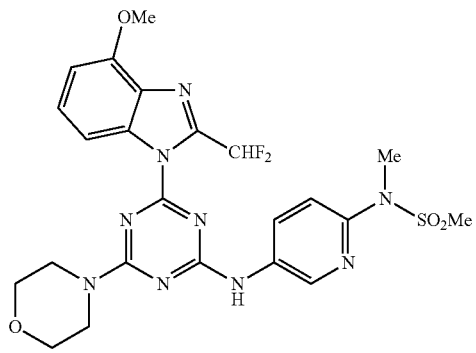 [SMILES: COc1cccc2c1nc(C(F)F)n2-c1nc(Nc2ccc(N(C)S(C)(=O)=O)nc2)nc(N2CCOCC2)n1]

To 0.652 g (4.69 mmol) of 2-amino-5-nitropyridine in THF (5 mL) was added 3.5 mL of NaHMDS (2M solution in THF) at 0° C. After 20 min, a solution of 1.085 g (4.97 mmol) of di-tert-butyl dicarbonate in THF (6 mL) was added, and the mixture was slowly warmed to room temperature overnight. Water was added, and the mixture was extracted with EtOAc (×4). The combined organic layers were washed with brine, dried ($Na_2SO_4$), and concentrated. Purification by flash column chromatography on silica, eluting with hexanes-EtOAc (7:3), gave 0.695 g (62% yield) of tert-butyl 5-nitro-2-pyridinylcarbamate as an orange powder: $^1$H NMR (CDCl$_3$) δ9.19 (dd, J=2.8, 0.5 Hz, 1H), 8.93 (br s, 1H), 8.46 (ddd, J=9.4, 2.8, 0.5 Hz, 1H), 8.20 (dd, J=9.5, 0.5 Hz, 1H), 1.59 (s, 9H); LCMS (APCI$^-$) m/z: 238 (MH$^+$, 100%).

To 0.378 g (1.58 mmol) of the above nitro compound in DMF (6 mL) at 0° C. was added 0.067 g (2.80 mmol) of sodium hydride. After 20 min, 0.12 mL (1.93 mmol) of methyl iodide was added, and the mixture was stirred for 2 hrs. Water was added, and the mixture was extracted with EtOAc (×4). The combined organic layer was washed successively with 1M HCl, sat. NaHCO$_3$ solution, and brine, dried (Na$_2$SO$_4$), and concentrated, to give 0.40 g (99% yield) of tert-butyl methyl(5-nitro-2-pyridinyl)carbamate: $^1$H NMR (CDCl$_3$) δ9.19 (d, J=2.7 Hz, 1H), 8.36 (dd, J=9.4, 2.7 Hz, 1H), 8.14 (dd, J=9.4, 0.3 Hz, 1H), 3.50 (s, 3H), 1.57 (s, 9H); LCMS (APCI$^-$) m/z: 253 (MH$^+$, 100%).

To 0.40 g (1.58 mmol) of the above nitro compound in MeOH (25 mL) was added 0.4 g of 10% Pd/C and the mixture was stirred under hydrogen (40 in Hg) for 4 hrs. After filtration through celite the reaction mixture was concentrated, to give 0.36 g (97% yield) of tert-butyl 5-amino-2-pyridin-2-yl (methyl)carbamate, as a yellow oil: $^1$H NMR (DMSO-d$_6$) δ7.70 (dd, J=2.9, 0.5 Hz, 1H), 7.07 (d, J=8.6 Hz, 1H), 6.93 (dd, J=8.6, 2.9 Hz, 1H), 3.12 (s, 3H), 1.39 (s, 9H).

To 0.356 g (1.53 mmol) of the above amine in THF (3 mL) was added 0.70 mL of n-butyllithium (2.5 M solution in hexanes) and the mixture was stirred for 10 min. A solution of 0.21 g (0.52 mmol) of 1-[4-chloro-6-(4-morpholinyl)-1,3,5-triazin-2-yl]-2-(difluoromethyl)-4-methoxy-1H-benzimidazole in THF (5 mL) was added, and the resulting mixture was stirred for 1 hr. The reaction mixture was neutralized with acetic acid, diluted with water, and extracted with EtOAc. The organic layer was washed with water and aq. NH$_3$, and dried. The solvent was removed under vacuum, and the product mixture was purified by flash column chromatography, eluting with CH$_2$Cl$_2$/EtOAc (3:1), to give 0.075 g (13% yield) of tert-butyl 5-{[4-[2-(difluoromethyl)-4-methoxy-1H-benzimidazol-1-yl]-6-(4-morpholinyl)-1,3,5-triazin-2-yl]amino}-2-pyridinyl(methyl)carbamate, as a yellow powder: $^1$H NMR (DMSO-d$_6$) δ10.11 (s, 1H), 8.68-7.41 (m, 5H), 7.61 (d, J=9.0 Hz, 1H), 6.97 (d, J=8.1 Hz, 1H), 3.98 (s, 3H), 3.83 (s, 4H), 3.74-3.73 (m, 4H), 3.29 (s, 3H), 1.47 (s, 9H); LCMS (APCI$^+$) m/z: 585 (MH$^+$, 100%).

To 0.0750 g (0.13 mmol) of the above carbamate in CH$_2$Cl$_2$ (3 mL) was added 0.1 mL (1.30 mmol) of trifluoroacetic acid and the mixture was stirred for 5 hrs. After dilution with CH$_2$Cl$_2$, the mixture was treated with H$_2$O and aq. NH$_3$, and the organic layer was washed with brine, dried (Na$_2$SO$_4$), and concentrated. The residue was recrystallized from EtOH/CH$_2$Cl$_2$ to give 0.0472 g (75% yield) of N$^5$-[4-[2-(difluoromethyl)-4-methoxy-1H-benzimidazol-1-yl]-6-(4-morpholinyl)-1,3,5-triazin-2-yl]-N$^2$-methyl-2,5-pyridinediamine: mp 218-221° C.; $^1$H NMR (CDCl$_3$) δ8.31-7.73 (m, 2H), 7.62 (dd, J=8.8, 2.6 Hz, 1H), 7.56-7.31 (m, 2H), 6.82-6.80 (m, 2H), 6.46 (d, J=8.8 Hz, 1H), 4.76 (br s, 1H), 4.04 (s, 3H), 3.89 (s, 4H), 3.79 (s, 4H), 2.96 (s, 3H); HRMS (ESI) M+H$^+$ Calcd. for $C_{22}H_{24}F_2N_9O_2$: m/z 484.2016. Found: m/z 484.2023.

To 30 mg (0.06 mmol) of the above methylamine in CH$_2$Cl$_2$ (2 mL) at 0° C. was added 0.01 mL (0.07 mmol) of Et$_3$N, and after 10 min 5 μL (0.06 mmol) of methanesulfonyl chloride was added, and the mixture was stirred for 1 hr. Water was added, and the mixture was extracted with EtOAc. The organic layer washed with brine, dried, and the solvent was removed. Chromatography on silica, eluting first with hexanes/EtOAc (1:1) then with CH$_2$Cl$_2$/EtOAc (1:1), gave 0.019 g (55% yield) of N-(5-{[4-[2-(difluoromethyl)-4-methoxy-1H-benzimidazol-1-yl]-6-(4-morpholinyl)-1,3,5-triazin-2-yl]amino}-2-pyridinyl)-N-methylmethanesulfonamide, as a white powder: mp 250-253° C.; $^1$H NMR (CDCl$_3$) δ8.61 (s, broad, 1H), 8.11-7.25 (m, 6H), 6.81 (d, J=8.0 Hz, 1H), 4.02 (s, 3H), 3.91 (s, 4H), 3.82-3.80 (m, 4H), 3.41 (s, 3H), 3.01 (s, 3H); HRMS (ESI) M+H$^+$ Calcd. for $C_{23}H_{26}F_2N_9O_4S$: m/z 562.1791. Found: m/z 562.1785.

Example 102

Biological Activity

A. Inhibition of Isolated Enzyme

Compounds were evaluated for their ability to inhibit Class I PI 3-kinase enzymes p110δ/p85, p110α/p85, and p110β/p85. Reaction mixtures comprising 0.1 μg of a recombinant enzyme, 10 μg of L-α-phosphatidylinositol, and 2× Lipid Kinase Buffer (40 mM Tris-HCl, pH 7.4, 200 mM NaCl, 1 mM EDTA), which contains either DMSO only as a control or the test compound in DMSO (the final DMSO concentration is 1%), were activated by the addition of an ATP mix (5 mM MgCl$_2$, 100 μM ATP, and 0.1 μL [γ$^{33}$P]ATP). Reactions were incubated at room temperature for 1 hr, and then stopped by the addition of 1M HCl. The lipids were then extracted using a two step procedure. Firstly, 200 μL of chloroform/methanol (1:1) was added, the biphasic reactions mixed and centrifuged briefly, and the inorganic phase was removed and discarded. Following this, 80 μL of methanol:HCl (1:1) was added and the same procedure followed. The organic phase (70 μL) was then transferred to a clean 1.6 mL tube and the reactions were dried using a Speedvac, with no heating, for 30 min. The reactions were spotted onto TLC plates (Merck Ltd) and developed for 1 hr in propanol-1:2 M acetic acid (13:7). The TLC plates were then dried at room temperature and quantified using a phosphorimager (StormImager, Amersham). Nine compound concentrations were used for each test compound to determine its $IC_{50}$ value. Each experiment was performed twice and the average $IC_{50}$ value is used herein. The results are summarized in Table 1.

B. Cellular Growth Inhibition.

The compounds were evaluated against two early passage human cell lines NZB5 and NZOV9 (Marshall et al., *Oncol. Res.* 2004, 14, 297). The cells were grown in ITS medium (α-modified minimal essential medium supplemented insulin, transferrin, selenite, and 5% fetal bovine serum) and grown on 96-well tissue culture plates under an atmosphere of 5% $O_2$, 5% $CO_2$, and 90% $N_2$. Individual wells contained 500-1,000 cells (depending on the growth rate) in a volume of 150 μL. Compounds were added at 10-fold concentration steps to a maximum of 20 μM and plates were incubated for five days, with $^3H$-thymidine being added over the last 6 hrs. Cells were harvested and incorporated radioactivity measured. Duplicate samples were analyzed for each compound dose with multiple control samples. Data were fitted by a least-squares method to an exponential of the form $y=y_0+ae^{-bx}$, where y is the radioactivity (corrected for background and normalized to 100% of the control), x is the radiation dose, and $y_0$, a, and b are variables, and the $IC_{50}$ value defined as the compound concentration reducing $^3H$-thymidine levels by 50%. The results are summarized in Table 1.

TABLE 1

Biological Activity

| Example | Enzyme $IC_{50}$* | | | Cell $IC_{50}$* | |
|---|---|---|---|---|---|
| | p110α | p110β | p110δ | NZB5 | NZOV9 |
| 1 | B | A | A | C | B |
| 2 | A | B | A | B | B |
| 3 | A | A | A | B | A |
| 4 | B | B | B | B | B |
| 5 | A | A | A | B | A |
| 6 | A | A | A | B | A |
| 7 | B | C | B | B | B |
| 8 | A | B | A | B | A |
| 9 | A | B | A | A | A |
| 10 | A | B | A | B | A |
| 11 | A | C | A | B | B |
| 12 | A | B | A | B | B |
| 13 | A | B | A | B | A |
| 14 | A | A | A | B | A |
| 15 | A | B | A | B | A |
| 16 | A | | A | C | B |
| 17 | A | A | A | B | A |
| 18 | A | B | A | B | A |
| 19 | B | B | A | B | B |
| 20 | A | B | A | A | A |
| 21 | A | B | A | B | B |
| 22 | A | B | A | B | A |
| 23 | A | A | A | B | A |
| 24 | B | C | A | | |
| 25 | A | | | | |
| 26 | B | | | | |
| 27 | A | | | | |
| 28 | A | | | | |
| 29 | A | | | | |
| 30 | A | | | | |
| 31 | A | | | | |
| 32 | A | | | B | A |
| 33 | A | | | A | A |
| 34 | A | | | B | A |
| 35 | A | | | A | A |
| 36 | A | | | B | A |

TABLE 1-continued

Biological Activity

| Example | Enzyme $IC_{50}$* | | | Cell $IC_{50}$* | |
|---|---|---|---|---|---|
| | p110α | p110β | p110δ | NZB5 | NZOV9 |
| 37 | A | | | B | A |
| 38 | A | | | B | A |
| 39 | A | | | B | A |
| 40 | A | | | B | A |
| 41 | A | | | | |
| 42 | A | | | B | A |
| 43 | A | | | | |
| 44 | A | | | B | A |
| 45 | A | | A | B | A |
| 46 | A | | | B | A |
| 47 | A | | A | B | A |
| 48 | A | | A | | |
| 49 | A | | A | | |
| 50 | A | | A | B | B |
| 51 | A | | A | C | B |
| 52 | | | | C | C |
| 53 | B | | A | C | B |
| 54 | B | | A | B | A |
| 55 | A | | A | | |
| 56 | A | | A | | |
| 58 | A | | A | | |
| 59 | B | C | A | | |
| 61 | A | | A | | |
| 63 | B | C | B | B | B |
| 64 | A | B | B | B | A |
| 65 | A | B | B | B | B |
| 66 | A | C | B | B | B |
| 67 | A | C | B | B | B |
| 68 | A | C | B | B | A |
| 69 | A | C | A | B | A |
| 70 | A | C | A | A | A |
| 71 | A | C | A | A | A |
| 72 | A | | B | | |
| 73 | B | | B | | |
| 74 | A | | B | | |
| 75 | B | | B | | |
| 76 | B | | B | | |
| 77 | B | | B | | |
| 78 | A | C | B | B | A |
| 79 | A | C | B | B | A |
| 80 | A | | A | | |
| 81 | A | | A | | |
| 82 | A | | A | | |
| 83 | B | | B | | |
| 84 | A | B | A | A | C |
| 85 | B | | C | B | B |
| 86 | B | | C | | |
| 87 | A | | B | | |
| 88 | A | | B | | |
| 89 | A | | B | C | B |
| 90 | A | C | B | B | A |
| 91 | A | C | B | A | A |
| 92 | A | B | B | B | B |
| 93 | A | | A | | |
| 94 | B | | B | | |
| 95 | B | | C | | |
| 96 | A | | B | | |
| 97 | A | | A | | |
| 98 | A | | B | | |
| 99 | A | B | B | A | A |
| 100 | A | | A | B | A |
| 101 | A | B | A | A | A |

*A. <0.1 μM; B. 0.1-1.0 μM; C. >1.0 μM

Example 103

Pharmacological Stability

Pharmacological stability of 2-(difluoromethyl)-1-[4-[4-(methylsulfonyl)-1-piperazinyl]-6-(4-morpholinyl)-1,3,5-triazin-2-yl]-1H-benzimidazole ("the sulfonamide," Example 1) and 1-[4-(4-acetyl-1-piperazinyl)-6-(4-morpholinyl)-1,3,5-triazin-2-yl]-2-(difluoromethyl)-1H-benzimidazole ("the carboxamide," EP 1864665 and WO 2006/095906) were incubated in human plasma at 37° C. for 20 hrs. The sulfonamide displayed a greater than five-fold increase in stability compared to the carboxamide.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method for the treatment of a PI3K-mediated cancer, comprising administration to a mammal in need thereof, a therapeutically effective dose of a composition in an amount effective to inhibit PI3K enzyme activity, comprising a compound of Formula IA:

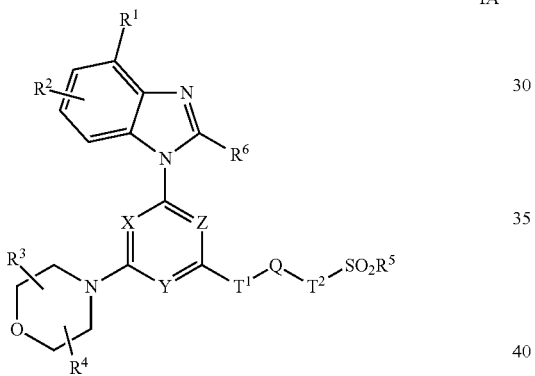

IA or a pharmaceutically acceptable salt thereof;
wherein:
$R^1$ and $R^2$ are each independently (a) hydrogen, cyano, halo, or nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (c) —C(O)$R^{1a}$, —C(O)OR$^{1b}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; wherein each R$^{1a}$, R$^{1b}$, R$^{1c}$, and R$^{1d}$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^{1b}$ and R$^{1c}$ together with the N atom to which they are attached form heterocyclyl;
$R^3$ and $R^4$ are each independently hydrogen or $C_{1-6}$ alkyl; or $R^3$ and $R^4$ are linked together to form a bond, $C_{1-6}$ alkylene, $C_{1-6}$ heteroalkylene, $C_{2-6}$ alkenylene, or $C_{2-6}$ heteroalkenylene;

$R^5$ is independently $C_{1-6}$ alkyl $C_{2-6}$ alkenyl, each optionally substituted with one or more substituents, each of which is independently selected from the group consisting of heterocyclyl and —NR$^f$R$^g$, or R$^5$ is —NR$^{5m}$R$^{5n}$, where R$^{5m}$ and R$^{5n}$ are each independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl;
$R^6$ is independently hydrogen or $C_{1-6}$ alkyl;
Q is $C_{1-6}$ alkylene, $C_{2-6}$ alkenylene, $C_{2-6}$ alkynylene, $C_{3-7}$ cycloalkylene, $C_{6-14}$ arylene, heteroarylene, or heterocyclylene;
$T^1$ is independently a bond, $C_{1-6}$ alkylene, —O—, or —NR$^8$—;
$T^2$ is independently a bond, $C_{1-6}$ alkylene, or —NR$^8$—; wherein each R$^8$ is independently hydrogen, $C_{1-6}$ alkyl, $C_{2-6}$ alkenyl, or $C_{2-6}$ alkynyl; and
with the proviso that at least one of the two atoms that are directly attached to the —SO$_2$— group is nitrogen;
X, Y, and Z are each independently a nitrogen atom or CR$^9$, with the proviso that at least two of X, Y, and Z are nitrogen atoms; where R$^9$ is hydrogen or $C_{1-6}$ alkyl;
wherein each alkyl, alkylene, heteroalkylene, alkenyl, alkenylene, heteroalkenylene, alkynyl, alkynylene, cycloalkyl, cycloalkylene, aryl, arylene, heteroaryl, heteroarylene, heterocyclyl, and heterocyclylene in $R^1$, $R^2$, $R^3$, $R^4$, $R^6$, $R^8$, $R^9$, $R^{1a}$, $R^{1b}$, $R^{1c}$, $R^{1d}$, $R^{5m}$, $R^{5n}$, Q, $T^1$, and $T^2$, is optionally substituted with one or more groups, each independently selected from (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each optionally substituted with one or more, in one embodiment, one, two, three, or four, substituents $Q^1$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more substituents $Q^1$; or (iii) R$^b$ and R$^c$ together with the N atom to which they are attached form heterocyclyl, optionally substituted with one or more substituents $Q^1$;
wherein each $Q^1$ is independently selected from the group consisting of (a) cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, —C(O)OR$^e$, —C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heterocyclyl.

2. The method of claim 1, wherein the pharmaceutically acceptable salt is the salt of an acid selected from the group consisting of acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

3. The method of claim 1, wherein the pharmaceutically acceptable salt is the salt of an acid selected from the group consisting of methanesulfonic acid, succinic acid, citric acid, and hydrochloric acid.

4. The method of claim 2, wherein $R^1$ is independently hydrogen, methoxy, or dimethylaminopropoxy;
$R^2$ is independently hydrogen or amino;
$R^3$ and $R^4$ are each independently hydrogen; or $R^3$ and $R^4$ are linked together to form ethylene;
$R^5$ is independently methyl, ethenyl, dimethylaminomethyl, dimethylaminoethyl, or dimethylaminopropyl;
$R^6$ is difluoromethyl;
Q is phenylene, optionally substituted with one or more groups;
$T^1$ is independently a bond, —O—, or —NR$^8$—;
$T^2$ is —NR$^8$—, with the proviso that the atom that is attached to —SO$_2$R$_5$ is nitrogen;
wherein each $R^8$ is independently hydrogen or methyl; and
X, Y, and Z are each a nitrogen atom.

5. The method of claim 4, wherein the pharmaceutically acceptable salt is the salt of an acid selected from the group consisting of methanesulfonic acid, succinic acid, citric acid, and hydrochloric acid.

6. The method of claim 2, wherein the compound of Formula IA is Formula V:

or a pharmaceutically acceptable salt thereof;

wherein
$R^1$ is independently hydrogen, methoxy, or dimethylaminopropoxy;
$R^2$ is independently hydrogen or amino;
$R^3$ and $R^4$ are hydrogen; or $R^3$ and $R^4$ are linked together to form ethylene;
$R^5$ is independently methyl, ethenyl, dimethylaminomethyl, dimethylaminoethyl, or dimethylaminopropyl;
$R^6$ is difluoromethyl;
U is N or CH;
G is —CH$_2$—, or —CH$_2$CH$_2$—; and
X, Y, and Z are each a nitrogen atom.

7. The method of claim 6, wherein the pharmaceutically acceptable salt is the salt of an acid selected from the group consisting of methanesulfonic acid, succinic acid, citric acid, and hydrochloric acid.

8. The method of claim 2, wherein the compound is N-{4-[4-[2-(difluoromethyl)-4-methoxy-1H-benzimidazol-1-yl]-6-(4-morpholinyl)-1,3,5-triazin-2-yl]phenyl}-2-(dimethylamino)ethanesulfonamide mesylate.

9. The method of claim 2, wherein the compound is N-{4-[4-[2-(difluoromethyl)-4-methoxy-1H-benzimidazol-1-yl]-6-(4-morpholinyl)-1,3,5-triazin-2-yl]phenyl}-2-(dimethylamino)-N-methylethanesulfonamide mesylate.

10. The method of claim 2, wherein the compound is N-[2-({4-[4-[2-(difluoromethyl)-4-methoxy-1H-benzimidazol-1-yl]-6-(4-morpholinyl)-1,3,5-triazin-2-yl]-1-piperidinyl}sulfonyl)ethyl]-N,N-dimethylamine hydrochloride.

11. The method of claim 2, wherein the PI3K-mediated cancer is hemangiosarcoma, mastocytosis, breast cancer, osteosarcoma, melanoma, lymphoma, renal cell carcinoma, astrocytoma, bladder cancer, non-small cell lung cancer, colon or rectal cancer, ovarian cancer, multiple myeloma, non-Hodgkin lymphoma, leukemia, or promyelocytic leukemia.

12. The method of claim 11, wherein the composition is an oral dosage form and is administered in an amount of between about 0.1 to about 50 mg/kg/day.

13. The method of claim 12, wherein the composition is an oral dosage form and is administered in an amount of between about 0.5 to about 25 mg/kg/day.

14. The method of claim 12, wherein the mammal is a dog or a cat.

15. The method of claim 7, wherein the PI3K-mediated cancer is hemangiosarcoma, mastocytosis, breast cancer, osteosarcoma, melanoma, lymphoma, renal cell carcinoma, astrocytoma, bladder cancer, non-small cell lung cancer, colon or rectal cancer, ovarian cancer, multiple myeloma, non-Hodgkin lymphoma, leukemia, or promyelocytic leukemia.

16. The method of claim 15, wherein the composition is an oral dosage form and is administered in an amount of between about 0.1 to about 50 mg/kg/day.

17. The method of claim 16, wherein the composition is an oral dosage form and is administered in an amount of between about 0.5 to about 25 mg/kg/day.

18. The method of claim 16, wherein the mammal is a dog or a cat.

19. The method of claim 9, wherein the PI3K-mediated cancer is hemangiosarcoma, mastocytosis, breast cancer, osteosarcoma, melanoma, lymphoma, renal cell carcinoma, astrocytoma, bladder cancer, non-small cell lung cancer, colon or rectal cancer, ovarian cancer, multiple myeloma, non-Hodgkin lymphoma, leukemia, or promyelocytic leukemia.

20. The method of claim 19, wherein the composition is an oral dosage form and is administered in an amount of between about 0.1 to about 50 mg/kg/day.

21. The method of claim 20, wherein the composition is an oral dosage form and is administered in an amount of between about 0.5 to about 25 mg/kg/day.

22. The method of claim 20, wherein the mammal is a dog or a cat.

* * * * *